United States Patent
Li et al.

(10) Patent No.: US 12,240,876 B2
(45) Date of Patent: Mar. 4, 2025

(54) LIVER-SPECIFIC Wnt SIGNAL ENHANCING MOLECULES AND USES THEREOF

(71) Applicant: Surrozen Operating, Inc., South San Francisco, CA (US)

(72) Inventors: Yang Li, Mountain View, CA (US); Zhengjian Zhang, Albany, CA (US); Randall J. Brezski, Alameda, CA (US); Leonard Presta, San Francisco, CA (US); Thomas Lopez, Palo Alto, CA (US); Hui Chen, Foster City, CA (US); Helene Baribault, Redwood City, CA (US); Wen-Chen Yeh, Belmont, CA (US); Shengjiang Tu, Foster City, CA (US)

(73) Assignee: Surrozen Operating, Inc., South San Francisco, CA (US)

( * ) Notice: Subject to any disclaimer, the term of this patent is extended or adjusted under 35 U.S.C. 154(b) by 0 days.

(21) Appl. No.: 18/311,082

(22) Filed: May 2, 2023

(65) Prior Publication Data
US 2023/0374090 A1    Nov. 23, 2023

Related U.S. Application Data

(63) Continuation of application No. PCT/US2021/059564, filed on Nov. 16, 2021.

(60) Provisional application No. 63/248,157, filed on Sep. 24, 2021, provisional application No. 63/182,106, filed on Apr. 30, 2021, provisional application No. 63/114,457, filed on Nov. 16, 2020.

(51) Int. Cl.
| | |
|---|---|
| *C07K 14/47* | (2006.01) |
| *A61K 38/00* | (2006.01) |
| *A61P 1/16* | (2006.01) |
| *C07K 16/24* | (2006.01) |

(52) U.S. Cl.
CPC ............ *C07K 14/4705* (2013.01); *A61P 1/16* (2018.01); *C07K 16/24* (2013.01); *A61K 38/00* (2013.01); *C07K 2317/24* (2013.01); *C07K 2317/565* (2013.01); *C07K 2319/03* (2013.01)

(58) Field of Classification Search
None
See application file for complete search history.

(56) References Cited

U.S. PATENT DOCUMENTS

| | | |
|---|---|---|
| 4,946,778 A | 8/1990 | Ladner et al. |
| 5,091,513 A | 2/1992 | Huston et al. |
| 5,132,405 A | 7/1992 | Huston et al. |
| 6,528,624 B1 | 3/2003 | Idusogie et al. |
| 6,538,124 B1 | 3/2003 | Idusogie et al. |
| 7,297,775 B2 | 11/2007 | Idusogie et al. |
| 7,317,091 B2 | 1/2008 | Lazar et al. |
| 7,364,731 B2 | 4/2008 | Idusogie et al. |
| 7,657,380 B2 | 2/2010 | Lazar et al. |
| 7,662,925 B2 | 2/2010 | Lazar et al. |
| 8,278,036 B2 | 10/2012 | Kariko et al. |
| 8,507,442 B2 | 8/2013 | Gurney et al. |
| 8,691,966 B2 | 4/2014 | Kariko et al. |
| 8,748,089 B2 | 6/2014 | Kariko et al. |
| 8,835,108 B2 | 9/2014 | Kariko et al. |
| 8,969,526 B2 | 3/2015 | Baehner et al. |
| 9,296,826 B2 | 3/2016 | Cong et al. |
| 9,771,427 B2 | 9/2017 | Hofer et al. |
| 11,958,891 B2 | 4/2024 | Zhang et al. |
| 2003/0044409 A1 | 3/2003 | Carson et al. |
| 2007/0244061 A1 | 10/2007 | Niehrs et al. |
| 2008/0038272 A1 | 2/2008 | Buehring et al. |
| 2008/0131435 A1 | 6/2008 | Stavenhagen et al. |
| 2008/0138344 A1 | 6/2008 | Stavenhagen et al. |
| 2008/0267955 A1 | 10/2008 | Schluesener et al. |
| 2008/0286261 A1 | 11/2008 | Morgan et al. |
| 2009/0028869 A1 | 1/2009 | Dodel et al. |
| 2009/0092599 A1 | 4/2009 | Lazar et al. |
| 2010/0092457 A1 | 4/2010 | Aburatani et al. |
| 2010/0172895 A1 | 7/2010 | Boone et al. |
| 2013/0230521 A1 | 9/2013 | Nakamura et al. |
| 2014/0044713 A1 | 2/2014 | De Lau et al. |
| 2014/0105917 A1 | 4/2014 | Gurney |
| 2014/0328859 A1 | 11/2014 | Cong et al. |
| 2015/0299324 A1 | 10/2015 | Hofer et al. |
| 2016/0303232 A1 | 10/2016 | Adiwijaya et al. |
| 2017/0158775 A1 | 6/2017 | Linden et al. |
| 2017/0240633 A1 | 8/2017 | Wang et al. |
| 2017/0306029 A1 | 10/2017 | Garcia et al. |
| 2017/0349659 A1 | 12/2017 | Garcia et al. |
| 2018/0066067 A1 | 3/2018 | Cong et al. |
| 2018/0312604 A1 | 11/2018 | Throsby et al. |

(Continued)

FOREIGN PATENT DOCUMENTS

| | | |
|---|---|---|
| CN | 104080471 A | 10/2014 |
| CN | 104704001 A | 6/2015 |

(Continued)

OTHER PUBLICATIONS

Apte, U. et al. (Sep. 2009) Beta-catenin activation promotes liver regeneration after acetaminophen-induced injury. The American Journal of Pathology. 175(3):1056-1065. DOI: 10.2353/ajpath.2009. 080976.

Arumugam, T. et al. (Apr. 2015) "New Blocking Antibodies against Novel AGR2-C4.4A Pathway Reduce Growth and Metastasis of Pancreatic Tumors and Increase Survival in Mice" Molecular Cancer Therapeutics, 14(4):941-951.

Bhanot, P. et al. (Jul. 18, 1996) "A new member of the frizzled family from Drosophila functions as a Wingless receptor" Nature, 382:225-230.

Bhushan, B. et al. (Nov. 2014) Pro-regenerative signaling after acetaminophen-induced acute liver injury in mice identified using a novel incremental dose model. The American Journal of Pathology. 184(11):3013-3025. DOI: 10.1016/j.ajpath.2014.07.019.

(Continued)

*Primary Examiner* — Marianne P Allen
(74) *Attorney, Agent, or Firm* — Cooley LLP

(57) ABSTRACT

The present disclosure provides liver-specific Wnt signal enhancing molecules, and related methods of using these molecules to increase Wnt signaling in liver tissues and treat liver diseases and disorders.

10 Claims, 61 Drawing Sheets

Specification includes a Sequence Listing.

(56) References Cited

U.S. PATENT DOCUMENTS

| | | |
|---|---|---|
| 2020/0024338 A1 | 1/2020 | Luca et al. |
| 2020/0048324 A1 | 2/2020 | Zhang et al. |
| 2020/0199237 A1 | 6/2020 | Garcia et al. |
| 2020/0199238 A1 | 6/2020 | Garcia et al. |
| 2020/0308287 A1 | 10/2020 | Li et al. |
| 2021/0079089 A1 | 3/2021 | Li et al. |
| 2021/0087280 A1 | 3/2021 | Li et al. |
| 2021/0292422 A1 | 9/2021 | Li |
| 2021/0380678 A1 | 12/2021 | Zhang et al. |
| 2021/0403578 A1 | 12/2021 | Garcia et al. |
| 2022/0064337 A1 | 3/2022 | Li et al. |
| 2022/0112278 A1 | 4/2022 | Li et al. |
| 2022/0175884 A1 | 6/2022 | Lee et al. |
| 2022/0195053 A1 | 6/2022 | Li et al. |
| 2023/0138045 A1 | 5/2023 | Li |
| 2023/0183359 A1 | 6/2023 | Garcia et al. |
| 2024/0279303 A1 | 8/2024 | Zhang et al. |

FOREIGN PATENT DOCUMENTS

| | | |
|---|---|---|
| CN | 106714831 A | 5/2017 |
| CN | 108602888 A | 9/2018 |
| EP | 2305274 A1 | 4/2011 |
| EP | 2331136 B1 | 1/2018 |
| WO | WO-2004063351 A2 | 7/2004 |
| WO | WO-2006079372 A1 | 8/2006 |
| WO | WO-2006088494 A2 | 8/2006 |
| WO | WO-2006105338 A2 | 10/2006 |
| WO | WO-2007024249 A2 | 3/2007 |
| WO | WO-2008093646 A1 | 8/2008 |
| WO | WO-2010090513 A2 | 8/2010 |
| WO | WO-2010092457 A1 | 8/2010 |
| WO | WO-2011130624 A2 | 10/2011 |
| WO | WO-2012014076 A2 | 2/2012 |
| WO | WO-2012045075 A1 | 4/2012 |
| WO | WO-2012138453 A1 | 10/2012 |
| WO | WO-2012140274 A2 | 10/2012 |
| WO | WO-2013052523 A1 | 4/2013 |
| WO | WO-2013054307 A2 | 4/2013 |
| WO | WO-2013071047 A1 | 5/2013 |
| WO | WO-2013078199 A2 | 5/2013 |
| WO | WO-2013130364 A1 | 9/2013 |
| WO | WO-2013151666 A2 | 10/2013 |
| WO | WO-2014023709 A1 | 2/2014 |
| WO | WO-2014081507 A1 | 5/2014 |
| WO | WO-2014093924 A1 | 6/2014 |
| WO | WO-2014164253 A1 | 10/2014 |
| WO | WO-2015164392 A2 | 10/2015 |
| WO | WO-2016040895 A1 | 3/2016 |
| WO | WO-2016073906 A2 | 5/2016 |
| WO | WO-2016081640 A1 | 5/2016 |
| WO | WO-2017069628 A2 | 4/2017 |
| WO | WO-2017100467 A2 | 6/2017 |
| WO | WO-2018098363 A2 | 5/2018 |
| WO | WO-2018107116 A1 | 6/2018 |
| WO | WO-2018132572 A1 | 7/2018 |
| WO | WO-2018140821 A1 | 8/2018 |
| WO | WO-2018203567 A1 | 11/2018 |
| WO | WO-2018215614 A1 | 11/2018 |
| WO | WO-2019126398 A1 | 6/2019 |
| WO | WO-2019126399 A1 | 6/2019 |
| WO | WO-2019126401 A1 | 6/2019 |
| WO | WO-2020010308 A1 | 1/2020 |
| WO | WO-2020014271 A1 | 1/2020 |
| WO | WO-2020132356 A1 | 6/2020 |
| WO | WO-2020167848 A1 | 8/2020 |
| WO | WO-2020185960 A1 | 9/2020 |
| WO | WO-2020206005 A1 | 10/2020 |
| WO | WO-2020250156 A1 | 12/2020 |
| WO | WO-2021003054 A1 | 1/2021 |
| WO | WO-2021173726 A1 | 9/2021 |
| WO | WO-2022104280 A1 | 5/2022 |
| WO | WO-2022192445 A1 | 9/2022 |
| WO | WO-2023044348 A1 | 3/2023 |
| WO | WO-2023115048 A1 | 6/2023 |

OTHER PUBLICATIONS

Brott, B.K. and S.Y. Sokol (Sep. 2002) "Regulation of Wnt/LRP Signaling by Distinct Domains of Dickkopf Proteins" Mol Cell Biol, 22(17):6100-6110.

Clevers, H. et al. (Oct. 3, 2014) "An integral program for tissue renewal and regeneration: Wnt signaling and stem cell control" Science, 346(6205): 1248012-1- 1248012-7.

Colman, P. M. "Effects of amino acid sequence changes on antibody-antigen interactions", Research in Immunology, (Jan. 1994); 145(1):33-36.

D'Souza, A.A. et al. (2015) "Asialoglycoprotein receptor mediated hepatocyte targeting—Strategies and applications", Journal of Controlled Release, 203:126-139.

Eppink, B. et al. (Dec. 1, 2015) "Abstract C21: Generation of Wnt- and mitogenic receptor binding bispecific antibodies to target cancer stem cells" AACR-NCI-EORTC International Conference: Molecular Targets and Cancer Therapeutics; Nov. 5-9, 2015; Boston, MA. Molecular Cancer Therapeutics, 14(12 Suppl 2):Abstract C21, DOI: 10.1158/1535-7163.TARG-15-C21; 1 page.

Ettenberg S.A. et al. (Aug. 31, 2010) "Inhibition of tumorigenesis driven by different Wnt proteins requires blockade of distinct ligand-binding regions by LRP6 antibodies" Proc Natl Acad Sci USA, 107(35):15473-15478.

GenBank Accession No. AF177394.2 "*Homo sapiens* dickkopf-1 (DKK-1) mRNA, complete cds" Dec. 20, 2016, 2 pages.

GenBank Accession No. AF177395.1 "*Homo sapiens* dickkopf-2 (DKK-2) mRNA, complete cds" Dec. 20, 2016, 2 pages.

GenBank Accession No. NM_001466.4 "*Homo sapiens* frizzled class receptor 2 (FZD2), mRNA" Feb. 17, 2021, 5 pages.

GenBank Accession No. NM_002335.2 "*Homo sapiens* low density lipoprotein receptor-related protein 5 (LRP5), mRNA" May 3, 2014, 5 pages.

GenBank Accession No. NM_002336.2 "*Homo sapiens* LDL receptor related protein 6 (LRP6), mRNA" Oct. 20, 2018, 8 pages.

GenBank Accession No. NM_003391.3 "*Homo sapiens* Wnt family member 2 (WNT2), transcript variant 1, mRNA" Feb. 17, 2021, 4 pages.

GenBank Accession No. NM_003392.7 "*Homo sapiens* Wnt family member 5A (WNT5A), transcript variant 1, mRNA" Feb. 21, 2021, 5 pages.

GenBank Accession No. NM_003393.4 "*Homo sapiens* Wnt family member 8B (WNT8B), mRNA" Mar. 7, 2021, 4 pages.

GenBank Accession No. NM_003394.4 "*Homo sapiens* Wnt family member 10B (WNT10B), mRNA" Feb. 16, 2021, 4 pages.

GenBank Accession No. NM_003395.4 "*Homo sapiens* Wnt family member 9A (WNT9A), mRNA" Feb. 16, 2021, 4 pages.

GenBank Accession No. NM_003396.3 "*Homo sapiens* Wnt family member 9B (WNT9B), transcript variant 1, mRNA" Feb. 16, 2021, 4 pages.

GenBank Accession No. NM_003468.4 "*Homo sapiens* frizzled class receptor 5 (FZD5), mRNA" Feb. 18, 2021, 6 pages.

GenBank Accession No. NM_003505.2 "*Homo sapiens* frizzled class receptor 1 (FZD1), mRNA" Nov. 22, 2020, 4 pages.

GenBank Accession No. NM_003506.4 "*Homo sapiens* frizzled class receptor 6 (FZD6), transcript variant 1, mRNA" Feb. 16, 2021, 5 pages.

GenBank Accession No. NM_003507.2 "*Homo sapiens* frizzled class receptor 7 (FZD7), mRNA" Feb. 21, 2021, 5 pages.

GenBank Accession No. NM_003508.3 "*Homo sapiens* frizzled class receptor 9 (FZD9), mRNA" Feb. 17, 2021, 5 pages.

GenBank Accession No. NM_004185.4 "*Homo sapiens* Wnt family member 2B (WNT2B), transcript variant WNT-2B1, mRNA" Feb. 13, 2021, 4 pages.

GenBank Accession No. NM_004625.4 "*Homo sapiens* Wnt family member 7A (WNT7A), mRNA" Feb. 17, 2021, 5 pages.

GenBank Accession No. NM_004626.3 "*Homo sapiens* Wnt family member 11 (WNT11), mRNA" Feb. 17, 2021, 4 pages.

GenBank Accession No. NM_005430.4 "*Homo sapiens* Wnt family member 1 (WNT1), mRNA" Feb. 21, 2021, 4 pages.

GenBank Accession No. NM_006522.4 "*Homo sapiens* Wnt family member 6 (WNT6), mRNA" Feb. 16, 2021, 4 pages.

(56) References Cited

OTHER PUBLICATIONS

GenBank Accession No. NM_007197.4 "*Homo sapiens* frizzled class receptor 10 (FZD10), mRNA" Mar. 2, 2021, 5 pages.
GenBank Accession No. NM_012193.4 "*Homo sapiens* frizzled class receptor 4 (FZD4), mRNA" Mar. 16, 2021, 6 pages.
GenBank Accession No. NM_014419.4 "*Homo sapiens* dickkopf like acrosomal protein 1 (DKKL1), transcript variant 1, mRNA" Feb. 18, 2021, 4 pages.
GenBank Accession No. NM_014420.3 "*Homo sapiens* dickkopf WNT signaling pathway inhibitor 4 (DKK4), mRNA" Feb. 15, 2021, 4 pages.
GenBank Accession No. NM_014421.3 "*Homo sapiens* dickkopf WNT signaling pathway inhibitor 2 (DKK2), mRNA" Feb. 13, 2021, 4 pages.
GenBank Accession No. NM_015881.6 "*Homo sapiens* dickkopf WNT signaling pathway inhibitor 3 (DKK3), transcript variant 1, mRNA" Feb. 23, 2021, 5 pages.
GenBank Accession No. NM_016087.2 "*Homo sapiens* Wnt family member 16 (WNT16), transcript variant 2, mRNA" Jan. 18, 2021, 4 pages.
GenBank Accession No. NM_024494.2 "*Homo sapiens* Wnt family member 2B (WNT2B), transcript variant WNT-2B2, mRNA*Homo sapiens* Wnt family member 2B (WNT2B), transcript variant WNT-2B2, mRNA" Nov. 12, 2018, 4 pages.
GenBank Accession No. NM_025216.3 "*Homo sapiens* Wnt family member 10A (WNT10A), mRNA" Feb. 17, 2021, 4 pages.
GenBank Accession No. NM_030753.5 "*Homo sapiens* Wnt family member 3 (WNT3), mRNA" Mar. 2, 2021, 4 page.
GenBank Accession No. NM_030761.5 "*Homo sapiens* Wnt family member 4 (WNT4), mRNA" Feb. 15, 2021, 4 pages.
GenBank Accession No. NM_031866.3 "*Homo sapiens* frizzled class receptor 8 (FZD8), mRNA" Mar. 16, 2021, 5 pages.
GenBank Accession No. NM_032642.3 "*Homo sapiens* Wnt family member 5B (WNT5B), transcript variant 1, mRNA" Mar. 22, 2021, 4 pages.
GenBank Accession No. NM_033131.4 "*Homo sapiens* Wnt family member 3A (WNT3A), mRNA" Mar. 2, 2021, 4 pages.
GenBank Accession No. NM_058238.3 "*Homo sapiens* Wnt family member 7B (WNT7B), mRNA" Feb. 16, 2021, 4 pages.
GenBank Accession No. NM_058244.4 "*Homo sapiens* Wnt family member 8A (WNT8A), transcript variant 3, mRNA" Feb. 23, 2021, 4 pages.
GenBank Accession No. NM_145866.2 "*Homo sapiens* frizzled class receptor 3 (FZD3), transcript variant 2, mRNA" Feb. 21, 2021, 7 pages.
GenBank Accession No. NP_001017403.1 "leucine-rich repeat-containing G-protein coupled receptor 6 isoform 1 precursor [*Homo sapiens* ]" Mar. 2, 2021, 6 pages.
GenBank Accession No. NP_001017404.1 "leucine-rich repeat-containing G-protein coupled receptor 6 isoform 3 [*Homo sapiens* ]" Mar. 3, 2021, 4 pages.
GenBank Accession No. NP_001025042.2 "R-spondin-4 isoform 1 precursor [*Homo sapiens* ]" Dec. 12, 2020, 3 pages.
GenBank Accession No. NP_001033722.1 "R-spondin-1 isoform 1 precursor [*Homo sapiens*]" Feb. 20, 2021, 3 pages.
GenBank Accession No. NP_001035096.1 "R-spondin-4 isoform 2 precursor [*Homo sapiens*]" Dec. 12, 2020, 3 pages.
GenBank Accession No. NP_001193927.1 "E3 ubiquitin-protein ligase ZNRF3 isoform 1 precursor [*Homo sapiens*]" Feb. 17, 2021, 3 pages.
GenBank Accession No. NP_001229838.1 "R-spondin-1 isoform 2 [*Homo sapiens*]" Feb. 19, 2021, 3 pages.
GenBank Accession No. NP_001229839.1 "R-spondin-1 isoform 3 precursor [*Homo sapiens*]" Feb. 20, 2021, 3 pages.
GenBank Accession No. NP_001264155.1 "leucine-rich repeat-containing G-protein coupled receptor 5 isoform 2 precursor [*Homo sapiens*]" Mar. 22, 2021, 4 pages.
GenBank Accession No. NP_001264156.1 "leucine-rich repeat-containing G-protein coupled receptor 5 isoform 3 precursor [*Homo sapiens*]" Mar. 22, 2021, 4 pages.

GenBank Accession No. NP_001269792.1 "R-spondin-2 isoform 2 precursor [*Homo sapiens*]" Feb. 22, 2021, 3 pages.
GenBank Accession No. NP_001292473.1 "E3 ubiquitin-protein ligase RNF43 isoform 1 precursor [*Homo sapiens*]" Dec. 30, 2020, 4 pages.
GenBank Accession No. NP_001292474.1 "E3 ubiquitin-protein ligase RNF43 isoform 2 [*Homo sapiens*]" Feb. 14, 2021, 3 pages.
GenBank Accession No. NP_001304871.1 "R-spondin-2 isoform 3 [*Homo sapiens*]" Feb. 23, 2021, 3 pages.
GenBank Accession No. NP_001333361.1 "leucine-rich repeat-containing G-protein coupled receptor 4 isoform 2 precursor [*Homo sapiens*]" Mar. 16, 2021, 3 pages.
GenBank Accession No. NP_001662.1 "asialoglycoprotein receptor 1 isoform a [*Homo sapiens*]" Feb. 16, 2021, 3 pages.
GenBank Accession No. NP_003658.1 "leucine-rich repeat-containing G-protein coupled receptor 5 isoform 1 precursor [*Homo sapiens*]" Mar. 22, 2021, 4 pages.
GenBank Accession No. NP_036374.1 "dickkopf-related protein 1 precursor [*Homo sapiens*]" Mar. 3, 2021, 3 pages.
GenBank Accession No. NP_055236.1 "dickkopf-related protein 2 precursor [*Homo sapiens*]" Feb. 13, 2021, 3 pages.
GenBank Accession No. NP_060233.3 "E3 ubiquitin-protein ligase RNF43 isoform 1 precursor [*Homo sapiens*]" Dec. 15, 2020, 4 pages.
GenBank Accession No. NP_060960.2 "leucine-rich repeat-containing G-protein coupled receptor 4 isoform 1 precursor [*Homo sapiens*]" Mar. 16, 2021, 5 pages.
GenBank Accession No. NP_067649.2 "leucine-rich repeat-containing G-protein coupled receptor 6 isoform 2 [*Homo sapiens*]" Mar. 2, 2021, 4 pages.
GenBank Accession No. NP_115549.2 "E3 ubiquitin-protein ligase ZNRF3 isoform 2 [*Homo sapiens*]" Feb. 21, 2021, 3 pages.
GenBank Accession No. NP_116173.2 "R-spondin-3 precursor [*Homo sapiens*]" Mar. 16, 2021, 4 pages.
GenBank Accession No. NP_550436.1 "asialoglycoprotein receptor 2 isoform c [*Homo sapiens*]" Feb. 13, 2021, 3 pages.
GenBank Accession No. NP_848660.3 "R-spondin-2 isoform 1 precursor [*Homo sapiens*]" Feb. 16, 2021, 3 pages.
GenBank Accession No. XP_005582755.1 "Predicted: asialoglycoprotein receptor 1 isoform X1 [Macaca fascicularis]" Jan. 25, 2016, 2 pages.
GenBank Accession No. XP_006710646.1 "R-spondin-1 isoform X1 [*Homo sapiens*]" Feb. 28, 2021, 1 page.
GenBank Accession No. XP_011515320.1 "R-spondin-2 isoform X1 [*Homo sapiens*]" Feb. 28, 2021, 2 pages.
GenBank Accession No. XP_011515321.1 "R-spondin-2 isoform X2 [*Homo sapiens*]" Feb. 28, 2021, 2 pages.
GenBank Accession No. XP_011523257.1 "E3 ubiquitin-protein ligase RNF43 isoform X1 [*Homo sapiens*]" Feb. 28, 2021, 2 pages.
GenBank Accession No. XP_011523258.1 "E3 ubiquitin-protein ligase RNF43 isoform X2 [*Homo sapiens*]" Feb. 28, 2021, 2 pages.
GenBank Accession No. XP_016868884.1 "R-spondin-2 isoform X3 [*Homo sapiens*]" Feb. 28, 2021, 1 page.
GenBank Accession No. XP_016880289.1 "E3 ubiquitin-protein ligase RNF43 isoform X1 [*Homo sapiens*]" Feb. 28, 2021, 2 pages.
Gong, Y et al. (2010) "Wnt Isoform-Specific Interactions with Coreceptor Specify Inhibition or Potentiation of Signaling by LRP6 Antibodies" PLoS One, 5(9):e12682, doi:10.1371/journal.pone. 0012682; 17 pages.
Hao, H-X. et al. (May 10, 2012) "ZNRF3 promotes Wnt receptor turnover in an R-spondin-sensitive manner" Nature, 485(7397):195-200.
Heupel, W-M. et al. (Aug. 1, 2008) "Pemphigus Vulgaris IgG Directly Inhibit Desmoglein 3-Mediated Transinteraction" Journal of Immunology, 181(3):1825-1834.
Hombach, A.A. et al. (Jan. 1, 2012) "Antibody-IL 2 fusion proteins for tumor targeting" Antibody Engineering: Methods and Protocols, 2nd Ed. Methods in Molecular Biology, vol. 907, p. 611-626.
Ingham, P. W. (Oct. 1996) "Has the quest for a Wnt receptor finally frizzled out?" Trends Genet, 12(10):382-384.
International Search Report and Written Opinion for Application No. PCT/US2021/059564, mailed Apr. 15, 2022, 14 pages.

(56) References Cited

OTHER PUBLICATIONS

Invitation to Pay Fee for International Application No. PCT/US2021/059564 dated Feb. 1, 2022, 2 pages.
Jacobsen, B. et al. (Oct. 10, 2014) "C4.4A as a biomarker in pulmonary adenocarcinoma and squamous cell carcinoma" World Journal of Clinical Oncology, 5(4):621-632.
Jacobsen, F.W. et al. (Feb. 3, 2017) "Engineering an IgG Scaffold Lacking Effector Function with Optimized Developability" J Biol Chem, 292:1865-1875.
Janda, C.Y. et al. (May 11, 2017) "Surrogate Wnt agonists that phenocopy canonical Wnt and β-catenin signaling" Nature, 545(7653):234-237. HHS Public Access Author Manuscript, 35 pages.
Jin, Y-R. and J.K. Yoon (Dec. 2012) "The R-spondin family of proteins: Emerging regulators of WNT signaling" Int J Biochem Cell Biol, 44(12):2278-2287, doi:10.1016/j.biocel.2012.09.006.
Keerthivasan, S. et al. (Feb. 2014) "Wnt/Beta-catenin signaling in T-cells drives epigenetic imprinting of pro-inflammatory properties and promotes colitis and colon cancer" Sci Transl Med, 6(225):225ra28, doi: 10.1126/scitranslmed.3007607. NIH Public Access Author Manuscript, 28 pages.
Kim, K.-A. et al. (Jun. 2008) "R-Spondin Family Members Regulate the Wnt Pathway by a Common Mechanism" Mol Biol Cell, 19(6):2588-2596.
Knight, M.N. and K. Hankenson (2014) "R-spondins: Novel matricellular regulators of the skeleton" Matrix Biology, 37:157-161.
Krupnik, V.E. et al. (1999) "Functional and structural diversity of the human Dickkopf gene family" Gene, 238(2):301-313.
Li, L. et al. (Feb. 22, 2002) "Second Cysteine-rich Domain of Dickkopf-2 Activates Canonical Wnt Signaling Pathway via LRP-6 Independently of Dishevelled" J Biol Chem, 277(8):5977-5981.
Lo, M. et al. (Mar. 3, 2017) "Effector-attenuating Substitutions That Maintain Antibody Stability and Reduce Toxicity in Mice" J Biol Chem, 292:3900-3908.
Mannstadt, M. et al. (1999) "Receptors for PTH and PTHrP: their biological importance and functional properties" American Journal of Physiology, 277:F665-F675.
McMahon, A.P. (Jul. 1992) "The Wnt family of developmental regulators" Trends Genet, 8:236-242.
Meier, M. et al. (2000) Crystal Structure of the Carbohydrate Recognition Domain of the H1 Subunit of the Asialoglycoprotein Receptor. J Mol Biol. 300:857-865.
Miller, J.R. (Dec. 28, 2001) "The Wnts" Genome Biol, 3(1):3001.1-3001.15.
Moon, B-I. et al. (2015) "Functional Modulation of Regulatory T Cells by IL-2" PLoS One, 10(11):e0141864, doi:10.1371/journal.pone.0141864; 13 pages.
Ngora, H. et al. (Feb. 2012) "Membrane-Bound and Exosomal Metastasis-Associated C4.4A Promotes Migration by Associating with the α6β4 Integrin and MT1-MMP1,2" Neoplasia, 14(2):95-107.
Pace, L. et al. (2005) "IL-4 Modulation of CD4+ CD25+ T Regulatory Cell-Mediated Suppression" J Immunol, 174(12):7645-7653.
Papkoff, J. et al. (May 1996) "Wnt-1 Regulates Free Pools of Catenins and Stabilizes APC-Catenin Complexes" Mol Cell Biol, 16:2128-2134.
Paret, B. et al. (Jul. 10, 2005) "Ly6 family member C4.4A binds laminins 1 and 5, associates with Galectin-3 and supports cell migration" International Journal of Cancer, 115(5):724-733.
Paul, W.E. (1993) "Fv Structure and Diversity in Three Dimensions" in Fundamental Immunology, 3rd ed. Raven Press, NY; Chap. 9, pp. 292-295.
Perez De La Lastra, J.M. et al. (Apr. 1999) Epitope mapping of 10 monoclonal antibodies against the pig analogue of human membrane cofactor protein (MCP). Immunology, vol. 96, No. 4, pp. 663-670. DOI: 10.1046/j.1365-2567.1999.00732.x.
Rudikoff, S. et al. "Single amino acid substitution altering antigen-binding specificity", Proc Natl Acad Sci, (Mar. 1982); 79:1979-1983.
Russell, J.O. and S. P. Monga. (2018) Wnt/beta-Catenin Signaling in Liver Development, Homeostasis, and Pathobiology. Annu. Rev. Pathol. Mech. Dis, 13:351-378, DOI: 10.1146/annurev-pathol-020117-044010.
Sanhueza, C.A. et al. (2017) "Efficient Liver Targeting by Polyvalent Display of a Compact Ligand for the Asialoglycoprotein Receptor" J Am Chem Soc, 139:3528-3536.
Sato et al. (2011). "Long-term expansion of epithelial organoids from human colon, adenoma, adenocarcinoma, and Barrett's epithelium," Gastroenterology, 141: 1762-1772.
Sato, T. et al. (May 14, 2009) "Single Lgr5 stem cells build crypt-villus structures in vitro without a mesenchymal niche" Nature, 459:262-265, www.nature.com/doifinder/10.1038/nature07935; with "Methods", 1 page.
Scatchard et al., "The attractions of proteins for small molecules and ions," Ann. N.Y. Acad. Sci. (1949) 51:660-672.
Shilpi, S. et al. (Jul. 2018) Drug targeting strategies for liver cancer and other liver diseases. Moj Drug Design Development & Therapy, vol. 2, No. 4, pp. 171-177.
Skolnick J., et al., "From Genes to Protein Structure and Function: Novel Applications of Computational Approaches in the Genomic Era," Trends in Biotechnology, Jan. 2000, vol. 18, pp. 34-39.
Stockert, R.J. et al. (1991) "Structural Characteristics and Regulation of the Asialoglycoprotein Receptor" Targeted Diagnostics and Therapy 4:41-64.
Tao, Guo-Zhong et al. (Jun. 2013) Wnt/[beta]-Catenin Signaling Protects Mouse Liver against Oxidative Stress-induced Apoptosis through the Inhibition of Forkhead Transcription Factor FoxO3" J Biol Chem, 288(24): 17214-17224.
Thomason, H.A. et al. (2010) "Desmosomes: adhesive strength and signalling in health and disease" Biochemical Journal, 429(3):419-433.
UniProtKB, (Asgri_Human) Asialoglycoprotein receptor I. UniProtKB Accession No. P07306. Last Modified: Feb. 23, 2022. [online]. Retrieved Mar. 24, 2022 from: https://www.dot.uniprot.org/uniprot/P07306; 16 printed pages.
UniProtKB, Membrane protein. UniProtKB Accession No. A0A0M8ZAH5. Last Modified: Dec. 9, 2015. [online]. [Retrieved on Mar. 8, 2018]. Retrieved from the Internet: URL: http://www.uniprot.org/uniproUAOAOM8ZAH5 Protein, and Sequence (370 a.a.); 3 printed pages.
Witzigmann, D., et al., "Variable Asialoglycoprotein Receptor 1 Expression in Liver Disease: Implications for Therapeutic Intervention," Hepatology Research, Jun. 2016, vol. 46(7), pp. 686-696.
Worthen, C.A. and C.A. Enns (Mar. 6, 2014) "The role of hepatic transferring receptor 2 in the regulation of iron homeostasis in the body" Frontiers in Pharmacology, 5:34, 8 pages.
Xie, Y. et al. (Oct. 2013) "Interaction with both ZNRF3 and LGR4 is required for the signalling activity of R-spondin" EMBO Reports, 14(12):1120-1126.
Yan, H. et al. (Nov. 13, 2012) "Sodium taurocholate cotransporting polypeptide is a functional receptor for human hepatitis B and D virus" eLife, 1:e00049, http://dx.doi.org/10.7554/eLife.00049; 28 pages.
Yan, J-J. et al. (2015) "Active radar guides missile to its target: receptor-based targeted treatment of hepatocellular carcinoma by nanoparticulate systems" Tumor Biology, 36:55-67.
Yang, W.H. et al. (2018) Accelerated Aging and Clearance of Host Anti-inflammatory Enzymes by Discrete Pathogens Fuels Sepsis. Cell Host Microbe. 24(4):500-513.
Yang-Snyder, J. et al. (1996) "A frizzled homolog functions in a vertebrate Wnt signaling pathway" Curr Biol, 6:1302-1306.
You, J. et al. (2008) "Wnt pathway-related gene expression in inflammatory bowel disease" Dig Dis Sci, 53(4):1013-1019.
Zapata et al., "Engineering linear F(ab')2 fragments for efficient production in *Escherichia coli* and enhanced antiproliferative activity," Protein Engineering, Design and Selection, Oct. 1995, 8(10), pp. 1057-1062.
Zhang, Z. et al. (Aug. 2020) Tissue-targeted Rspondin mimetics for liver regeneration. Scientific Reports, vol. 10, No. 1, Article 13951; DOI: 10.1038/s41598-020-70912-3, 14 pages.

(56) References Cited

OTHER PUBLICATIONS

International Preliminary Report on Patentability for International Application No. PCT/US2021/059564, mailed May 16, 2023, 8 pages.
Andersen et al. "Anti-carcinoembryonic antigen single-chain variable fragment antibody variants bind mouse and human neonatal Fc receptor with different affinities that reveal distinct cross-species differences in serum half-life" Journal of Biological Chemistry (2012); 287(27):22927-22937.
GenBank Accession No. NP_005805.1 "cell surface A33 antigen precursor [*Homo sapiens*]" Jun. 3, 2022, 4 pages.
Roopenian et al. "The MHC class I-like IgG receptor controls perinatal IgG transport, IgG homeostasis, and fate of IgG-Fc-coupled drugs" The Journal of Immunology (2003); 170(7):3528-3533.
U.S. Appl. No. 18/896,546, filed Sep. 25, 2024, by Luca et al.
Almagro et al. "Progress and Challenges in the Design and Clinical Development of Antibodies for Cancer Therapy" Front Immunol. (2018); 8(1751):1-19.
Brown et al. "Tolerance to Single, but Not Multiple, Amino Acid Replacements in Antibody VH CDR2: A Means of Minimizing B Cell Wastage from Somatic Hypermutation" The Journal of Immunology (1996); 156(9):3285-3291.
Chiu et al. "Antibody Structure and Function: The Basis for Engineering Therapeutics" Antibodies (2019); 8(4):55, 1-80.
Grainger et al. "Mechanisms of Wnt signaling and control" Wiley Interdiscip Rev Syst Biol Med (2018); 10(5):e1422, 1-39.
Marvin et al. "Redesigning an antibody fragment for faster association with its antigen" Biochemistry (2003); 42(23):7077-7083.

FIG. 1

BOLD: Deamidation or isomerization risk
*ITALICS*: RSPO2

αASGR1-RSPO2 (1R34-DDNN/RA) Light Chain Variable Region:

SSELTQDPAVSVALGQTVRITCQGD¹*SLRSYYA*SWYQQKPGQAPVLVIYGKN¹*NRPSGIPDRFSGSSSGNTASLTITGAQAEDEADYYC*N²*SLERIGIYLSYVFG*GGTKLTVL (SEQ ID NO:23)

D¹: CDR_L1_D25, N¹: CDR_L2_N51, N²: CDR_L3_N88

αASGR1-RSPO2 (1R34-DDNN/RA) Heavy Chain Variable Region with mutant Rspo2:

NPICKGCLSCSKDNGCSRCQQKLFFFLRREGMRQYGECLHSCPSGYYGHRAPDMNRCARCRIENCDSCRSKDACTKCKVGFYLHRGRCFDECPDGFAPLE
ETMECVEGGGSGGGGSGGGGSGGGGSEVQLLESGGGLVQPGGSLRLSCAASGFTFSSYAMSWVRQAPGKGLEWVSAISGSGGSTYYAD¹⁵*SVKGRFTISRDNSK*NTLYLQMNSLRAEDTAVYYCAKDFSSRRWYLEYWGQGTLVTVSS (SEQ ID NO:24)

D¹: CDR_H2

| Position | Location | Mutant |
|---|---|---|
| 1 | CDR_H2 | D62 S, E, A |
| 2 | CDR_L1 | D25 S, E, A |
| 3 | CDR_L2 | N51 Q, S, A |
| 4 | CDR_L3 | N88 Q, S, A, L, E, H, T, R, K, Y, WT |

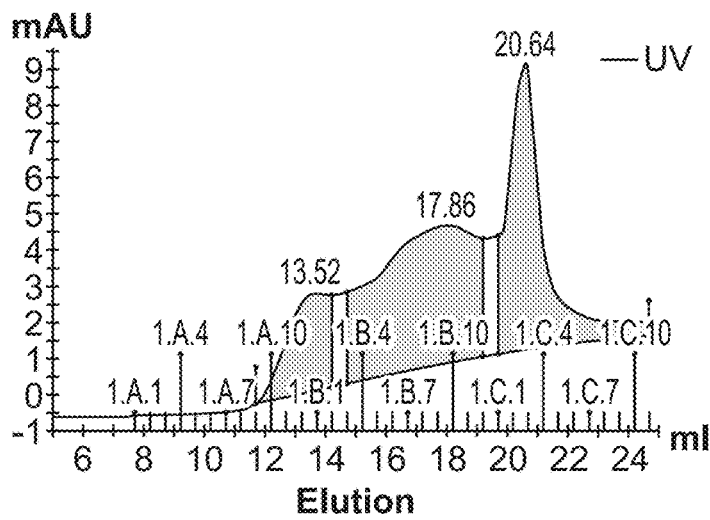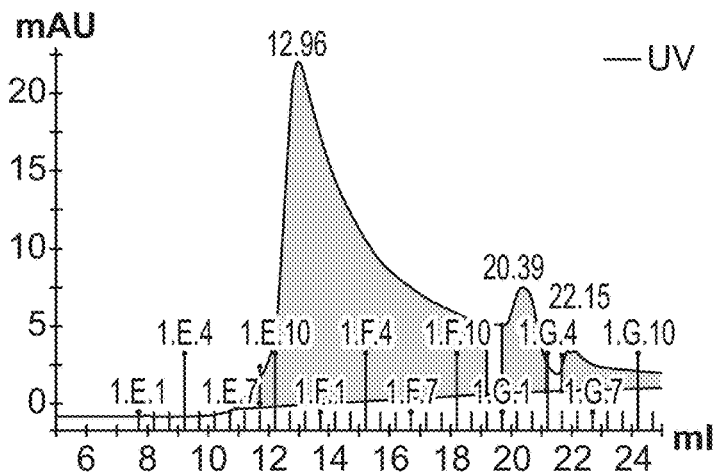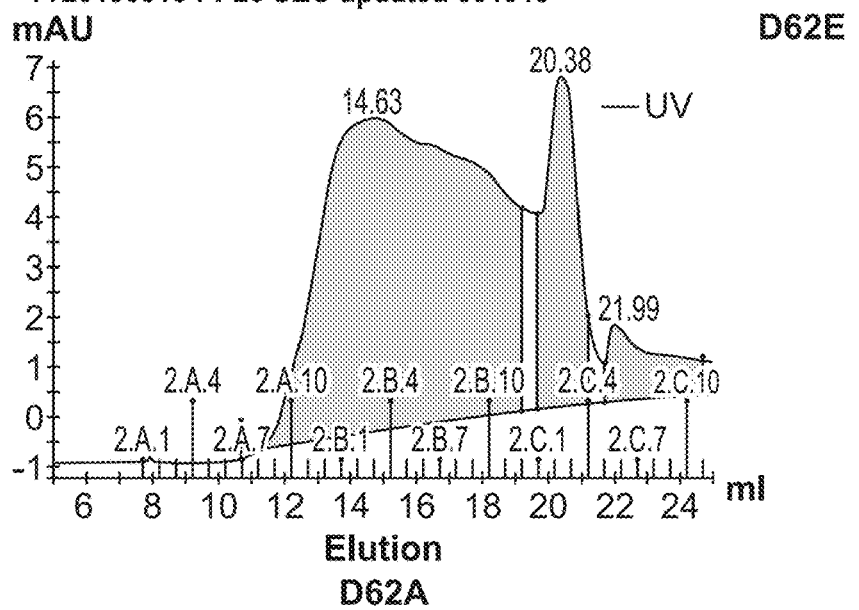
FIG. 2

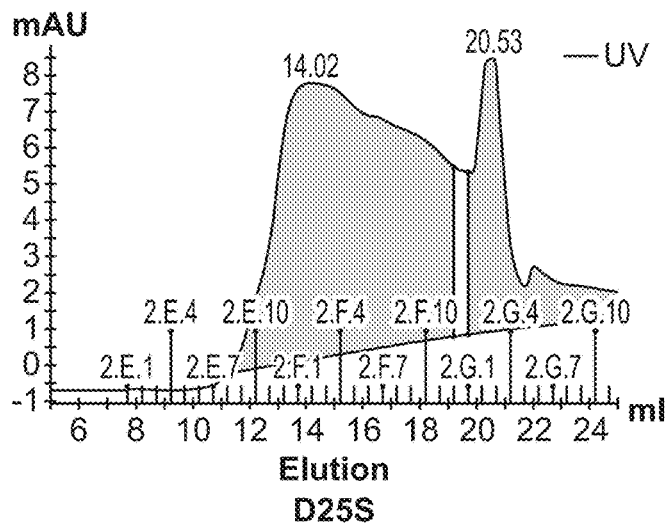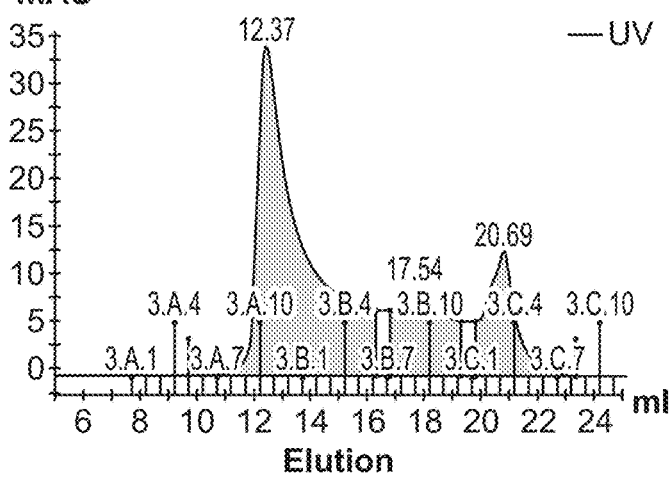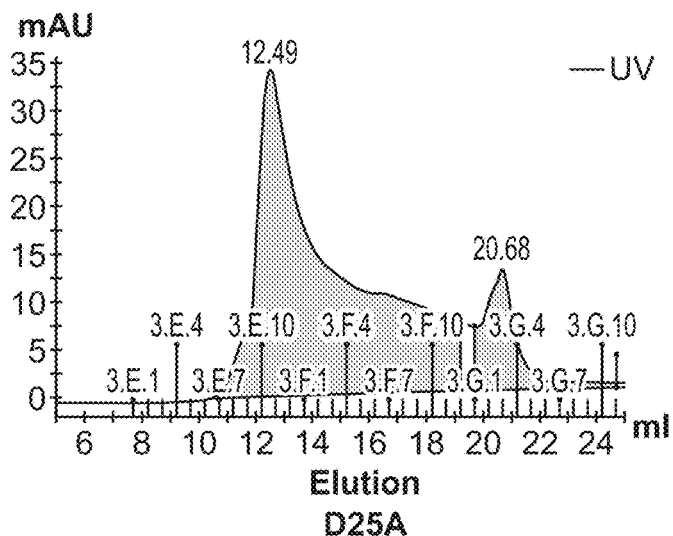
FIG. 3

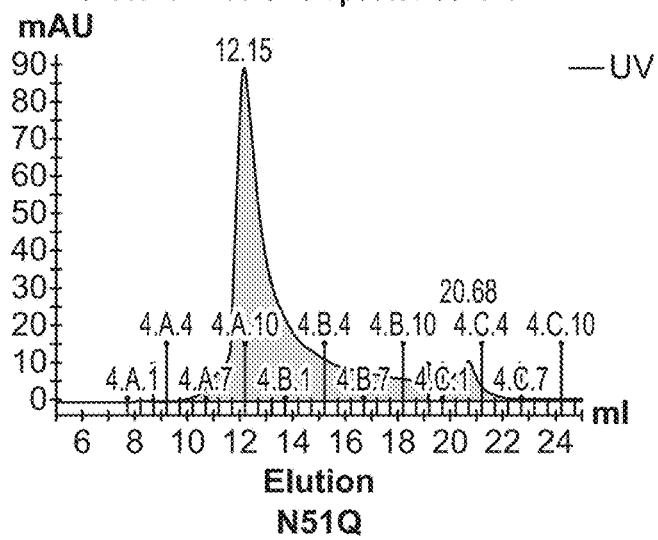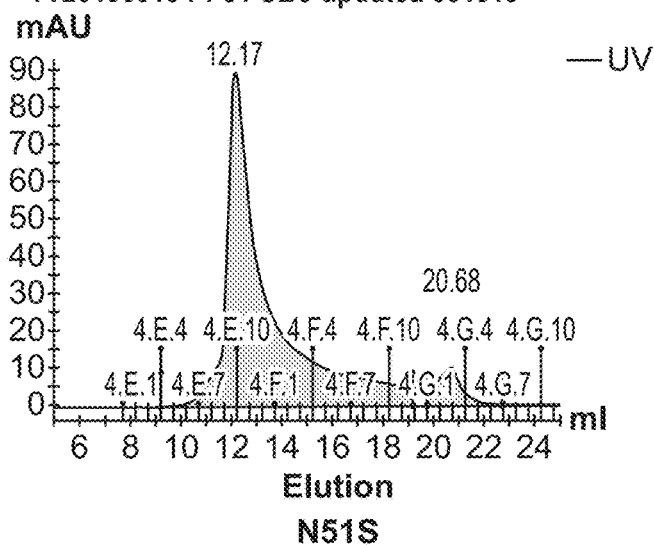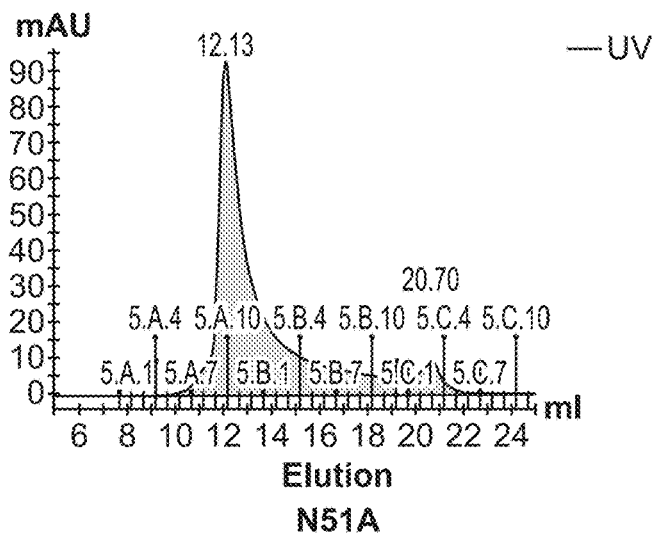
FIG. 4

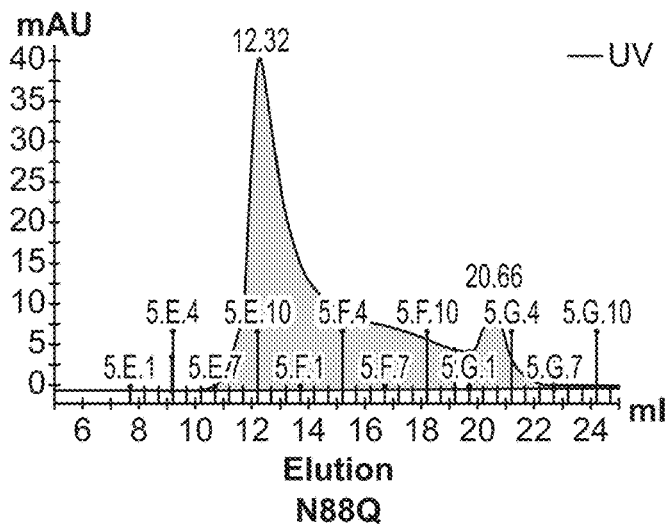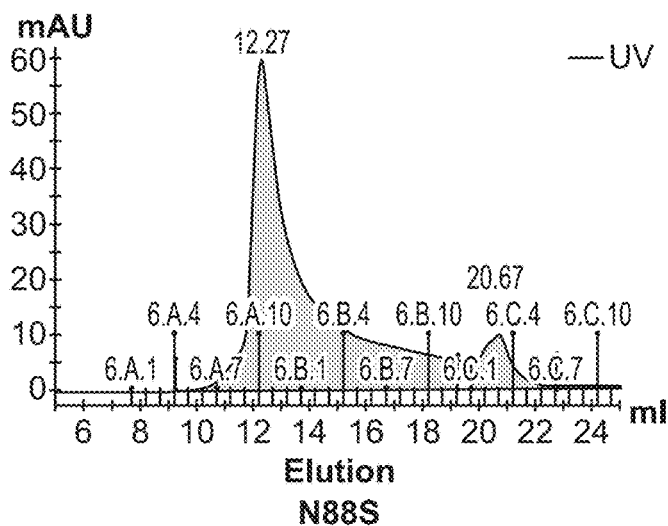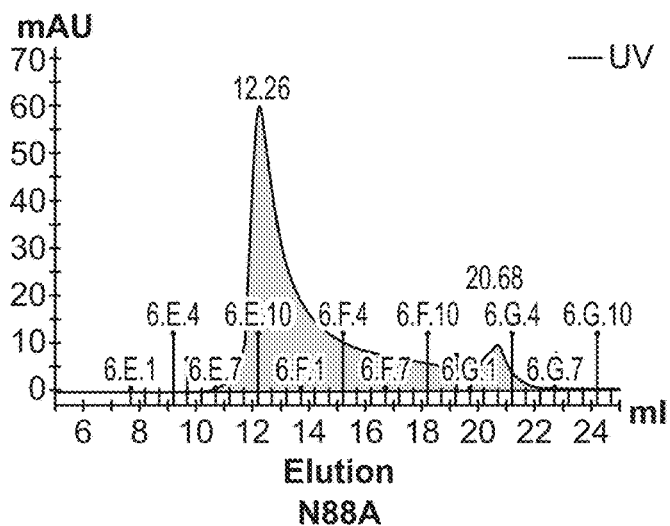
FIG. 5

| Name | STF EC50 ng/ml | STF EMAX (% of NG) | HIC (mono vs poly disperse) | Poly specificity (binding) | Tm/Tagg | Freeze/ thaw stability | ASGR1 binding $K_D$ (M) | ASGR1 $k_{on}$ (1/Ms) | ASGR1 $k_{off}$ (1/s) |
|---|---|---|---|---|---|---|---|---|---|
| DDNN-RA ("wild type") | 2.96 | 100% | mono | Heparin/ dsDNA/ KLH/LPS | 64.7/63.7 | Stable | 7.67E-09 | 2.36E+05 | 1.81E-03 |
| EEST-RA | 3.79 | 101% | mono | Heparin/ dsDNA/ KLH/LPS | 64.1/63.8 | Stable | 1.83E-08 | 1.74E+05 | 3.19E-03 |
| EESN-RA | 3.43 | 98% | mono | Heparin/ dsDNA/ KLH/LPS | 64.5/65.3 | Stable | 1.02E-08 | 2.24E+05 | 2.28E-03 |
| EEAN-RA | 2.60 | 101% | mono | Heparin/ dsDNA/ KLH/LPS | 64.0/64.0 | Stable | 1.77E-08 | 1.93E+05 | 3.41E-03 |
| EEAT-RA | 3.45 | 93% | mono | Heparin/ dsDNA/ KLH/LPS | 64.2/63.0 | Stable | 2.69E-08 | 1.48E+05 | 3.99E-03 |

FIG. 8

| Sample ID | Loading Sample | KD (M) | con(1/Ms) | Kdis(1/s) | Full R^2 |
|---|---|---|---|---|---|
| WILD TYPE | bio-ASGR1 | 3.13E-08 | 2.53E+05 | 7.89E-03 | 0.9987 |
| EESQ | bio-ASGR1 | 1.80E-06 | 7.38E+04 | 1.33E-01 | 0.991 |
| EESN | bio-ASGR1 | 1.09E-08 | 3.65E+05 | 3.96E-03 | 0.998 |
| EESL | bio-ASGR1 | 1.08E-04 | 1.42E+01 | 1.54E-03 | 0 |
| EESH | bio-ASGR1 | 1.36E-04 | 2.56E+03 | 3.49E-01 | 0.9118 |
| EESE | bio-ASGR1 | 9.59E-07 | 4.74E+04 | 4.55E-02 | 0.9908 |
| EESA | bio-ASGR1 | 2.14E-06 | 3.65E+05 | 7.82E-01 | 0.9961 |
| EEAQ | bio-ASGR1 | 1.51E-06 | 1.26E+05 | 1.90E-01 | 0.9947 |
| EEAN | bio-ASGR1 | 2.74E-06 | 3.38E+05 | 9.26E-01 | 0.9971 |
| EEAA | bio-ASGR1 | 2.57E-08 | 3.16E+05 | 8.14E-03 | 0.997 |
| EEST | bio-ASGR1 | 1.25E-08 | 3.09E+05 | 3.84E-03 | 0.9983 |
| EESR | bio-ASGR1 | 7.64E-08 | 2.41E+04 | 1.84E-03 | 0.9793 |
| EESK | bio-ASGR1 | 2.13E-06 | 4.09E+05 | 8.72E-01 | 0.9976 |
| EESY | bio-ASGR1 | 4.39E-07 | 7.91E+03 | 3.47E-03 | 0.9811 |
| EEAL | bio-ASGR1 | 1.55E-03 | 8.88E+01 | 1.38E-01 | 0.0226 |
| EEAE | bio-ASGR1 | 3.59E-06 | 2.02E+04 | 7.25E-02 | 0.9927 |
| EEAH | bio-ASGR1 | 2.35E-04 | 9.59E+03 | 2.25E+00 | 0.9593 |
| EEAT | bio-ASGR1 | 4.69E-08 | 1.55E+05 | 7.25E-03 | 0.9917 |
| EEAY | bio-ASGR1 | 6.13E-04 | 2.57E+03 | 1.58E+00 | 0.9632 |
| EEAR | bio-ASGR1 | 2.71E-03 | 3.50E+02 | 9.48E-01 | 0.9588 |

FIG. 9

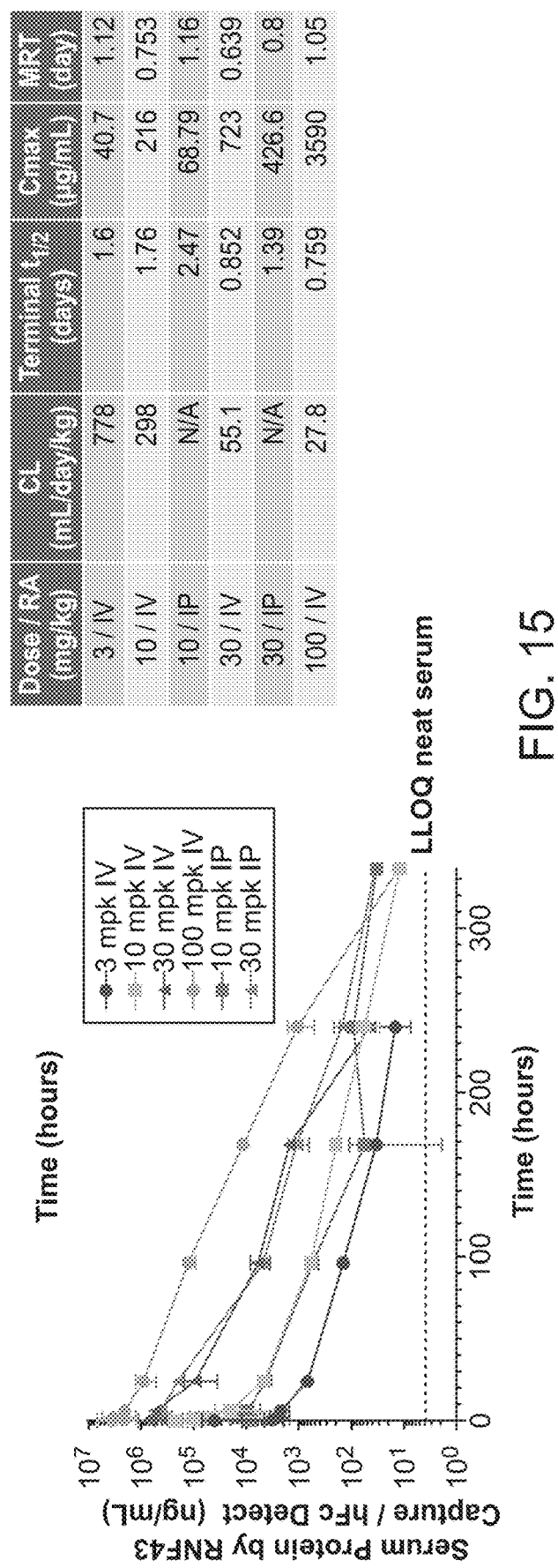
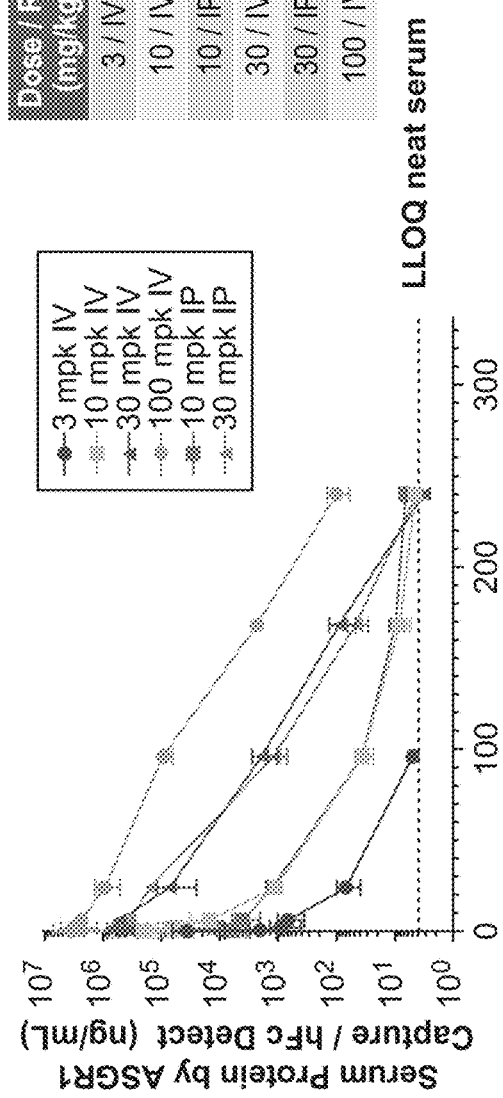
FIG. 15

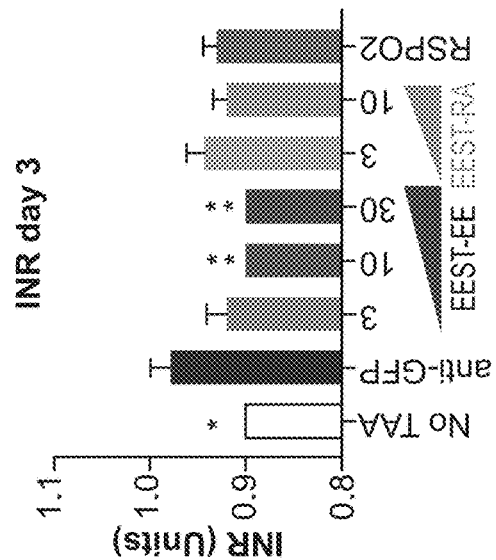
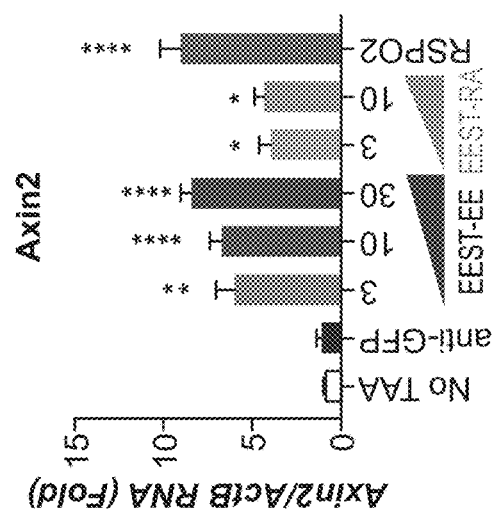
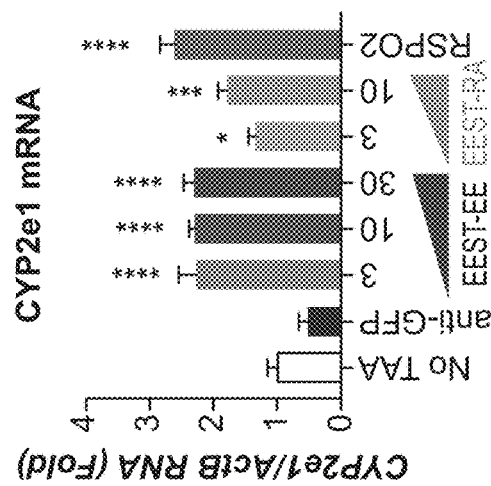
FIG. 19

>8M24_VH

QVQLQQSGAELARPGASVKLSCKASGYTFTNYGINWVKQRTGQGLEWIGEIFPRSDNTFYNEKFKGKATLTADKSSTTAYMELRSLTSEDSAVYFCARKGRDYGTSHYFDYWGQGTTLTVSS (SEQ ID NO:13)

>8M24_VL

DIQMTQSPASLSVSVGETVTITCRISENIYSNLAWYQQKQGKSPHLLVYAAINLADGVPSRFSGSGSGTQFSLKINSLQSEDFGSYYCQHFWGTPFTFGSGTKLEIK (SEQ ID NO:14)

>h8M24_VH_H1 (humanized H1)

EVQLVQSGAEVKKPGSSVKVSCKASGYTFTNYGINWVRQAPGQGLEWMGEIFPRSDNTFYAQKFQGRVTITADKSTSTAYMELSSLRSEDTAVYYCARKGRDYGTSIIYFDYWGQGTTVTVSS (SEQ ID NO:15)

>h8M24_VH_H2 (humanized H2)

EVQLVQSGAEVKKPGSSVKVSCKASGYTFTNYGINWVRQAPGQGLEWIGEIFPRSDNTFYAQKFQGRATLTADKSTSTAYMELSSLRSEDTAVYYCARKGRDYGTSHYFDYWGQGTTLTVSS (SEQ ID NO:16)

>h8M24_VL_L1 (humanized L1)

DIQMTQSPSSLSASVGDRVTITCRISENIYSNLAWYQQKPGKAPKLLIYAAINLADGVPSRFSGSGSGTDFTLTISSLQPEDFATYCQHFWGTPFTFGQGTKLEIK (SEQ ID NO:17)

>h8M24_VL_L2 (humanized L2)

DIQMTQSPSSLSASVGDRVTITCRISENIYSNLAWYQQKPGKAPKLLVYAAINLADGVPSRFSGSGSGTDFTLTISSLQPEDFGTYYCQHFWGTPFTFGQGTKLEIK (SEQ ID NO:18)

FIG. 25

8M24 (CDRs underlined)

LC
DIQMTQSPASLSVSVGETVTTTCRISENIYSNLAWYQQKQGKSPHLLVYAAINLADGVPSRFSGSGSGTQ
FSLKINSLQSEDFGSYYCQHFWGTPFTFGSGTKLEIK (SEQ ID NO: 14)

HC
QVQLQQSGAELARPGASVKLSCKASGYTFTNYGINWVKQRTGQLEWIGEIFPRSDNTFYNEKFKGKA
TLTADKSSTIAYMELRSLTSEDSAVYFCARKGRDYGTSHYFDYWGQGTTLTVSS (SEQ ID NO: 13)

FIG. 26A

8M24 variants explored

| | CDR_L2 | CDR_H1 | CDR_H2 | CDR_H3 | CDR_H3 |
|---|---|---|---|---|---|
| mutants | D56E,S,A | N31S,A,Q | N57Q,S,A,N | D102E,S,A | D110 WT |

FIG. 26B

| Name | SPR EC50 BMAX (ng/ml) | SPR BMAX Conc 2M24 | SDS PAGE | HIC (mono vs agg insects) | PDT specificity | Tm map | Freeze thaw stability | Oxd KD |
|---|---|---|---|---|---|---|---|---|
| 8M24 | 6.80 | 100% | good | mono | ^detectable dsDNA and Heparin binding | 64.5/65 | #stable | 3.9E-10 |
| EAQE | 9.52 | 95.9% | good | mono | ^ detectable dsDNA and Heparin binding | 66.0/79.0 | #stable | 1.09E-09 |
| EASE | 7.99 | 98.8% | good | mono | ^ detectable dsDNA and Heparin binding | 66.2/79.0 | #stable | 3.11E-10 |
| EAAE | 10.5 | 104% | good | mono | ^ detectable dsDNA and Heparin binding | 67.0/80.0 | #stable | 5.00E-10 |
| EANE | 14.6 | 104% | good | mono | ^ detectable dsDNA and Heparin binding | 68.6/ | #stable | <1.0E-12 |

```
Rspo1  MRLGLC-VVALVLSWTHLTISSRGIKGKRQRRISAEGSQACAKGCELCSEVNGCLKCSPK    59
Rspo2  MQFRLFSFALIILNCMDYSHCQGNR-WRRSKR-ASYVSNPICKGCLSCSKDNGCSRCQQK    58
Rspo3  MHLRLISWLFIILNFMEYIGSQNASRGRRQRRMHPNVSQGCQGGCATCSDYNGCLSCKPR    60
Rspo4  MRAPLCLLLL-VAHAVDMLA------LNRRKKQVGTGLGGNCTGCIICSEENGCSTCQQR    53
       *: *      :      .* ::          ** **. ***  *.:

Rspo1  LFILLERNDIRQVGVCLPSCPPGYFDARNPDMNKCIKCKIEHCEACFSHNFCTKCKEGLY   119
Rspo2  LFFFLRREGMRQYGECLHSCPSGYYGHRAPDMNRCARCRIENCDSCFSKDFCTKCKVGFY   118
Rspo3  LFFALERIGMKQIGVCLSSCPSGYYGTRYPDINKCTKCKADCDTCFNCNFCTKCKSGFY   119
Rspo4  LFLFIRREGIRQYGKCLHDCPPGYFGIRGQEVNRCKKCGATCESCFSQDFCTRCKRGFY   112
       **:  .:* .::.* * ** .** **.   *    ::*:*  *:*  *:::**.**. **  **

Rspo1  LHKGRCYPACPEGSSAANGTMECSSPAQCEMSEWSPWGPCSKKQQLCGFRRGSEERTRRV   179
Rspo2  LHRGRCFDECPDGFAPLEETMECVE--GCEVGHWSEWGTCSRNNRTCGFKWGLETRTRQI   176
Rspo3  LHLGKCLDNCPEGLEANNHTMECVSIVHCEVSEWNPWSPCTKKGKTCGFKRGTETRVREI   179
Rspo4  LYKGSCLPTCPPGTLAHQNTRSCQG--ECELGPWGGWSPCTHNGKTCGSAWGLESRVREA   170
       *:  *:  ** *   :  *  **   **:. *. *. *::: : **  * * *.*.

Rspo1  LHAPVGDHAACSDTKETRRCTVRRVPCPEGQKR--RKGGQGRRENANRNLARKESKE---   234
Rspo2  VKKPVKDTILCPTIAESRRCKMTMRHCPGGKRT--PKAKEKRNKKKKRKLIERAQEQHSV   234
Rspo3  IQHPSAKGNLCPPTNETRKCTVQRKKCQKGERG--KKGRERKRKKPNKGESKEAIPDSKS   237
Rspo4  GRAGHEEAATCQVLSESRKCPIQR-PCPGERSPGQKKGRKDRRPRKDRKLDRRLDVR---   226
       :  . * *:*:* : *   . *:  :  .:  ..

Rspo1  --AGAGS-RRRKGQQQQQ------QQGTVGPLTSAGPA   263  (SEQ ID NO:47)
Rspo2  FLA-----TDRANQ------------------------   243  (SEQ ID NO:48)
Rspo3  LESSKEIPEQRENKQQQKKRKVQDKQKSVSVSTVH----   272  (SEQ ID NO:49)
Rspo4  --------PRQPGLQP----------------------   234  (SEQ ID NO:50)
       : .
```

| Sample ID | Loading Sample | KD (M) | Kon (1/Ms) | Kdis (1/s) | Full R^2 |
|---|---|---|---|---|---|
| WildType | bio-ASGR1 | 3.13E-08 | 2.53E+05 | 7.89E-03 | 0.9987 |
| EESQ | bio-ASGR1 | 1.80E-06 | 7.38E+04 | 1.33E-01 | 0.991 |
| EESN | bio-ASGR1 | 1.09E-08 | 3.65E+05 | 3.96E-03 | 0.998 |
| EESL | bio-ASGR1 | 1.08E-04 | 1.42E+01 | 1.54E-03 | 0 |
| EESH | bio-ASGR1 | 1.36E-04 | 2.56E+03 | 3.49E-01 | 0.9118 |
| EESE | bio-ASGR1 | 9.59E-07 | 4.74E+04 | 4.55E-02 | 0.9908 |
| EESA | bio-ASGR1 | 2.14E-06 | 3.65E+05 | 7.82E-01 | 0.9961 |
| EEAQ | bio-ASGR1 | 1.51E-06 | 1.26E+05 | 1.90E-01 | 0.9947 |
| EEAN | bio-ASGR1 | 2.74E-06 | 3.38E+05 | 9.26E-01 | 0.9971 |
| EEAA | bio-ASGR1 | 2.57E-08 | 3.16E+05 | 8.14E-03 | 0.997 |
| EEST | bio-ASGR1 | 1.25E-08 | 3.09E+05 | 3.84E-03 | 0.9983 |
| EESR | bio-ASGR1 | 7.64E-08 | 2.41E+04 | 1.84E-03 | 0.9793 |
| EESK | bio-ASGR1 | 2.13E-06 | 4.09E+05 | 8.72E-01 | 0.9976 |
| EESY | bio-ASGR1 | 4.39E-07 | 7.91E+03 | 3.47E-03 | 0.9811 |
| EEAL | bio-ASGR1 | 1.55E-03 | 8.88E+01 | 1.38E-01 | 0.0226 |
| EEAE | bio-ASGR1 | 3.59E-06 | 2.02E+04 | 7.25E-02 | 0.9927 |
| EEAH | bio-ASGR1 | 2.35E-04 | 9.59E+03 | 2.25E+00 | 0.9593 |
| EEAT | bio-ASGR1 | 4.69E-08 | 1.55E+05 | 7.25E-03 | 0.9917 |
| EEAY | bio-ASGR1 | 6.13E-04 | 2.57E+03 | 1.58E+00 | 0.9632 |
| EEAR | bio-ASGR1 | 2.71E-03 | 3.50E+02 | 9.48E-01 | 0.9588 |

SEQUENCE LISTING

```
Sequence total quantity: 63
SEQ ID NO: 1              moltype = AA  length = 215
FEATURE                   Location/Qualifiers
source                    1..215
                          mol_type = protein
                          organism = Homo sapiens
SEQUENCE: 1
SSELTQDPAV SVALGQTVRI TCQGDSLRSY YASWYQQKPG QAPVLVIYGK NNRPSGIPDR   60
FSGSSSGNTA SLTITGAQAE DEADYYCNSL ERIGYLSYVF GGGTKLTVLG QPKAAPSVTL  120
FPPSSEELQA NKATLVCLIS DFYPGAVTVA WKADSSPVKA GVETTTPSKQ SNNKYAASSY  180
LSLTPEQWKS HRSYSCQVTH EGSTVEKTVA PTECS                             215

SEQ ID NO: 2              moltype = AA  length = 572
FEATURE                   Location/Qualifiers
REGION                    1..572
                          note = Fusion construct 1R34-DDNN/RA heavy chain fused to
                          RSPO2
source                    1..572
                          mol_type = protein
                          organism = synthetic construct
SEQUENCE: 2
NPICKGCLSC SKDNGCSRCQ QKLFFFLRRE GMRQYGECLH SCPSGYYGHR APDMNRCARC   60
RIENCDSCRS KDACTKCKVG FYLHRGRCFD ECPDGFAPLE ETMECVEGGG GSGSGGSGGG  120
GSEVQLLESG GGLVQPGGSL RLSCAASGFT FSSYAMSWVR QAPGKGLEWV SAISGSGGST  180
```

```
YYADSVKGRF TISRDNSKNT LYLQMNSLRA EDTAVYYCAK DFSSRRWYLE YWGQGTLVTV    240
SSASTKGPSV FPLAPSSKST SGGTAALGCL VKDYFPEPVT VSWNSGALTS GVHTFPAVLQ    300
SSGLYSLSSV VTVPSSSLGT QTYICNVNHK PSNTKVDKKV EPKSCDKTHT CPPCPAPELL    360
GGPSVFLFPP KPKDTLMISR TPEVTCVVVD VSHEDPEVKF NWYVDGVEVH NAKTKPREEQ    420
YGSTYRVVSV LTVLHQDWLN GKEYKCKVSN KALPAPIEKT ISKAKGQPRE PQVYTLPPSR    480
EEMTKNQVSL TCLVKGFYPS DIAVEWESNG QPENNYKTTP PVLDSDGSFF LYSKLTVDKS    540
RWQQGNVFSC SVMHEALHNH YTQKSLSLSP GK                                  572

SEQ ID NO: 3              moltype = AA  length = 107
FEATURE                   Location/Qualifiers
REGION                    1..107
                          note = Humanized VL domain modified from 8M24 antibody
source                    1..107
                          mol_type = protein
                          organism = synthetic construct
SEQUENCE: 3
DIQMTQSPSS LSASVGDRVT ITCRISENIY SNLAWYQQKP GKAPKLLIYA AINLADGVPS    60
RFSGSGSGTD FTLTISSLQP EDFATYYCQH FWGTPFTFGQ GTKLEIK                  107

SEQ ID NO: 4              moltype = AA  length = 244
FEATURE                   Location/Qualifiers
REGION                    1..244
                          note = fusion construct heavy chain variable domain fused
                           to RSPO2
source                    1..244
                          mol_type = protein
                          organism = synthetic construct
SEQUENCE: 4
NPICKGCLSC SKDNGCSRCQ QKLFFFLRRE GMRQYGECLH SCPSGYYGHR APDMNRCARC    60
RIENCDSCRS KDACTKCKVG FYLHRGRCFD ECPDGFAPLE ETMECVEGGG GSGGGGSGGG    120
GSEVQLVQSG AEVKKPGSSV KVSCKASGYT FTNYGINWVR QAPGQGLEWM GEIFPRSDNT    180
FYAQKFQGRV TITADKSTST AYMELSSLRS EDTAVYYCAR KGRDYGTSHY FDYWGQGTTV    240
TVSS                                                                 244

SEQ ID NO: 5              moltype = AA  length = 214
FEATURE                   Location/Qualifiers
REGION                    1..214
                          note = Humanized VL chain modified from 8M24 antibody
source                    1..214
                          mol_type = protein
                          organism = synthetic construct
SEQUENCE: 5
DIQMTQSPSS LSASVGDRVT ITCRISENIY SNLAWYQQKP GKAPKLLIYA AINLADGVPS    60
RFSGSGSGTD FTLTISSLQP EDFATYYCQH FWGTPFTFGQ GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 6              moltype = AA  length = 574
FEATURE                   Location/Qualifiers
REGION                    1..574
                          note = fusion construct heavy chain fused to RSPO2
source                    1..574
                          mol_type = protein
                          organism = synthetic construct
SEQUENCE: 6
NPICKGCLSC SKDNGCSRCQ QKLFFFLRRE GMRQYGECLH SCPSGYYGHR APDMNRCARC    60
RIENCDSCRS KDACTKCKVG FYLHRGRCFD ECPDGFAPLE ETMECVEGGG GSGGGGSGGG    120
GSEVQLVQSG AEVKKPGSSV KVSCKASGYT FTNYGINWVR QAPGQGLEWM GEIFPRSDNT    180
FYAQKFQGRV TITADKSTST AYMELSSLRS EDTAVYYCAR KGRDYGTSHY FDYWGQGTTV    240
TVSSASTKGP SVFPLAPSSK STSGGTAALG CLVKDYFPEP VTVSWNSGAL TSGVHTFPAV    300
LQSSGLYSLS SVVTVPSSSL GTQTYICNVN HKPSNTKVDK KVEPKSCDKT HTCPPCPAPE    360
LLGGPSVFLF PPKPKDTLMI SRTPEVTCVV VDVSHEDPEV KFNWYVDGVE VHNAKTKPRE    420
EQYGSTYRVV SVLTVLHQDW LNGKEYKCKV SNKALPAPIE KTISKAKGQP REPQVYTLPP    480
SREEMTKNQV SLTCLVKGFY PSDIAVEWES NGQPENNYKT TPPVLDSDGS FFLYSKLTVD    540
KSRWQQGNVF SCSVMHEALH NHYTQKSLSL SPGK                                574

SEQ ID NO: 7              moltype = AA  length = 215
FEATURE                   Location/Qualifiers
REGION                    1..215
                          note = mutated light chain sequence
source                    1..215
                          mol_type = protein
                          organism = synthetic construct
SEQUENCE: 7
SSELTQDPAV SVALGQTVRI TCQGESLRSY YASWYQQKPG QAPVLVIYGK SNRPSGIPDR    60
FSGSSSGNTA SLTITGAQAE DEADYYCTSL ERIGYLSYVF GGGTKLTVLG QPKAAPSVTL    120
FPPSSEELQA NKATLVCLIS DFYPGAVTVA WKADSSPVKA GVETTTPSKQ SNNKYAASSY    180
LSLTPEQWKS HRSYSCQVTH EGSTVEKTVA PTECS                               215
```

```
SEQ ID NO: 8              moltype = AA   length = 572
FEATURE                   Location/Qualifiers
REGION                    1..572
                          note = fusion construct mutated EEST/EE heavy chain fused
                            to RSPO2
source                    1..572
                          mol_type = protein
                          organism = synthetic construct
SEQUENCE: 8
NPICKGCLSC SKDNGCSRCQ QKLFFFLRRE GMRQYGECLH SCPSGYYGHR APDMNRCARC    60
RIENCDSCES KDECTKCKVG FYLHRGRCFD ECPDGFAPLE ETMECVEGGG GSGGGGSGGG   120
GSEVQLLESG GGLVQPGGSL RLSCAASGFT FSSYAMSWVR QAPGKGLEWV SAISGSGGST   180
YYAESVKGRF TISRDNSKNT LYLQMNSLRA EDTAVYYCAK DFSSRRWYLE YWGQGTLVTV   240
SSASTKGPSV FPLAPSSKST SGGTAALGCL VKDYFPEPVT VSWNSGALTS GVHTFPAVLQ   300
SSGLYSLSSV VTVPSSSLGT QTYICNVNHK PSNTKVDKKV EPKSCDKTHT CPPCPAPELL   360
GGPSVFLFPP KPKDTLMISR TPEVTCVVVD VSHEDPEVKF NWYVDGVEVH NAKTKPREEQ   420
YGSTYRVVSV LTVLHQDWLN GKEYKCKVSN KALPAPIEKT ISKAKGQPRE PQVYTLPPSR   480
EEMTKNQVSL TCLVKGFYPS DIAVEWESNG QPENNYKTTP PVLDSDGSFF LYSKLTVDKS   540
RWQQGNVFSC SVMHEALHNH YTQKSLSLSP GK                                572

SEQ ID NO: 9              moltype = AA   length = 215
FEATURE                   Location/Qualifiers
REGION                    1..215
                          note = mutated 1R34-EEST/RA light chain
source                    1..215
                          mol_type = protein
                          organism = synthetic construct
SEQUENCE: 9
SSELTQDPAV SVALGQTVRI TCQGESLRSY YASWYQQKPG QAPVLVIYGK SNRPSGIPDR    60
FSGSSSGNTA SLTITGAQAE DEADYYCTSL ERIGYLSYVF GGGTKLTVLG QPKAAPSVTL   120
FPPSSEELQA NKATLVCLIS DFYPGAVTVA WKADSSPVKA GVETTTPSKQ SNNKYAASSY   180
LSLTPEQWKS HRSYSCQVTH EGSTVEKTVA PTECS                             215

SEQ ID NO: 10             moltype = AA   length = 572
FEATURE                   Location/Qualifiers
REGION                    1..572
                          note = fusion construct mutated 1R34-EEST/RA heavy chain
                            fused to RSPO2
source                    1..572
                          mol_type = protein
                          organism = synthetic construct
SEQUENCE: 10
NPICKGCLSC SKDNGCSRCQ QKLFFFLRRE GMRQYGECLH SCPSGYYGHR APDMNRCARC    60
RIENCDSCRS KDACTKCKVG FYLHRGRCFD ECPDGFAPLE ETMECVEGGG GSGGGGSGGG   120
GSEVQLLESG GGLVQPGGSL RLSCAASGFT FSSYAMSWVR QAPGKGLEWV SAISGSGGST   180
YYAESVKGRF TISRDNSKNT LYLQMNSLRA EDTAVYYCAK DFSSRRWYLE YWGQGTLVTV   240
SSASTKGPSV FPLAPSSKST SGGTAALGCL VKDYFPEPVT VSWNSGALTS GVHTFPAVLQ   300
SSGLYSLSSV VTVPSSSLGT QTYICNVNHK PSNTKVDKKV EPKSCDKTHT CPPCPAPELL   360
GGPSVFLFPP KPKDTLMISR TPEVTCVVVD VSHEDPEVKF NWYVDGVEVH NAKTKPREEQ   420
YGSTYRVVSV LTVLHQDWLN GKEYKCKVSN KALPAPIEKT ISKAKGQPRE PQVYTLPPSR   480
EEMTKNQVSL TCLVKGFYPS DIAVEWESNG QPENNYKTTP PVLDSDGSFF LYSKLTVDKS   540
RWQQGNVFSC SVMHEALHNH YTQKSLSLSP GK                                572

SEQ ID NO: 11             moltype = AA   length = 215
FEATURE                   Location/Qualifiers
REGION                    1..215
                          note = mutated 1R34-EEAT/EE light chain
source                    1..215
                          mol_type = protein
                          organism = synthetic construct
SEQUENCE: 11
SSELTQDPAV SVALGQTVRI TCQGESLRSY YASWYQQKPG QAPVLVIYGK ANRPSGIPDR    60
FSGSSSGNTA SLTITGAQAE DEADYYCTSL ERIGYLSYVF GGGTKLTVLG QPKAAPSVTL   120
FPPSSEELQA NKATLVCLIS DFYPGAVTVA WKADSSPVKA GVETTTPSKQ SNNKYAASSY   180
LSLTPEQWKS HRSYSCQVTH EGSTVEKTVA PTECS                             215

SEQ ID NO: 12             moltype = AA   length = 572
FEATURE                   Location/Qualifiers
REGION                    1..572
                          note = fusion construct mutated 1R34-EEAT/EE heavy chain
                            fused to RSPO2
source                    1..572
                          mol_type = protein
                          organism = synthetic construct
SEQUENCE: 12
NPICKGCLSC SKDNGCSRCQ QKLFFFLRRE GMRQYGECLH SCPSGYYGHR APDMNRCARC    60
RIENCDSCES KDECTKCKVG FYLHRGRCFD ECPDGFAPLE ETMECVEGGG GSGGGGSGGG   120
GSEVQLLESG GGLVQPGGSL RLSCAASGFT FSSYAMSWVR QAPGKGLEWV SAISGSGGST   180
YYAESVKGRF TISRDNSKNT LYLQMNSLRA EDTAVYYCAK DFSSRRWYLE YWGQGTLVTV   240
```

```
SSASTKGPSV FPLAPSSKST SGGTAALGCL VKDYFPEPVT VSWNSGALTS GVHTFPAVLQ    300
SSGLYSLSSV VTVPSSSLGT QTYICNVNHK PSNTKVDKKV EPKSCDKTHT CPPCPAPELL    360
GGPSVFLFPP KPKDTLMISR TPEVTCVVVD VSHEDPEVKF NWYVDGVEVH NAKTKPREEQ    420
YGSTYRVVSV LTVLHQDWLN GKEYKCKVSN KALPAPIEKT ISKAKGQPRE PQVYTLPPSR    480
EEMTKNQVSL TCLVKGFYPS DIAVEWESNG QPENNYKTTP PVLDSDGSFF LYSKLTVDKS    540
RWQQGNVFSC SVMHEALHNH YTQKSLSLSP GK                                  572

SEQ ID NO: 13            moltype = AA  length = 122
FEATURE                  Location/Qualifiers
REGION                   1..122
                         note = 8M24 antibody heavy chain variable domain
source                   1..122
                         mol_type = protein
                         organism = synthetic construct
SEQUENCE: 13
QVQLQQSGAE LARPGASVKL SCKASGYTFT NYGINWVKQR TGQGLEWIGE IFPRSDNTFY     60
NEKFKGKATL TADKSSTTAY MELRSLTSED SAVYFCARKG RDYGTSHYFD YWGQGTTLTV    120
SS                                                                  122

SEQ ID NO: 14            moltype = AA  length = 107
FEATURE                  Location/Qualifiers
REGION                   1..107
                         note = 8M24 antibody light chain variable domain
source                   1..107
                         mol_type = protein
                         organism = synthetic construct
SEQUENCE: 14
DIQMTQSPAS LSVSVGETVT ITCRISENIY SNLAWYQQKQ GKSPHLLVYA AINLADGVPS     60
RFSGSGSGTQ FSLKINSLQS EDFGSYYCQH FWGTPFTFGS GTKLEIK                  107

SEQ ID NO: 15            moltype = AA  length = 122
FEATURE                  Location/Qualifiers
REGION                   1..122
                         note = 8M24 antibody heavy chain variable domain (humanized
                            1)
source                   1..122
                         mol_type = protein
                         organism = synthetic construct
SEQUENCE: 15
EVQLVQSGAE VKKPGSSVKV SCKASGYTFT NYGINWVRQA PGQGLEWMGE IFPRSDNTFY     60
AQKFQGRVTI TADKSTSTAY MELSSLRSED TAVYYCARKG RDYGTSHYFD YWGQGTTVTV    120
SS                                                                  122

SEQ ID NO: 16            moltype = AA  length = 122
FEATURE                  Location/Qualifiers
REGION                   1..122
                         note = 8M24 antibody heavy chain variable domain (humanized
                            2)
source                   1..122
                         mol_type = protein
                         organism = synthetic construct
SEQUENCE: 16
EVQLVQSGAE VKKPGSSVKV SCKASGYTFT NYGINWVRQA PGQGLEWIGE IFPRSDNTFY     60
AQKFQGRATL TADKSTSTAY MELSSLRSED TAVYYCARKG RDYGTSHYFD YWGQGTTLTV    120
SS                                                                  122

SEQ ID NO: 17            moltype = AA  length = 107
FEATURE                  Location/Qualifiers
REGION                   1..107
                         note = 8M24 antibody light chain variable domain (humanized
                            1)
source                   1..107
                         mol_type = protein
                         organism = synthetic construct
SEQUENCE: 17
DIQMTQSPSS LSASVGDRVT ITCRISENIY SNLAWYQQKP GKAPKLLIYA AINLADGVPS     60
RFSGSGSGTD FTLTISSLQP EDFATYYCQH FWGTPFTFGQ GTKLEIK                  107

SEQ ID NO: 18            moltype = AA  length = 107
FEATURE                  Location/Qualifiers
REGION                   1..107
                         note = 8M24 antibod light chain variable domain (humanized
                            2)
source                   1..107
                         mol_type = protein
                         organism = synthetic construct
SEQUENCE: 18
DIQMTQSPSS LSASVGDRVT ITCRISENIY SNLAWYQQKP GKAPKLLVYA AINLADGVPS     60
RFSGSGSGTD FTLTISSLQP EDFGTYYCQH FWGTPFTFGQ GTKLEIK                  107
```

```
SEQ ID NO: 19            moltype = AA   length = 107
FEATURE                  Location/Qualifiers
REGION                   1..107
                         note = 8M24-EASE-RA light chain variable domain
source                   1..107
                         mol_type = protein
                         organism = synthetic construct
SEQUENCE: 19
DIQMTQSPSS LSASVGDRVT ITCRISENIY SNLAWYQQKP GKAPKLLIYA AINLAEGVPS    60
RFSGSGSGTD FTLTISSLQP EDFATYYCQH FWGTPFTFGQ GTKLEIK                 107

SEQ ID NO: 20            moltype = AA   length = 244
FEATURE                  Location/Qualifiers
REGION                   1..244
                         note = fusion construct 8M24-EASE-RA heavy chain variable
                           domain fused to RSPO2
source                   1..244
                         mol_type = protein
                         organism = synthetic construct
SEQUENCE: 20
NPICKGCLSC SKDNGCSRCQ QKLFFFLRRE GMRQYGECLH SCPSGYYGHR APDMNRCARC    60
RIENCDSCRS KDACTKCKVG FYLHRGRCFD ECPDGFAPLE ETMECVEGGG GSGGGGSGGG   120
GSEVQLVQSG AEVKKPGSSV KVSCKASGYT FTAYGINWVR QAPGQGLEWM GEIFPRSDST   180
FYAQKFQGRV TITADKSTST AYMELSSLRS EDTAVYYCAR KGREYGTSHY FDYWGQGTTV   240
TVSS                                                               244

SEQ ID NO: 21            moltype = AA   length = 214
FEATURE                  Location/Qualifiers
REGION                   1..214
                         note = 8M24-EASE-EE light chain
source                   1..214
                         mol_type = protein
                         organism = synthetic construct
SEQUENCE: 21
DIQMTQSPSS LSASVGDRVT ITCRISENIY SNLAWYQQKP GKAPKLLIYA AINLAEGVPS    60
RFSGSGSGTD FTLTISSLQP EDFATYYCQH FWGTPFTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 22            moltype = AA   length = 574
FEATURE                  Location/Qualifiers
REGION                   1..574
                         note = fusion construct 8M24-EASE-EE heavy chain fused to
                           RSPO2
source                   1..574
                         mol_type = protein
                         organism = synthetic construct
SEQUENCE: 22
NPICKGCLSC SKDNGCSRCQ QKLFFFLRRE GMRQYGECLH SCPSGYYGHR APDMNRCARC    60
RIENCDSCES KDECTKCKVG FYLHRGRCFD ECPDGFAPLE ETMECVEGGG GSGGGGSGGG   120
GSEVQLVQSG AEVKKPGSSV KVSCKASGYT FTAYGINWVR QAPGQGLEWM GEIFPRSDST   180
FYAQKFQGRV TITADKSTST AYMELSSLRS EDTAVYYCAR KGREYGTSHY FDYWGQGTTV   240
TVSSASTKGP SVFPLAPSSK STSGGTAALG CLVKDYFPEP VTVSWNSGAL TSGVHTFPAV   300
LQSSGLYSLS SVVTVPSSSL GTQTYICNVN HKPSNTKVDK KVEPKSCDKT HTCPPCPAPE   360
LLGGPSVFLF PPKPKDTLMI SRTPEVTCVV VDVSHEDPEV KFNWYVDGVE VHNAKTKPRE   420
EQYGSTYRVV SVLTVLHQDW LNGKEYKCKV SNKALPAPIE KTISKAKGQP REPQVYTLPP   480
SREEMTKNQV SLTCLVKGFY PSDIAVEWES NGQPENNYKT TPPVLDSDGS FFLYSKLTVD   540
KSRWQQGNVF SCSVMHEALH NHYTQKSLSL SPGK                              574

SEQ ID NO: 23            moltype = AA   length = 109
FEATURE                  Location/Qualifiers
REGION                   1..109
                         note = 1R34-DDNN/RA light chain variable domain
source                   1..109
                         mol_type = protein
                         organism = synthetic construct
SEQUENCE: 23
SSELTQDPAV SVALGQTVRI TCQGDSLRSY YASWYQQKPG QAPVLVIYGK NNRPSGIPDR    60
FSGSSSGNTA SLTITGAQAE DEADYYCNSL ERIGYLSYVF GGGTKLTVL              109

SEQ ID NO: 24            moltype = AA   length = 242
FEATURE                  Location/Qualifiers
REGION                   1..242
                         note = fusion construct 1R34-DDNN/RA heavy chain variable
                           domain fused to RSPO2
source                   1..242
                         mol_type = protein
                         organism = synthetic construct
```

```
SEQUENCE: 24
NPICKGCLSC SKDNGCSRCQ QKLFFFLRRE GMRQYGECLH SCPSGYYGHR APDMNRCARC    60
RIENCDSCRS KDACTKCKVG FYLHRGRCFD ECPDGFAPLE ETMECVEGGG GSGSGGSGGG   120
GSEVQLLESG GGLVQPGGSL RLSCAASGFT FSSYAMSWVR QAPGKGLEWV SAISGSGGST   180
YYADSVKGRF TISRDNSKNT LYLQMNSLRA EDTAVYYCAK DFSSRRWYLE YWGQGTLVTV   240
SS                                                                 242

SEQ ID NO: 25           moltype = AA  length = 214
FEATURE                 Location/Qualifiers
REGION                  1..214
                        note = 8M24-EASE light chain
source                  1..214
                        mol_type = protein
                        organism = synthetic construct
SEQUENCE: 25
DIQMTQSPSS LSASVGDRVT ITCRISENIY SNLAWYQQKP GKAPKLLIYA AINLAEGVPS    60
RFSGSGSGTD FTLTISSLQP EDFATYYCQH FWGTPFTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 26           moltype = AA  length = 574
FEATURE                 Location/Qualifiers
REGION                  1..574
                        note = fusion construct 8M24-EASE heavy chain fused to
                         RSPO2 (human IgG1_N297G)
source                  1..574
                        mol_type = protein
                        organism = synthetic construct
SEQUENCE: 26
NPICKGCLSC SKDNGCSRCQ QKLFFFLRRE GMRQYGECLH SCPSGYYGHR APDMNRCARC    60
RIENCDSCRS KDACTKCKVG FYLHRGRCFD ECPDGFAPLE ETMECVEGGG GSGGGGSGGG   120
GSEVQLVQSG AEVKKPGSSV KVSCKASGYT FTAYGINWVR QAPGQGLEWM GEIFPRSDST   180
FYAQKFQGRV TITADKSTST AYMELSSLRS EDTAVYYCAR KGREYGTSHY FDYWGQGTTV   240
TVSSASTKGP SVFPLAPSSK STSGGTAALG CLVKDYFPEP VTVSWNSGAL TSGVHTFPAV   300
LQSSGLYSLS SVVTVPSSSL GTQTYICNVN HKPSNTKVDK KVEPKSCDKT HTCPPCPAPE   360
LLGGPSVFLF PPKPKDTLMI SRTPEVTCVV VDVSHEDPEV KFNWYVDGVE VHNAKTKPRE   420
EQYGSTYRVV SVLTVLHQDW LNGKEYKCKV SNKALPAPIE KTISKAKGQP REPQVYTLPP   480
SREEMTKNQV SLTCLVKGFY PSDIAVEWES NGQPENNYKT TPPVLDSDGS FFLYSKLTVD   540
KSRWQQGNVF SCSVMHEALH NHYTQKSLSL SPGK                               574

SEQ ID NO: 27           moltype = AA  length = 109
FEATURE                 Location/Qualifiers
REGION                  1..109
                        note = 1R34-EEST/EE light chain variable domain
source                  1..109
                        mol_type = protein
                        organism = synthetic construct
SEQUENCE: 27
SSELTQDPAV SVALGQTVRI TCQGESLRSY YASWYQQKPG QAPVLVIYGK SNRPSGIPDR    60
FSGSSSGNTA SLTITGAQAE DEADYYCTSL ERIGYLSYVF GGGTKLTVL               109

SEQ ID NO: 28           moltype = AA  length = 242
FEATURE                 Location/Qualifiers
REGION                  1..242
                        note = Made in Labe - fusion construct 1R34-EEST/EE heavy
                         chain variable region fused to RSPO2
source                  1..242
                        mol_type = protein
                        organism = synthetic construct
SEQUENCE: 28
NPICKGCLSC SKDNGCSRCQ QKLFFFLRRE GMRQYGECLH SCPSGYYGHR APDMNRCARC    60
RIENCDSCES KDECTKCKVG FYLHRGRCFD ECPDGFAPLE ETMECVEGGG GSGGGGSGGG   120
GSEVQLLESG GGLVQPGGSL RLSCAASGFT FSSYAMSWVR QAPGKGLEWV SAISGSGGST   180
YYAESVKGRF TISRDNSKNT LYLQMNSLRA EDTAVYYCAK DFSSRRWYLE YWGQGTLVTV   240
SS                                                                 242

SEQ ID NO: 29           moltype = AA  length = 107
FEATURE                 Location/Qualifiers
REGION                  1..107
                        note = modified R-spondin-2
source                  1..107
                        mol_type = protein
                        organism = synthetic construct
SEQUENCE: 29
NPICKGCLSC SKDNGCSRCQ QKLFFFLRRE GMRQYGECLH SCPSGYYGHR APDMNRCARC    60
RIENCDSCRS KDACTKCKVG FYLHRGRCFD ECPDGFAPLE ETMECVE                 107

SEQ ID NO: 30           moltype = AA  length = 107
FEATURE                 Location/Qualifiers
```

```
REGION                     1..107
                           note = modified R-spondin-2
source                     1..107
                           mol_type = protein
                           organism = synthetic construct
SEQUENCE: 30
NPICKGCLSC SKDNGCSRCQ QKLFFFLRRE GMRQYGECLH SCPSGYYGHR APDMNRCARC    60
RIENCDSCAS KDACTKCKVG FYLHRGRCFD ECPDGFAPLE ETMECVE                 107

SEQ ID NO: 31              moltype = AA  length = 107
FEATURE                    Location/Qualifiers
REGION                     1..107
                           note = modified R-spondin-2
source                     1..107
                           mol_type = protein
                           organism = synthetic construct
SEQUENCE: 31
NPICKGCLSC SKDNGCSRCQ QKLFFFLRRE GMRQYGECLH SCPSGYYGHR APDMNRCARC    60
RIENCDSCES KDACTKCKVG FYLHRGRCFD ECPDGFAPLE ETMECVE                 107

SEQ ID NO: 32              moltype = AA  length = 107
FEATURE                    Location/Qualifiers
REGION                     1..107
                           note = modified R-spondin-2
source                     1..107
                           mol_type = protein
                           organism = synthetic construct
SEQUENCE: 32
NPICKGCLSC SKDNGCSRCQ QKLFFFLRRE GMRQYGECLH SCPSGYYGHR APDMNRCARC    60
RIENCDSCES KDECTKCKVG FYLHRGRCFD ECPDGFAPLE ETMECVE                 107

SEQ ID NO: 33              moltype = AA  length = 450
FEATURE                    Location/Qualifiers
REGION                     1..450
                           note = 1R34-DDNN/RA heavy chain
source                     1..450
                           mol_type = protein
                           organism = synthetic construct
SEQUENCE: 33
EVQLLESGGG LVQPGGSLRL SCAASGFTFS SYAMSWVRQA PGKGLEWVSA ISGSGGSTYY    60
ADSVKGRFTI SRDNSKNTLY LQMNSLRAED TAVYYCAKDF SSRRWYLEYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYG   300
STYRVVSVLT VLHQDWLNGK EYKCKVSNKA LPAPIEKTIS KAKGQPREPQ VYTLPPSREE   360
MTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                   450

SEQ ID NO: 34              moltype = AA  length = 5
FEATURE                    Location/Qualifiers
REGION                     1..5
                           note = 1R34-EEST/EE CDRH1
source                     1..5
                           mol_type = protein
                           organism = synthetic construct
SEQUENCE: 34
SYAMS                                                                 5

SEQ ID NO: 35              moltype = AA  length = 17
FEATURE                    Location/Qualifiers
REGION                     1..17
                           note = 1R34-EEST/EE CDRH2
source                     1..17
                           mol_type = protein
                           organism = synthetic construct
SEQUENCE: 35
AISGSGGSTY YEDSVKG                                                   17

SEQ ID NO: 36              moltype = AA  length = 11
FEATURE                    Location/Qualifiers
REGION                     1..11
                           note = 1R34-EEST/EE CDRH3
source                     1..11
                           mol_type = protein
                           organism = synthetic construct
SEQUENCE: 36
DFSSRRWYLE Y                                                         11

SEQ ID NO: 37              moltype = AA  length = 11
```

```
FEATURE                 Location/Qualifiers
REGION                  1..11
                        note = 1R34-EEST/EE CDRL1
source                  1..11
                        mol_type = protein
                        organism = synthetic construct
SEQUENCE: 37
QGESLRSYYA S                                                           11

SEQ ID NO: 38           moltype = AA  length = 8
FEATURE                 Location/Qualifiers
REGION                  1..8
                        note = 1R34-EEST/EE CDRL2
source                  1..8
                        mol_type = protein
                        organism = synthetic construct
SEQUENCE: 38
YGKSNRPS                                                               8

SEQ ID NO: 39           moltype = AA  length = 13
FEATURE                 Location/Qualifiers
REGION                  1..13
                        note = 1R34-EEST/EE CDRL3
source                  1..13
                        mol_type = protein
                        organism = synthetic construct
SEQUENCE: 39
CTSLERIGYL SYV                                                         13

SEQ ID NO: 40           moltype = AA  length = 8
FEATURE                 Location/Qualifiers
REGION                  1..8
                        note = 1R34-EEAT/EE CDRL2
source                  1..8
                        mol_type = protein
                        organism = synthetic construct
SEQUENCE: 40
YGKANRPS                                                               8

SEQ ID NO: 41           moltype = AA  length = 11
FEATURE                 Location/Qualifiers
REGION                  1..11
                        note = 8M24-EASE CDRL1
source                  1..11
                        mol_type = protein
                        organism = synthetic construct
SEQUENCE: 41
RISENIYSNL A                                                           11

SEQ ID NO: 42           moltype = AA  length = 7
FEATURE                 Location/Qualifiers
REGION                  1..7
                        note = 8M24-EASE CDRL2
source                  1..7
                        mol_type = protein
                        organism = synthetic construct
SEQUENCE: 42
AAINLAE                                                                7

SEQ ID NO: 43           moltype = AA  length = 9
FEATURE                 Location/Qualifiers
REGION                  1..9
                        note = 8M24-EASE CDRL3
source                  1..9
                        mol_type = protein
                        organism = synthetic construct
SEQUENCE: 43
QHFWGTPFT                                                              9

SEQ ID NO: 44           moltype = AA  length = 5
FEATURE                 Location/Qualifiers
REGION                  1..5
                        note = 8M24-EASE CDRH1
source                  1..5
                        mol_type = protein
                        organism = synthetic construct
SEQUENCE: 44
AYGIN                                                                  5
```

```
SEQ ID NO: 45                  moltype = AA  length = 17
FEATURE                        Location/Qualifiers
REGION                         1..17
                               note = 8M24-EASE CDRH2
source                         1..17
                               mol_type = protein
                               organism = synthetic construct
SEQUENCE: 45
EIFPRSDSTF YAQKFQG                                                 17

SEQ ID NO: 46                  moltype = AA  length = 13
FEATURE                        Location/Qualifiers
REGION                         1..13
                               note = 8M24-EASE CDRH3
source                         1..13
                               mol_type = protein
                               organism = synthetic construct
SEQUENCE: 46
KGREYGTSHY FDY                                                     13

SEQ ID NO: 47                  moltype = AA  length = 263
FEATURE                        Location/Qualifiers
source                         1..263
                               mol_type = protein
                               organism = Homo sapiens
SEQUENCE: 47
MRLGLCVVAL VLSWTHLTIS SRGIKGKRQR RISAEGSQAC AKGCELCSEV NGCLKCSPKL   60
FILLERNDIR QVGVCLPSCP PGYFDARNPD MNKCIKCKIE HCEACFSHNF CTKCKEGLYL  120
HKGRCYPACP EGSSAANGTM ECSSPAQCEM SEWSPWGPCS KKQQLCGFRR GSEERTRRVL  180
HAPVGDHAAC SDTKETRRCT VRRVPCPEGQ KRRKGGQGRR ENANRNLARK ESKEAGAGSR  240
RRKGQQQQQQ QGTVGPLTSA GPA                                         263

SEQ ID NO: 48                  moltype = AA  length = 243
FEATURE                        Location/Qualifiers
source                         1..243
                               mol_type = protein
                               organism = Homo sapiens
SEQUENCE: 48
MQFRLFSFAL IILNCMDYSH CQGNRWRRSK RASYVSNPIC KGCLSCSKDN GCSRCQQKLF   60
FFLRREGMRQ YGECLHSCPS GYYGHRAPDM NRCARCRIEN CDSCFSKDFC TKCKVGFYLH  120
RGRCFDECPD GFAPLEETME CVEGCEVGHW SEWGTCSRNN RTCGFKWGLE TRTRQIVKKP  180
VKDTILCPTI AESRRCKMTM RHCPGGKRTP KAKEKRNKKK KRKLIERAQE QHSVFLATDR  240
ANQ                                                                243

SEQ ID NO: 49                  moltype = AA  length = 272
FEATURE                        Location/Qualifiers
source                         1..272
                               mol_type = protein
                               organism = Homo sapiens
SEQUENCE: 49
MHLRLISWLF IILNFMEYIG SQNASRGRRQ RRMHPNVSQG CQGGCATCSD YNGCLSCKPR   60
LFFALERIGM KQIGVCLSSC PSGYYGTRYP DINKCTKCKA DCDTCFNKNF CTKCKSGFYL  120
HLGKCLDNCP EGLEANNHTM ECVSIVHCEV SEWNPWSPCT KKGKTCGFKR GTETRVREII  180
QHPSAKGNLC PPTNETRKCT VQRKKCQKGE RGKKGRERKR KKPNKGESKE AIPDSKSLES  240
SKEIPEQREN KQQQKKRKVQ DKQKSVSVST VH                                272

SEQ ID NO: 50                  moltype = AA  length = 234
FEATURE                        Location/Qualifiers
source                         1..234
                               mol_type = protein
                               organism = Homo sapiens
SEQUENCE: 50
MRAPLCLLLL VAHAVDMLAL NRRKKQVGTG LGGNCTGCII CSEENGCSTC QQRLFLFIRR   60
EGIRQYGKCL HDCPPGYFGI RGQEVNRCKK CGATCESCFS QDFCIRCKRQ FYLYKGKCLP  120
TCPPGTLAHQ NTRECQGECE LGPWGGWSPC THNGKTCGSA WGLESRVREA GRAGHEEAAT  180
CQVLSESRKC PIQRPCPGER SPGQKKGRKD RRPRKDRKLD RRLDVRPRQP GLQP         234

SEQ ID NO: 51                  moltype = AA  length = 574
FEATURE                        Location/Qualifiers
REGION                         1..574
                               note = fusion construct 8M24-EASE-RA heavy chain fused to
                                 RSPO2
source                         1..574
                               mol_type = protein
                               organism = synthetic construct
SEQUENCE: 51
NPICKGCLSC SKDNGCSRCQ QKLFFFLRRE GMRQYGECLH SCPSGYYGHR APDMNRCARC   60
RIENCDSCRS KDACTKCKVG FYLHRGRCFD ECPDGFAPLE ETMECVEGGG GSGGGGSGGG  120
GSEVQLVQSG AEVKKPGSSV KVSCKASGYT FTAYGINWVR QAPGQGLEWM GEIFPRSDST  180
```

```
FYAQKFQGRV TITADKSTST AYMELSSLRS EDTAVYYCAR KGREYGTSHY FDYWGQGTTV    240
TVSSASTKGP SVFPLAPSSK STSGGTAALG CLVKDYFPEP VTVSWNSGAL TSGVHTFPAV    300
LQSSGLYSLS SVVTVPSSSL GTQTYICNVN HKPSNTKVDK KVEPKSCDKT HTCPPCPAPE    360
LLGGPSVFLF PPKPKDTLMI SRTPEVTCVV VDVSHEDPEV KFNWYVDGVE VHNAKTKPRE    420
EQYGSTYRVV SVLTVLHQDW LNGKEYKCKV SNKALPAPIE KTISKAKGQP REPQVYTLPP    480
SREEMTKNQV SLTCLVKGFY PSDIAVEWES NGQPENNYKT TPPVLDSDGS FFLYSKLTVD    540
KSRWQQGNVF SCSVMHEALH NHYTQKSLSL SPGK                                574

SEQ ID NO: 52           moltype = AA   length = 169
FEATURE                 Location/Qualifiers
REGION                  1..169
                        note = modified human ASGR1
source                  1..169
                        mol_type = protein
                        organism = synthetic construct
SEQUENCE: 52
HHHHHHHHGS GSGLNDIFEA QKIEWHESGS GCPVNWVEHE RSCYWFSRSG KAWADADNYC     60
RLEDAHLVVV TSWEEQKFVQ HHIGPVNTWM GLHDQNGPWK WVDGTDYETG FKNWRPEQPD    120
DWYGHGLGGG EDCAHFTDDG RWNDDVCQRP YRWVCETELD KASQEPPLL                169

SEQ ID NO: 53           moltype = AA   length = 214
FEATURE                 Location/Qualifiers
REGION                  1..214
                        note = 8M24L1 Light-chain
source                  1..214
                        mol_type = protein
                        organism = synthetic construct
SEQUENCE: 53
DIQMTQSPSS LSASVGDRVT ITCRISENIY SNLAWYQQKP GKAPKLLIYA AINLADGVPS     60
RFSGSGSGTD FTLTISSLQP EDFATYYCQH FWGTPFTFGQ GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 54           moltype = AA   length = 236
FEATURE                 Location/Qualifiers
REGION                  1..236
                        note = 8M24H1 Heavy-chain
source                  1..236
                        mol_type = protein
                        organism = synthetic construct
SEQUENCE: 54
EVQLVQSGAE VKKPGSSVKV SCKASGYTFT NYGINWVRQA PGQGLEWMGE IFPRSDNTFY     60
AQKFQGRVTI TADKSTSTAY MELSSLRSED TAVYYCARKG RDYGTSHYFD YWGQGTTVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCGSGSG HHHHHH        236

SEQ ID NO: 55           moltype = AA   length = 4
FEATURE                 Location/Qualifiers
REGION                  1..4
                        note = peptide linker
source                  1..4
                        mol_type = protein
                        organism = synthetic construct
SEQUENCE: 55
GGGG                                                                   4

SEQ ID NO: 56           moltype = AA   length = 5
FEATURE                 Location/Qualifiers
REGION                  1..5
                        note = peptide linker
source                  1..5
                        mol_type = protein
                        organism = synthetic construct
SEQUENCE: 56
GGGGG                                                                  5

SEQ ID NO: 57           moltype = AA   length = 7
FEATURE                 Location/Qualifiers
REGION                  1..7
                        note = peptide linker
source                  1..7
                        mol_type = protein
                        organism = synthetic construct
SEQUENCE: 57
GGGGGGG                                                                7

SEQ ID NO: 58           moltype = AA   length = 5
FEATURE                 Location/Qualifiers
```

```
REGION                  1..5
                        note = peptide linker
source                  1..5
                        mol_type = protein
                        organism = synthetic construct
SEQUENCE: 58
GGGGS                                                                          5

SEQ ID NO: 59           moltype = AA  length = 6
FEATURE                 Location/Qualifiers
REGION                  1..6
                        note = peptide linker
source                  1..6
                        mol_type = protein
                        organism = synthetic construct
SEQUENCE: 59
GGGGGK                                                                         6

SEQ ID NO: 60           moltype = AA  length = 7
FEATURE                 Location/Qualifiers
REGION                  1..7
                        note = peptide linker
source                  1..7
                        mol_type = protein
                        organism = synthetic construct
SEQUENCE: 60
GGGGGKR                                                                        7

SEQ ID NO: 61           moltype = AA  length = 8
FEATURE                 Location/Qualifiers
REGION                  1..8
                        note = peptide linker
source                  1..8
                        mol_type = protein
                        organism = synthetic construct
SEQUENCE: 61
GGGKGGGG                                                                       8

SEQ ID NO: 62           moltype = AA  length = 15
FEATURE                 Location/Qualifiers
REGION                  1..15
                        note = peptide linker
source                  1..15
                        mol_type = protein
                        organism = synthetic construct
SEQUENCE: 62
GGGGSGGGGS GGGGS                                                              15

SEQ ID NO: 63           moltype = AA  length = 17
FEATURE                 Location/Qualifiers
source                  1..17
                        mol_type = protein
                        organism = synthetic construct
REGION                  1..17
                        note = 1R34-EEST/EE CDRH2
SEQUENCE: 63
AISGSGGSTY YAESVKG                                                            17
```

LIVER-SPECIFIC Wnt SIGNAL ENHANCING MOLECULES AND USES THEREOF

CROSS REFERENCES TO RELATED APPLICATIONS

This application is a continuation of International Application No. PCT/US2021/059564, filed Nov. 16, 2021, which claims priority to U.S. Provisional Application No. 63/114,457, filed Nov. 16, 2020, U.S. Provisional Application No. 63/182,106, filed Apr. 30, 2021, and U.S. Provisional Application No. 63/248,157, filed Sep. 24, 2021, each of which is incorporated herein in its entirety for all purposes.

STATEMENT REGARDING SEQUENCE LISTING

The Sequence Listing XML associated with this application is provided in XML file format and is hereby incorporated by reference into the specification. The name of the XML file containing the Sequence Listing XML is SRZN_019_03US_ST26.xml. The XML file is 88,713 bytes, and created on Oct. 3, 2024, and is being submitted electronically via USPTO Patent Center.

FIELD OF THE INVENTION

The present disclosure relates to liver-specific Wnt signal enhancing molecules, e.g., fusion proteins, comprising a domain that binds an E3 ubiquitin ligase, ZNRF3 or RNF43, and a liver-specific cell surface receptor binding domain, as well as related methods of using the liver-specific Wnt signal enhancing molecules to mediate liver-specific internalization or sequestration of the E3 ligases, ZNRF3/RNF43, thus stabilizing Wnt receptors and enhancing Wnt signaling in a liver-specific manner, and to treat and prevent a variety of diseases and disorders.

BACKGROUND OF THE INVENTION

Wnt ("Wingless-related integration site" or "Wingless and Int-1" or "Wingless-Int") ligands and their signals play key roles in the control of development, homeostasis and regeneration of many essential organs and tissues, including bone, liver, skin, stomach, intestine, kidney, central nervous system, mammary gland, oral mucosa, taste bud, ovary, cochlea and many other tissues (reviewed, e.g., by Clevers, Loh, and Nusse, 2014; 346:1248012). Modulation of Wnt signaling pathways has potential for treatment of degenerative diseases and tissue injuries. To achieve this goal, it is desirous to develop strategies to modulate Wnt signaling activity in a liver-specific or cell type-specific manner to avoid unwanted effects. One of the challenges for modulating Wnt signaling as a therapeutic is the existence of multiple Wnt ligands and Wnt receptors, Frizzled 1-10 (Fzd1-10), with many tissues expressing multiple and overlapping Fzds. Canonical Wnt signals also involve Low-density lipoprotein (LDL) receptor-related protein 5 (LRP5) or Low-density lipoprotein (LDL) receptor-related protein 6 (LRP6) as co-receptors, which are broadly expressed in various tissues, in addition to Fzds.

R-spondins 1-4 are a family of ligands that amplify Wnt signals. Each of the R-spondins work through a receptor complex that contains Zinc and Ring Finger 3 (ZNRF3) or Ring Finger Protein 43 (RNF43) on one end and a Leucine-rich repeat-containing G-protein coupled receptor 4-6 (LGR4-6) on the other (reviewed, e.g., by Knight and Hankenson 2014, Matrix Biology; 37: 157-161). R-spondins might also work through additional mechanisms of action. ZNRF3 and RNF43 are two membrane-bound E3 ligases specifically targeting Wnt receptors (Fzd1-10 and LRP5 or LRP6) for degradation. Binding of an R-spondin to ZNRF3/RNF43 and LGR4-6 causes clearance or sequestration of the ternary complex, which removes E3 ligases from Wnt receptors and stabilizes Wnt receptors, resulting in enhanced Wnt signals. Each R-spondin contains two Furin domains (1 and 2), with Furin domain 1 binding to ZNRF3/RNF43, and Furin domain 2 binding to LGR4-6. Fragments of R-spondins containing Furin domains 1 and 2 are sufficient for amplifying Wnt signaling. While R-spondin effects depend on Wnt signals, since both LGR4-6 and ZNRF3/RNF43 are widely expressed in various tissues, the effects of R-spondins are not tissue-specific.

There is clearly a need in the art for liver-specific Wnt signal enhancing molecules for the treatment and prevention of specific diseases and disorders. The present invention addresses this need by providing compositions and methods useful for enhancing Wnt activity in a liver-specific manner.

SUMMARY OF THE INVENTION

The present invention relates to liver-specific Wnt signal enhancing molecules and uses thereof, e.g., in increasing Wnt signaling in a target tissue and treating disease and conditions that would benefit from increased Wnt signaling. In particular embodiments, the tissue is liver.

In one embodiment, the present invention provides a liver-specific Wnt signal enhancing molecule, or a pharmaceutically acceptable salt thereof, comprising a first domain that specifically binds one or more transmembrane E3 ubiquitin ligases selected from ZNRF3 and RNF43, and a second domain that specifically binds a liver-specific cell surface molecule, wherein the molecule increases Wnt signaling in the tissue. In certain embodiments, the second domain specifically binds a liver-specific cell surface molecule and increases Wnt signaling in the liver or liver cells. In various embodiments, either or both of the first domain and the second domain are polypeptides, antibodies, small molecules, natural ligands, non-natural ligands, or variants thereof.

In particular embodiments of Wnt signal enhancing molecules, the first domain comprises a first polypeptide sequence and/or the second domain comprises a second polypeptide sequence. In particular embodiments, the molecule comprises a fusion protein comprising the first polypeptide sequence and the second polypeptide sequence.

In certain embodiments, the first polypeptide sequence comprises an R-Spondin sequence or a fragment or variant thereof. In particular embodiments, the R-spondin is an R-spondin-1, an R-spondin-2, an R-spondin-3, or an R-spondin-4, e.g., a human R-spondin-1-4. In certain embodiments, the first polypeptide sequence comprises an R-spondin Furin domain 1 or a fragment or variant thereof. In particular embodiments, the first polypeptide sequence is a wild-type R-spondin-derived sequence or a modified sequence. In addition, the first polypeptide sequence could have increased, similar, or reduced binding to LGR4-6 as compared to the corresponding native full length R-spondin. In some embodiments, the the R-spondin or the R-spondin Furin domain 1 has at least 50%, at least 60%, at least 70%, at least 80%, at least 90%, or at least 95% identity to any of the R-spondins or R-spondin Furin 1 domains present in SEQ ID NOs:29-32 or 47-50. In certain embodiments, the first polypeptide is an antibody or antigen-binding fragment thereof that specifically binds ZNRF3 and/or RNF43. In particular embodiments, the first polypeptide is an antibody or an antigen-binding fragment thereof, comprising: a) CDRH1, CDRH2 and CDRH3 sequences set forth herein; and/or b) CDRL1, CDRL2 and CDRL3 sequences set forth herein, or a variant of said antibody, or antigen-binding fragment thereof, comprising one or more amino acid modifications, wherein said variant comprises less than 8 amino acid substitutions in said CDR sequences. In particular embodiments, the first polypeptide is an antibody or an antigen-binding fragment thereof, comprising a nanobody, VH or VL sequence set forth herein, or a fragment or variant thereof.

In certain embodiments, the second polypeptide sequence is a polypeptide, an antibody or fragment or variant thereof, or a ligand or fragment or variant thereof. In certain embodiments, the second polypeptide is an antibody or antigen-binding fragment thereof that specifically binds ASGR1 and/or ASGR2. In particular embodiments, the second polypeptide is an antibody or an antigen-binding fragment thereof, comprising: a) CDRH1, CDRH2 and CDRH3 sequences set forth herein; and/or b) CDRL1, CDRL2 and CDRL3 sequences set forth herein, or a variant of said antibody, or antigen-binding fragment thereof, comprising one or more amino acid modifications, wherein said variant comprises less than 8 amino acid substitutions in said CDR sequences. In particular embodiments, the first polypeptide is an antibody or an antigen-binding fragment thereof, comprising a nanobody, VH or VL sequence set forth herein, or a fragment or variant thereof.

In certain illustrative embodiments of the liver-specific Wnt signal enhancing molecules disclosed herein: the tissue is liver tissue, and the cell surface receptor is asialoglycoprotein receptor 1 (ASGR1), asialoglycoprotein receptor 2 (ASGR2), transferrin receptor 2 (TFR2) or solute carrier family 10 member 1 (SLC10A1).

In particular embodiments of the liver-specific Wnt signal enhancing molecules described herein, the first domain and the second domain are joined by a linker moiety. In certain embodiments, the linker moiety is a peptidyl linker sequence. In particular embodiments, the peptidyl linker sequence comprises one or more amino acids selected from the group consisting of: Glycine, Asparagine, Serine, Threonine and Alanine.

In particular embodiments, the liver-specific Wnt signal enhancing molecules described herein consist of a single polypeptide, e.g., a fusion protein comprising the first domain and the second domain. In certain embodiments, the liver-specific Wnt signal enhancing molecules described herein comprise two or more polypeptides, such as dimers or multimers comprising two or more fusion proteins, each comprising the first domain and the second domain, wherein the two or more polypeptides are linked, e.g., through a linker moiety or via a bond between amino acid residues in each of the two or more polypeptides, e.g., an intermolecular disulfide bond between cysteine residues. In particular embodiments, the liver-specific Wnt signal enhancing molecules described herein comprise two or more polypeptide sequences. For example, a liver-specific Wnt signal enhancing molecule may comprise antibody heavy and light chains (or antigen-binding fragments thereof) that constitute either the first domain or the second domain, wherein the other domain (i.e., the second domain or first domain) is linked to the antibody heavy chain or light chain, either as a fusion protein (e.g., directly or via a peptide linker) or via a linker moiety. In particular embodiments, the other domain is linked to the N-terminus of the heavy chain, the C-terminus of the heavy chain, the N-terminus of the light chain, or the C-terminus of the light chain. Such structures may be referred to herein as appended IgG scaffolds or formats.

In related embodiments, the disclosure provides a liver-specific Wnt ("Wingless-related integration site" or "Wingless and Int-1" or "Wingless-Int") signal enhancing molecule, or a pharmaceutically acceptable salt thereof, comprising a first domain that specifically binds one or more transmembrane E3 ubiquitin ligases selected from Zinc and Ring Finger 3 (ZNRF3) and Ring Finger Protein 43 (RNF43), and a second domain that specifically binds asialoglycoprotein receptor 1 (ASGR1), wherein: (a) the first domain comprises a modified R-spondin polypeptide, or a fragment or variant thereof; and (b) the second domain comprises a modified antibody, or antigen-binding fragment thereof, comprising: CDRH1, CDRH2 and CDRH3 sequences; and CDRL1, CDRL2 and CDRL3 sequences. In certain embodiments, the R-spondin polypeptide, or fragment or variant thereof, comprises a Furin domain 1 sequence and, optionally, a wild-type or mutated Furin domain 2 sequence, or a fragment or variant thereof, wherein the R-spondin polypeptide or fragment or variant thereof has reduced binding to Leucine-rich repeat-containing G-protein coupled receptors 4-6 (LGR4-6) as compared to a full length, wild-type R-spondin polypeptide. In certain embodiments, the R-spondin polypeptide or fragment or variant thereof comprises amino acid substitutions at positions corresponding to amino acids 105 and 109 of human R-spondin 2. In certain embodiments, the amino acid substitutions are: (a) F105R, F105A, or F105E; and (b) F109A or F109E. In particular embodiments, the two amino acid substitutions are: (a) F105R and F109A; (b) F105A and F109A; (c) F105E and F109A; or (d) F105E and F109E. In particular embodiments, the combination of the CDRH1, CDRH2, CDRH3, CDRL1, CDRL2, and CDRL3 sequences are selected from the following: (a) SYAMS (SEQ ID NO:34), AISGSGGSTYYEDSVKG (SEQ ID NO: 35), DFSSRRWYLEY (SEQ ID NO: 36), QGESLRSYYAS (SEQ ID NO: 37), YGKSNRPS (SEQ ID NO: 38), and CTSLERIGYLSYV (SEQ ID NO: 39), respectively; (b) SYAMS (SEQ ID NO: 34), AISGSGGSTYYEDSVKG (SEQ ID NO: 35), DFSSRRWYLEY (SEQ ID NO: 36), QGESLRSYYAS (SEQ ID NO: 37), YGKANRPS (SEQ ID NO: 40), and CTSLERIGYLSYV (SEQ ID NO: 39), respectively; or (c) RISENIYSNLA (SEQ ID NO: 41), AAINLAE (SEQ ID NO:42), QHFWGTPFT (SEQ ID NO: 43), AYGIN (SEQ ID NO: 44), EIFPRSDSTFYNEKFKG (SEQ ID NO:45), and KGREYGTSHYFDY (SEQ ID NO:46), respectively. In certain embodiments, the second domain comprises an antibody light chain polypeptide and an antibody heavy chain polypeptide, and wherein the first domain is fused to the N-terminus of the antibody heavy chain polypeptide, optionally via a linker moiety. In particular embodiments, the linker moiety is a peptidyl linker sequence. In certain embodiments, the linker sequence comprises one or more amino acids selected from the group consisting of: Glycine, Asparagine, Serine, Threonine and Alanine. In certain embodiments, the Wnt signal enhancing molecule comprises two antibody light chain polypeptides and two fusion polypeptides, wherein each fusion polypeptide comprises the modified R-spondin polypeptide or fragment or variant thereof fused to the N-terminus of the antibody heavy chain polypeptide via a linker moiety, optionally a peptidyl linker sequence, wherein the two fusion polypeptides are linked to each other, and the two antibody light chain polypeptides are each linked to different heavy chain polypeptides of the the fusion polypeptides. In particular embodiments, the molecule comprises: (i) the two antibody light chain polypeptides comprise a variable region sequence having at least 95% identity to the variable region sequence in any one of SEQ ID NOs: 1, 3, 5, 7, 9, 11, 14, 17, 18, 19, 21, 23, 25, or 27, or a variable region thereof; and/or (ii) the two antibody heavy chain polypeptides comprise a variable region sequence having at least 95% identity to the variable region sequence in any one of SEQ ID NOs: 2, 4, 6, 8, 10, 12, 13, 15, 16, 20, 22, 24, 26, 28, 33, or 51, or a variable region thereof. In certain embodiments, the two fusion polypeptides each comprise a sequence having at least 95% identity to any one of SEQ ID NOs: 2, 4, 6, 8, 10, 12, 13, 14, 15, 16, 20, 22, 24, 26, 28, 33, or 51, or a variable region thereof. In certain embodiments, the two antibody light chain polypeptides comprise a sequence having at least 95% identity to SEQ ID NO:7, or a variable region thereof, and the two fusion polypeptides each comprise a sequence having at least 95% identity to SEQ ID NO:8, or a variable region thereof. In certain embodiments, the two antibody light chain polypeptides comprise a sequence having at least 95% identity to SEQ ID NO:25, or a variable region thereof, and the two fusion polypeptides each comprise a sequence having at least 95% identity to SEQ ID NO:26, or a variable region thereof.

In another related embodiment, the disclosure provides a polypeptide comprising a sequence having at least 95% identity to any one of SEQ ID NOs:1-28, 33, or 51, or a variable region thereof, optionally wherein the polypeptide comprises one of the following sets of CDRs: (a) SYAMS (SEQ ID NO: 34), AISGSGGSTYYEDSVKG (SEQ ID NO: 35), and DFSSRRWYLEY (SEQ ID NO: 36); (b) QGESLRSYYAS (SEQ ID NO:37), YGKSNRPS (SEQ ID NO: 38), and CTSLERIGYLSYV (SEQ ID NO: 39); (c) QGESLRSYYAS (SEQ ID NO: 37), YGKANRPS (SEQ ID NO: 40), and CTSLERIGYLSYV (SEQ ID NO: 39); (d) RISENIYSNLA (SEQ ID NO: 41), AAINLAE (SEQ ID NO: 42), and QHFWGTPFT (SEQ ID NO: 43); or (e) AYGIN (SEQ ID NO: 44), EIFPRSDSTFYNEKFKG (SEQ ID NO: 45), and KGREYGTSHYFDY (SEQ ID NO: 46). In certain embodiments, the polypeptide is a fusion protein comprising a modified R-spondin polypeptide or fragment or variant thereof fused to the N-terminus of an antibody heavy chain polypeptide via a linker moiety, optionally a peptidyl linker sequence, wherein the R-spondin polypeptide or fragment or variant thereof comprises two amino acid substitutions at positions corresponding to amino acids 105 and 109 of human R-spondin 2. In certain embodiments, the two amino acid substitutions are: (a) F105R, F105A, or F105E; and (b) F109A or F109E. In certain embodiments, the two amino acid substitutions are: (a) F105R and F109A; (b) F105A and F109A; (c) F105E and F109A; or (d) F105E and F109E. In certain embodiments, the antibody heavy chain polypeptide comprises a combination of CDRH1, CDRH2, and CDRH3 sequences selected from the following: (a) SYAMS (SEQ ID NO: 34), AISGSGGSTYYEDSVKG (SEQ ID NO: 35), DFSSRRWYLEY (SEQ ID NO: 36), respectively; or (b) RISENIYSNLA (SEQ ID NO: 41), AAINLAE (SEQ ID NO: 42), QHFWGTPFT (SEQ ID NO: 43), respectively. In particular embodiments, the polypeptide comprises a modified antibody light chain polypeptide. In certain embodiments, the modified antibody light chain polypeptide comprises a combination of CDRL1, CDRL2, and CDRL3 sequences selected from the following: (a) QGESLRSYYAS (SEQ ID NO: 37), YGKSNRPS (SEQ ID NO: 38), and CTSLERIGYLSYV (SEQ ID NO: 39), respectively; (b) QGESLRSYYAS (SEQ ID NO: 37), YGKANRPS (SEQ ID NO: 40), and CTSLERIGYLSYV (SEQ ID NO: 39), respectively; or (c) AYGIN (SEQ ID NO: 44), EIFPRSDSTFYNEKFKG (SEQ ID NO: 45), and KGREYGTSHYFDY (SEQ ID NO: 46), respectively.

In another related embodiment, the disclosure provides a nucleic acid sequence encoding any of the polypeptides disclosed herein, such as an antibody light chain polypeptide or fusion polypeptide disclosed herein, or a polypeptide having at least 95% identity to any one of SEQ ID NOs:1-33 or 51, or a variable region thereof. In particular embodiments, the nucleic acid sequence is DNA or mRNA.

In another embodiment, the disclosure provides a vector comprising a nucleic acid sequence disclosed herein. In certain embodiments, the vector is an expression vector comprising a promoter sequence operatively linked to the nucleic acid sequence. In certain embodiments, the vector is a virus comprising a promoter sequence operatively linked to the nucleic acid sequence.

In a related embodiment, the disclosure provides a host cell comprising the vector disclosed herein. In a further related embodiment, the disclosure provides a process for producing an antibody light chain polypeptide or fusion polypeptide disclosed herein, comprising culturing the host cell under conditions wherein the polypeptide is expressed by the expression vector. In certain embodiments, the method comprises the step of isolating the fusion polypeptide produced.

In a related embodiment, the disclosure provides a pharmaceutical composition comprising: a) a molecule disclosed herein, a nucleic acid sequence disclosed herein, the vector disclosed herein, or a host cell disclosed herein; and b) a pharmaceutically acceptable diluent, adjuvant or carrier.

In another embodiment, the present invention provides a pharmaceutical composition comprising a liver-specific Wnt signal enhancing molecule described herein, or a pharmaceutically acceptable salt thereof, and a pharmaceutically acceptable diluent, adjuvant or carrier.

In another embodiment, the present invention provides a pharmaceutical composition comprising a polynucleotide comprising a nucleic acid sequence encoding a liver-specific Wnt signal enhancing molecule described herein, or a pharmaceutically acceptable salt thereof, and a pharmaceutically acceptable diluent, adjuvant or carrier. In particular embodiments, the nucleic acid sequence comprises DNA or mRNA, optionally a modified mRNA.

In another embodiment, the present invention provides a pharmaceutical composition comprising a vector comprising a nucleic acid sequence encoding a liver-specific Wnt signal enhancing molecule, or a pharmaceutically acceptable salt thereof, and a pharmaceutically acceptable diluent, adjuvant or carrier. In particular embodiments, the vector comprises a promoter operatively linked to the nucleic acid sequence, which drives expression of the liver-specific Wnt signal enhancing molecule. In certain embodiments, the vector is an expression vector or a viral vector.

In another embodiment, the disclosure provides a method for increasing Wnt ("Wingless-related integration site" or "Wingless and Int-1" or "Wingless-Int") signaling in a liver tissue, comprising contacting the liver tissue with: a) the Wnt signal enhancing molecule disclosed herein; b) a nucleic acid disclosed herein; c) a vector disclosed herein; d) a host cell disclosed herein; or e) a pharmaceutical composition disclosed herein, wherein the molecule binds the liver tissue and sequesters or increases endocytosis of one or more transmembrane E3 ubiquitin ligase selected from Zinc and Ring Finger 3 (ZNRF3) and Ring Finger Protein 43 (RNF43) in the liver tissue.

In a related embodiment, the disclosure provides a method for treating or preventing a liver disease or liver disorder in a subject in need thereof, wherein the liver disease or liver disorder is associated with reduced Wnt ("Wingless-related integration site" or "Wingless and Int-1" or "Wingless-Int") signaling or would benefit from increased Wnt signaling, comprising administering to the subject an effective amount of: a) a molecule disclosed herein; b) a nucleic acid disclosed herein; c) a vector disclosed herein; d) a host cell disclosed herein; or e) the pharmaceutical composition disclosed. In particular embodiments, the liver disease or liver disorder is selected from the group consisting of: acute liver failure of all causes, acute liver failure drug-induced, acute on chronic liver failure (ACLF), acute decompensation of the liver, ascites due to cirrhosis, hyponatremia in patients with cirrhosis, hepatorenal syndrome-acute kidney injury (HRS-AKI), hepatic encephalopathy, alcoholic liver diseases, chronic liver failure of all causes, decompensated liver failure, late stage compensated liver failure, cirrhosis, liver fibrosis of all causes, portal hypertension, chronic liver insufficiency of all causes, end stage liver disease (ESLD), nonalcoholic steatohepatitis (NASH), nonalcoholic fatty liver disease (NAFLD) (fatty liver), alcoholic hepatitis, acute alcoholic hepatitis (AAH) or severe alcoholic hepatitis, chronic alcoholic hepatitis, alcoholic liver disease (ALD) (also called alcohol-related liver disease (ARLD)), hepatitis C virus-induced liver diseases (HCV), hepatitis B virus-induced liver diseases (HBV), other viral hepatitis (e.g., hepatitis A virus-induced liver diseases (HAV) and hepatitis D virus-induced liver diseases (HDV)), primary biliary cirrhosis, autoimmune hepatitis, livery surgery, liver injury, veno-occlusive disease (VOD), sinusoidal obstructive syndrome (SOS), primary biliary cholangitis (PBC), primary sclerosing cholangitis (PSC), liver transplantation, "small for size" syndrome in liver surgery and transplantation, congenital liver disease and disorders, liver failure due to APAP (acetominophen) overdose, acetaminophen-induced liver injury, and any other liver disease or disorder resulting from genetic diseases, degeneration, aging, drugs, or injuries.

In certain embodiments, the liver disease or liver disorder is selected from acute alcoholic hepatitis, acute liver failure (including but not limited to acute liver failure (ALF) due to acetaminophen (APAP) overdose), acute on chronic liver failure (ACLF), acute decompensation of the liver, ascites due to cirrhosis, hyponatremia in patients with cirrhosis, hepatorenal syndrome-acute kidney injury (HRS-AKI), hepatic encephalopathy, or liver cirrhosis. In certain embodiments, the liver disease is alcoholic hepatitis, e.g., acute alcoholic hepatitis or severe alcoholic hepatitis. In particular embodiments, the molecule, nucleic acid, vector, host cell, or pharmaceutical composition is administered parenterally, orally, intramuscularly, or locally to the liver. In particular embodiments, the subject is a mammal, optionally a human.

In a related embodiment, the disclosure provides a method of generating, culturing, or maintaining liver cells, liver tissue, or a liver organoid, comprising contact the cells, tissue, or organoid with: a) a molecule disclosed herein; b) a nucleic acid disclosed herein; c) a vector disclosed herein; d) a host cell disclosed herein; or e) a pharmaceutical composition disclosed herein. In some embodiments, the method is for maintaining viability of liver tissue ex vivo, comprising contacting liver tissue obtained from a donor, optionally by perfusing the liver tissue ex vivo with a composition comprising the molecule. In some embodiments, the method is for maintaining viability of liver tissue, comprising contacting donor liver tissue in vivo with a composition comprising the molecule. In some embodiments, the method is for generating or maintaining a liver organoid culture, comprising contacting the liver organoid culture, optionally by culturing the liver organoid culture in a medium comprising the molecule.

In a further embodiment, the present invention includes a method for increasing Wnt signaling in a target tissue, comprising contacting the target tissue with a liver-specific Wnt signal enhancing molecule described herein, wherein the second domain specifically binds a cell-specific surface molecule on the target tissue, and wherein the liver-specific Wnt signal enhancing molecule binds the target tissue and sequesters or increases endocytosis of one or more transmembrane E3 ubiquitin ligase selected from ZNRF3 and RNF43 in the target tissue.

In particular embodiments, the target tissue or cell is contacted with a polynucleotide comprising a nucleic acid sequence encoding the liver-specific Wnt signal enhancing molecule, or a vector comprising a nucleic acid sequence encoding the liver-specific Wnt signal enhancing molecule, e.g., an expression vector or viral vector.

In yet another related embodiment, the present invention includes a method for treating or preventing a disease or condition in a subject in need thereof, wherein the disease or condition is associated with reduced Wnt signaling or would benefit from increased Wnt signaling, comprising providing to the subject an effective amount of a pharmaceutical composition comprising the liver-specific Wnt signal enhancing molecule, or a pharmaceutically acceptable salt thereof, either alone or in combination with a Wnt, Norrin, or a Wnt activating/mimetic molecule. In particular embodiments, the method is performed using a pharmaceutical composition comprising a polynucleotide comprising a nucleic acid sequence encoding the liver-specific Wnt signal enhancing molecule (e.g., a DNA or mRNA), or a vector comprising a nucleic acid sequence encoding the liver-specific Wnt signal enhancing molecule (e.g., an expression vector or viral vector).

In particular embodiments of any of the methods of treatment described herein, the disease or disorder is a liver disease or disorder of a tissue selected from the group consisting of: acute liver failure of all causes, acute liver failure drug-induced, acute on chronic liver failure (ACLF), acute decompensation of the liver, ascites due to cirrhosis, hyponatremia in patients with cirrhosis, hepatorenal syndrome-acute kidney injury (HRS-AKI), hepatic encephalopathy, alcoholic liver diseases, chronic liver failure of all causes, decompensated liver failure, late stage compensated liver failure, cirrhosis, liver fibrosis of all causes, portal hypertension, chronic liver insufficiency of all causes, end stage liver disease (ESLD), nonalcoholic steatohepatitis (NASH), nonalcoholic fatty liver disease (NAFLD) (fatty liver), alcoholic hepatitis, acute alcoholic hepatitis (AAH), chronic alcoholic hepatitis, alcoholic liver disease (ALD) (also called alcohol-related liver disease (ARLD), hepatitis C virus-induced liver diseases (HCV), hepatitis B virus-induced liver diseases (HBV), other viral hepatitis (e.g., hepatitis A virus-induced liver diseases (HAV) and hepatitis D virus-induced liver diseases (HDV)), primary biliary cirrhosis, autoimmune hepatitis, livery surgery, liver injury, veno-occlusive disease (VOD), sinusoidal obstructive syndrome (SOS), primary biliary cholangitis (PBC), primary sclerosing cholangitis (PSC), liver transplantation, "small for size" syndrome in liver surgery and transplantation, congenital liver disease and disorders, liver failure due to APAP (acetominophen) overdose, and any other liver disease or disorder resulting from genetic diseases, degeneration, aging, drugs, or injuries. In certain embodiments, the liver disease is alcoholic hepatitis, e.g., acute alcoholic hepatitis or severe alcoholic hepatitis. In particular embodiments of any of the methods of treatment or prevention described herein, the pharmaceutical composition is provided systemically, parenterally, orally, intramuscularly, locally, or topically. In particular embodiments, the subject is a mammal, optionally a human.

In particular embodiments, the antibody or antigen-binding fragment thereof comprises a heavy chain variable region or light chain variable region, or a heavy chain or light chain, comprising an amino acid sequence having at least 90% identity to an amino acid sequence disclosed herein, e.g., SEQ ID NOs: 1-28, 33, or 51, or a fragment or variant thereof, e.g., a variable domain of the sequence.

BRIEF DESCRIPTION OF THE DRAWINGS

Features of the disclosure are set forth with particularity in the appended claims. A better understanding of the features and advantages of the present invention will be obtained by reference to the following detailed description that sets forth illustrative embodiments, in which the principles of the invention are utilized, and the accompanying drawings.

FIG. 1 shows the light chain variable domain sequence and the fusion polypeptide heavy chain variable domain-RSPO2 sequence for an initial αASGR1-RSPO2 Wnt signaling enhancer molecule. CDRs are underlined, and deamidation or isomerization risks are in bold. Various amino acid replacements made to remove the risks are shown for each position.

FIG. 2 provides SEC profile graphs of variants of the initial (ASGR1-RSPO2 Wnt signaling enhancer molecule with various amino acid substitutions at the D62 position in CDR H2.

FIG. 3 provides SEC profile graphs of variants of the initial (αASGR1-RSPO2 Wnt signaling enhancer molecule with various amino acid substitutions at the D25 position in CDR L1.

FIG. 4 provides SEC profile graphs of variants of the initial αASGR1-RSPO2 Wnt signaling enhancer molecule with various amino acid substitutions at the N51 position in CDR L2

FIG. 5 provides SEC profile graphs of variants of the initial αASGR1-RSPO2 Wnt signaling enhancer molecule with various amino acid substitutions at the N88 position in CDR L3.

FIG. 8 is a table summarizing the results of the indicated assays for Wnt signaling enhancer molecules comprising the indicated combinations of point mutations as compared to the initial αASGR1-RSPO2 Wnt signaling enhancer molecule (wild type).

FIG. 9 is a table summarizing ASGR1 binding assay results for Wnt signaling enhancer molecules comprising the indicated combinations of point mutations as compared to the initial αASGR1-RSPO2 Wnt signaling enhancer molecule (wild type).

FIG. 15 provides the pharmacokinetic profile of the EEST-EE Wnt signal enhancing molecule in mice following administration either IV at 3, 10, 30, 100 mg/kg or i.p. at 10 or 30 mg/kg.

FIG. 19 shows INR (left), Axin2 (middle), and CYP2e1 mRNA (right) following administration of the indicated amounts of the Wnt signal enhancing molecules, EEST-EE or EEST-RA.

FIG. 25 provides the sequences of the variable domains of the 8M24 antibody heavy and light chains, and of various humanized versions thereof.

FIG. 26A provides the sequence of the VH and VL domains of the 8M24 antibody. CDRs are underlines, and amino acids that were modified are shown in bold.

FIG. 26B shows the various amino acid substitutions made at each indicated position within the 8M24 CDRs.

FIG. 28 is a table summarizing the characteristics of various 8M24 Wnt signaling enhancer molecules comprising the indicated combination of point mutations.

FIG. 38 shows an alignment of all four human R-spondin proteins (Rspo1 (SEQ ID NO:47); Rspo2 (SEQ ID NC:48); Rspo3 (SEQ ID NO:49); and Rspo4 (SEQ ID NO:50), with the Furin domain 1 (Fu1) and 2 (Fu2) shaded in light and dark shading, respectively. The Fu1 domain generally corresponds to: about amino acid residues 38-94 of SEQ ID NO:47; about amino acid residues 37-93 of SEQ ID NO:48; about amino acid residues 39-95 of SEQ ID NO:49; and about amino acid residues 32-88 of SEQ ID NO:50. The Fu2 domain generally corresponds to: about amino acid residues 97-144 of SEQ ID NO:47; about amino acid residues 96-143 of SEQ ID NO:48; about amino acid residues 98-144 of SEQ ID NO:49; and about amino acid residues 91-137 of SEQ ID NO:50.

FIGS. 39A-C show binding of various Wnt signal enhancing molecules comprising the indicated combinations of point mutations as compared to the initial αASGR1-RSPO2 Wnt signaling enhancer molecule (NG or "wild type"). FIG. 39A is a table showing kinetic fir parameters from the data in FIGS. 39B and 39C. Data was fit using the bivalent analyte model in the ForteBIO Data Analysis Software. FIGS. 39B-39C provide data from serial dilutions of the various Wnt signal enhancing molecules tested for binding using biotinylated ASGR1 captured on streptavidin sensors using the Octet Red96e.

DETAILED DESCRIPTION OF THE INVENTION

Figure 6:
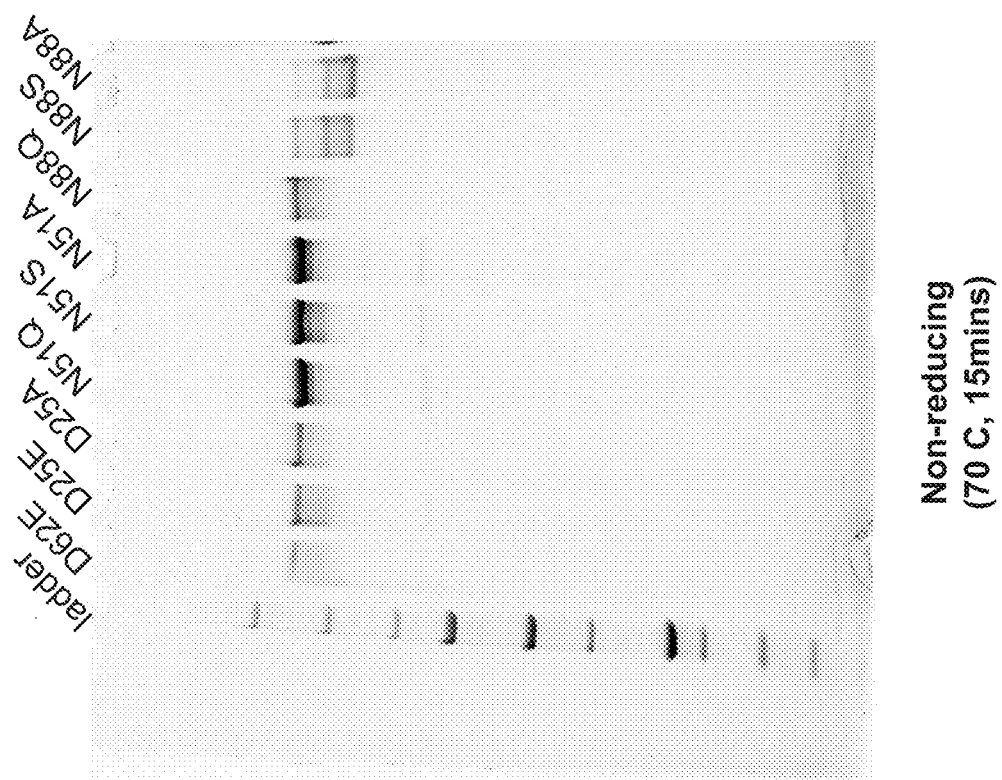
FIG. 6 shows SDS-PAGE gel analysis of expression and folding of Wnt signaling enhancer molecules comprising the indicated point mutations as compared to the initial αASGR1-RSPO2 Wnt signaling enhancer molecule, under non-reducing (left panel) or reducing (right panel) conditions.

The present disclosure provides liver-specific Wnt signal enhancing molecules, where in certain embodiments, the molecules: 1) selectively bind to a liver-specific cell surface receptor; 2) mediate internalization or sequestration of ZNRF3/RNF43 in the targeted liver tissue or cells; and/or 3) enhance Wnt signaling in a liver-specific manner. In certain embodiments, the molecules are fusion proteins. In certain embodiments, the molecules are antibodies having an additional appended binding domain. Also provided are pharmaceutical compositions and methods for the use of any of the molecules and compositions disclosed herein for enhancing, i.e., increasing, Wnt signaling in liver tissue or liver cells, e.g., for the treatment or prophylaxis of a liver disease or disorder. These and other objects, advantages, and features of the invention will become apparent to those persons skilled in the art upon reading the details of the compositions and methods as more fully described below.

Definitions

A "vector" as used herein refers to a macromolecule or association of macromolecules that comprises or associates with a polynucleotide and which can be used to mediate delivery of the polynucleotide to a cell. Illustrative vectors include, for example, plasmids, viral vectors, liposomes, and other gene delivery vehicles.

The term "polynucleotide" refers to a polymeric form of nucleotides of any length, including deoxyribonucleotides or ribonucleotides, or analogs thereof. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

A polynucleotide or polypeptide (sequence-of-interest) has a certain percent "sequence identity" to another polynucleotide or polypeptide (reference sequence), meaning that, when aligned, that percentage of bases or amino acids are the same when comparing the two sequences. As understood in the art, sequence identity refers to the percentage identity obtained when sequences are aligned for maximum correspondence over a comparison window (e.g., a specified region of each of the sequences), which may be calculated by any of the algorithms described herein using default parameters, which are expected to generate the same alignment, in most cases, when applied to similar sequences. Identity is calculated, unless specified otherwise, across the full length of the reference sequence. Thus, a sequence-of-interest "shares at least x % identity to" a reference sequence if, when the sequence-of-interest is aligned to the reference sequence, at least x % (rounded down) of the residues in the sequence-of-interest are aligned as an exact match to a corresponding residue in the reference sequence. Gaps may be introduced into the sequence-of-interest and/or the reference sequence to maximize correspondence over the comparison window.

Sequence similarity (i.e., identity) can be determined in a number of different manners. To determine sequence identity, sequences can be aligned using the methods and computer programs, including BLAST (e.g., BLAST and BLAST 2.0 algorithms, which are described in Altschul et al. (1990) J. Mol. Biol. 215: 403-410 and Altschul et al. (1997) Nucleic acids Res. 25: 3389-3402, respectively), publicly available through the National Center for Biotechnology Information (NCBI), e.g., over the worldwide web at ncbi.nlm.nih.gov/BLAST/, such as BLASTP or BLASTN. For example, sequence identity may be determined by using the stand-alone executable BLAST engine program for blasting two sequences (bl2seq), which can be retrieved from the NCBI ftp site, using the default parameters (Tatusova and Madden, FEMS Microbiol Lett. 1999, 174, 247-250). Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See Meth. Mol. Biol. 70: 173-137 (1997). Also, the GAP program using the Needleman and Wunsch alignment method can be utilized to align sequences. See J. Mol. Biol. 48: 443-453 (1970). Of interest is the BestFit program using the local homology algorithm of Smith and Waterman (Advances in Applied Mathematics 2: 482-489 (1981) to determine sequence identity. The gap generation penalty will generally range from 1 to 5, usually 2 to 4 and in many embodiments will be 3 The gap extension penalty will generally range from about 0.01 to 0.20 and in many instances will be 0.10. The program has default parameters determined by the sequences inputted to be compared. The sequence identity may be determined using the default parameters determined by the program. This program is available also from Genetics Computing Group (GCG) package, from Madison, Wis., USA. Another program of interest is the FastDB algorithm. FastDB is described in Current Methods in Sequence Comparison and Analysis, Macromolecule Sequencing and Synthesis, Selected Methods and Applications, pp. 127-149, 1988, Alan R. Liss, Inc. Percent sequence identity is calculated by FastDB based upon the following parameters: Mismatch Penalty: 1.00; Gap Penalty: 1.00; Gap Size Penalty: 0.33; and Joining Penalty: 30.0. Another program of interest is CLUSTAL from uniprot.org and available at https://www.cbi.ac.uk/Tools/msa/clustalo/. Unless indicated to the contrary, sequence identity is determined using the BLAST algorithm (e.g., bl2seq) with default parameters.

"Recombinant," as applied to a polynucleotide means that the polynucleotide is the product of various combinations of cloning, restriction or ligation steps, and other procedures that result in a construct that us distinct from a polynucleotide found in nature.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter.

"Operatively linked" or "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

An "expression vector" is a vector comprising a region which encodes a gene product of interest, and is used for effecting the expression of the gene product in an intended target cell. An expression vector also comprises control elements operatively linked to the encoding region to facilitate expression of the gene product in the target. The combination of control elements and a gene or genes to which they are operably linked for expression is sometimes referred to as an "expression cassette," a large number of which are known and available in the art or can be readily constructed from components that are available in the art.

As used herein, the terms "polypeptide," "peptide," and "protein" refer to polymers of amino acids of any length. The terms also encompass an amino acid polymer that has been modified; for example, to include disulfide bond formation, glycosylation, lipidation, phosphorylation, or conjugation with a labeling component.

As used herein, the term "antibody" means an isolated or recombinant binding agent that comprises the necessary variable region sequences to specifically bind an antigenic epitope. Therefore, an antibody is any form of antibody or fragment thereof that exhibits the desired biological activity, e.g., binding the specific target antigen. Thus, it is used in the broadest sense and specifically covers monoclonal antibodies (including full-length monoclonal antibodies), polyclonal antibodies, human antibodies, humanized antibodies, chimeric antibodies, nanobodies, diabodies, multispecific antibodies (e.g., bispecific antibodies), and antibody fragments including but not limited to scFv, Fab, and $Fab_2$, so long as they exhibit the desired biological activity.

"Antibody fragments" comprise a portion of an intact antibody, for example, the antigen-binding or variable region of the intact antibody. Examples of antibody fragments include Fab, Fab', $F(ab')_2$, and Fv fragments; diabodies; linear antibodies (e.g., Zapata et al., Protein Eng. 8(10): 1057-1062 (1995)); single-chain antibody molecules (e.g., scFv); and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an $F(ab')_2$ fragment that has two antigen combining sites and is still capable of cross-linking antigen.

By "comprising," it is meant that the recited elements are required in, for example, the composition, method, kit, etc., but other elements may be included to form the, for example, composition, method, kit etc. within the scope of the claim. For example, an expression cassette "comprising" a gene encoding a therapeutic polypeptide operably linked to a promoter is an expression cassette that may include other elements in addition to the gene and promoter, e.g., polyadenylation sequence, enhancer elements, other genes, linker domains, etc.

By "consisting essentially of," it is meant a limitation of the scope of the, for example, composition, method, kit, etc., described to the specified materials or steps that do not materially affect the basic and novel characteristic(s) of the, for example, composition, method, kit, etc. For example, an expression cassette "consisting essentially of" a gene encoding a therapeutic polypeptide operably linked to a promoter and a polyadenylation sequence may include additional sequences, e.g., linker sequences, so long as they do not materially affect the transcription or translation of the gene. As another example, a variant, or mutant, polypeptide fragment "consisting essentially of" a recited sequence has the amino acid sequence of the recited sequence plus or minus about 10 amino acid residues at the boundaries of the sequence based upon the full length naïve polypeptide from which it was derived, e.g. 10, 9, 8, 7, 6, 5, 4, 3, 2 or 1 residue less than the recited bounding amino acid residue, or 1, 2, 3, 4, 5, 6, 7, 8, 9, or 10 residues more than the recited bounding amino acid residue.

By "consisting of," it is meant the exclusion from the composition, method, or kit of any element, step, or ingredient not specified in the claim. For example, a polypeptide or polypeptide domain "consisting of" a recited sequence contains only the recited sequence.

An "expression vector" as used herein encompasses a vector, e.g. plasmid, minicircle, viral vector, liposome, and the like as discussed herein or as known in the art, comprising a polynucleotide which encodes a gene product of interest, and is used for effecting the expression of a gene product in an intended target cell. An expression vector also comprises control elements operatively linked to the encoding region to facilitate expression of the gene product in the target. The combination of control elements, e.g., promoters, enhancers, UTRs, miRNA targeting sequences, etc., and a gene or genes to which they are operably linked for expression is sometimes referred to as an "expression cassette." Many such control elements are known and available in the art or can be readily constructed from components that are available in the art.

A "promoter" as used herein encompasses a DNA sequence that directs the binding of RNA polymerase and thereby promotes RNA synthesis, i.e., a minimal sequence sufficient to direct transcription. Promoters and corresponding protein or polypeptide expression may be ubiquitous, meaning strongly active in a wide range of cells, tissues and species or cell-type specific, liver-specific, or species specific. Promoters may be "constitutive," meaning continually active, or "inducible," meaning the promoter can be activated or deactivated by the presence or absence of biotic or abiotic factors. Also included in the nucleic acid constructs or vectors of the invention are enhancer sequences that may or may not be contiguous with the promoter sequence.

Enhancer sequences influence promoter-dependent gene expression and may be located in the 5' or 3' regions of the native gene.

The term "native" or "wild-type" as used herein refers to a nucleotide sequence, e.g., gene, or gene product, e.g., RNA or protein, that is present in a wild-type cell, tissue, organ or organism. The term "variant" as used herein refers to a mutant of a reference polynucleotide or polypeptide sequence, for example a native polynucleotide or polypeptide sequence, i.e., having less than 100% sequence identity with the reference polynucleotide or polypeptide sequence. Put another way, a variant comprises at least one amino acid difference (e.g., amino acid substitution, amino acid insertion, amino acid deletion) relative to a reference polynucleotide sequence, e.g., a native polynucleotide or polypeptide sequence. For example, a variant may be a polynucleotide having a sequence identity of 50% or more, 60% or more, or 70% or more with a full length native polynucleotide sequence, e.g. an identity of 75% or 80% or more, such as 85%, 90%, or 95% or more, for example, 98% or 99% identity with the full length native polynucleotide sequence. As another example, a variant may be a polypeptide having a sequence identity of 70% or more with a full length native polypeptide sequence, e.g., an identity of 75% or 80% or more, such as 85%, 90%, or 95% or more, for example, 98% or 99% identity with the full length native polypeptide sequence. Variants may also include variant fragments of a reference, e.g., native, sequence sharing a sequence identity of 70% or more with a fragment of the reference, e.g., native, sequence, e.g. an identity of 75% or 80% or more, such as 85%, 90%, or 95% or more, for example, 98% or 99% identity with the native sequence.

As used herein, the terms "biological activity" and "biologically active" refer to the activity attributed to a particular biological element in a cell. For example, the "biological activity" of an R-spondin, or fragment or variant thereof refers to the ability to enhance Wnt signals. As another example, the biological activity of a polypeptide or functional fragment or variant thereof refers to the ability of the polypeptide or functional fragment or variant thereof to carry out its native functions of, e.g., binding, enzymatic activity, etc. As a third example, the biological activity of a gene regulatory element, e.g., promoter, enhancer, Kozak sequence, and the like, refers to the ability of the regulatory element or functional fragment or variant thereof to regulate, i.e., promote, enhance, or activate the translation of, respectively, the expression of the gene to which it is operably linked.

The terms "administering" or "introducing" or "providing", as used herein, refer to delivery of a composition to a cell, to cells, tissues and/or organs of a subject, or to a subject. Such administering or introducing may take place in vivo, in vitro or ex vivo.

The terms "treatment", "treating" and the like are used herein to generally mean obtaining a desired pharmacologic and/or physiologic effect. The effect may be prophylactic in terms of completely or partially preventing a disease or symptom thereof, e.g., reducing the likelihood that the disease or symptom thereof occurs in the subject, and/or may be therapeutic in terms of a partial or complete cure for a disease and/or adverse effect attributable to the disease. "Treatment" as used herein covers any treatment of a disease in a mammal, and includes: (a) inhibiting the disease, i.e., arresting its development partially or completely; or (b) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "host," "subject," and "patient" are used interchangeably herein, and refer to a mammal, including, but not limited to, human and non-human primates, including simians and humans; mammalian sport animals (e.g., horses); mammalian farm animals (e.g., sheep, goats, etc.); mammalian pets (dogs, cats, etc.); and rodents (e.g., mice, rats, etc.).

The various compositions and methods of the invention are described below. Although particular compositions and methods are exemplified herein, it is understood that any of a number of alternative compositions and methods are applicable and suitable for use in practicing the invention. It will also be understood that an evaluation of the expression constructs and methods of the invention may be carried out using procedures standard in the art.

The practice of the present invention will employ, unless otherwise indicated, conventional techniques of cell biology, molecular biology (including recombinant techniques), microbiology, biochemistry and immunology, which are within the scope of those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991), each of which is expressly incorporated by reference herein.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5%, or up to 1% of a given value. Alternatively, particularly with respect to biological systems or processes, the term can mean within an order of magnitude, e.g., within 5-fold or within 2-fold, of a value. Where particular values are described in the application and claims, unless otherwise stated the term "about" meaning within an acceptable error range for the particular value should be assumed.

All publications mentioned herein are incorporated herein by reference to disclose and describe the methods and/or materials in connection with which the publications are cited. It is understood that the present disclosure supersedes any disclosure of an incorporated publication to the extent there is a contradiction.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Unless otherwise indicated, all terms used herein have the same meaning as they would to one skilled in the art and the practice of the present invention will employ, conventional techniques of microbiology and recombinant DNA technology, which are within the knowledge of those of skill of the art.

Sequences

The following table (Table A) is a listing of representative sequences and associated sequence identifier numbers. CDRs are underlined in plain font. For each heavy and light chain sequence, the CDRs are consecutively CDR1, CDR2, and CDR3. Linker sequences are shown in bold plain font, and RSPO2 sequences are shown in italics. Thus, heavy and light chain sequences, and variable domains thereof, can be readily determined based on the provided sequences. Heavy chain constant domains are double underlined. In particular embodiments, the sequences are a polypeptide sequence present within the indicated liver-specific Wnt signal enhancing molecule. In particular embodiments, the Wnt signal enhancing molecule comprises two of the heavy chain fusion protein sequences and two of the light chain sequences, e.g., in an antibody format, wherein the two heavy chain fusion protein sequences are bound to each other and each of the two light chain sequences are bound to a different heavy chain fusion protein sequence. In particular embodiments, the Wnt signal enhancing molecule comprises two heavy chain fusion protein sequences comprising the CDRs present within any of these sequences and two light chain sequences present within any of these sequences, e.g., in an antibody format, wherein the two heavy chain fusion protein sequences are bound to each other and each of the two light chain sequences are bound to a different heavy chain fusion protein sequence. In particular embodiments, the Wnt signal enhancing molecule comprises two heavy chain fusion protein sequences, each comprising the CDRs present within any of these sequences, and two light chain sequences, each comprising the CDRs present within any of these sequences, e.g., in an antibody format, wherein the two heavy chain fusion protein sequences are bound to each other and each of the two light chain sequences are bound to a different heavy chain fusion protein sequence. In particular embodiments, each of the two heavy chain fusion protein sequences and/or each of the two light chain sequences have at least 90%, at least 95%, at least 98% or at least 99% identify to any of the disclosed sequence, and in particular embodiments, the amino acid modifications, e.g., insertions, deletions, or substitutions, are not present within a CDR. In particular embodiments, the amino acid modifications do not occur at any of (a) F105R, F105A, or F105E; and/or (b) F109A or F109E.

TABLE A

Sequences of representative liver-specific Wnt signal enhancing molecules, 1R34-DDNN/RA, 8M24-v1, 1R34-EEST/EE, 1R34-EEST/RA, 1R34-EEAT/EE, 8M24 humanized 1, 8M24 humanized 2, 8M24-EASE-RA, 8M24-EASE-EE, 1R34-DDNN/RA, which include two of the indicated light chain sequences and two of the indicated heavy chain fusion sequences in an antibody format, e.g., a bilaterally symmetric, bispecific molecule: (a) that comprises or consists of an IgG to which 2 Rspo2 domains have been fused, wherein (i) one (1) Rspo2 domain is fused to each heavy chain of the IgG, (ii) each arm of the IgG binds a liver-specific cell surface receptor binding domain (e.g., ASGR1) and (b) where the binding of such IgG arms activates downstream signaling

| SEQ ID NO: | Description | Sequence |
|---|---|---|
| 1 | 1R34-DDNN/RA light chain (human lambda 2 light chain) | SSELTQDPAVSVALGQTVRITCQGDSLRSYYASWYQQKPG QAPVLVIYGKNNRPSGIPDRFSGSSSGNTASLTITGAQAED EADYYCNSLERIGYLSYVFGGGTKLTVLGQPKAAPSVTLF PPSSEELQANKATLVCLISDFYPGAVTVAWKADSSPVKAG VETTTPSKQSNNKYAASSYLSLTPEQWKSHRSYSCQVTHE GSTVEKTVAPTECS |
| 2 | 1R34-DDNN/RA heavy chain fused to RSPO2 (human IgG1_N297G; constant domains double underlined) | *NPICKGCLSCSKDNGCSRCQQKLFFFLRREGMRQYGECLHSC PSGYYGHRAPDMNRCARCRIENCDSCRSKDACTKCKVGFYL HRGRCFDECPDGFAPLEETMECVE*__GGGGSGSGGSGGGS__ EVQLLESGGGLVQPGGSLRLSCAASGFTFSSYAMSWVRQA PGKGLEWVSAISGSGGSTYYADSVKGRFTISRDNSKNTLY LQMNSLRAEDTAVYYCAKDFSSRRWYLEYWGQGTLVTV SSASTKGPSVFPLAPSSKSTSGGTAALGCLVKDYFPEPVTV SWNSGALTSGVHTFPAVLQSSGLYSLSSVVTVPSSSLGTQT YICNVNHKPSNTKVDKKVEPKSCDKTHTCPPCPAPELLGG PSVFLFPPKPKDTLMISRTPEVTCVVVDVSHEDPEVKENW YVDGVEVHNAKTKPREEQYGSTYRVVSVLTVLHQDWLN GKEYKCKVSNKALPAPIEKTISKAKGQPREPQVYTLPPSRE EMTKNQVSLTCLVKGFYPSDIAVEWESNGQPENNYKTTPP VLDSDGSFFLYSKLTVDKSRWQQGNVFSCSVMHEALHNH YTQKSLSLSPGK |

TABLE A-continued

Sequences of representative liver-specific Wnt signal enhancing molecules, 1R34-DDNN/RA, 8M24-v1, 1R34-EEST/EE, 1R34-EEST/RA, 1R34-EEAT/EE, 8M24 humanized 1, 8M24 humanized 2, 8M24-EASE-RA, 8M24-EASE-EE, 1R34-DDNN/RA, which include two of the indicated light chain sequences and two of the indicated heavy chain fusion sequences in an antibody format, e.g., a bilaterally symmetric, bispecific molecule: (a) that comprises or consists of an IgG to which 2 Rspo2 domains have been fused, wherein (i) one (1) Rspo2 domain is fused to each heavy chain of the IgG, (ii) each arm of the IgG binds a liver-specific cell surface receptor binding domain (e.g., ASGR1) and (b) where the binding of such IgG arms activates downstream signaling

| SEQ ID NO: | Description | Sequence |
|---|---|---|
| 3 | 8M24-v1 light chain variable domain | DIQMTQSPSSLSASVGDRVTITCRISENIYSNLAWYQQKPG KAPKLLIYAAINLADGVPSRFSGSGSGTDFTLTISSLQPEDF ATYYCQHFWGTPFTFGQGTKLEIK |
| 4 | 8M24-v1 heavy chain variable domain fused to RSPO2 | NPICKGCLSCSKDNGCSRCQQKLFFFLRREGMRQYGECLHSC PSGYYGHRAPDMNRCARCRIENCDSCRSKDACTKCKVGFYL HRGRCFDECPDGFAPLEETMECVEGGGGSGGGGSGGGGS EVQLVQSGAEVKKPGSSVKVSCKASGYTFTNYGINWVRQ APGQGLEWMGEIFPRSDNTFYAQKFQGRVTITADKSTSTA YMELSSLRSEDTAVYYCARKGRDYGTSHYFDYWGQGTT VTVSS |
| 5 | 8M24-v1 light chain | DIQMTQSPSSLSASVGDRVTITCRISENIYSNLAWYQQKPG KAPKLLIYAAINLADGVPSRFSGSGSGTDFTLTISSLQPEDF ATYYCQHFWGTPFTFGQGTKLEIKRTVAAPSVFIFPPSDEQL KSGTASVVCLLNNFYPREAKVQWKVDNALQSGNSQESVTEQDS KDSTYSLSSTLTLSKADYEKHKVYACEVTHQGLSSPVTKSFNRG EC |
| 6 | 8M24-v1 heavy chain fused to RSPO2 (constant domains double underlined) | NPICKGCLSCSKDNGCSRCQQKLFFFLRREGMRQYGECLHSC PSGYYGHRAPDMNRCARCRIENCDSCRSKDACTKCKVGFYL HRGRCFDECPDGFAPLEETMECVEGGGGSGGGGSGGGGS EVQLVQSGAEVKKPGSSVKVSCKASGYTFTNYGINWVRQ APGQGLEWMGEIFPRSDNTFYAQKFQGRVTITADKSTSTA YMELSSLRSEDTAVYYCARKGRDYGTSHYFDYWGQGTT VTVSSASTKGPSVFPLAPSSKSTSGGTAALGCLVKDYFPEP VTVSWNSGALTSGVHTFPAVLQSSGLYSLSSVVTVPSSSLG TQTYICNVNHKPSNTKVDKKVEPKSCDKTHTCPPCPAPEL LGGPSVFLFPPKPKDTLMISRTPEVTCVVVDVSHEDPEVKF NWYVDGVEVHNAKTKPREEQYGSTYRVVSVLTVLHQDW LNGKEYKCKVSNKALPAPIEKTISKAKGQPREPQVYTLPPS REEMTKNQVSLTCLVKGFYPSDIAVEWESNGQPENNYKTT PPVLDSDGSFFLYSKLTVDKSRWQQGNVFSCSVMHEALH NHYTQKSLSLSPGK |
| 7 | 1R34-EEST/EE light chain | SSELTQDPAVSVALGQTVRITCQGESLRSYYASWYQQKPG QAPVLVIYGKSNRPSGIPDRFSGSSSGNTASLTITGAQAEDE ADYYCTSLERIGYLSYVFGGGTKLTVLGQPKAAPSVTLFPP SSEELQANKATLVCLISDFYPGAVTVAWKADSSPVKAGVE TTTPSKQSNNKYAASSYLSLTPEQWKSHRSYSCQVTHEGS TVEKTVAPTECS |
| 8 | 1R34-EEST/EE heavy chain fused to RSPO2 | NPICKGCLSCSKDNGCSRCQQKLFFFLRREGMRQYGECLHSC PSGYYGHRAPDMNRCARCRIENCDSCESKDECTKCKVGFYL HRGRCFDECPDGFAPLEETMECVEGGGGSGGGGSGGGGS EVQLLESGGGLVQPGGSLRLSCAASGFTFSSYAMSWVRQA PGKGLEWVSAISGSGGSTYYAESVKGRFTISRDNSKNTLY LQMNSLRAEDTAVYYCAKDFSSRRWYLEYWGQGTLVTV SSASTKGPSVFPLAPSSKSTSGGTAALGCLVKDYFPEPVTV SWNSGALTSGVHTFPAVLQSSGLYSLSSVVTVPSSSLGTQT YICNVNHKPSNTKVDKKVEPKSCDKTHTCPPCPAPELLGG PSVFLFPPKPKDTLMISRTPEVTCVVVDVSHEDPEVKFNW YVDGVEVHNAKTKPREEQYGSTYRVVSVLTVLHQDWLN GKEYKCKVSNKALPAPIEKTISKAKGQPREPQVYTLPPSRE EMTKNQVSLTCLVKGFYPSDIAVEWESNGQPENNYKTTPP VIDSDGSFFLYSKLTVDKSRWQQGNVFSCSVMHEALHNH YTQKSLSLSPGK |
| 9 | 1R34-EEST/RA light chain | SSELTQDPAVSVALGQTVRITCQGESLRSYYASWYQQKPG QAPVLVIYGKSNRPSGIPDRFSGSSSGNTASLTITGAQAEDE ADYYCTSLERIGYLSYVFGGGTKLTVLGQPKAAPSVTLFPP SSEELQANKATLVCLISDFYPGAVTVAWKADSSPVKAGVE TTTPSKQSNNKYAASSYLSLTPEQWKSHRSYSCQVTHEGS TVEKTVAPTECS |

TABLE A-continued

Sequences of representative liver-specific Wnt signal enhancing molecules, 1R34-DDNN/RA, 8M24-v1, 1R34-EEST/EE, 1R34-EEST/RA, 1R34-EEAT/EE, 8M24 humanized 1, 8M24 humanized 2, 8M24-EASE-RA, 8M24-EASE-EE, 1R34-DDNN/RA, which include two of the indicated light chain sequences and two of the indicated heavy chain fusion sequences in an antibody format, e.g., a bilaterally symmetric, bispecific molecule: (a) that comprises or consists of an IgG to which 2 Rspo2 domains have been fused, wherein (i) one (1) Rspo2 domain is fused to each heavy chain of the IgG, (ii) each arm of the IgG binds a liver-specific cell surface receptor binding domain (e.g., ASGR1) and (b) where the binding of such IgG arms activates downstream signaling

| SEQ ID NO: | Description | Sequence |
|---|---|---|
| 10 | 1R34-EEST/RA heavy chain fused to RSPO2 | NPICKGCLSCSKDNGCSRCQQKLFFFLRREGMRQYGECLHSCPSGYYGHRAPDMNRCARCRIENCDSCRSKDACTKCKVGFYLHRGRCFDECPDGFAPLEETMECVEGGGGSGGGGSGGGGSEVQLLESGGGLVQPGGSLRLSCAASGFTFSSYAMSWVRQAPGKGLEWVSAISGSGGSTYYAESVKGRFTISRDNSKNTLYLQMNSLRAEDTAVYYCAKDFSSRRWYLEYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYGSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVESCSVMHEALHNHYTQKSLSLSPGK |
| 11 | 1R34-EEAT/EE light chain | SSELTQDPAVSVALGQTVRITCQGESLRSYYASWYQQKPGQAPVLVIYGKANRPSGIPDRFSGSSSGNTASLTITGAQAEDEADYYCTSLERIGYLSYVFGGGTKLTVLGQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |
| 12 | 1R34-EEAT/EE heavy chain fused to RSPO2 | NPICKGCLSCSKDNGCSRCQQKLFFFLRREGMRQYGECLHSCPSGYYGHRAPDMNRCARCRIENCDSCESKDECTKCKVGFYLHRGRCFDECPDGFAPLEETMECVEGGGGSGGGGSGGGGSEVQLLESGGGLVQPGGSLRLSCAASGFTFSSYAMSWVRQAPGKGLEWVSAISGSGGSTYYAESVKGRFTISRDNSKNTLYLQMNSLRAEDTAVYYCAKDFSSRRWYLEYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKENWYVDGVEVHNAKTKPREEQYGSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 13 | 8M24 antibody heavy chain variable domain | QVQLQQSGAELARPGASVKLSCKASGYTFTNYGINWVKQRTGQGLEWIGEIFPRSDNTFYNEKFKGKATLTADKSSTTAYMELRSLTSEDSAVYFCARKGRDYGTSHYFDYWGQGTTLTVSS |
| 14 | 8M24 antibody light chain variable domain | DIQMTQSPASLSVSVGETVTITCRISENIYSNLAWYQQKQGKSPHLLVYAAINLADGVPSRFSGSGSGTQFSLKINSLQSEDFGSYYCQHFWGTPFTFGSGTKLEIK |
| 15 | 8M24 antibody heavy chain variable domain (humanized 1) | EVQLVQSGAEVKKPGSSVKVSCKASGYTFTNYGINWVRQAPGQGLEWMGEIFPRSDNTFYAQKFQGRVTITADKSTSTAYMELSSLRSEDTAVYYCARKGRDYGTSHYFDYWGQGTTVTVSS |
| 16 | 8M24 antibody heavy chain variable domain (humanized 2) | EVQLVQSGAEVKKPGSSVKVSCKASGYTFTNYGINWVRQAPGQGLEWIGEIFPRSDNTFYAQKFQGRATLTADKSTSTAYMELSSLRSEDTAVYYCARKGRDYGTSHYFDYWGQGTTLTVSS |
| 17 | 8M24 antibody light chain variable domain (humanized 1) | DIQMTQSPSSLSASVGDRVTITCRISENIYSNLAWYQQKPGKAPKLLIYAAINLADGVPSRFSGSGSGTDFTLTISSLQPEDFATYYCQHFWGTPFTFGQGTKLEIK |

TABLE A-continued

Sequences of representative liver-specific Wnt signal enhancing molecules, 1R34-DDNN/RA, 8M24-v1, 1R34-EEST/EE, 1R34-EEST/RA, 1R34-EEAT/EE, 8M24 humanized 1, 8M24 humanized 2, 8M24-EASE-RA, 8M24-EASE-EE, 1R34-DDNN/RA, which include two of the indicated light chain sequences and two of the indicated heavy chain fusion sequences in an antibody format, e.g., a bilaterally symmetric, bispecific molecule: (a) that comprises or consists of an IgG to which 2 Rspo2 domains have been fused, wherein (i) one (1) Rspo2 domain is fused to each heavy chain of the IgG, (ii) each arm of the IgG binds a liver-specific cell surface receptor binding domain (e.g., ASGR1) and (b) where the binding of such IgG arms activates downstream signaling

| SEQ ID NO: | Description | Sequence |
| --- | --- | --- |
| 18 | 8M24 antibody light chain variable domain (humanized 2) | DIQMTQSPSSLSASVGDRVTITCRISENIYSNLAWYQQKPG KAPKLLVYAAINLADGVPSRFSGSGSGTDFTLTISSLQPEDF GTYYCQHFWGTPFTFGQGTKLEIK |
| 19 | 8M24-EASE-RA light chain variable domain | DIQMTQSPSSLSASVGDRVTITCRISENIYSNLAWYQQKPG KAPKLLIYAAINLAEGVPSRFSGSGSGTDFTLTISSLQPEDF ATYYCQHFWGTPFTFGQGTKLEIK |
| 20 | 8M24-EASE-RA heavy chain variable domain fused to RSPO2 | NPICKGCLSCSKDNGCSRCQQKLFFFLRREGMRQYGECLHSC PSGYYGHRAPDMNRCARCRIENCDSCRSKDACTKCKVGFYL HRGRCFDECPDGFAPLEETMECVEGGGGSGGGGSGGGGS EVQLVQSGAEVKKPGSSVKVSCKASGYTFTAYGINWVRQ APGQGLEWMGEIFPRSDSTFYAQKFQGRVTITADKSTSTA YMELSSLRSEDTAVYYCARKGREYGTSHYFDYWGQGTTV TVSS |
| 21 | 8M24-EASE-EE light chain | DIQMTQSPSSLSASVGDRVTITCRISENIYSNLAWYQQKPG KAPKLLIYAAINLAEGVPSRFSGSGSGTDFTLTISSLQPEDF ATYYCQHFWGTPFTFGQGTKLEIKRTVAAPSVFIFPPSDEQ LKSGTASVVCLLNNFYPREAKVQWKVDNALQSGNSQESV TEQDSKDSTYSLSSTLTLSKADYEKHKVYACEVTHQGLSS PVTKSFNRGEC |
| 22 | 8M24-EASE-EE heavy chain fused to RSPO2 | NPICKGCLSCSKDNGCSRCQQKLFFFLRREGMRQYGECLHSC PSGYYGHRAPDMNRCARCRIENCDSCESKDECTKCKVGFYL HRGRCFDECPDGFAPLEETMECVEGGGGSGGGGSGGGGS EVQLVQSGAEVKKPGSSVKVSCKASGYTFTAYGINWVRQ APGQGLEWMGEIFPRSDSTFYAQKFQGRVTITADKSTSTA YMELSSLRSEDTAVYYCARKGREYGTSHYFDYWGQGTTV TVSSASTKGPSVFPLAPSSKSTSGGTAALGCLVKDYFPEPV TVSWNSGALTSGVHTFPAVLQSSGLYSLSSVVTVPSSSLGT QTYICNVNHKPSNTKVDKKVEPKSCDKTHTCPPCPAPELL GGPSVELFPPKPKDTLMISRTPEVTCVVVDVSHEDPEVKFN WYVDGVEVHNAKTKPREEQYGSTYRVVSVLTVLHQDWL NGKEYKCKVSNKALPAPIEKTISKAKGQPREPQVYTLPPSR EEMTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 23 | 1R34-DDNN/RA light chain variable domain | SSELTQDPAVSVALGQTVRITCQGDSLRSYYASWYQQKPG QAPVLVIYGKNNRPSGIPDRFSGSSSGNTASLTITGAQAED EADYYCNSLERIGYLSYVFGGGTKLTVL |
| 24 | 1R34-DDNN/RA heavy chain variable domain fused to RSPO2 | NPICKGCLSCSKDNGCSRCQQKLFFFLRREGMRQYGECLHSC PSGYYGHRAPDMNRCARCRIENCDSCRSKDACTKCKVGFYLH RGRCFDECPDGFAPLEETMECVEGGGGSGSGGGGGSEV QLLESGGGLVQPGGSLRLSCAASGFTFSSYAMSWVRQAPG KGLEWVSAISGSGGSTYYADSVKGRFTISRDNSKNTLYLQ MNSLRAEDTAVYYCAKDFSSRRWYLEYWGQGTLVTVSS |
| 25 | 8M24-EASE light chain (human kappa light chain) | DIQMTQSPSSLSASVGDRVTITCRISENIYSNLAWYQQKPG KAPKLLIYAAINLAEGVPSRFSGSGSGTDFTLTISSLQPEDF ATYYCQHFWGTPFTFGQGTKLEIKRTVAAPSVFIFPPSDEQL KSGTASVVCLLNNFYPREAKVQWKVDNALQSGNSQESVTEQDS KDSTYSLSSTLTLSKADYEKHKVYACEVTHQGLSSPVTKSFNRG EC |
| 26 | 8M24-EASE | NPICKGCLSCSKDNGCSRCQQKLFFFLRREGMRQYGECLHSC PSGYYGHRAPDMNRCARCRIENCDSCRSKDACTKCKVGFYL HRGRCFDECPDGFAPLEETMECVEGGGGSGGGGSGGGGS EVQLVQSGAEVKKPGSSVKVSCKASGYTFTAYGINWVRQ APGQGLEWMGEIFPRSDSTFYAQKFQGRVTITADKSTSTA |

TABLE A-continued

Sequences of representative liver-specific Wnt signal enhancing molecules, 1R34-
DDNN/RA, 8M24-v1, 1R34-EEST/EE, 1R34-EEST/RA, 1R34-EEAT/EE, 8M24 humanized
1, 8M24 humanized 2, 8M24-EASE-RA, 8M24-EASE-EE, 1R34-DDNN/RA, which include
two of the indicated light chain sequences and two of the indicated heavy chain fusion
sequences in an antibody format, e.g., a bilaterally symmetric, bispecific molecule: (a) that
comprises or consists of an IgG to which 2 Rspo2 domains have been fused, wherein (i) one
(1) Rspo2 domain is fused to each heavy chain of the IgG, (ii) each arm of the IgG binds a
liver-specific cell surface receptor binding domain (e.g., ASGR1) and (b) where the binding
of such IgG arms activates downstream signaling

| SEQ ID NO: | Description | Sequence |
|---|---|---|
|  | heavy chain fused to RSPO2 (human IgG1_N297G) | YMELSSLRSEDTAVYYCARKGREYGTSHYFDYWGQGTTV TVSSASTKGPSVFPLAPSSKSTSGGTAALGCLVKDYFPEPV TVSWNSGALTSGVHTFPAVLQSSGLYSLSSVVTVPSSSLGT QTYICNVNHKPSNTKVDKKVEPKSCDKTHTCPPCPAPELL GGPSVFLFPPKPKDTLMISRTPEVTCVVVDVSHEDPEVKFN WYVDGVEVHNAKTKPREEQYGSTYRVVSVLTVLHQDWL NGKEYKCKVSNKALPAPIEKTISKAKGQPREPQVYTLPPSR EEMTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 27 | 1R34-EEST/EE light chain variable domain | SSELTQDPAVSVALGQTVRITCQGESLRSYYASWYQQKPG QAPVLVIYGKSNRPSGIPDRFSGSSSGNTASLTITGAQAEDE ADYYCTSLERIGYLSYVFGGGTKLTVL |
| 28 | 1R34-EEST/EE heavy chain variable region fused to RSPO2 | NPICKGCLSCSKDNGCSRCQQKLFFFLRREGMRQYGECLHSC PSGYYGHRAPDMNRCARCRIENCDSCESKDECTKCKVGFYL HRGRCFDECPDGFAPLEETMECVEGGGGSGGGGSGGGGS EVQLLESGGGLVQPGGSLRLSCAASGFTFSSYAMSWVRQA PGKGLEWVSAISGSGGSTYYAESVKGRFTISRDNSKNTLY LQMNSLRAEDTAVYYCAKDFSSRRWYLEYWGQGTLVTV SS |
| 29 | Modified R-spondin-2 | NPICKGCLSCSKDNGCSRCQQKLFFFLRREGMRQYGECLH SCPSGYYGHRAPDMNRCARCRIENCDSCRSKDACTKCKV GFYLHRGRCFDECPDGFAPLEETMECVE |
| 30 | Modified R-spondin-2 | NPICKGCLSCSKDNGCSRCQQKLFFFLRREGMRQYGECLH SCPSGYYGHRAPDMNRCARCRIENCDSCASKDACTKCKV GFYLHRGRCFDECPDGFAPLEETMECVE |
| 31 | Modified R-spondin-2 | NPICKGCLSCSKDNGCSRCQQKLFFFLRREGMRQYGECLH SCPSGYYGHRAPDMNRCARCRIENCDSCESKDACTKCKV GFYLHRGRCFDECPDGFAPLEETMECVE |
| 32 | Modified R-spondin-2 | NPICKGCLSCSKDNGCSRCQQKLFFFLRREGMRQYGECLH SCPSGYYGHRAPDMNRCARCRIENCDSCESKDECTKCKV GFYLHRGRCFDECPDGFAPLEETMECVE |
| 33 | 1R34-DDNN/RA heavy chain | EVQLLESGGGLVQPGGSLRLSCAASGFTFSSYAMSWVRQA PGKGLEWVSAISGSGGSTYYADSVKGRFTISRDNSKNTLY LQMNSLRAEDTAVYYCAKDFSSRRWYLEYWGQGTLVTV SSASTKGPSVFPLAPSSKSTSGGTAALGCLVKDYFPEPVTV SWNSGALTSGVHTFPAVLQSSGLYSLSSVVTVPSSSLGTQT YICNVNHKPSNTKVDKKVEPKSCDKTHTCPPCPAPELLGG PSVFLFPPKPKDTLMISRTPEVTCVVVDVSHEDPEVKFNW YVDGVEVHNAKTKPREEQYGSTYRVVSVLTVLHQDWLN GKEYKCKVSNKALPAPIEKTISKAKGQPREPQVYTLPPSRE EMTKNQVSLTCLVKGFYPSDIAVEWESNGQPENNYKTTPP VLDSDGSFFLYSKLTVDKSRWQQGNVFSCSVMHEALHNH YTQKSLSLSPGK |
| 34 | 1R34-EEST/EE CDRH1 | SYAMS |
| 35 | 1R34-EEST/EE CDRH2 | AISGSGGSTYYEDSVKG |
| 36 | 1R34-EEST/EE CDRH3 | DFSSRRWYLEY |

TABLE A-continued

Sequences of representative liver-specific Wnt signal enhancing molecules, 1R34-DDNN/RA, 8M24-v1, 1R34-EEST/EE, 1R34-EEST/RA, 1R34-EEAT/EE, 8M24 humanized 1, 8M24 humanized 2, 8M24-EASE-RA, 8M24-EASE-EE, 1R34-DDNN/RA, which include two of the indicated light chain sequences and two of the indicated heavy chain fusion sequences in an antibody format, e.g., a bilaterally symmetric, bispecific molecule: (a) that comprises or consists of an IgG to which 2 Rspo2 domains have been fused, wherein (i) one (1) Rspo2 domain is fused to each heavy chain of the IgG, (ii) each arm of the IgG binds a liver-specific cell surface receptor binding domain (e.g., ASGR1) and (b) where the binding of such IgG arms activates downstream signaling

| SEQ ID NO: | Description | Sequence |
|---|---|---|
| 37 | 1R34-EEST/EE CDRL1 | QGESLRSYYAS |
| 38 | 1R34-EEST/EE CDRL2 | YGKSNRPS |
| 39 | 1R34-EEST/EE CDRL3 | CTSLERIGYLSYV |
| 40 | 1R34-EEAT/EE CDRL2 | YGKANRPS |
| 41 | 8M24-EASE CDRL1 | RISENIYSNLA |
| 42 | 8M24-EASE CDRL2 | AAINLAE |
| 43 | 8M24-EASE CDRL3 | QHFWGTPFT |
| 44 | 8M24-EASE CDRH1 | AYGIN |
| 45 | 8M24-EASE CDRH2 | EIFPRSDSTFYAQKFQG |
| 46 | 8M24-EASE CDRH3 | KGREYGTSHYFDY |
| 47 | Rspo1 | MRLGLCVVALVLSWTHLTISSRGIKGKRQRRISAEGSQAC AKGCELCSEVNGCLKCSPKLFILLERNDIRQVGVCLPSCPP GYFDARNPDMNKCIKCKIEHCEACFSHNFCTKCKEGLYLH KGRCYPACPEGSSAANGTMECSSPAQCEMSEWSPWGPCS KKQQLCGFRRGSEERTRRVLHAPVGDHAACSDTKETRRC TVRRVPCPEGQKRRKGGQGRRENANRNLARKESKEAGAG SRRRKGQQQQQQQGTVGPLTSAGPA |
| 48 | Rspo2 | MQFRLFSFALIILNCMDYSHCQGNRWRRSKRASYVSNPIC KGCLSCSKDNGCSRCQQKLFFFLRREGMRQYGECLHSCPS GYYGHRAPDMNRCARCRIENCDSCFSKDFCTKCKVGFYL HRGRCFDECPDGFAPLEETMECVEGCEVGHWSEWGTCSR NNRTCGFKWGLETRTRQIVKKPVKDTILCPTIAESRRCKM TMRHCPGGKRTPKAKEKRNKKKKRKLIERAQEQHSVFLA TDRANQ |
| 49 | Rspo3 | MHLRLISWLFIILNFMEYIGSQNASRGRRQRRMHPNVSQG CQGGCATCSDYNGCLSCKPRLFFALERIGMKQIGVCLSSCP SGYYGTRYPDINKCTKCKADCDTCFNKNFCTKCKSGFYLH LGKCLDNCPEGLEANNHTMECVSIVHCEVSEWNPWSPCT KKGKTCGFKRGTETRVREIIQHPSAKGNLCPPTNETRKCTV QRKKCQKGERGKKGRERKRKKPNKGESKEAIPDSKSLESS KEIPEQRENKQQQKKRKVQDKQKSVSVSTVH |
| 50 | Rspo4 | MRAPLCLLLLVAHAVDMLALNRRKKQVGTGLGGNCTGCI ICSEENGCSTCQQRLFLFIRREGIRQYGKCLHDCPPGYFGIR GQEVNRCKKCGATCESCFSQDFCIRCKRQFYLYKGKCLPT CPPGTLAHQNTRECQGECELGPWGGWSPCTHNGKTCGSA WGLESRVREAGRAGHEEAATCQVLSESRKCPIQRPCPGER SPGQKKGRKDRRPRKDRKLDRRLDVRPRQPGLQP |

TABLE A-continued

Sequences of representative liver-specific Wnt signal enhancing molecules, 1R34-DDNN/RA, 8M24-v1, 1R34-EEST/EE, 1R34-EEST/RA, 1R34-EEAT/EE, 8M24 humanized 1, 8M24 humanized 2, 8M24-EASE-RA, 8M24-EASE-EE, 1R34-DDNN/RA, which include two of the indicated light chain sequences and two of the indicated heavy chain fusion sequences in an antibody format, e.g., a bilaterally symmetric, bispecific molecule: (a) that comprises or consists of an IgG to which 2 Rspo2 domains have been fused, wherein (i) one (1) Rspo2 domain is fused to each heavy chain of the IgG, (ii) each arm of the IgG binds a liver-specific cell surface receptor binding domain (e.g., ASGR1) and (b) where the binding of such IgG arms activates downstream signaling

| SEQ ID NO: | Description | Sequence |
|---|---|---|
| 51 | 8M24-EASE-RA heavy chain fused to RSPO2 | NPICKGCLSCSKDNGCSRCQQKLFFFLRREGMRQYGECLHSC PSGYYGHRAPDMNRCARCRIENCDSCRSKDACTKCKVGFYL HRGRCFDECPDGFAPLEETMECVEGGGGSGGGGGGGGS EVQLVQSGAEVKKPGSSVKVSCKASGYTFTAYGINWVRQ APGQGLEWMGEIFPRSDSTFYAQKFQGRVTITADKSTSTA YMELSSLRSEDTAVYYCARKGREYGTSHYFDYWGQGTTV TVSSASTKGPSVFPLAPSSKSTSGGTAALGCLVKDYFPEPV TVSWNSGALTSGVHTFPAVLQSSGLYSLSSVVTVPSSSLGT QTYICNVNHKPSNTKVDKKVEPKSCDKTHTCPPCPAPELL GGPSVFLFPPKPKDTLMISRTPEVTCVVVDVSHEDPEVKFN WYVDGVEVHNAKTKPREEQYGSTYRVVSVLTVLHQDWL NGKEYKCKVSNKALPAPIEKTISKAKGQPREPQVYTLPPSR EEMTKNQVSLTCLVKGFYPSDIAVEWESNGQPENNYKTTP PVLDSDGSFFLYSKLTVDKSRWQQGNVFSCSVMHEALHN HYTQKSLSLSPGK |
| 52 | HuASGR1-CBD P07306 154-291 | HHHHHHHHGSGSGLNDIFEAQKIEWHESGSGCPVNWVEH ERSCYWFSRSGKAWADADNYCRLEDAHLVVVTSWEEQK FVQHHIGPVNTWMGLHDQNGPWKWVDGTDYETGFKNW RPEQPDDWYGHGLGGGEDCAHFTDDGRWNDDVCQRPYR WVCETELDKASQEPPLL |
| 53 | 8M24L1 Light-chain | DIQMTQSPSSLSASVGDRVTITCRISENIYSNLAWYQQKPG KAPKLLIYAAINLADGVPSRFSGSGSGTDFTLTISSLQPEDF ATYYCQHFWGTPFTFGQGTKLEIKRTVAAPSVFIFPPSDEQ LKSGTASVVCLLNNFYPREAKVQWKVDNALQSGNSQESV TEQDSKDSTYSLSSTLTLSKADYEKHKVYACEVTHQGLSS PVTKSFNRGEC |
| 54 | 8M24H1 Heavy-chain | EVQLVQSGAEVKKPGSSVKVSCKASGYTFTNYGINWVRQ APGQGLEWMGEIFPRSDNTFYAQKFQGRVTITADKSTSTA YMELSSLRSEDTAVYYCARKGRDYGTSHYFDYWGQGTT VTVSSASTKGPSVFPLAPSSKSTSGGTAALGCLVKDYFPEP VTVSWNSGALTSGVHTFPAVLQSSGLYSLSSVVTVPSSSLG TQTYICNVNHKPSNTKVDKKVEPKSCGSGSGHHHHHH |

In particular embodiments, the sequences are a polypeptide sequence present within the indicated liver-specific Wnt signal enhancing molecules comprise one or more of any of the polypeptides shown in Table A or a variant thereof, or any combination thereof. In particular embodiments, the Wnt signal enhancing molecule comprises two of the heavy chain fusion protein sequences and two of the light chain sequences, e.g., in an antibody format, wherein the two heavy chain fusion protein sequences are bound to each other and each of the two light chain sequences are bound to a different heavy chain fusion protein sequence. In particular embodiments, the Wnt signal enhancing molecule comprises two heavy chain fusion protein sequences comprising the CDRs present within any of these sequences and two light chain sequences present within any of these sequences, e.g., in an antibody format, wherein the two heavy chain fusion protein sequences are bound to each other and each of the two light chain sequences are bound to a different heavy chain fusion protein sequence. In particular embodiments, the Wnt signal enhancing molecule comprises two heavy chain fusion protein sequences, each comprising the CDRs present within any of these sequences, and two light chain sequences, each comprising the CDRs present within any of these sequences, e.g., in an antibody format, wherein the two heavy chain fusion protein sequences are bound to each other and each of the two light chain sequences are bound to a different heavy chain fusion protein sequence. In particular embodiments, each of the two heavy chain fusion protein sequences and/or each of the two light chain sequences are variants of any of the disclosed sequences and have at least 90%, at least 95%, at least 98% or at least 99% identify to any of the disclosed sequences, and in particular embodiments, any amino acid modifications, e.g., insertions, deletions, or substitutions, are not present within a CDR. In particular embodiments, the amino acid modifications do not occur at any of (a) F105R, F105A, or F105E; and/or (b) F109A or F109E. In particular embodiments, variants of the heavy chain comprise N297G. In particular embodiments, the RPOS2 sequences present in the variants comprise the F105R and F109A substitutions. In particular embodiments, the RPOS2 sequences present in the variants comprise the F105E and F109E substitutions. In particular embodiments, the molecules comprise the amino acid substitutions as compared to parental or wild type for any of the following constructs: EEST/FE, EEST/RA, EEAT/EE, EESN/RA, EEAN/RA, 8M24-EAASE-0RA, or 8M24-EASE-EE.

Liver-Specific Wnt Signal Enhancing Molecules

In certain aspects, the present disclosure provides liver-specific Wnt signal enhancing molecules capable of enhancing Wnt activity in a liver-specific manner. In certain embodiments, the liver-specific Wnt signal enhancing molecules are bi-functional molecules comprising a first domain that binds to one or more ZNRF3 and/or RNF43 ligases, and a second domain that binds to liver tissue and/or liver cells. Each of the first domain and the second domain may be any moiety capable of binding to the ligase complex or targeted tissue or cell, respectively. For example, each of the first domain and the second domain may be, but are not limited to, a moiety selected from: a polypeptide (e.g., an antibody or antigen-binding fragment thereof or a peptide or polypeptide different from an antibody), a small molecule, and a natural ligand or a variant, fragment or derivative thereof. In certain embodiments, the natural ligand is a polypeptide, a small molecule, an ion, an amino acid, a lipid, or a sugar molecule. The first domain and the second domain may be the same type of moiety as each other, or they may be different types of moieties. In certain embodiments, the liver-specific Wnt signal enhancing molecules bind to a liver-specific cell surface receptor. In particular embodiments, the liver-specific Wnt signal enhancing molecules increase or enhance Wnt signaling by at least 50%, at least two-fold, at least three-fold, at least five-fold, at least ten-fold, at least twenty-fold, at least thirty-fold, at least forty-fold, or at least fifty-fold in liver tissue or liver cells, e.g., as compared to a negative control.

Liver-specific Wnt signal enhancing molecules may have different formats. In particular embodiments, the liver-specific Wnt signal enhancing molecules are fusion proteins comprising a first polypeptide sequence that binds to ZNRF3/RNF43 and a second polypeptide sequence that binds to liver tissue or liver cells. In certain embodiments, the two polypeptide sequences may be fused directly or via a linker. In certain embodiments, the liver-specific Wnt signal enhancing molecules comprise two or more polypeptides, such as dimers or multimers comprising two or more fusion proteins, each comprising the first domain and the second domain, wherein the two or more polypeptides are linked, e.g., through a linker moiety or via a bond between amino acid residues in each of the two or more polypeptides, e.g., an intermolecular disulfide bond between cysteine residues.

In particular embodiments, a liver-specific Wnt signal enhancing molecule is an antibody comprising antibody heavy and light chains (or antigen-binding fragments thereof) that constitute either the first domain or the second domain, wherein the other domain (i.e., the second domain or first domain) is linked to the antibody heavy chain or light chain, either as a fusion protein or via a linker moiety. In particular embodiments, the other domain is linked to the N-terminus of the heavy chain, the C-terminus of the heavy chain, the N-terminus of the light chain, or the C-terminus of the light chain. Such structures may be referred to herein as appended IgG scaffolds. For example, a liver-specific Wnt signal enhancing molecule can be an antibody that binds a liver-specific cell surface receptor, wherein a binding domain that binds ZNRF3/RNF43 is fused or appended to either the heavy chain or light chain of the antibody that binds the tissue- or cell-specific receptor. In particular embodiments, a liver-specific Wnt signal enhancing molecule is an antibody or antigen-binding fragment thereof that binds ASGR1 or ASGR2, wherein a binding domain that binds ZNRF3/RNF43 is fused or appended to either the heavy chain or light chain of the antibody or antigen-binding fragment thereof. In particular embodiments, the binding domain that binds ZNRF3/RNF43 is derived from an Rspo polypeptide, and in some embodiments, it comprises Fu1 and Fu2 domains, wherein the Fu1 and Fu2 domains optionally comprise one or more amino acid modifications, including any of those disclosed herein, e.g., F105R, F105E, F109A, or F109E.

In certain embodiments, the liver-specific Wnt signal enhancing molecules comprise a first domain ("action module") that binds ZNRF3/RNF43 and a second domain ("targeting module") that binds a liver-specific receptor, e.g., with high affinity. In certain embodiments, each of these two domains has substantially reduced activity or is inactive in enhancing Wnt signals by itself. However, when the liver-specific Wnt signal enhancing molecules engage with liver tissue or cells that express the liver-specific receptor, E3 ligases ZNRF3/RNF43 are recruited to a ternary complex with the liver-specific receptors, leading them to be sequestered, and/or cleared from the cell surface via receptor-mediated endocytosis. The net result is to enhance Wnt signals in a liver-specific manner.

In certain embodiments, the action module is a binder to ZNRF3/RNF43 E3 ligases, and it can be designed based on R-spondins, e.g., R-spondins-1-4, including but not limited to human R-spondins-1-4. In certain embodiments, the action module is an R-spondin, e.g., a wild-type R-spondin-1-4, optionally a human R-spondin-1-4, or a variant or fragment thereof. In particular embodiments, it is a variant of any of R-spondins-1-4 having at least 80%, at least 85%, at least 90%, at least 95%, at least 98%, or at least 99% sequence identity to the corresponding wild-type R-spondin-1-4 sequence. In certain embodiments, the action module comprises or consists of a Furin domain 1 of an R-spondin, e.g., any of R-spondins 1-4, which bind ZNRF3/RNF43. Extended versions of Furin domain 1 (including, but not limited to, those with a mutated Furin domain 2 that no longer binds to LGR4-6 or has reduced binding to LGR4-6) or engineered antibodies or any other derivatives or any engineered polypeptides different from antibodies that are able to bind specifically to ZNRF3/RNF43 can also be used. In certain embodiments, the action module comprises one or more Furin domain 1 of an R-spondin. In certain embodiments, it does not comprise a Furin domain 2 of an R-spondin, or it comprises a modified or variant Furin domain 2 of an R-spondin, e.g., a Furin domain 2 with reduced activity as compared to the wild-type Furin domain 2. In certain embodiments, an action module comprises a Furin domain 1 but not a Furin domain 2 of R-spondin. In certain embodiments, an action module comprises two or more Furin domain 1 or multimers of a Furin domain 1. The action domain may comprise one or more wild-type Furin domain 1 of an R-spondin. In particular embodiments, the action module comprises a modified or variant Furin domain 1 of an R-spondin that has increased activity, e.g., binding to ZNRF3/RNF43, as compared to the wild-type Furin domain 1. Variants having increased binding to ZNRF3/RNF43 may be identified, e.g., by screening a phage or yeast display library comprising variants of an R-spondin Furin domain 1. Peptides or polypeptides unrelated to R-spondin Furin domain 1 but with binding to ZNRF3/RNF43 may also be identified through screening. Action modules may further comprise additional moieties or polypeptide sequences, e.g., additional amino acid residues to stabilize the structure of the action module or liver-specific Wnt signal enhancing molecule in which it is present.

R-spondins are capable of amplifying Wnt signals. The minimal functional unit of R-spondin is composed of two Furin domains, Furin domain 1 that binds to ZNRF3/RNF43 E3 ligases, and Furin domain 2 that binds to LGR4-6, bringing together a ternary complex of R-spondin, LGR, and the E3 ligases. This results in internalization of the whole complex and removal of ZNRF3/RNF43 away from their targets of destruction. Furin domain 1 alone is not fully functional, but it is capable of binding to both ZNRF3 and RNF43.

The action module of the liver-specific Wnt signal enhancing molecules described herein can be, but is not limited to, any functional moiety that can bind to the ZNRF3/RNF43 ligases, e.g., polypeptides or organic chemicals. In particular embodiments, the action module, for example a polypeptide comprising the Furin domain 1 of an R-spondin, either alone or together with the targeting module, is substantially inactive in non-target tissues, so as to minimize potential off-target effects. The action module is fused to or bound to a targeting module in the context of a liver-specific Wnt signal enhancing molecule, and when the liver-specific Wnt signal enhancing molecule engages with target tissue that express the liver-specific receptor, E3 ligases ZNRF3/RNF43 are recruited to a ternary complex with the liver-specific receptors, leading them to be relocated on the cell surface, sequestered, and/or cleared from the cell surface.

In certain embodiments, the action module comprises a fragment or variant of an R-spondin polypeptide (e.g., any of R-spondins 1-4), or a functional fragment or variant thereof. In particular embodiments, the action module comprises a fragment of a wild-type R-spondin, and in other embodiments, the action module comprises a fragment of an R-spondin comprising one or more amino acid modifications. The R-spondin may be any R-spondin known in the art or a homolog thereof, including R-spondins from any animal species, including but not limited to mammalian species, such as human R-spondins. R-spondins have been identified and described, and their polypeptide and encoding polynucleotide sequences are known and available in the art. In particular embodiments, the R-spondin polypeptide is a human R-spondin or a homolog found in other vertebrates or non-vertebrates, e.g., a mouse R-spondin. Amino acid sequences of human R-spondin 1, human R-spondin 2, human R-spondin 3, and human R-spondin 4, and the Furin domains 1 thereof, are provided in FIG. 38 and SEQ ID NOs:47-50, respectively. Their homologues and variants are available from general database search, such as https://www.dot.ncbi.dot.nlm.dot.nih.dot.gov/protein/. The present invention includes (but is not limited to) action modules comprising or consisting of fragments and variants of any of these or other R-spondins. In various embodiments, variants of any of the R-spondin polypeptides and fragments thereof comprise one or more amino acid modifications, e.g., deletions, additions, or substitutions as compared to the wild-type R-spondin polypeptide. The modification(s) may be present in any region of the variant of R-spondin or a fragment thereof, including but not limited to a Furin domain 1 and/or a Furin domain 2. It is understood that amino acid modifications outside of the Furin domain 1 or Furin domain 2 may alter the resulting variant such that the resulting variant has reduced LGR4-6 binding activity as compared to the wild-type R-spondin or fragment thereof.

In certain embodiments, the action module comprises or consists of an R-spondin sequence, e.g., a full length or wild-type R-spondin-1, -2, -3 or -4, optionally a human R-spondin-1, -2, -3, or -4, or a variant or fragment thereof. In particular embodiments, it is a variant of any of R-spondins-1-4 having at least 80%, at least 85%, at least 90%, at least 95%, at least 98%, or at least 99% sequence identity to the corresponding wild-type R-spondin-1-4 sequence. In certain embodiments, the action module comprises or consists of a full length R-spondin (e.g., any of R-spondins-1-4) comprising one or more amino acid modifications, including but not limited to any of those disclosed herein. In certain embodiments, the action module comprises or consists of a fragment of a wild-type or modified R-spondin (e.g., any of R-spondins-1-4). In particular embodiments, the fragment is able to bind to ZNRF3 and/or RNF43. In certain embodiments, the action module comprises the Furin domain 1 of an R-spondin protein, or fragments or variants of R-spondin proteins. In certain embodiments, the action module comprises or consists of one or more (e.g., one, two or three or more Furin domain 1 of an R-spondin protein (e.g., R-spondin-1-4), or a variant thereof having at least 85%, at least 90%, at least 95%, at least 98% or at least 99% sequence identify to an R-spondin Furin domain 1. In certain embodiments, the action module comprises an R-spondin Furin 1 domain or variant or fragment thereof and an R-spondin Furin 2 domain or variant or fragment thereof. In certain embodiments, the action module comprises an antibody, or antigen binding fragment thereof, that bind ZNRF3/RNF43. In particular embodiments, the action module specifically binds to either ZNRF3 or RNF43.

In certain embodiments, the action module comprises one or more Furin domain 1 of an R-spondin, e.g., human R-spondin 1 or human R-spondin 2, or a variant thereof. In certain embodiments, the action module comprises one or more Furin domain 1 of an R-spondin, but it does not comprise a Furin domain 2 of an R-spondin. In certain embodiments, the action module comprises one or more Furin domain 1 of an R-spondin, and it comprises a modified or variant Furin domain 2 of an R-spondin, e.g., a Furin domain 2 with reduced activity as compared to the wild-type Furin domain 2. In certain embodiments, the action module comprises an R-spondin protein having a modified or variant Furin domain 2 of an R-spondin, e.g., a Furin domain 2 with reduced activity as compared to the wild-type Furin domain 2. In certain embodiments, an action module comprises two or more Furin domains 1, or variants thereof, or multimers of a Furin domain 1 or variant thereof. In certain embodiments, the action module comprises a variant R-spondin Furin 1 domain comprising one or more point mutations, e.g., at amino acid residues corresponding to K58, H76, S77, R86, and/or N91 of human R-spondin 2. In certain embodiments, the action module comprises a variant R-spondin Furin 2 domain comprising one or more point mutations, e.g., at amino acid residues corresponding to F105, F109 and/or K121 of human R-spondin 2. In particular embodiments, the action module comprises a modified or variant Furin domain 1 of an R-spondin that has increased activity, e.g., binding to ZNRF3/RNF43, as compared to the wild-type Furin domain 1. Action modules may further comprise additional moieties or polypeptide sequences, e.g., additional amino acid residues to stabilize the structure of the action module or liver-specific Wnt signal enhancing molecule in which it is present. In certain embodiments, an action module comprises a peptide or polypeptide without obvious/strong sequence homology to R-spondins but has binding affinity to ZNRF3/RNF43 comparable to or higher than the binding affinity of R-spondins to ZNRF3/RNF43.

In certain embodiments, the action module comprises a Furin domain 1 of an R-spondin polypeptide (e.g., a human R-spondin), or a functional fragment or variant thereof, and a modified or variant Furin domain 2 of an R-spondin polypeptide (e.g., a human R-spondin), wherein the modified Furin domain 2 has reduced binding affinity to LGR4-6 as compared to the corresponding wild-type Furin domain 2. In certain embodiments, the Furin domain 2 comprises one or more point mutations, e.g., at amino acid residues corresponding to F105 and/or F109 of human R-spondin 2. The skilled artisan can readily determine the corresponding amino acid residues in other R-spondin polypeptides by comparing their amino acid sequences to human R-spondin 2. In certain embodiments, the action module comprises a Furin domain 1 or variant thereof and a Furin domain 2 or variant thereof, wherein the Furin domain 1 and/or Furin domain 2 comprises one or more point mutations. The one or more point mutations within the action module (as compared to the corresponding wild-type R-spondin sequence) may occur at any amino acid residues within the Furin domain 1 and/or Furin domain 2, including but not limited to, e.g., at amino acid residues K58, H76, S77, R86, N91, F105, F109, or K121 and other residues that can be modified to reduce the binding affinity to LGR4-6. Regions of the Furin domain 1 and Furin domain 2 of human R-spondin 1 that are important for its functional activity have been identified, including conserved hydrophilic residues S48, N51, R66, R70 and Q71, and less conserved, hydrophobic residues, L46, L54, 162 and L64, which are important for binding to the E3 ligases. In addition, in the human R-spondin 1 Furin domain 1, amino acid residues K59, S78, D85, R87, N88 and N92 form a hydrophilic interaction surface with LGR5, and the FSHNF amino acid sequence has been identified as a loop important for the hydrophobic surface. In particular embodiments, action modules comprising R-spondin Furin domain 1 and/or Furin domain 2 may comprise one or more mutations within any of these regions, surfaces or amino acid residues.

In particular embodiments, action modules comprising R-spondin Furin domain 1 and/or Furin domain 2 may comprise one or more mutations or other alternations beyond these regions, surfaces or amino acid residues, which indirectly compromise LGR4-6 binding by affecting the structure and/or stability of the binding surface.

In certain embodiments, action modules comprising R-spondin Furin domain 1 and/or Furin domain 2 may comprise one or more mutations at any amino acid residues, including but not limited to any of those depicted in the accompanying Examples. In particular embodiments, the action module comprises a modified Furin domain 2 comprising amino acid substitutions at amino acid residues F10 and/or F109. In particular embodiments, the action module comprises a Furin 1 domain and a modified Furin domain 2 comprising amino acid substitutions at amino acid residues F105 and/or F109. In particular embodiments, the action module comprises a modified Furin 1 domain and a modified Furin 2 domain, where in certain embodiments, the modified Furin 1 domain comprises one or more amino acid modifications at amino acids R65, R69 and/or Q70, and the modified Furin domain comprises one or more amino acid modification at amino acids F105 and/or F109. In certain embodiments, the modified R-spondin polypeptide or fragment or variant thereof comprises amino acid substitutions at positions corresponding to amino acids F105 and F109 of human R-spondin 2. In certain embodiments the two amino acid substitutions include: (a) F105R, F105A, or F105E; and (b) F109A or F109E. In particular embodiments, the two amino acid substitutions are: (a) F105R and F109A; (b) F105A and F109A; (c) F105E and F109A; or (d) F105E and F109E. In certain embodiments, the modified R-spondin polypeptide or fragment or variant thereof has at least 80%, at least 85%, at least 90%, at least 95%, at least 98%, at least 99%, or 100% sequence identity to any of SEQ ID NOs: 29-32. In certain embodiments, the modified R-spondin polypeptide or fragment or variant thereof has at least 80%, at least 85%, at least 90%, at least 95%, at least 98%, at least 99%, or 100% sequence identity to any of SEQ ID NOs: 29-32, and comprises one of the following combinations of amino acid substitutions: (a) F105R and F109A; (b) F105A and F109A; (c) F105E and F109A; or (d) F105E and F109E. In particular embodiments, the modified Furin domain 2 has binding affinity to LGR4-6 less than 80%, less than 50%, less than 20%, or less than 10% the binding of the corresponding wild-type Furin domain 2, e.g., in the context of the full length R-spondin protein.

In certain embodiments, the action module comprises a Furin domain 1 of an R-spondin polypeptide (e.g., a human R-spondin), or a functional fragment or variant thereof, and an unmodified Furin domain 2 of an R-spondin polypeptide (e.g., a human R-spondin). While in certain embodiments, a modified Furin domain 2 having reduced binding affinity to LGR4-6 as compared to the corresponding wild-type Furin domain 2 is more desirable to increase the specificity of tissue targeting, in particular embodiments, the unmodified Furin domain 2 combined with the targeting module has improved tissue targeting over wild-type R-spondin without targeting module, and has utility in certain contexts.

In certain embodiments, the action module comprises a wild-type or modified R-spondin Furin domain 1, e.g., from any of R-spondin-1, -2, -3, -4, optionally human R-spondins-1, -2, -3 or -4. In particular embodiments, the action module comprises the R-spondin Furin 1 domain and a wild-type or modified R-spondin Furin 2 domain, e.g., from any of R-spondin-1, -2, -3, -4, optionally human R-spondins-1, -2, -3 or -4. In particular embodiments, the action module comprises the first R-spondin Furin 1 domain and a second wild-type or modified R-spondin Furin 1 domain, e.g., from any of R-spondin-1, -2, -3, -4, optionally human R-spondins-1, -2, -3 or -4. In particular embodiments, the modified Furin domain 2 has comparable binding affinity to LGR4-6 or a binding affinity to LGR4-6 of less than 80%, less than 50%, less than 20%, or less than 10% the binding of the corresponding wild-type Furin domain 2, e.g., in the context of the full length R-spondin protein.

In certain embodiments, the action module comprises an antibody or antigen-binding fragment thereof that specifically binds ZNRF3 and/or RNF43. In particular embodiments, the action module comprises an antibody or antigen-binding fragment thereof that binds to human RNF43 (hRNF43, NCBI reference sequence XP_011523257.1, residues 44-198) or human ZNRF3 (hZNRF3; NCBI reference sequence NP_001193927.1, residues 56-219). In particular embodiments, the action module is an antibody or an antigen-binding fragment thereof, comprising a nanobody, VH or VL sequence, or a fragment or variant thereof.

In certain embodiments, the targeting module specifically binds to a liver-specific surface molecule, e.g., a liver-specific surface receptor, and can be, e.g., natural ligands, antibodies, or synthetic chemicals. In particular embodiments, the liver-specific surface molecule is preferentially expressed on liver organ, liver tissue, and/or liver cells. In particular embodiments, the liver-specific surface molecule has increased or enhanced expression on liver tissue or liver cells as compared to one or more other non-targeted organs, tissues or cell types. In certain embodiments, the liver-specific surface molecule is preferentially expressed on the surface of the liver organ, liver tissue or liver cell as compared to one or more other organ, tissue or cell type, respectively. For example, in particular embodiments, a cell surface receptor is considered to be liver-specific or liver-specific cell surface molecule if it is expressed at levels at least two-fold, at least five-fold, at least 10-fold, at least 20-fold, at least 30-fold, at least 40-fold, at least 50-fold, at least 100-fold, at least 500-fold, or at least 1000-fold higher in the liver organ, tissue or cell than it is expressed in one or more, five or more, all other organs, tissues or cells, or an average of all other organs, tissue or cells, respectively. In certain embodiments, the liver-specific or liver-specific cell surface molecule is a cell surface receptor, e.g., a polypeptide receptor comprising a region located within the cell surface membrane and an extracellular region to which the targeting module can bind. In various embodiments, the methods described herein may be practiced by specifically targeting cell surface molecules that are only expressed on liver tissue or a subset of tissues including the liver tissue, or by specifically targeting cell surface molecules that have higher levels of expression on liver tissue as compared to all, most, or a substantial number of other tissues, e.g., higher expression on the liver tissue than on at least two, at least five, at least ten, or at least twenty other tissues.

Liver-specific cell surface receptors are known in the art. Examples of liver-specific surface receptors include but are not limited to, ASGR1, ASGR2, TFR2, and SLC10A1. Additional receptors for liver delivery are described, e.g., by Yan et al., Tumor Biology, 2015; 36:55-67.

In certain embodiments, the targeting module comprises an antibody or antigen-binding fragment thereof that specifically binds ASGR1 and/or ASGR2. In particular embodiments, the targeting module comprises an antibody or an antigen-binding fragment thereof, comprising: a) CDRH1, CDRH2 and CDRH3 sequences set forth herein; and/or b) CDRL1, CDRL2 and CDRL3 sequences set forth herein, or a variant of said antibody, or antigen-binding fragment thereof, comprising one or more amino acid modifications, wherein said variant comprises less than 8 amino acid substitutions in said CDR sequences (e.g., less than 7, less than 6, less than 5, less than 4, less than 3, or less than 2). In certain embodiments, the targeting module comprises an antibody heavy chain variable domain comprising CDRs of SEQ ID NOs:34, 35, and 36, and an antibody light chain variable domain comprising CDRs of SEQ ID NOs:37, 38, and 39. In certain embodiments, the targeting module comprises an antibody heavy chain variable domain comprising CDRs of SEQ ID NOs:34, 35, and 36, and an antibody light chain variable domain comprising CDRs of SEQ ID NOs: 37, 40, and 39. In certain embodiments, the targeting module comprises an antibody light chain variable domain comprising CDRs of SEQ ID NOs:41, 42, and 43, and an antibody heavy chain variable domain comprising CDRs of SEQ ID NOs:44, 45, and 46.

As used herein, a cell surface molecule is said to be liver-specific if a greater amount of the molecule is present on liver cells or liver tissue as compared to one or more other cell or tissue types, or any other cell or tissue type. In certain embodiments, the greater amount is at least two-fold, at least five-fold, at least 10-fold, at least 20-fold, at least 50-fold, or at least 100-fold as compared to the amount in the one or more other cell or tissue types, or any other cell or tissue type. For example, in particular embodiments, a cell surface receptor is considered to be a liver-specific or cell-specific cell surface molecule if it is expressed at levels at least two-fold, at least five-fold, at least 10-fold, at least 20-fold, at least 30-fold, at least 40-fold, at least 50-fold, at least 100-fold, at least 500-fold, or at least 1000-fold higher in the target organ, tissue or cell than it is expressed in one or more, five or more, all other organs, tissues or cells, or an average of all other organs, tissue or cells, respectively. In certain embodiments, the liver-specific or cell-specific cell surface molecule is a cell surface receptor, e.g., a polypeptide receptor comprising a region located within the cell surface membrane and an extracellular region to which the targeting module can bind.

In particular embodiments, the targeting module binds to a liver-specific surface molecule. The targeting modules that bind to each liver-specific surface molecules can be, but are not limited to, antibodies or antigen-binding fragments thereof, peptides, natural ligands of tissue- or cell-specific receptors, or their derivatives, and synthetic small molecules, etc.

In certain embodiments, the liver-specific Wnt signal enhancing molecule binds to specific liver cell types, e.g., specific cell types associated with a target tissue. For example, in liver tissue, the targeting module may bind to hepatocytes, precursors and stem cells of hepatocytes, biliary tract cells, and/or endothelial or other vascular cells.

The asialoglycoprotein receptor (ASGPR) is comprised of ASGR1 and ASGR2 (reviewed, for example by Stockert, Morell and Ashwell, 1991, Targeted Diagnostics and Therapy 4: 41-64). This receptor is a transmembrane protein that plays a critical role in serum glycoprotein homeostasis by mediating the endocytosis and lysosomal degradation of glycoproteins with exposed terminal galactose or N-acetylgalactosamine residues. Thus, natural and synthetic ligands of AGPR include, but are not limited to, galactosylated cholinesterase, galactose (Gal) and N-acetylgalactosamine (GalNAc), GalNAc containing molecules such as GalNAc-terminating glycoproteins, and mono-, oligo-, or poly-saccharide containing molecules or nano-particles (reviewed, for example, by D'Souza and Devarajan 2015, Journal of Controlled Release, 203:126-139.

In various embodiments, the liver-specific surface molecules are liver-specific cell surface receptors. For liver, these include, but are not limited to, ASGR1 and ASGR2. In particular embodiments, the targeting module binds to human ASGR1 (hASGR1; NCBI reference sequence NP_001662.1, residues 62-291), human ASGR2 (hASGR2; NCBI reference sequence NP_550436.1, residues 66-292), cynomolgus ASGR1 (cynoASGR1, sequence ID XP_005582755.1, residues 62-291), or cynomolgus ASGR2 (cynoASGR2).

In certain embodiments, the targeting module comprises an antibody or antigen-binding fragment thereof, comprising CDRH1, CDRH2 and CDRH3 sequences set forth herein; and/or CDRL1, CDRL2 and CDRL3 sequences set forth herein, or a variant of said antibody, or antigen-binding fragment thereof, comprising one or more amino acid modifications, wherein said variant comprises less than 8 amino acid substitutions in said CDR sequences. In particular embodiments, the isolated antibody, or antigen-binding fragment thereof comprises a heavy chain variable region, light chain variable region, nanobody, or scFv sequence comprising an amino acid sequence having at least 90% or at least 95% identity to a sequence disclosed herein, e.g., disclosed in any one of SEQ ID NOs:1-24 or 29. In particular embodiments, the targeting module comprises a variable heavy chain region having at least 90% or at least 95% identity to the variable heavy domain depicted in any one of SEQ ID NOs: 2, 4, 6, 8, 10, 12, 13, 15, 16, 20, 22, 24, 26, 28, 33, or 51. In particular embodiments, the targeting module comprises a variable light chain region having at least 90% or at least 95% identity to the variable light domain depicted in any one of SEQ ID NOs:1, 3, 5, 7, 9, 11, 14, 17, 18, 19, 21, 23, 25, or 27. In particular embodiments, the targeting module comprises a heavy chain having at least 90% or at least 95% identity to the heavy chain depicted in any one of SEQ ID NOs:2, 6, 8, 10, 12, 22, 26, 33, or 51. In particular embodiments, the targeting module comprises a light chain having at least 90% or at least 95% identity to the light chain depicted in any one of SEQ ID NOs:1, 5, 7, 9, 11, 21, or 25. In particular embodiments, the constant region of the light chain and/or heavy chain is an IgG1 or IgG2.

In certain embodiments, Wnt signal enhancing molecules comprise a fusion protein, e.g., a fusion protein comprising an antibody heavy or light chain of the targeting domain fused to an action domain. In certain embodiments, the two regions of the fusion protein (e.g., the targeting domain region and the action domain are fused via a linker moiety. In certain embodiments, the linker is made up of amino acids linked together by peptide bonds. In particular embodiments, the linker comprises, in length, from 1 up to about 40 amino acid residues, from 1 up to about 20 amino acid residues, or from 1 to about 10 amino acid residues. In certain embodiments, the amino acid residues in the linker are from among the twenty canonical amino acids, and in certain embodiments, selected from cysteine, glycine, alanine, proline, asparagine, glutamine, and/or serine. In certain embodiments, a linker comprises one or more non-natural amino acids. In some embodiments, a peptidyl linker is made up of a majority of amino acids that are sterically unhindered, such as glycine, serine, and alanine linked by a peptide bond. Certain linkers include polyglycines, polyserines, and polyalanines, or combinations of any of these. Some exemplary peptidyl linkers are poly(Gly)1-8, particularly (Gly)3, (Gly)4 (SEQ ID NO:55), (Gly)5 (SEQ ID NO: 56), and (Gly)7 (SEQ ID NO: 57), as well as, poly(Gly)4 Ser (SEQ ID NO: 58), poly(Gly-Ala)2-4 and poly(Ala)1-8. Other specific examples of peptidyl linkers include (Gly) 5Lys (SEQ ID NO: 59), and (Gly)5LysArg (SEQ ID NO: 60). To explain the above nomenclature, for example, (Gly) 3Lys(Gly)4 means Gly-Gly-Gly-Lys-Gly-Gly-Gly-Gly (SEQ ID NO: 61). Other combinations of Gly and Ala are also useful. Additionally, a peptidyl linker can also comprise a non-peptidyl segment such as a 6 carbon aliphatic molecule of the formula —CH2-CH2-CH2-CH2-CH2-CH2-. The peptidyl linkers can be altered to form derivatives as described herein. In particular embodiments, the linker is any of those identified in any of SEQ ID NOs: 2, 4, 6, 8, 10, 12, 20, 22, 24, 26, or 28.

Illustrative non-peptidyl linkers include, for example, alkyl linkers such as —NH—(CH2)s-C(O)—, wherein s=2-20. These alkyl linkers may further be substituted by any non-sterically hindering group such as lower alkyl (e.g., C1-C6) lower acyl, halogen (e.g., Cl, Br), CN, NH$_2$, phenyl, etc. Non-peptide portions of the inventive composition of matter, such as non-peptidyl linkers or non-peptide half-life extending moieties can be synthesized by conventional organic chemistry reactions. Chemical groups that find use in linking binding domains include carbamate; amide (amine plus carboxylic acid); ester (alcohol plus carboxylic acid), thioether (haloalkane plus sulfhydryl; maleimide plus sulfhydryl), Schiff's base (amine plus aldehyde), urea (amine plus isocyanate), thiourea (amine plus isothiocyanate), sulfonamide (amine plus sulfonyl chloride), disulfide; hydrazone, lipids, and the like, as known in the art.

The linkage between domains may comprise spacers, e.g. alkyl spacers, which may be linear or branched, usually linear, and may include one or more unsaturated bonds; usually having from one to about 300 carbon atoms; more usually from about one to 25 carbon atoms; and may be from about three to 12 carbon atoms. Spacers of this type may also comprise heteroatoms or functional groups, including amines, ethers, phosphodiesters, and the like. Specific structures of interest include: $(CH_2CH_2O)n$ where n is from 1 to about 12; $(CH_2CH_2NH)n$, where n is from 1 to about 12; $[(CH_2)n(C=O)NH(CH_2)_m]_z$, where n and m are from 1 to about 6, and z is from 1 to about 10; $[(CH_2)nOPO_3(CH_2)_m]_z$ where n and m are from 1 to about 6, and z is from 1 to about 10. Such linkers may include polyethylene glycol, which may be linear or branched.

In particular embodiments, the liver-specific Wnt signal enhancing molecule, or a pharmaceutically acceptable salt thereof, comprises a first domain that specifically binds one or more transmembrane E3 ubiquitin ligases selected from Zinc and Ring Finger 3 (ZNRF3) and Ring Finger Protein 43 (RNF43), and a second domain that specifically binds asialoglycoprotein receptor 1 (ASGR1) and/or asialoglycoprotein receptor 2 (ASGR2), wherein: (a) the first domain comprises an Rspo sequence or fragment or variant thereof; and/or (b) the second domain comprises an antibody or antigen-binding fragment thereof comprising: (i) CDRH1, CDRH2 and CDRH3 sequences set forth herein; and/or (ii) CDRL1, CDRL2 and CDRL3 sequences set forth herein, or a variant of said antibody, or antigen-binding fragment thereof, comprising one or more amino acid modifications, wherein said variant comprises less than 8 amino acid substitutions in said CDR sequences. In particular embodiments, it comprises a polypeptide having at least 80%, at least 85%, at least 90%, at least 95%, at least 98%, or at least 99% identity to any of SEQ ID NOs:1-29. It particular embodiments, the polypeptide includes the CDR sequences identified in any of SEQ ID NOs:1-46 or 51, or any other sequence disclosed herein.

An action module or targeting module, e.g., an antibody or antigen-binding fragment thereof, that "specifically binds to" or is "specific for" a particular cell surface polypeptide or receptor is one that binds to that particular polypeptide or receptor without substantially binding to any other polypeptide or polypeptide epitope. In some embodiments, the action modules and targeting modules of the present disclosure specifically bind to ZNRF3/RNF43 or a liver-specific cell surface molecule (e.g., receptor), respectively, with dissociation constants ($K_d$) equal to or lower than 1000 nM, equal to or lower than 100 nM, equal to or lower than 10 nM, equal to or lower than 1 nM, equal to or lower than 0.5 nM, equal to or lower than 0.1 nM, equal to or lower than 0.01 nM, equal to or lower than 0.005 nM, equal to or lower than 0.001 nM, or equal to or lower than 0.0005 nM, when measured at a temperature of about 4° C., 25° C., 37° C. or 42° C. Affinities of binders, e.g., antibodies, can be readily determined using conventional techniques, for example, those described by Scatchard et al. (Ann. N. Y. Acad. Sci. USA 51:660 (1949), ELISA assays, biolayer interferometry (BLI) assays, and surface plasmon resonance (SPR) assays). Binding properties of an antibody to antigens, cells or tissues thereof may generally be determined and assessed using immunodetection methods including, for example, immunofluorescence-based assays, such as immuno-histochemistry (IHC) and/or fluorescence-activated cell sorting (FACS).

In certain embodiments, the action module and/or the targeting module of the liver-specific Wnt signal enhancing molecule are polypeptides, whereas in other embodiments, the action module and/or the targeting module of the liver-specific Wnt signaling molecule are small organic molecules. In certain embodiments, the action module and the targeting module are both polypeptides, e.g., antibodies or antigen binding fragments thereof. In certain embodiments, the action module and the targeting module of a liver-specific Wnt signal enhancing molecule are covalently bound to each other. In certain embodiments, the action module and the targeting module of a liver-specific Wnt signal enhancing fusion molecule are non-covalently bound to each other. In certain embodiments, the action module and the targeting module of a liver-specific Wnt signal enhancing molecule are present within the same fusion protein. In other embodiments, the action module is present within a first polypeptide further comprising a first binding domain, and the targeting module is present within a second polypeptide further comprising a second binding domain, wherein the first and second binding domain bind to each other. In some embodiments, the first and second binding domain are the same or variants thereof, such as, e.g., an Fc polypeptide. In some embodiments, the first and second binding domain are different from each other. In particular embodiments, the present invention includes the use of fragments or variants of any of the targeting modules or action modules described herein, including functional fragments or variants of the reference molecule.

In certain embodiments, a liver-specific Wnt signal enhancing molecule (e.g., a fusion protein) has a formula selected from: $R_1$-L-$R_2$, and $R_2$-L-$R_1$, wherein $R_1$ is an action module that binds ZNRF3/RNF43, $R_2$ is a targeting module that binds a liver-specific cell surface receptor, and L is a linker, and wherein L may be absent or present. Each of $R_1$ and R2 may be any of the various action modules and targeting modules described herein, respectively. Each of $R_1$ and $R_2$ may be any moiety capable of binding to one or more of the E3 ligases (ZNRF3 or RNF43), or targeted tissue or cell, respectively. For example, each of $R_1$ and $R_2$ may be, but are not limited to, a moiety selected from: a polypeptide (e.g., an antibody or antigen-binding fragment thereof or a peptide or polypeptide different from an antibody), a small molecule, and a natural ligand or a variant, fragment or derivative thereof. In certain embodiments, the natural ligand is a polypeptide, a small molecule, an ion, an amino acid, a lipid, or a sugar molecule. The action module and the targeting module (i.e., $R_1$ and $R_2$) may be the same type of moiety as each other, or they may be different types of moieties. In particular embodiments, $R_2$ is an antibody of antigen-binding fragment thereof, and in certain embodiments, $R_2$ comprises an Fc protein or analog thereof.

In certain embodiments, a liver-specific Wnt signal enhancing molecule comprises a single molecule (e.g., polypeptide), whereas in other embodiments, a Wnt signal enhancing fusion molecule comprises two or more molecules (e.g., polypeptides) bound to each other, e.g., non-covalently bound to each other. For example, in one embodiment, a liver-specific Wnt signal enhancing fusion comprises two molecules having formulas $R_3$-$L_1$ and $R_4$-$L_2$, respectively, wherein $R_3$ is an action module, $R_4$ is a targeting module, and wherein the $L_1$ and $L_2$ groups bind to each other, e.g., to form a dimer. In various embodiments, the $L_1$ and $L_2$ groups are the same as each other or different from one another. One example of an $L_1$ or $L_2$ group is an Fc sequence, e.g., murine Fc2b or human Fc1, each of which is known in the art. Each of $R_3$ and $R_4$ may be any of the various action modules and targeting modules described herein, respectively. Each of $R_3$ and $R_4$ may be any moiety capable of binding to one or more of the E3 ligases (ZNRF3 and/or RNF43), or targeted tissue or cell, respectively.

In particular embodiments, a liver-specific Wnt signal enhancing molecule comprises an antibody or binding fragments thereof that binds one or more of the E3 ligases (ZNRF3 and/or RNF43), wherein the antibody heavy chain and/or the antibody light chain comprises an appended binding domain that binds a targeted tissue or cell.

In particular embodiments, a liver-specific Wnt signal enhancing molecule comprises an antibody, or one or more binding fragment thereof, that binds a targeted tissue or cell, wherein the antibody heavy chain and/or the antibody light chain comprises an appended binding domain that binds one or more of the E3 ligases (ZNRF3 and/or RNF43). The appended binding domain may be directly fused to the N-terminus or C-terminus of the antibody, e.g., as a heavy chain or light chain fusion protein, or it may be appended to the heavy chain or light chain via a linker moiety, e.g., to the N-terminus, C-terminus, or an internal amino acid of the heavy chain or light chain. In certain embodiments, the antibody is an IgG, e.g., an IgG1 or IgG2. In certain embodiments, the liver-specific Wnt signal enhancing molecule comprises four polypeptides, including two antibody light chains and two antibody heavy chains, wherein one or more of the antibody heavy chains, and/or the antibody lights chains further comprise an appended binding domain that binds one or more of the E3 ligases (ZNRF3 and/or RNF43), such as an Rspo2 variant disclosed herein. In particular embodiments, the appended binding domain is linked to one or both of the antibody heavy chains and/or light chains (or binding fragments thereof) via a linker, such as any disclosed herein. In certain embodiments, the two antibody heavy chains are linked via one or more disulfide bonds, and each of the antibody light chains is linked to a different antibody heavy chain via one or more disulfide bond. In particular embodiments, each of the light chains in the antibody-like Wnt signal enhancing molecule are the same. In particular embodiments, each of the heavy chains in the antibody-like Wnt signal enhancing molecule are the same. In particular embodiments, each of the light chains in the antibody-like Wnt signal enhancing molecule are different. In particular embodiments, each of the heavy chains in the antibody-like Wnt signal enhancing molecule are different. In particular embodiments, the Wnt signal enhancing molecule comprises two different light chains and/or two different heavy chains that each bind different liver-specific cell surface molecules. In particular embodiments, the Wnt signal enhancing molecule comprises two different light chains and/or two different heavy chains that each bind different E3 ligases. In various embodiments, the binding domain is appended to either the heavy chain or light chain. In particular embodiments, a liver-specific Wnt signal enhancing molecule comprises two antibody light chains and two antibody heavy chains of an antibody that specifically binds to a liver-specific cell surface molecule, e.g., ASGR1 or ASGR2, wherein a binding domain that binds one or more of the E3 ligases (ZNRF3 and/or RNF43) is appended to the N-terminus of the two antibody heavy chains. In particular embodiments, the binding domain that binds one or more of the E3 ligases is an Rspo or a fragment or variant thereof. In certain embodiments, the Rspo has at least 90%, at least 95%, at least 98%, or at least 99% sequence identity to any one of SEQ ID NOs:29-32 or SEQ ID NOs:47-50, or a fragment thereof. In particular embodiments, the liver-specific Wnt signal enhancing molecule comprises two heavy chain fusion proteins and two light chain fusion proteins disclosed in Table A, e.g., the liver-specific Wnt signal enhancing molecule is 1R34-DDNN/RA, 8M24-v1, 1R34-EEST/EE, 1R34-EEST/RA, 1R34-EEAT/EE, 8M24 humanized 1, 8M24 humanized 2, 8M24-EASE-RA, 8M24-EASE-EE, or 1R34-DDNN/RA.

In certain embodiments, a liver-specific Wnt signal enhancing molecule, or a pharmaceutically acceptable salt thereof, comprises a first domain that specifically binds one or more transmembrane E3 ubiquitin ligases selected from Zinc and Ring Finger 3 (ZNRF3) and Ring Finger Protein 43 (RNF43), and a second domain that specifically binds asialoglycoprotein receptor 1 (ASGR1), wherein:
(a) the first domain comprises a modified R-spondin polypeptide or a fragment or variant thereof; and
(b) the second domain comprises a modified antibody or antigen-binding fragment thereof comprising: CDRH1, CDRH2 and CDRH3 sequences; and CDRL1, CDRL2 and CDRL3 sequences.

In particular embodiments, the second domain comprises two modified antibody light chains and two modified antibody heavy chains, wherein the first domain is appended to the N-terminus of each of the antibody heavy chain. Thus, in particular embodiments, the Wnt signal enhancing molecules comprise two modified antibody light chains derived from an antibody that binds to ASGR1 and two fusion proteins, each fusion protein comprising a modified antibody heavy chain derived from the antibody that binds to ASGR1 with an R-spondin polypeptide (or fragment thereof) fused to its N-terminus, optionally via a linker moiety. In particular embodiments, the R-spondin polypeptide is a modified R-spondin polypeptide, e.g., a modified Rspo-2 polypeptide comprising one or more amino acid modifications as compared to wild type human Rspo-2.

In certain embodiments, the modified R-spondin polypeptide or fragment or variant thereof comprises amino acid substitutions at positions corresponding to amino acids F105 and F109 of human R-spondin 2. In certain embodiments the two amino acid substitutions include: (a) F105R, F105A, or F105E; and (b) F109A or F109E. In particular embodiments, the two amino acid substitutions are: (a) F105R and F109A; (b) F105A and F109A; (c) F105E and F109A; or (d) F105E and F109E. In certain embodiments, the modified R-spondin polypeptide or fragment or variant thereof has at least 80%, at least 85%, at least 90%, at least 95%, at least 98%, at least 99%, or 100% sequence identity to any of the following:

(SEQ ID NO: 29)
NPICKGCLSCSKDNGCSRCQQKLFFFLRREGMRQYGECLHSCPSGYYGH
RAPDMNRCARCRIENCDSC<u>R</u>SKD<u>A</u>CTKCKVGFYLHRGRCFDECPDGFAP
LEETMECVE;

(SEQ ID NO: 30)
NPICKGCLSCSKDNGCSRCQQKLFFFLRREGMRQYGECLHSCPSGYYGH
RAPDMNRCARCRIENCDSC<u>A</u>SKD<u>A</u>CTKCKVGFYLHRGRCFDECPDGFAP
LEETMECVE;

(SEQ ID NO: 31)
NPICKGCLSCSKDNGCSRCQQKLFFFLRREGMRQYGECLHSCPSGYYGH
RAPDMNRCARCRIENCDSC<u>E</u>SKD<u>A</u>CTKCKVGFYLHRGRCFDECPDGFAP
LEETMECVE:
or (SEQ ID NO: 32)
NPICKGCLSCSKDNGCSRCQQKLFFFLRREGMRQYGECLHSCPSGYYGH
RAPDMNRCARCRIENCDSC<u>E</u>SKD<u>E</u>CTKCKVGFYLHRGRCFDECPDGFAP
LEETMECVE.

In particular embodiments, the modified antibody heavy chain derived from the antibody that binds to ASGR1 is fused to the modified R-spondin polypeptide via a linker moiety, including any of those disclosed herein. In particular embodiments, the linker moiety is a peptidyl linker comprising or having the following sequence: GGGGSGGGGSGGGGS (SEQ ID NO: 62).

In particular embodiments, the modified heavy chain variable region comprises a sequence having at least 90% or at least 95% identity to any one of SEQ ID NOs:2, 4, 6, 8, 10, 12, 13, 14, 15, 16, 20, 22, 24, 26, 28, 33, or 51. In particular embodiments, the modified light chain variable region comprises a sequence having at least 90% or at least 95% identify to any one of SEQ ID NOs:1, 3, 5, 7, 9, 11, 14, 17, 18, 19, 21, 23, 25, or 27. In particular embodiments, the amino acid modifications, e.g., insertions, deletions, or substitutions, are not present with in a CDR. In particular embodiments, the amino acid modifications do not occur at any of (a) F105R, F105A, or F105E; and/or (b) F109A or F109E.

In particular embodiments, the modified heavy chain comprises a sequence having at least 90% or at least 95% identity to any one of SEQ ID NOs: 2, 6, 8, 10, 12, 22, 26, or 33, or a fragment thereof comprising the heavy chain sequence or heavy chain variable domain sequence (e.g., absent the RSPO2 and linker sequences). In particular embodiments, the modified light chain comprises a sequence having at least 90% or at least 95% identify to any one of SEQ ID NOs:1, 5, 7, 9, 11, 21, or 25. In particular embodiments, the amino acid modifications, e.g., insertions, deletions, or substitutions, are not present with in a CDR. In particular embodiments, the amino acid modifications do not occur at any of(a) F105R, F105A, or F105E; and/or (b) F109A or F109E. In particular embodiments, variants of the heavy chain comprise N297G. In particular embodiments, the RPOS2 sequences present in the variants comprise the F105R and F109A substitutions. In particular embodiments, the RPOS2 sequences present in the variants comprise the F105E and F109E substitutions. In particular embodiments, the molecules comprise the amino acid substitutions as compared to parental or wild type for any of the following constructs: EEST/EE, EEST/RA, EEAT/EE, EESN/RA, EEAN/RA, 8M24-EAASE-RA, or 8M24-EASE-EE.

In particular embodiments, the two fusion polypeptides each comprise a sequence having at least 95% identity to any one of SEQ ID NOs: 2, 4, 6, 8, 10, 12, 13, 14, 15, 16, 20, 22, 24, 26, 28, 33, or 51.

In certain embodiments, the modified heavy chain and modified light chain sequences are derived from an anti-ASGR1 antibody comprising the following heavy chain and light chain sequences or have at least 90%, at least 95%, at least 98%, or at least 99% identity to the following heavy chain and light chain sequences (shown with CDRs underlined):

(SEQ ID NO: 1)
SSELTQDPAVSVALGQTVRITC<u>QGDSLRSYYAS</u>WYQQKPGQAPVLVIY<u>G</u>

<u>KNNRPSGIPDRFSGSSSGNTASLTITGAQAEDEADYYC</u><u>NSLERIGYLSY</u>

VFGGGTKLTVLGQPKAAPSVTLFPPSSEELQANKATLVCLISDFYPGAV

TVAWKADSSPVKAGVETTTPSKQSNNKYAASSYLSLTPEQWKSHRSYSC

QVTHEGSTVEKTVAPTECS;
and

Heavy chain:
(SEQ ID NO: 33)
EVQLLESGGGLVQPGGSLRLSCAASGFTFS<u>SYAMS</u>WVRQAPGKGLEWVS <u>AISGSGGSTYYADSVKGRFTISRDNSKNTLYLQMNSLRAEDTAVYYCAK</u>

<u>DFSSRRWYLEYWGQGTLVTVSSASTKGPSVFPLAPSSKSTSGGTAALGC</u>

LVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFL

FPPKPKDTLMISRTPEVTCVVVDVSHEDPEVKFNWYVDGVEVHNAKTKP

-continued

REEQYGSTYRVVSVLTVLHQDWLNGKEYKCKVSNKALPAPIEKTISKAK

GQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQ

KSLSLSPGK.

In particular embodiments, the light chain comprises an amino acid substitution at one or more amino acid positions selected from D25, N51, and N88 (shown in bold above). In particular embodiments, all three positions are substituted. In certain embodiments, D25 is substituted with E. In certain embodiments, N51 is substituted with S or A. In certain embodiments, N88 is substituted with T. In one embodiment, D25 is substituted with E, N51 is substituted with S, and N88 is substituted with T (EST). In one embodiment, D25 is substituted with E, N51 is substituted with A, and N88 is substituted with T (EAT). In particular embodiments, any of the Wnt signal enhancing molecules disclosed herein comprises a light chain variable domain having at least 90%, at least 95%, at least 98%, or at least 99% identity to the variable domain of SEQ ID NO:1, optionally further comprising an amino acid substitution at one or more amino acid positions selected from D25, N51, and N88, including any of the substitutions disclosed above.

In particular embodiments, the heavy chain comprises an amino acid substitution at D62 (shown in bold above). In certain embodiments, D62 is substituted with E (E). In particular embodiments, any of the Wnt signal enhancing molecules disclosed herein comprises a heavy chain variable domain having at least 90%, at least 95%, at least 98%, or at least 99% identity to the variable domain of SEQ ID NO:33, optionally further comprising an amino acid substitution at D62, including any of the substitutions disclosed above.

In particular embodiments, the modified antibody portion of the molecule (or variable domain thereof) comprises the following combination of amino acid substitutions: (a) in the heavy chain, D62 is substituted with E; and (b) in the light chain, D25 is substituted with E, N51 is substituted with S, and N88 is substituted with T (EEST). In particular embodiments, the modified antibody portion of the molecule (or variable domain thereof) comprises the following combination of amino acid substitutions: (a) in the heavy chain, D62 is substituted with E; and (b) in the light chain, D25 is substituted with E, N51 is substituted with A, and N88 is substituted with T (EEAT).

Thus, in certain embodiments, the modified anti-ASGR1 antibody portion of the molecule comprises any of the following combinations of CDRH1, CDRH2, CDRH3, CDRL1, CDRL2, and CDRL3 sequences:

(a)

SYAMS, (SEQ ID NO: 34)

AISGSGGSTYYEDSVKG, (SEQ ID NO: 35)

DFSSRRWYLEY, (SEQ ID NO: 36)

QGESLRSYYAS, (SEQ ID NO: 37)

YGKSNRPS, (SEQ ID NO: 38)
and

CTSLERIGYLSYV, respectively; (SEQ ID NO: 39)
or (b)

SYAMS, (SEQ ID NO: 34)

AISGSGGSTYYEDSVKG, (SEQ ID NO: 35)

DFSSRRWYLEY, (SEQ ID NO: 36)

QGESLRSYYAS, (SEQ ID NO: 37)

YGKANRPS, (SEQ ID NO: 40)
and

CTSLERIGYLSYV, respectively. (SEQ ID NO: 39)

In certain embodiments, the modified anti-ASGR1 antibody portion of the molecule comprises the VH and VL domains comprising any of these combinations of CDRs in the context of the parental sequence, or a variant thereof having at least 80%, at least 85%, at least 90%, at least 95%, at least 98%, or at least 99% identity to the VH or VL domain. In particular embodiments, any of the variants disclosed herein do not comprise any additional amino acid modifications in their CDR sequences (other than those described herein).

In particular embodiments, the two antibody light chain polypeptides comprise a sequence having at least 95% identity to any one of SEQ ID NOs: 1, 5, 7, 9, 11, 21, 25, or a variable region thereof.

In certain embodiments, the two antibody light chain polypeptides comprise a sequence having at least 95% identity to SEQ ID NO:1 or a variable region thereof, and the two fusion polypeptides each comprise a sequence having at least 95% identity to SEQ ID NO:2 or a variable region thereof.

In certain embodiments, the two antibody light chain polypeptides comprise a sequence having at least 95% identity to SEQ ID NO:7 or a variable region thereof, and the two fusion polypeptides each comprise a sequence having at least 95% identity to SEQ ID NO:8 or a variable region thereof.

In certain embodiments, the two antibody light chain polypeptides comprise a sequence having at least 95% identity to SEQ ID NO:7 or a variable region thereof, and the two fusion polypeptides each comprise a sequence having at least 95% identity to SEQ ID NO:10 or a variable region thereof.

In certain embodiments, the two antibody light chain polypeptides comprise a sequence having at least 95% identity to SEQ ID NO:11 or a variable region thereof, and the two fusion polypeptides each comprise a sequence having at least 95% identity to SEQ ID NO:12 or a variable region thereof.

In particular embodiments, the two fusion polypeptides each comprise a sequence having at least 95% identity to any one of SEQ ID NOs: 2, 4, 6, 8, 10, 12, 13, 14, 15, 16, 20, 22, 24, 26, 28, 33, or 51, or a variable region thereof.

In certain embodiments, the modified heavy chain and modified light chain sequences are derived from the 8M24 anti-ASGR1 antibody comprising the following heavy chain and light chain sequences or have at least 90%, at least 95%, at least 98%, or at least 99% identity to the following heavy chain and light chain sequences (shown with CDRs underlined):

(SEQ ID NO: 5)
DIQMTQSPSSLSASVGDRVTITC<u>RISENIYSNLA</u>WYQQKPGKAPKLLIY

<u>AAINLAD</u>GVPSRFSGSGSGTDFTLTISSLQPEDFATYYC<u>QHFWGTPFTF</u>

GQGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

Heavy chain:
(SEQ ID NO: 51)
EVQLVQSGAEVKKPGSSVKVSCKASGYTFTNYGINWVRQAPGQGLEWMG <u>EIFPRSDNTFYAQKFQ</u>GRVTITADKSTSTAYMELSSLRSEDTAVYYCAR <u>KGRDYGTSHYFDY</u>WGQGTTVTVSSASTKGPSVFPLAPSSKSTSGGTAAL

GCLVKDYFPEPVTVSWNSGALTSGVHTFPAVLQSSGLYSLSSVVTVPSS

SLGTQTYICNVNHKPSNTKVDKKVEPKSCDKTHTCPPCPAPELLGGPSV

FLFPPKPKDTLMISRTPEVTCVVVDVSHEDPEVKFNWYVDGVEVHNAKT

KPREEQYGSTYRVVSVLTVLHQDWLNGKEYKCKVSNKALPAPIEKTISK

AKGQPREPQVYTLPPSREEMTKNQVSLTCLVKGFYPSDIAVEWESNGQP

ENNYKTTPPVLDSDGSFFLYSKLTVDKSRWQQGNVFSCSVMHEALHNHY

TQKSLSLSPGK.

In particular embodiments, the light chain comprises an amino acid substitution at amino acid position D56 (shown in bold above). In certain embodiments, D56 is substituted with E, S, or A. In particular embodiments, D56 is substituted with E (E). In particular embodiments, any of the Wnt signal enhancing molecules disclosed herein comprises a light chain variable domain having at least 90%, at least 95%, at least 98%, or at least 99% identity to the variable domain of SEQ ID NO:5, optionally further comprising an amino acid substitution at D56, including any of the substitutions disclosed above.

In particular embodiments, the heavy chain comprises an amino acid substitution at one or more amino acid positions selected from N31, N57, or D102 (shown in bold above). In particular embodiments, all three positions are substituted. In certain embodiments, N31 is substituted with A or Q. In certain embodiments, N57 is substituted with S, A, or N. In certain embodiments, D102 is substituted with E, S, or A. In one embodiment, N31 is substituted with A, N57 is substituted with S, and D102 is substituted with E (ASE). In particular embodiments, N31 is substituted with A, N57 is substituted with S, D102 is substituted with E, and D110 is not substituted (ASED). In particular embodiments, any of the Wnt signal enhancing molecules disclosed herein comprises a heavy chain variable domain having at least 90%, at least 95%, at least 98%, or at least 99% identity to the variable domain of any one of SEQ ID NOs:20, 22, or 51, optionally further comprising an amino acid substitution at one or more amino acid positions selected from N31, N57, or D102, including any of the substitutions disclosed above.

In particular embodiments, the modified antibody portion of the molecule comprises the following combination of amino acid substitutions: (a) in the light chain, D56 is substituted with E; and (b) in the heavy chain, N31 is substituted with A, N57 is substituted with S, D102 is substituted with E, and D110 is not substituted (EASE).

Thus, in certain embodiments, the modified anti-ASGR1 antibody portion of the molecule comprises the following combination of CDRH1, CDRH2, CDRH3, CDRL1, CDRL2, and CDRL3 sequences:

(SEQ ID NO: 41)
RISENIYSNLA, (SEQ ID NO: 42)
AAINLAE, (SEQ ID NO: 43)
QHFWGTPFT, (SEQ ID NO: 44)
AYGIN, (SEQ ID NO: 45)
EIFPRSDSTFYNEKFKG,
and (SEQ ID NO: 46)
KGREYGTSHYFDY, respectively.

In certain embodiments, the modified anti-ASGR1 antibody portion of the molecule comprises the VH and VL domains comprising any of these combinations of CDRs in the context of the parental sequence, or a variant thereof having at least 80%, at least 85%, at least 90%, at least 95%, at least 98%, or at least 99% identity to the VH or VL domain. In particular embodiments, the variants do not comprise any additional amino acid modifications in their CDR sequences (other than those described herein).

In certain embodiments, the two antibody light chain polypeptides, or variable domains thereof, comprise a sequence having at least 90% or at least 95% identity to any one of SEQ ID NOs: 3, 5, 14, 17, 18, 19, 21, or 25, or a variable region thereof. In certain embodiments, the two fusion polypeptides, or antibody heavy chain polypeptides or variable domains thereof, each comprise a sequence having at least 90% or at least 95% identity to any one of SEQ ID NOs: 4, 6, 13, 15, 16, 20, 22, or 26, or a variable region thereof. In particular embodiments, the two antibody light chain polypeptides each comprise a sequence having at least 95% identity to SEQ ID NO:25 or a variable region thereof, and the two fusion polypeptides each comprise a sequence having at least 95% identity to SEQ ID NO:26, or a variable region thereof.

In certain embodiments, the light chain polypeptide comprises the sequence:

(SEQ ID NO: 25)
DIQMTQSPSSLSASVGDRVTITC<u>RISENIYSNLA</u>WYQQKPGKAPKLLIY

<u>AAINLAE</u>GVPSRFSGSGSGTDFTLTISSLQPEDFATYYC<u>QHFWGTPFTF</u>

GQGTKLEIK, wherein the CDR sequences are underlined; and in certain embodiments, the heavy chain fusion polypeptide comprises the sequence:

(SEQ ID NO: 26)
*NPICKGCLSCSKDNGCSRCQQKLFFFLRREGMRQYGECLHSCPSGYYGH*

*RAPDMNRCARCRIENCDSC<u>R</u>SKD<u>A</u>CTKCKVGFYLHRGRCFDECPDGFA*

-continued

*PLEETMECVE*GGGGSGGGGSGGGGSEVQLVQSGAEVKKPGSSVKVSCKA

SGYTFT<u>AYGINW</u>VRQAPGQGLEWMG<u>EIFPRSDSTFYAQKFQ</u>GRVTITAD

KSTSTAYMELSSLRSEDTAVYYCAR<u>KGREYGTSHYFDYW</u>GQGTTVTVSS, wherein the Rspo2 domain is italicized, the linker is in bold, and the CDR sequences are underlined. In related embodiments, the R and A shown in bold are replaced with E and E.

It is understood that the Wnt signal enhancing molecules may comprise various combinations of action modules and targeting modules. Thus, any of the variant anti-ASGR1 antibody sequences (or fragments thereof) nay be combined with various other action modules, including but not limited to any disclosed herein.

The present disclosure further provides polypeptides comprising any of the light chains or fusion polypeptides disclosed herein, and polypeptides comprising a sequence having at least 80%, at least 85%, at least 90%, at least 95%, at least 98%, or at least 99% sequence identity to any of the light chains or fusion polypeptides disclosed herein, as well as functional or binding fragments thereof, e.g., VH or VL domains. The skilled artisan can readily determine the light chain region of any of the polypeptides disclosed herein based on the information provided in the table of sequences, and by comparing these sequences to others disclosed herein.

In certain embodiments, the liver-specific Wnt signal enhancing molecules (e.g., fusion proteins) increase Wnt signaling in a liver tissue or liver cell contacted with the fusion protein. In particular embodiments, Wnt signaling in the liver tissue or liver cell is increased by at least 50%, at least two-fold, at least three-fold, at least four-fold, at least five-fold, or at least ten-fold.

Liver-specific Wnt signal enhancing molecules may be produced by standard methods of organic synthesis and molecular biology known and available in the art. For example, a liver-specific Wnt signal enhancing fusion protein may be generated by fusing a targeting module (e.g., an antibody or antigen-binding fragment thereof that bind ASGR1 or ASGR2) to an action module (e.g., human R-spondin 2 Furin domain 1 alone, corresponding to amino acid residues N37-R95, or human R-spondin 2 Furin domain 1 followed by a Furin domain 2, in which the Furin domain 2 interaction with the LGR proteins is abolished or compromised by point mutations, e.g., F105A and F109A, singly or in combination). In certain embodiments, the targeting module and action module are fused by a linker, e.g., a glycine-serine linker, with either domain located at the N-terminus of the liver-specific Wnt signal enhancing molecule. In certain embodiments, the targeting module and action module are fused by a protein linker (e.g., albumin). Additional ways of "fusing" the targeting module with the action module include, but are not limited to, "knob-in-hole" or leucine zipper mediated dimerization, for example. DNA sequences encoding the targeting module, the action module (and, optionally, a linker) may be genetically engineered to encode the desired fusion protein.

For liver-specific Wnt signal enhancing molecules and domains thereof (e.g., fusion molecules, antibody heavy and light chains), the DNA sequences encoding different parts of the fusion proteins may be inserted into bacterial or eukaryotic expression vectors using standard molecular cloning techniques, and expressed in appropriate host cells. The expressed proteins may be purified to homogeneity using standard techniques in protein science such as affinity, ion-exchange, and size-exclusion chromatography. The present disclosure also includes functional fragments and variants of any of the polypeptide action modules, targeting modules, and fusion proteins described herein, including variants having at least 50%, at least 60%, at least 70%, at least 80%, at least 85%, at least 90%, at least 95%, at least 98% or at least 99% polypeptide sequence identity to an action module, targeting module, or fusion protein described herein. Such variants may comprise one or more amino acid modifications as compared to any of the sequences disclosed herein, e.g., one or more amino acid deletion, insertion or substitution. In particular embodiments, functional fragments and variants of liver-specific Wnt signal enhancing fusion proteins have at least 5%, at least 10%, at least 20%, at least 30%, at least 40%, at least 50%, at least 60%, at least 70%, at least 80% at least 90% at least 100% or more Wnt signal enhancing activity as compared to the liver-specific Wnt signal enhancing fusion protein from which they were derived. In certain embodiments, functional fragments and variants of polypeptide action modules have at least 5%, at least 10%, at least 20%, at least 30%, at least 40%, at least 50%, at least 60%, at least 70%, at least 80% at least 90% at least 100% or more Wnt signal enhancing activity as compared to the action module from which they were derived (when measured in the context of the entire liver-specific Wnt signal enhancing molecule). In certain embodiments, functional fragments and variants of targeting modules have at least 5%, at least 10%, at least 20%, at least 30%, at least 40%, at least 50%, at least 60%, at least 70%, at least 80% at least 90% at least 100% or more binding activity as compared to the targeting module from which they were derived.

The present disclosure also includes polynucleotides or nucleic acid sequences that encode one or more liver-specific Wnt signal enhancing molecules or components thereof, e.g., proteins, fusion proteins or variants thereof, described herein, and vectors comprising these polynucleotides, including expression vectors, and cells comprising these vectors. In certain embodiments, the polynucleotides or nucleic acid sequences are DNA or RNA. In particular embodiments, the RNA is messenger RNA (mRNA). In certain embodiments, the RNA is a modified mRNA comprising one or more modified nucleosides. Modified mRNAs comprising one or more modified nucleoside have been described as having advantages over unmodified mRNAs, including increase stability, higher expression levels and reduced immunogenicity. Non-limiting examples of modified mRNAs that may be used according to the present invention are described, e.g., in PCT Patent Application Publication Nos. WO2011/130624, WO2012/138453, WO2013052523, WO2013151666, WO2013/071047, WO2013/078199, WO2012045075, WO2014081507, WO2014093924, WO2014164253, US Patent Nos: U.S. Pat. No. 8,278,036 (describing modified mRNAs comprising pseudouridine), U.S. Pat. No. 8,691,966 (describing modified mRNAs comprising pseudouridine and/or N1-methylpseudouridine), U.S. Pat. No. 8,835,108 (describing modified mRNAs comprising 5-methylcytidine, U.S. Pat. No. 8,748,089 (describing modified mRNAs comprising pseudouridine or 1-methylpseudouridine). In particular embodiments, the modified mRNA sequence encoding the liver-specific Wnt signal enhancing polypeptide comprises at least one modification as compared to an unmodified A, G, U or C ribonucleoside. In particular embodiments, the at least one modified nucleosides include N1-methylpseudouridine and/ or 5-methylcytidine. In particular embodiments, the modified mRNA comprises a 5' terminal cap sequence followed by a sequence encoding the liver-specific Wnt signal enhancing polypeptide, following by a 3' tailing sequence, such as a polyA or a polyA-G sequence.

In particular embodiments, the polynucleotide is a vector, e.g., an expression vector, and the expression vector comprises a polynucleotide sequence encoding a liver-specific Wnt signal enhancing fusion molecule (e.g., a fusion protein or one or both chains of an appended antibody) described herein operably linked to a promoter sequence, e.g., a promoter sequence that drives expression of the polynucleotide in a cell. In certain embodiments, the vector is a viral vector, e.g., a virus comprising a polynucleotide comprising an expression cassette comprising a promoter operably linked to a DNA or RNA sequence encoding the liver-specific Wnt signal enhancing polypeptide. In particular embodiments, the expression cassette comprises 5' and/or 3' cellular or viral UTRs or the derivatives thereof.

The present disclosure also includes functional fragments and variants of the polynucleotides described herein, including variants having at least 50%, at least 60%, at least 70%, at least 80%, at least 85%, at least 90%, at least 95%, at least 98% or at least 99% polynucleotide sequence identity to a polynucleotide described herein. Such variants may comprise one or more nucleotide or nucleoside modifications as compared to any of the sequences disclosed herein, e.g., one or more nucleotide deletion, insertion or substitution. In particular embodiments, the polynucleotides described herein are codon-optimized, e.g., to enhance expression of the encoded polypeptide in a host cell. In particular embodiments, polynucleotide variants comprise one or more modified nucleotide or nucleoside.

The present disclosure also includes cells comprising a polynucleotide or vector that encodes a liver-specific Wnt signal enhancing molecule, e.g., fusion protein, or portion or domain thereof, described herein. In certain embodiments, the cell is a host cell, such as, e.g., an HEK293 cell that may be used to produce liver-specific Wnt signal enhancing fusion proteins. In preparing the subject compositions, any host cells may be employed, including but not limited to, for example, mammalian cells (e.g. 293 cells), insect cells (e.g., SF9 cells), microorganisms and yeast. In certain embodiments, the cells are heterologous or autologous to a subject treated with a liver-specific Wnt signal enhancing polypeptide described herein. In particular embodiments, the cells were obtained from the subject and transduced with a viral vector described herein. In particular embodiments, the transduced cells are delivered to the subject for treatment.

The present disclosure also includes pharmaceutical compositions comprising one or more liver-specific Wnt signal enhancing molecules (e.g., fusion proteins or antibody-based constructs), or one or more polynucleotides or vectors comprising sequences encoding a liver-specific Wnt signal enhancing molecule or portion thereof.

Wnt signaling may be measured using techniques and assays known and available in the art. In certain embodiments, an increase in Wnt signaling is determined using a cell line corresponding to a target tissue or cell type. In particular embodiments, the cell line contains a reporter plasmid with a marker gene (e.g., a luciferase gene) under the control of a Wnt signal-responsive promoter. Enhanced reporter activity of the cells in response to Wnt3a, Wnt3a conditioned media, recombinant sources of Wnt3a, or a Wnt mimetic agonist by the addition of either Furin domain 1 alone (or together with Furin domain 2, with the F105A and/or F109A point mutations) as a negative control or functional R-spondin (full length or Furin domains 1 and 2) as a positive control may be determined. Reporter activity in response to the liver-specific Wnt signal enhancing molecules may also be determined by contacting the reporter cell line with the tissue specific Wnt signal enhancing molecule. The negative control may be substantially, significantly, or completely negative for reporter activity, and the liver-specific Wnt signal enhancing molecule and positive control should show an increase in Wnt signaling response as an increase in reporter activity. Additional controls may include an anti-ASGR1 antibody alone (negative), a fusion protein in which an anti-GFP antibody is used in place of an anti-ASGR1 antibody (negative), and intact Furin domain 1-Furin domain 2 protein (positive). Tissue specificity of the liver-specific Wnt signal enhancing molecule may be determined by similarly measuring the reporter activity in response to treatment with the liver-specific Wnt signal enhancing molecule in cell types or tissues other than those targeted. In certain embodiments, reporter activity is higher in the targeted tissue bound by the liver-specific Wnt signal enhancing molecule as compared to non-targeted tissues, e.g., at least 50%, at least two-fold, at least three-fold, at least four-fold, at least five-fold, or at least ten-fold higher.

In particular embodiments, a liver-specific Wnt signal enhancing polypeptide comprises any combination of action module and targeting module, including any combination of any of the action modules and targeting modules described herein. In particular embodiments, they are joined by a linker, e.g., albumin (e.g., human serum albumin), a peptidyl linker, or a non-peptidyl linker, where the targeting and action modules are on the N- and C-termini of the linker, e.g., Fc or albumin, peptidyl linker, or non-peptidyl linker.

The liver-specific Wnt signal enhancing molecules can also be joined to a moiety such as a polyethylene glycol (PEG), Fe, albumin, etc. as known in the art to enhance stability in vivo.

One example of a liver-specific Wnt signal enhancing molecule is a Wnt signal enhancing polypeptide comprising an action module comprising a variant or fragment of an R-spondin (e.g., human R-spondin 2) having reduced ability to enhance Wnt signaling and a targeting module that specifically binds ASGR1, ASGR2, TFR2, or SLC10A1, wherein the tissue specific Wnt signal enhancing polypeptide increases Wnt signaling in liver tissue and may be used to treat a disease or condition of liver tissue.

Illustrative, non-limiting examples of liver-specific Wnt signal enhancing molecules include those described in the accompanying Examples and sequences. In particular embodiments, a liver-specific Wnt signal enhancing molecule comprises two or more polypeptide sequences disclosed herein, e.g., in the appended IgG or antibody format. Polypeptides disclosed herein include but are not limited to polypeptides comprising or consisting of a sequence having at least 80%, at least 85%, at least 90%, at least 95%, at least 98%, or at least 99% identity to any of the sequences set forth herein and fragments and variants thereof. In particular embodiments, polypeptides comprise the action module or targeting module present within any of the sequences set forth herein, and fragments and variants thereof. In certain embodiments, the polypeptides have activity as an action module and/or a targeting module.

Illustrative, non-limiting examples of polynucleotides disclosed herein include any that encode for any of the polypeptides, variants and fragments described herein, including those described above. In certain embodiments, the polynucleotides encode polypeptides that have activity as a functional domain and/or a targeting module.

Pharmaceutical Compositions

Pharmaceutical compositions comprising a liver-specific Wnt signal enhancing molecule or antibody or antigen-binding fragment thereof described herein and one or more pharmaceutically acceptable diluent, carrier, or excipient are also disclosed. In particular embodiments, the Wnt signal enhancing molecule is selected from any of those disclosed herein, or comprises any of the polypeptide sequences disclosed herein, e.g., the Wnt signal enhancing molecules referred to as EEST-EE, EEST-RA, EEAT-EE, or 8M24 EASE-EE or 8M24 EASE-RA.

In further embodiments, pharmaceutical compositions comprising a polynucleotide comprising a nucleic acid sequence encoding a liver-specific Wnt signal enhancing molecule or antibody or antigen-binding fragment thereof described herein described herein and one or more pharmaceutically acceptable diluent, carrier, or excipient are also disclosed. In certain embodiments, the polynucleotides are DNA or mRNA, e.g., a modified mRNA. In particular embodiments, the polynucleotides are modified mRNAs further comprising a 5' cap sequence and/or a 3' tailing sequence, e.g., a polyA tail. In other embodiments, the polynucleotides are expression cassettes comprising a promoter operatively linked to the coding sequences.

In further embodiments, pharmaceutical compositions comprising an expression vector, e.g., a viral vector, comprising a polynucleotide comprising a nucleic acid sequence encoding a liver-specific Wnt signal enhancing molecule or antibody or antigen-binding fragment thereof described herein described herein and one or more pharmaceutically acceptable diluent, carrier, or excipient are also disclosed.

The present invention further contemplates a pharmaceutical composition comprising a cell comprising an expression vector comprising a polynucleotide comprising a promoter operatively linked to a nucleic acid encoding a liver-specific Wnt signal enhancing molecule or antibody or antigen-binding fragment thereof described herein described herein and one or more pharmaceutically acceptable diluent, carrier, or excipient. In particular embodiments, the cell is a heterologous cell or an autologous cell obtained from the subject to be treated. In particular embodiments, the cell is a stem cell, e.g., an adipose-derived stem cell or a hematopoietic stem cell.

The subject molecules can be combined with pharmaceutically-acceptable carriers, diluents and reagents useful in preparing a formulation that is generally safe, non-toxic, and desirable, and includes excipients that are acceptable for mammalian, e.g., human or primate, use. Such excipients can be solid, liquid, semisolid, or, in the case of an aerosol composition, gaseous. Examples of such carriers or diluents include, but are not limited to, water, saline, Ringer's solutions, dextrose solution, and 5% human serum albumin. Supplementary active compounds can also be incorporated into the formulations. Solutions or suspensions used for the formulations can include a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates; detergents such as Tween 20 to prevent aggregation; and compounds for the adjustment of tonicity such as sodium chloride or dextrose. The pH can be adjusted with acids or bases, such as hydrochloric acid or sodium hydroxide. In particular embodiments, the pharmaceutical compositions are sterile.

Pharmaceutical compositions may further include sterile aqueous solutions or dispersions and sterile powders for the extemporaneous preparation of sterile injectable solutions or dispersion. For intravenous administration, suitable carriers include physiological saline, bacteriostatic water, or phosphate buffered saline (PBS). In some cases, the composition is sterile and should be fluid to the extent that easy syringability exists. In certain embodiments, it is stable under the conditions of manufacture and storage and is preserved against the contaminating action of microorganisms such as bacteria and fungi. The carrier can be, e.g., a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the internal compositions can be brought about by including in the composition an agent which delays absorption, for example, aluminum monostearate and gelatin.

Sterile solutions can be prepared by incorporating the liver-specific Wnt signal enhancing molecule in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

In one embodiment, the pharmaceutical compositions are prepared with carriers that will protect the fusion protein against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions can also be used as pharmaceutically acceptable carriers. These can be prepared according to methods known to those skilled in the art.

It may be advantageous to formulate the pharmaceutical compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser, e.g. syringe, e.g. a prefilled syringe, together with instructions for administration.

The pharmaceutical compositions of the invention encompass any pharmaceutically acceptable salts, esters, or salts of such esters, or any other compound which, upon administration to an animal comprising a human, is capable of providing (directly or indirectly) the biologically active liver-specific Wnt signal enhancing molecule.

The present invention includes pharmaceutically acceptable salts of the liver-specific Wnt signal enhancing molecules described herein. The term "pharmaceutically acceptable salt" refers to physiologically and pharmaceutically acceptable salts of the compounds of the invention: i.e., salts that retain the desired biological activity of the parent compound and do not impart undesired toxicological effects thereto. A variety of pharmaceutically acceptable salts are known in the art and described, e.g., in "Remington's Pharmaceutical Sciences", 17th edition, Alfonso R. Gennaro (Ed.), Mark Publishing Company, Easton, PA, USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in J. Pharm. Sci. 66: 2 (1977). Also, for a review on suitable salts, see "Handbook of Pharmaceutical Salts: Properties, Selection, and Use" by Stahl and Wermuth (Wiley-VCH, 2002).

Pharmaceutically acceptable base addition salts are formed with metals or amines, such as alkali and alkaline earth metals or organic amines. Metals used as cations comprise sodium, potassium, magnesium, calcium, and the like. Amines comprise N—N'-dibenzylethylenediamine, chloroprocaine, choline, diethanolamine, dicyclohexylamine, ethylenediamine, N-methylglucamine, and procaine (see, for example, Berge et al., "Pharmaceutical Salts," J. Pharma Sci., 1977, 66, 119). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

In some embodiments, the pharmaceutical composition provided herein comprise a therapeutically effective amount of a liver-specific Wnt signal enhancing molecule described herein in admixture with a pharmaceutically acceptable carrier, diluent and/or excipient, for example saline, phosphate buffered saline, phosphate and amino acids, polymers, polyols, sugar, buffers, preservatives and other proteins. Exemplary amino acids, polymers and sugars and the like are octylphenoxy polyethoxy ethanol compounds, polyethylene glycol monostearate compounds, polyoxyethylene sorbitan fatty, acid esters, sucrose, fructose, dextrose, maltose, glucose, mannitol, dextran, sorbitol, inositol, galactitol, xylitol, lactose, trehalose, bovine or human serum albumin, citrate, acetate, Ringer's and Hank's solutions, cysteine, arginine, carnitine, alanine, glycine, lysine, valine, leucine, polyvinylpyrrolidone, polyethylene and glycol. Preferably, this formulation is stable for at least six months at 4° C.

In some embodiments, the pharmaceutical composition provided herein comprises a buffer, such as phosphate buffered saline (PBS) or sodium phosphate/sodium sulfate, tris buffer, glycine buffer, sterile water and other buffers known to the ordinarily skilled artisan such as those described by Good et al. (1966) Biochemistry 5:467. The pH of the buffer may be in the range of 6.5 to 7.75, preferably 7 to 7.5, and most preferably 7.2 to 7.4.

Methods for Increasing Wnt Activity or Wnt Receptor Cell Surface Expression

Liver-specific Wnt signal enhancing molecules, exemplified herein with respect to fusion proteins, may be used to increase Wnt signaling in liver tissue or liver cells. In particular embodiments, the Wnt signaling is canonical Wnt signaling. Thus, in some aspects, the present invention provides a method for increasing or enhancing Wnt signaling in liver tissue or liver cells, comprising contacting the liver tissue or cell with an effective amount of a liver-specific Wnt signal enhancing molecule disclosed herein, wherein the molecule comprises a targeting module that binds to a cell surface receptor on the target tissue or cell in a tissue- or cell-specific manner. In particular embodiments, the Wnt signal enhancing molecule is selected from any of those disclosed herein, or comprises any of the polypeptide sequences disclosed herein, e.g., the Wnt signal enhancing molecules referred to as EEST-EE, EEST-RA, EEAT-EE, or 8M24 EASE-EE or 8M24 EASE-RA. In certain embodiments, the Wnt signal enhancing molecule is EEST-EE. In certain embodiments, the Wnt signal enhancing molecule is 8M24 EASE-EE or 8M2 EASE-RA. In some embodiments, contacting occurs in vitro, ex vivo, or in vivo, e.g., the subject liver-specific Wnt signal enhancing molecule is administered or provided to a subject. In particular embodiments, the cell is a cultured cell, and the contacting occurs in vitro.

In related aspects, the present invention provides a method for increasing Wnt signaling in a liver tissue or cells, comprising contacting the target tissue or cell with an effective amount of one or more polynucleotide comprising a nucleic acid sequence encoding a liver-specific Wnt signal enhancing molecule disclosed herein, wherein the molecule comprises a targeting module that binds to a cell surface receptor on the target tissue or cell in a tissue- or cell-specific manner. In particular embodiments, the Wnt signal enhancing molecule is selected from any of those disclosed herein, or comprises any of the polypeptide sequences disclosed herein, e.g., the Wnt signal enhancing molecules referred to as EEST-EE, EEST-RA, EEAT-EE, or 8M24 EASE-EE or 8M24 EASE-RA. In certain embodiments, the polynucleotides are DNA or mRNA, e.g., a modified mRNA. In particular embodiments, the Wnt signal enhancing molecule is EEST-EE. In certain embodiments, the Wnt signal enhancing molecule is 8M24 EASE-EE or 8M2 EASE-RA. In certain embodiments, the polynucleotides are modified mRNAs further comprising a 5' cap sequence and/or a 3' tailing sequence, e.g., a polyA tail. In other embodiments, the polynucleotides are expression cassettes comprising a promoter operatively linked to the coding sequences.

In related aspects, the present invention provides a method for increasing Wnt signaling in liver tissue or cells, comprising contacting the target tissue or cell with an effective amount of one or more vector comprising a nucleic acid sequence encoding a liver-specific Wnt signal enhancing molecule of the present invention, wherein the molecule comprises a targeting module that binds to a cell surface receptor on the liver tissue or cell in a liver-specific manner. In particular embodiments, the Wnt signal enhancing molecule is selected from any of those disclosed herein, or comprises any of the polypeptide sequences disclosed herein, e.g., the Wnt signal enhancing molecules referred to as EEST-EE, EEST-RA, EEAT-EE, or 8M24 EASE-EE or 8M24 EASE-RA. In particular embodiments, the Wnt signal enhancing molecule is EEST-EE. In certain embodiments, the Wnt signal enhancing molecule is 8M24 EASE-EE or 8M2 EASE-RA. In certain embodiments, the vector is an expression vector, and may comprise a promoter operatively linked to the nucleic acid sequence. In particular embodiments, the vector is a viral vector.

In related aspects, the present invention provides a method for increasing Wnt signaling in liver tissue or cells, comprising contacting the target tissue with an effective amount of a cell comprising one or more nucleic acid sequence encoding a liver-specific Wnt signal enhancing molecule of the present invention, wherein the molecule comprises a targeting module that binds to a cell surface receptor on the liver tissue or cells in a liver-specific manner. In particular embodiments, the Wnt signal enhancing molecule is selected from any of those disclosed herein, or comprises any of the polypeptide sequences disclosed herein, e.g., the Wnt signal enhancing molecules referred to as EEST-EE, EEST-RA, EEAT-EE, or 8M24 EASE-EE or 8M24 EASE-RA. In particular embodiments, the Wnt signal enhancing molecule is EEST-EE. In certain embodiments, the Wnt signal enhancing molecule is 8M24 EASE-EE or 8M2 EASE-RA. In particular embodiments, the cell is a heterologous cell or an autologous cell obtained from the subject to be treated. In certain embodiments, the cell was transduced with a vector comprising an expression cassette encoding the liver-specific Wnt signal enhancing molecule. In particular embodiments, the cell is a stem cell, e.g., an adipose-derived stem cell or a hematopoietic stem cell.

Any of the methods described herein for increasing Wnt signalling may also be used to increase the number of Frizzled (Fz) receptors on the surface of targeted cells, e.g., liver tissue cells. In certain embodiments, the number of Fz receptors of the surface of the targeted cells is increase by at least 10%, at least 20%, at least 30%, at least 40%, at least 50%, at least 60%, at least 70%, at least 80%, at least 90%, at least two-fold, at least five-fold, or at least 10-fold. In particular embodiments, the Fz receptors include one or more of human frizzled proteins Fz1, Fz2, Fz3, Fz4, Fz5, Fz6, Fz7, Fz8, Fz9, and Fz10. For example, the disclosure provides a method for increasing Fz receptors on the surface of liver cells, comprising contacting the liver cells with an effective amount of liver-specific Wnt signal enhancing molecule disclosed herein, wherein the molecule comprises a targeting module that binds to a cell surface receptor on the liver tissue or cells in a liver-specific manner. In particular embodiments, the targeting module binds ASGR1 or ASGR2. In certain embodiments, the targeting module comprises an antibody or antigen-binding fragment thereof disclosed herein. In particular embodiments, the Wnt signal enhancing molecule is selected from any of those disclosed herein, or comprises any of the polypeptide sequences disclosed herein, e.g., the Wnt signal enhancing molecules referred to as EEST-EE, EEST-RA, EEAT-EE, or 8M24 EASE-EE or 8M24 EASE-RA. In particular embodiments, the Wnt signal enhancing molecule is EEST-EE. In certain embodiments, the Wnt signal enhancing molecule is 8M24 EASE-EE or 8M2 EASE-RA. In some embodiments, contacting occurs in vitro, ex vivo, or in vivo, e.g., the liver-specific Wnt signal enhancing molecule is administered or provided to a subject. In particular embodiments, the cell is a cultured cell, and the contacting occurs in vitro. In certain embodiments, the liver cell or tissue is initially contacted with the Wnt signal enhancing molecule directly, whereas in other related embodiments, the liver tissue or cell is initially contacted with a polynucleotide encoding the Wnt signal enhancing molecule, e.g., an expression vector, whereby the cell takes up the polynucleotide and expresses the Wnt signal enhancing molecule.

Any of the methods described herein for increasing Wnt signalling may also be used to increase Ki-67 on liver tissue or liver cells.

Methods for Treating Diseases and Disorders

Liver-specific Wnt signal enhancing molecules, exemplified herein with respect to fusion proteins, may be used in to treat a disease, disorder or condition, for example, by increasing Wnt signaling in a targeted liver cell, tissue or organ. Thus, in some aspects, the present invention provides a method for treating a disease or condition in a subject in need thereof, e.g., a disease or disorder associated with reduced Wnt signaling, or for which increased Wnt signaling would provide a therapeutic benefit, comprising contacting the subject with an effective amount of a composition of the present disclosure. In particular embodiments, the composition is a pharmaceutical composition comprising any of: a liver-specific Wnt signal enhancing molecule, e.g., a small molecule or a polypeptide; one or more polynucleotide comprising a nucleic acid sequence encoding a liver-specific Wnt signal enhancing molecule, e.g., a DNA or mRNA, optionally a modified mRNA; one or more vector comprising a nucleic acid sequence encoding a liver-specific Wnt signal enhancing molecule, e.g., an expression vector or viral vector; or a cell comprising one or more nucleic acid sequence encoding a liver-specific Wnt signal enhancing molecule, e.g., a cell transduced with an expression vector or viral vector encoding a liver-specific Wnt signal enhancing molecule. In particular embodiments, the Wnt signal enhancing molecule is selected from any of those disclosed herein, or comprises any of the polypeptide sequences disclosed herein, e.g., the Wnt signal enhancing molecules referred to as EEST-EE, EEST-RA, EEAT-EE, or 8M24 EASE-EE or 8M24 EASE-RA. In particular embodiments, the Wnt signal enhancing molecule is EEST-EE. In certain embodiments, the Wnt signal enhancing molecule is 8M24 EASE-EE or 8M2 EASE-RA. In particular embodiments, the disease or condition is a pathological disease or disorder, or an injury, e.g., an injury resulting from a wound. In certain embodiments, the wound may be the result of another therapeutic treatment. In certain embodiments, the disease or condition comprises impaired tissue repair, healing or regeneration, or would benefit from increased tissue repair, healing or regeneration. In some embodiments, contacting occurs in vivo, i.e., the subject composition is administered to a subject.

In related aspects, the present invention provides a method for treating a disease or condition, e.g., a disease or disorder associated with reduced Wnt signaling, or for which increased Wnt signaling would provide a therapeutic benefit, comprising administering to or contacting a subject in need thereof with a pharmaceutical composition comprising an effective amount of a liver-specific Wnt signal enhancing molecule of the present invention, wherein the molecule comprises a targeting module that binds to a cell surface receptor on the target tissue or cell in a tissue- or cell-specific manner. In particular embodiments, the Wnt signal enhancing molecule is selected from any of those disclosed herein, or comprises any of the polypeptide sequences disclosed herein, e.g., the Wnt signal enhancing molecules referred to as EEST-EE, EEST-RA, EEAT-EE, or 8M24 EASE-EE or 8M24 EASE-RA. In particular embodiments, the Wnt signal enhancing molecule is EEST-EE. In certain embodiments, the Wnt signal enhancing molecule is 8M24 EASE-EE or 8M2 EASE-RA.

In related aspects, the present invention provides a method for treating a disease or condition, e.g., a disease or disorder associated with reduced Wnt signaling, or for which increased Wnt signaling would provide a therapeutic benefit, comprising administering to or contacting a subject in need thereof with a pharmaceutical composition comprising an effective amount of one or more polynucleotide comprising a nucleic acid sequence encoding a liver-specific Wnt signal enhancing molecule of the present invention, wherein the molecule comprises a targeting module that binds to a cell surface receptor on the target tissue or cell in a tissue- or cell-specific manner. In particular embodiments, the Wnt signal enhancing molecule is selected from any of those disclosed herein, or comprises any of the polypeptide sequences disclosed herein, e.g., the Wnt signal enhancing molecules referred to as EEST-EE, EEST-RA, EEAT-EE, or 8M24 EASE-EE or 8M24 EASE-RA. In particular embodiments, the Wnt signal enhancing molecule is EEST-EE. In certain embodiments, the Wnt signal enhancing molecule is 8M24 EASE-EE or 8M2 EASE-RA.

In related aspects, the present invention provides a method for treating a disease or condition, e.g., a disease or disorder associated with reduced Wnt signaling, or for which increased Wnt signaling would provide a therapeutic benefit, comprising contacting a subject in need thereof with a pharmaceutical composition comprising an effective amount of one or more vector comprising a nucleic acid sequence encoding a liver-specific Wnt signal enhancing molecule of the present invention, wherein the molecule comprises a targeting module that binds to a cell surface receptor on the target tissue or cell in a tissue- or cell-specific manner. In particular embodiments, the Wnt signal enhancing molecule is selected from any of those disclosed herein, or comprises any of the polypeptide sequences disclosed herein, e.g., the Wnt signal enhancing molecules referred to as EEST-EE, EEST-RA, EEAT-EE, or 8M24 EASE-EE or 8M24 EASE-RA. In particular embodiments, the Wnt signal enhancing molecule is EEST-EE. In certain embodiments, the Wnt signal enhancing molecule is 8M24 EASE-EE or 8M2 EASE-RA.

In related aspects, the present invention provides a method for treating a disease or condition, e.g., a disease or disorder associated with reduced Wnt signaling, or for which increased Wnt signaling would provide a therapeutic benefit, comprising contacting a subject in need thereof with a pharmaceutical composition comprising an effective amount of a cell comprising one or more nucleic acid sequence encoding a liver-specific Wnt signal enhancing molecule of the present invention, wherein the molecule comprises a targeting module that binds to a cell surface receptor on the target tissue or cell in a tissue- or cell-specific manner In particular embodiments, the cell is a stem cell, e.g., an adipose-derived stem cell or a hematopoietic stem cell. In particular embodiments, the Wnt signal enhancing molecule is selected from any of those disclosed herein, or comprises any of the polypeptide sequences disclosed herein, e.g., the Wnt signal enhancing molecules referred to as EEST-EE, EEST-RA, EEAT-EE, or 8M24 EASE-EE or 8M24 EASE-RA. In particular embodiments, the Wnt signal enhancing molecule is EEST-EE. In certain embodiments, the Wnt signal enhancing molecule is 8M24 EASE-EE or 8M2 EASE-RA.

Wnt signaling plays key roles in the developmental process and maintenance of stem cells. Reactivation of Wnt signals is associated with regeneration and repair of most tissues after injuries and diseases. Liver-specific Wnt signal enhancing molecules may provide benefit of healing and tissue repair in response to liver injuries and diseases. Causes of liver tissue damage and loss include but are not limited to aging, degeneration, hereditary conditions, infection and inflammation, traumatic injuries, toxins/metabolic-induced toxicities, or other pathological conditions. Wnt signals and enhancers of Wnt signals have been shown to activate adult, tissue-resident stem cells. In some embodiments, the compounds of the invention are administered for use in treating diseased or damaged liver tissue, for use in liver tissue regeneration and for use in liver cell growth and proliferation, and/or for use in liver tissue engineering.

Human diseases associated with mutations of the Wnt pathway provide strong evidence for enhancement of Wnt signals in the treatment and prevention of diseases. Preclinical in vivo and in vitro studies provide additional evidence of involvement of Wnt signals in many disease conditions and further support utilization of liver-specific Wnt signal enhancing molecules in various human diseases. For example, compositions of the present invention may also be used in enhanced regeneration of liver cells, e.g., liver regeneration, treatment of cirrhosis, enhancement of liver transplantations, treatment of acute liver failure, treatment of chronic liver diseases with hepatitis (A, B, or C) virus infection or post-antiviral drug therapies, alcoholic liver diseases, including alcoholic hepatitis, e.g., acute or severe alcoholic hepatitis, non-alcoholic liver diseases with steatosis or steatohepatitis, and the like. The compositions of this invention may treat diseases and disorders including, without limitation, conditions in which regenerative liver tissue or cell growth is desired. In certain embodiments, the compositions are used to treat, for example, acute on chronic liver failure (ACLF), acute decompensation of the liver, ascites due to cirrhosis, hyponatremia in patients with cirrhosis, hepatorenal syndrome-acute kidney injury (HRS-AKI), or hepatic encephalopathy. In particular embodiments, the composition comprises a Wnt signal enhancing molecule is selected from any of those disclosed herein, or comprises any of the polypeptide sequences disclosed herein, e.g., the Wnt signal enhancing molecules referred to as EEST-EE, EEST-RA, EEAT-EE, or 8M24 EASE-EE or 8M24 EASE-RA. In particular embodiments, the Wnt signal enhancing molecule is EEST-EE. In certain embodiments, the Wnt signal enhancing molecule is 8M24 EASE-EE or 8M2 EASE-RA. In certain embodiments, the method is used to treat alcoholic hepatitis, e.g., acute alcoholic hepatitis or severe alcoholic hepatitis, and the Wnt signal enhancing molecule is EEST-EE, and in particular embodiments, the Wnt signal enhancing molecule is administered intravenously. In certain embodiments, the method is used to treat alcoholic hepatitis, e.g., acute alcoholic hepatitis or severe alcoholic hepatitis, and the Wnt signal enhancing molecule is 8M24 EASE-EE or 8M2 EASE-RA, and in particular embodiments, the Wnt signal enhancing molecule is administered intravenously.

Specific populations of proliferating cells for homeostatic renewal of hepatocytes have been identified through lineage tracing studies, for example Axin2-positive cells in pericentral region. Lineage tracing studies also identified additional potential liver progenitor cells, including but not limited to Lgr-positive cells. The self-renewing liver cells and other populations of potential progenitor cells, including Lgr5-positive and Axin2-positive cells, are identified to be capable of regeneration responding to Wnt signals and/or R-spondins following injuries. Numerous preclinical models of acute liver injury and failure and chronic liver diseases showed recovery and regeneration of hepatocytes benefit from enhancing Wnt signals. In certain embodiments, the compositions of this invention may be used in treatment of, e.g., acute liver failure of all causes, acute liver failure drug-induced, acute on chronic liver failure (ACLF), acute decompensation of the liver, ascites due to cirrhosis, hyponatremia in patients with cirrhosis, hepatorenal syndrome-acute kidney injury (HRS-AKI), hepatic encephalopathy, alcoholic liver diseases, chronic liver failure of all causes, decompensated liver failure, late stage compensated liver failure, cirrhosis, liver fibrosis of all causes, portal hypertension, chronic liver insufficiency of all causes, end stage liver disease (ESLD), nonalcoholic steatohepatitis (NASH), nonalcoholic fatty liver disease (NAFLD) (fatty liver), alcoholic hepatitis, acute alcoholic hepatitis (AAH), chronic alcoholic hepatitis, alcoholic liver disease (ALD) (also called alcohol-related liver disease (ARLD), hepatitis C virus-induced liver diseases (HCV), hepatitis B virus-induced liver diseases (HBV), other viral hepatitis (e.g., hepatitis A virus-induced liver diseases (HAV) and hepatitis D virus-induced liver diseases (HDV)), primary biliary cirrhosis, autoimmune hepatitis, livery surgery, liver injury, veno-occlusive disease (VOD), sinusoidal obstructive syndrome (SOS), primary biliary cholangitis (PBC), primary sclerosing cholangitis (PSC), liver transplantation, "small for size" syndrome in liver surgery and transplantation, congenital liver disease and disorders, liver failure due to APAP (acetaminophen) overdose, and any other liver disease or disorder resulting from genetic diseases, degeneration, aging, drugs, or injuries. They may also be used to enhance regeneration of liver cells, in vivo or in vitro. In certain embodiments, the method results in increased hepatocyte regeneration, improvised liver function, and/or decreased fibrosis. Methods for regeneration of liver tissue benefit from administration of the compounds of the invention, which can be systemic or localized. These include, but are not limited to, methods of systemic administration and methods of localized administration, e.g., by injection into the liver tissue, by injection into veins or blood vessels leading into the liver, by implantation of a sustained release formulation, and the like. In particular embodiments, the composition comprises a Wnt signal enhancing molecule is selected from any of those disclosed herein, or comprises any of the polypeptide sequences disclosed herein, e.g., the Wnt signal enhancing molecules referred to as EEST-EE, EEST-RA, EEAT-EE, or 8M24 EASE-EE or 8M24 EASE-RA. In particular embodiments, the Wnt signal enhancing molecule is EEST-EE. In certain embodiments, the Wnt signal enhancing molecule is 8M24 EASE-EE or 8M2 EASE-RA.

In particular embodiments, a liver-specific Wnt signal enhancing molecule disclosed herein is used to treat, inhibit, or prevent alcoholic hepatitis (AH), such as acute alcoholic hepatitis (AAH), also referred to as severe alcoholic hepatitis (severe AH). AAH (or severe AH) is a severe form of alcohol-related liver disease associated with significant short-term mortality. Alcoholic hepatitis typically occurs after more than 10 years of regular heavy alcohol use; average consumption in one study was 100 g/day (the equivalent of 10 drinks per day). The typical patient presents with recent onset of jaundice, ascites, and proximal muscle loss. Fever and leukocytosis also are common but should prompt an evaluation for infection, especially spontaneous bacterial peritonitis. Liver biopsy in these patients shows steatosis, swollen hepatocytes containing eosinophilic inclusion (Mallory) bodies, and a prominent neutrophilic inflammatory cell infiltrate. Because of the accuracy of clinical diagnosis, biopsy is rarely required, relying instead on clinical and laboratory features for diagnosis. Acute alcoholic hepatitis (AH) is a serious form of acute decompensation of alcoholic liver disease (ALD) that develops in heavy drinkers and is characterized by rapid onset of jaundice, malaise, anorexia, tender hepatomegaly, and features of the systemic inflammatory response syndrome (SIRS). Severe or acute alcoholic hepatitis (AH) is a catastrophic disease with a very high 180-day mortality and typically requires hospitalization. It can present as acute on chronic liver failure with worse prognosis in the presence of infections and higher grades of liver disease severity. Patients may have a recent history of heavy alcohol consumption within three months of presentation with jaundice and characteristic liver enzyme elevation pattern with coagulopathy, hepatic encephalopathy, variceal bleeding and sepsis that results in extrahepatic organ failures, as well as other potential symptoms, such as itching and/or fever. In particular embodiments, the liver-specific Wnt signal enhancing molecule is selected from any of those disclosed herein, or comprises any of the polypeptide sequences disclosed herein, e.g., the Wnt signal enhancing molecules referred to as EEST-EE, EEST-RA, EEAT-EE, or 8M24 EASE-EE or 8M24 EASE-RA. In certain embodiments, the Wnt signal enhancing molecule is EEST-EE. In certain embodiments, the Wnt signal enhancing molecule is 8M24 EASE-EE or 8M2 EASE-RA. In particular embodiments, it is administered intravenously. In certain embodiments, the method results in increased hepatocyte regeneration, improvised liver function, and/or decreased fibrosis.

The compositions of the present invention may be used to treat end stage liver disease (ESLD). ESLD or chronic liver failure is often the result of severe liver cirrhosis and the resultant liver fibrosis. ESLD is manifested by the development of ascites, variceal hemorrhage, hepatic encephalopathy and/or liver function impairment (e.g., decompensated liver disease). Common diseases or disorders associated with ESLD include: alcoholic hepatitis, chronic hepatitis C infection, chronic hepatitis B infection, chronic hepatitis D infection, non-alcoholic fatty liver disease (NAFLD), including non-alcoholic steatohepatitis (NASH), and inherited diseases such as cystic fibrosis, alpha-1 anti-trypsin deficiency, hemochromatosis, Wilson disease, galactosemia, and glycogen storage disease. Prolonged exposure to drugs, toxic chemicals, parasitic infections, and repeated heart failures with liver congestion can also result in ESLD. In particular embodiments, the composition comprises a Wnt signal enhancing molecule is selected from any of those disclosed herein, or comprises any of the polypeptide sequences disclosed herein, e.g., the Wnt signal enhancing molecules referred to as EEST-EE, EEST-RA, EEAT-EE, or 8M24 EASE-EE or 8M24 EASE-RA. In certain embodiments, the Wnt signal enhancing molecule is EEST-EE. In certain embodiments, the Wnt signal enhancing molecule is 8M24 EASE-EE or 8M2 EASE-RA. In particular embodiments, it is administered intravenously. In certain embodiments, the method results in increased hepatocyte regeneration, improvised liver function, and/or decreased fibrosis.

In particular embodiments, a composition is administered parenterally, e.g., intravenously, orally, rectally, or by injection. In some embodiments, it is administered locally, e.g., topically or intramuscularly. In some embodiments, a composition is administered to target tissues, e.g., to liver. Methods of the invention may be practiced in vivo or ex vivo. In some embodiments, the contacting of a target cell or tissue with a liver-specific Wnt signal enhancing molecule is performed ex vivo, with subsequent implantation of the cells or tissues, e.g., activated stem or progenitor cells, into the subject. The skilled artisan can determine an appropriate site of and route of administration based on the disease or disorder being treated. Methods of administration include, but are not limited to, methods of systemic administration and methods of localized administration, e.g., by injection into the liver tissue, by injection into veins or blood vessels leading into the liver, by implantation of a sustained release formulation, and the like.

The dose and dosage regimen may depend upon a variety of factors readily determined by a physician, such as the nature of the disease or disorder, the characteristics of the subject, and the subject's history. In particular embodiments, the amount of liver-specific Wnt signal enhancing molecule, e.g., fusion protein, administered or provided to the subject is in the range of about 0.01 mg/kg to about 50 mg/kg, 0.1 mg/kg to about 500 mg/kg, or about 0.1 mg/kg to about 50 mg/kg of the subject's body weight.

In certain embodiments, the subject may be any mammal, e.g., human, rodent (e.g. mice, rats, gerbils), rabbit, feline, canine, goat, ovine, pig, equine, bovine, or primate.

In some embodiments, the subject method results in a therapeutic benefit, e.g., inhibiting or preventing the development of a liver disease or disorder, halting the progression of a liver disease or disorder, reversing the progression of a liver disease or disorder, etc. In some embodiments, the methods increase hepatocyte regeneration, increase liver function, and/or decrease liver fibrosis. In some embodiments, the subject method comprises the step of detecting that a therapeutic benefit has been achieved. The ordinarily skilled artisan will appreciate that such measures of therapeutic efficacy will be applicable to the particular disease or disorder being modified, and will recognize the appropriate detection methods to use to measure therapeutic efficacy.

In certain embodiments, the disclosure provides a method for treating or preventing a disease or disorder associated with reduced Wnt signaling or that would benefit from increased Wnt signaling activity in liver tissue, such as, for example, any of the diseases or disorders disclosed herein that would benefit from liver regeneration, comprising providing to a subject in need thereof a pharmaceutical composition comprising a Wnt signal enhancing molecule comprising a targeting module that binds liver tissue, e.g., a targeting module that specifically binds to ASGR1, wherein the Wnt signal enhancing molecule increases or enhances Wnt signaling in the subject's liver tissue. In particular embodiments, the composition comprises a Wnt signal enhancing molecule is selected from any of those disclosed herein, or comprises any of the polypeptide sequences disclosed herein, e.g., the Wnt signal enhancing molecules referred to as EEST-EE, EEST-RA, EEAT-EE, or 8M24 EASE-EE or 8M24 EASE-RA. In certain embodiments, the Wnt signal enhancing molecule is EEST-EE. In certain embodiments, the Wnt signal enhancing molecule is 8M24 EASE-EE or 8M2 EASE-RA. In certain embodiments, the pharmaceutical composition is administered orally or systemically, e.g., parenterally. In particular embodiments, the Wnt signal enhancing molecule comprises an action module comprising an R-spondin Furin domain 1 or a fragment or variant thereof and, optionally, a mutated Furin domain 2 or a fragment or variant thereof. Methods for Producing or Maintaining Liver Cells, Tissue, and Organoids Other embodiments relate, in part, to the use of the molecules disclosed herein to promote or enhance the growth or proliferation of liver cells, liver tissue, and organoids, for example, by contacting liver cells, liver tissue, or liver organoids with one or more Wnt signal enhancing molecule disclosed herein, e.g., 1R34-EEST-EE, 8M24-EASE-EE, or 8M24-EASE-RA. In certain embodiments, the Wnt signal enhancing molecule is EEST-EE. In certain embodiments, the Wnt signal enhancing molecule is 8M24 EASE-EE or 8M2 EASE-RA In certain embodiments, the methods may be used to enhance growth or proliferation, or maintain or increase viability of liver cells, liver tissue, or liver organoids. In certain embodiments, the liver cells, liver tissue, or liver organoid are contacted ex vivo, in vitro, or in vivo. Methods disclosed herein may be used to generate and/or maintain liver cells, tissue, or organoids for therapeutic use, e.g., to be transplanted or grafted into a subject. They may also be used to generate and/or maintain liver cells, tissue, or organoids for research use. The Wnt signal enhancing molecules have widespread applications in non-therapeutic methods, for example in vitro research methods.

In certain embodiments, liver tissue is contacted with a Wnt signal enhancing molecule to maintain viability of the liver tissue. In particular embodiments, the liver tissue is donor liver tissue to be transplanted to a recipient in need thereof. In certain embodiments, donor liver tissue is perfused in vivo with a solution comprising a Wnt signal enhancing molecule disclosed here, e.g., before the liver tissue is removed from the donor. In certain embodiments, donor liver tissue is perfused ex vivo with a solution comprising a Wnt signal enhancing molecule disclosed here, e.g., during storage or during transport from a donor to a recipient. In particular embodiment, the liver tissue contacted with a Wnt signal enhancing molecule remains viable for transplantation for at least 10%, at least 20%, at least 50%, or at least 100% longer than if it was not contacted with the Wnt signal enhancing molecule.

In certain embodiments, a liver organoid culture is generated, grown, or maintained by contacting it with one or more Wnt signaling molecules disclosed herein. In particular embodiments, the Wnt signal enhancing molecule is present in the culture media used to grow or maintain the liver organoid tissue.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular biology, cell biology and biochemistry can be found in such standard textbooks as "Molecular Cloning: A Laboratory Manual, 3rd Ed." (Sambrook et al., Harbor Laboratory Press 2001); "Short Protocols in Molecular Biology, 4th Ed." (Ausubel et al. eds., John Wiley & Sons 1999); "Protein Methods" (Bollag et al., John Wiley & Sons 1996); "Nonviral Vectors for Gene Therapy" (Wagner et al. eds., Academic Press 1999); "Viral Vectors" (Kaplift & Loewy eds., Academic Press 1995); "Immunology Methods Manual" (I. Lefkovits ed., Academic Press 1997); and "Cell and Tissue Culture: Laboratory Procedures in Biotechnology" (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

Materials and methods employed in the following Examples include the following.

Protein production: All recombinant proteins were produced in Expi293F cells (Thermo Fisher Scientific) by transient transfection unless otherwise specified. All IgG-based and Fc-containing constructs were purified with CaptivA Protein A affinity resin (Repligen) and eluted with 0.1 M glycine pH 3.3. All proteins were further polished with Superdex 200 Increase 10/300 GL (GE Healthcare Life Sciences) size-exclusion chromatography (SEC) using 1×HBS buffer (20 mM HEPES pH 7.4, 150 mM NaCl) or 2×HBS buffer (40 mM HEPES pH 7.4, 300 mM NaCl). Proteins were supplemented with glycerol to 10% for long term storage at −80° C. All proteins tested were examined by SDS-polyacrylamide electrophoresis and estimated to be at least 90% pure.

SuperTop Flash (STF) assay: Wnt signaling activity was measured using cell lines containing a luciferase gene controlled by a Wnt-responsive promoter (Super Top Flash reporter assay, STF) as reported (Janda et al., 2017; Nature 545:234). In brief, cells were seeded at a density of 10,000 per well in 96-well plates 24 hr prior to treatment, then treated by RSPO or mimetic proteins overnight either alone or together with 100 pM WNT3A surrogate, R2M3-26. Cells were lysed with Luciferase Cell Culture Lysis Reagent (Promega) and activity was measured with Luciferase Assay System (Promega) using vendor suggested procedures. Data were plotted as average−/+standard deviation of triplicates and fitted by non-linear regression using Prism (GraphPad Software).

Semi-quantitative PCR analysis of gene expression: RNA from mouse tissues (liver and small intestine samples) was extracted using the MagMAX™ mirVana™ Total RNA Isolation Kit (ThermoFisher, A27828). cDNA was produced using the high-Capacity cDNA Reverse Transcription Kit (ThermoFisher, 43-688-14) or the SuperScript™ IV VILO™ Master Mix (ThermoFisher, Cat. No. 11756050). Mouse Axin2 and Ki67 mRNA expression were measured by using TaqMan® Fast Advanced Master Mix (ThermoFisher, 4444963) and the Mm00443610_m1 Axin2, Mm01278617_m1 Ki67, Mm01300555_g1 wnt1, Mm00470018_m1 wnt2, Mm00437336_m1 wnt3, Mm01194003_m1 wnt4, Mm00437347_m1 wnt5a, Mm01183986_m1 wnt5b, Mm00437353_m1 wnt6, Mm00437356_m1 wnt7a, Mm01301717_m1 wnt7b, Mm01157914_g1 wnt8a, Mm00457102_m1 wnt9b, Mm00442104_m1 wnt10b, Mm00437327_g1 wnt11, Mm00446420_m1 wnt16, Mm00507077_m1 rspo1, Mm00555790_m1 rspo2, Mm01188251_m1 rspo3, and Mm00615419_m1 rspo4 probes (ThermoFisher, 4331182). Values were normalized to expression of constitutive Actin B gene using the Mm02619580_g1 probe (ThermoFisher, 4351368).

Polyspecificity Assay: ELISA method was used to examine binding to non-target antigens, including human insulin (Sigma 91077C-100MG), keyhole limpet hemocyanin (KLH) (Sigma H7017-50MG), lipopolysaccharides from E. coli (LPS) (SigmaL3012-10MG), double-stranded DNA (dsDNA) (Sigma D1626-5G), and heparin. Before use, dsDNA was sheared to 200~200 bp using sonication. Corning® 96-well EIA/RIA Easy Wash™ Clear Flat Bottom Polystyrene High Bind Microplate (Corning 3369) was coated with 50 ul KLH, LPS, and dsDNA in PBS at 10 mg/ml over night at 4° C. Insulin was coated at 5 mg/ml. Heparin coated plates were purchased (Thermo Scientific C995X60). The coated plates were blocked with 300 µl 300 SuperBlock (Thermo 37516) at room temperature for 1 hr, then probed with 100 µl proteins of interest (antibodies or fusions) at 1000, 250, 125, 62.5 mg/ml at room temperature for 1 hr (or overnight at 4° C.). Anti-hFc-HRP (Jackson IR 109-035-098) was used to for detection and chemiluminescence quantification.

Protein Thermal Stability Assay: Protein thermal stability was measured using the Uncle instrument (Unchained Labs). Reaction was performed by adding the protein sample in 1×HBS buffer to the Unis then sealed by the silicone seals and closed in the frame. The fluorescent reading was measured at the UV266 nm and Blue 473 nm in the temperature range from 15° C. to 95° C. with the increment of 1° C. per minute. The Tm/Tagg was obtained using the Uncle data analysis software.

Mouse studies: Six-week old C57Bl/6J male mice were obtained from Jackson Laboratories (Bar Harbor, ME, USA) and were group-housed. All animal experimentation was in accordance with the criteria of the "Guide for the Care and Use of Laboratory Animals" prepared by the National Academy of Sciences. Protocols for animal experimentation were approved by the Surrozen Institutional Animal Care and Use Committee. Mice were acclimatized a minimum of two days prior to initiating experiments. Mice had unlimited access to purified, laboratory-grade acidified water and were fed ad libitum (2018 Teklad global 18% protein rodent diet). Mice were kept on a 12/12-hour light/dark cycle in a 30% to 70% humidity environment and room temperature ranging from 20° C. to 26° C.

In cases where the mice were humanized for human ASGR gene expression, each mouse was dosed with $1\times10^{11}$ ssAAV8-CAG-hASGR1 genome copies (Vector Biolabs, Malvern, PA) intravenously on day 0. On day 7, mice were injected intraperitoneally (i.p.) with αGFP, Fc-RSPO2-WT, αGFP-RSPO2-RA or αASGR1-RSPO2-RA. At indicated times after protein dosing, mice were anesthetized with isoflurane and blood was removed by cardiac puncture. A portion of the left liver lobe and duodenum were collected for analysis.

Semi-quantitative PCR analysis of gene expression in $CCl_4$ studies: RNA from mouse tissues (liver samples) was extracted using the MagMAX™ mirVana™ Total RNA Isolation Kit (ThermoFisher, A27828). cDNA was produced using the high-Capacity cDNA Reverse Transcription Kit (ThermoFisher, 43-688-14) or the SuperScript™ IV VILO™ Master Mix (ThermoFisher, Cat. No. 11756050). Mouse mRNA expression were measured by using TaqMan® Fast Advanced Master Mix (ThermoFisher, 4444963) and the Mm00443610_m1 Axin2, Mm00432359_m1 Ccnd1, Mm01278617_m1 Mki67. Values were normalized to expression of constitutive Actin B gene using the Mm02619580_g1 probe (ThermoFisher, 4351368).

Serum Chemistry: Blood was collected from the tail tip on day 7, and during termination via cardiac puncture at day 14. The serum was separated by centrifuging the blood in serum separation tubes with gel (Fisher, 22030401) at 10,000 RPM for 7 minutes. Supernatant were transferred to a new tube and kept at −20° C. until analysis. Serum samples were analyzed using a VetAxcel clinical analyzer, alkaline phosphatase and albumin assay kits (404200-3, SA2002 and SA2001, Alfa-Wasserman Diagnostic Technologies, respectively)

Histological Analysis and Immunofluorescence: Formalin-fixed and paraffin-embedded liver samples were sectioned and stained with the anti-Ki-67 rabbit antibodies (Fisher, 50245564), anti-HNF4α antibodies (Abcam, ab199431), Goat Anti-Rat IgG H&L (Alexa Fluor® 488) (ab150157) and Donkey Anti-Rabbit IgG H&L (Alexa Fluor® 647) (ab150075). Whole histological liver sections were stained with Picrosirius Red (PSR) using standard procedure and scanned to a digital image. Image J was used to quantify the percentage of section stained with PSR.

Example 1

Development and Characterization of Liver-Specific Wnt Signal Enhancing Molecules ASGR is a hetero-oligomer composed of two polypeptides, ASGR1 and ASGR2, that are predominantly expressed on hepatocytes and goes through rapid endocytosis. To create a liver-specific RSPO-like Wnt signaling enhancer molecules, the asialoglycoprotein receptor (ASGR) was targeted.

A number of IgG-like, liver-specific Wnt signaling enhancer molecules were produced, each comprising two anti-ASGR1 antibody light chains, and two anti-ASGR1 antibody heavy chains having a modified RSPO2 polypeptide fused to their N-termini via a linker sequence (αASGR1-RSPO2 constructs). In this design, the anti-ASGR1 antibody part of the molecule is a "targeting module" that provides liver specificity, while the RSPO2 part of the molecule functions as an "action module" that interacts with the E3 ligases. The Wnt signaling enhancer molecules comprise an IgG1 backbone unless indicated otherwise.

The initial αASGR1-RSPO2 Wnt signaling enhancer molecule made comprised an αASGR1 binding domain that binds the stalk region of ASGR1, and is referred to as 1R34-DDNN/RA. The sequence of the light chains of the 1R34-DDNA/RA molecule is provided below with the CDRs underlined:

```
                                           (SEQ ID NO: 1)
SSELTQDPAVSVALGQTVRITCQGDSLRSYYASWYQQKPGQAPVLVIYG

KNNRPSGIPDRFSGSSSGNTASLTITGAQAEDEADYYCNSLERIGYLSY

VFGGGTKLTVLGQPKAAPSVTLFPPSSEELQANKATLVCLISDFYPGAV

TVAWKADSSPVKAGVETTTPSKQSNNKYAASSYLSLTPEQWKSHRSYSC

QVTHEGSTVEKTVAPTECS.
```

The sequence of the heavy chains with the fused RSPO2 sequence for the 1R34-DDNA/RA molecule is shown below with the CDRs underlined, the RSPO2 sequence italicized, and the linker sequence in bold:

```
                                           (SEQ ID NO: 2)
NPICKGCLSCSKDNGCSRCQQKLFFFLRREGMRQYGECLHSCPSGYYGH

RAPDMNRCARCRIENCDSCRSKDACTKCKVGFYLHRGRCFDECPDGFA
```

```
PLEETMECVEGGGGSGGGGSGGGGSEVQLLESGGGLVQPGGSLRLSCAA

SGFTFSSYAMSWVRQAPGKGLEWVSAISGSGGSTYYADSVKGRFTISRD

NSKNTLYLQMNSLRAEDTAVYYCAKDFSSRRWYLEYWGQGTLVTVSSAS

TKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDV

SHEDPEVKFNWYVDGVEVHNAKTKPREEQYGSTYRVVSVLTVLHQDWLN

GKEYKCKVSNKALPAPIEKTISKAKGQPREPQVYTLPPSREEMTKNQVS

LTCLVKGFYPSDIAVEWESNGQPENNYKTTPPVLDSDGSFFLYSKLTVD

KSRWQQGNVFSCSVMHEALHNHYTQKSLSLSPGK.
```

Two amino acid substitutions as compared to the wild type human RSPO2 sequence are shown as bold, italicized, and underlined.

The subsequent αASGR1-RSPO2 Wnt signaling enhancer molecule, 8M24-v1, comprised an αASGR1 binding domain that binds the carbohydrate binding domain of ASGR1 and was derived from the 8M24 antibody. The sequence of the variable domain of the light chains of the 8M24-v1 molecule is provided below with the CDRs underlined:

```
                                           (SEQ ID NO: 3)
DIQMTQSPSSLSASVGDRVTITCRISENIYSNLAWYQQKPGKAPKLLIY

AAINLADGVPSRFSGSGSGTDFTLTISSLQPEDFATYYCQHFWGTPFTF

GQGTKLEIK.
```

The sequence of the light chains of the 8M24-v1 molecule is provided below with the CDRs underlined:

```
                                           (SEQ ID NO: 5)
DIQMTQSPSSLSASVGDRVTITCRISENIYSNLAWYQQKPGKAPKLLIY

AAINLADGVPSRFSGSGSGTDFTLTISSLQPEDFATYYCQHFWGTPFTF

GQGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.
```

The sequence of the variable domain of the heavy chains with the fused RSPO2 sequence of the 8M24v1 molecule is shown below with the CDRs underlined, the RSPO2 sequence italicized and the linker sequence in bold:

```
                                           (SEQ ID NO: 4)
NPICKGCLSCSKDNGCSRCQQKLFFFLRREGMRQYGECLHSCPSGYYGH

RAPDMNRCARCRIENCDSCRSKDACTKCKVGFYLHRGRCFDECPDGFAP

LEETMECVEGGGGSGGGGSGGGGSEVQLVQSGAEVKKPGSSVKVSCKAS

GYTFTNYGINWVRQAPGQGLEWMGEIFPRSDNTFYAQKFQGRVTITADK

STSTAYMELSSLRSEDTAVYYCARKGRDYGTSHYFDYWGQGTTVTVSS.
```

Two amino acid substitutions as compared to the wild type human RSPO2 sequence are shown as bold, italicized, and underlined.

Modifications to each of these two starting molecules were made for testing, to identify modified forms having superior characteristics.

1R34-DDNA/RA Molecule Modifications

Various amino acid modifications of the initial αASGR1-RSPO2 Wnt signaling enhancer molecule, 1R34-DDNA/RA, were made and tested to identify molecules with improved properties. FIG. 1 provides the amino acid sequences of the 1R34-DDNA/RA starting molecule's light chain polypeptides and heavy chain-Rspo2 fusion polypeptides, and indicates the amino acid residues that were modified in the variants in bold. All molecules included an N297G substitution in the IgG1 backbone (NG). In some molecules, to abolish LGR binding by the RSPO2 polypeptide, point mutations were introduced into two highly conserved hydrophobic residues within the Fu2 domain of RSPO2 that are reported to be critical for binding to LGR proteins, F105 and F109. The 1R34-DDNA/RA heavy chain sequence shown in FIG. 1 includes F105R and F109A substitutions as compared to the wild-type RSPO2 sequence, which are italicized and underlined.

Four Asn and Asp sites with the potential for deamidation or Asp isomerization liabilities are present in the CDRs of the ASGR1 binding IgG portion of the 1R34-DDNA/RA Wnt signaling enhancer molecules (shown in bold in FIG. 1). Various amino acid substitutions were made at each of these positions. The molecules were engineered using standard molecular biology techniques and expressed by transient transfection in Expi293 cells, and then subjected to 2 column purification (Protein A followed by SEC). The resulting molecules were tested for their potential to be introduced into the Wnt signaling enhancer molecules to eliminate deamidation or Asp isomerization liabilities.

Surprisingly, the D62 position in CDR2 of the heavy chain showed limited flexibility to be replaced by other amino acids. As shown in FIG. 2, D62 mutated to Ser or Ala resulted in substantial changes in SEC profile of the molecules, suggesting that these mutations disrupted folding of the molecule, whereas mutation to Glu maintained folding. This latter mutation also retained STF activity (data not shown).

Similarly, the D25 position in CDR1 of the light chain could not be replaced by serine, since it disrupted protein folding, as shown in FIG. 3. However, substitution of D25 with Glu or Ala maintained protein folding and STF activity (FIG. 3 and data not shown).

The N51 position in CDR2 of the light chain had the flexibility to be replaced by Gln, Ser, or Ala (FIG. 4). Each of these substitutions maintained STF activity, although STF activity was somewhat reduced with the Gln mutation at position 51 (data not shown).

Figure 41:
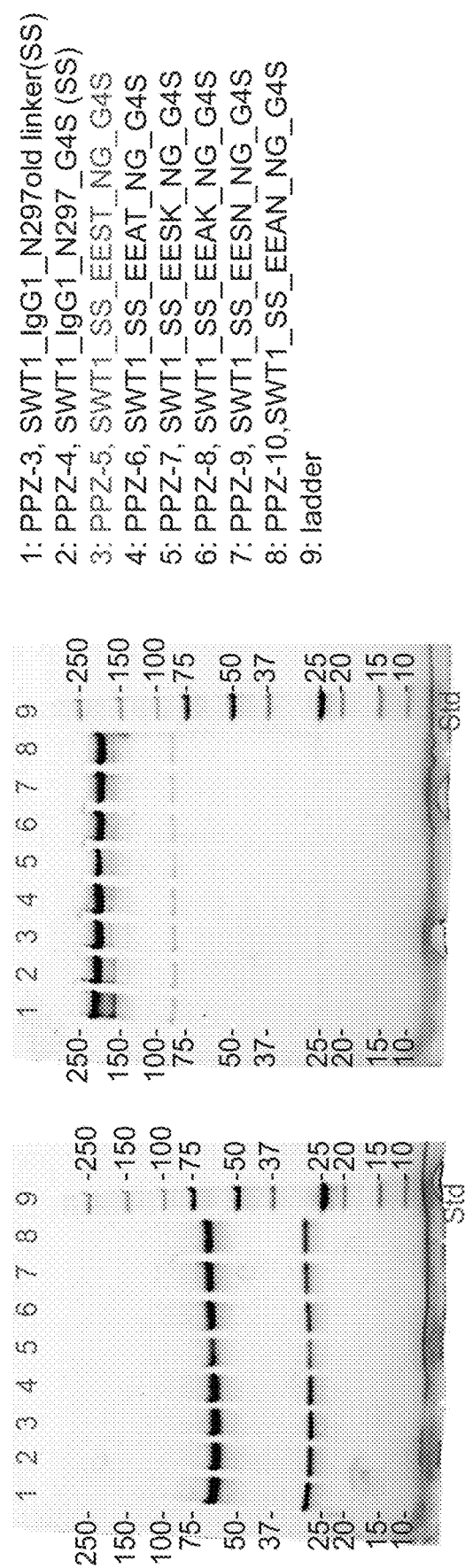
FIG. 41 shows the stability of constructs with the indicated combinations of amino acid substitutions.
Figure 42:
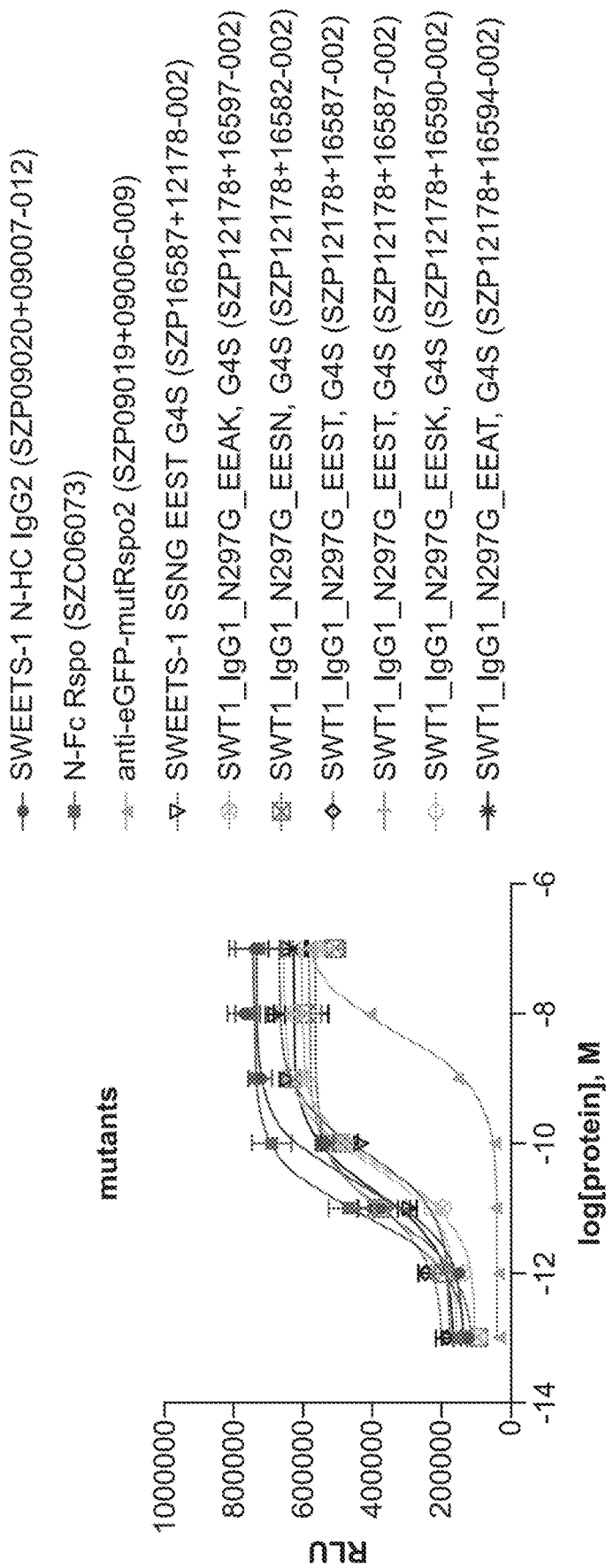
FIG. 42 shows STF activity of constructs with the indicated combinations of amino acid substitutions.

Modification of the N88 position in CDR3 of the light chain did not affect protein SEC profile when replaced by Gln, Ser, or Ala, as shown in FIG. 5. Each of these substitutions maintained STF activity, although STF activity was somewhat reduced with the Gln mutation at position 88 (data not shown). However, SDS-PAGE analysis revealed that although the N88S and N88A mutants were well expressed, the mutation to S or A caused non-properly folded proteins, as shown in FIG. 6. In combination with other mutants, LC N88Q compromised activity and L88A compromised integrity. Further modifications of the N88 position in CD3 to His (EESH), Thr (EEST), Arg (EESR), or Lys (EESK) (and other amino acid residues) were made in the background of heavy chain CDR2 D62E, light chain CDR1 D25E, and light chain CDR2 N51S substitutions, and tested in Huh-7 and Hek-293 cells (FIGS. 50A-D). Mutants EESH and EESR had reduced STF activity, possibly due to interrupting binding sites on the cell surface. Mutants EEST, EESK, and EEAT had comparable STF activity to WT, whereas the following combination of mutations had reduced activity: EESL, EESE, EESH, EESR, EESY, EEAL, EEAE, EEAH, EEAY, and EEAR. Protein folding of various combinations of mutants with different amino acids replacing N88 was also examined (FIG. 41). Combinations of sequences with similar activity were compared, and EEST had the EEST had the highest Emax and lowest EC50 (FIG. 42). Surprisingly, mutation of N88 to Thr maintained both STF activity and proper protein folding (FIG. 41).

Preferred substitutions at the various modified positions were selected based on activity and are shown in Table 1, with preferred amino acid substitutions highlighted in bold (WT indicates wild type).

TABLE 1

| Position | Location | Mutant 1 |
| --- | --- | --- |
| 1 | CDR_H2 | D62 S, E, A |
| 2 | CDR_L1 | D25 S, E, A |
| 3 | CDR_L2 | N51 Q, S, A |
| 4 | CDR_L3 | N88 Q, S, A, L, E, H, T, R, K, Y, WT |

Figure 7:
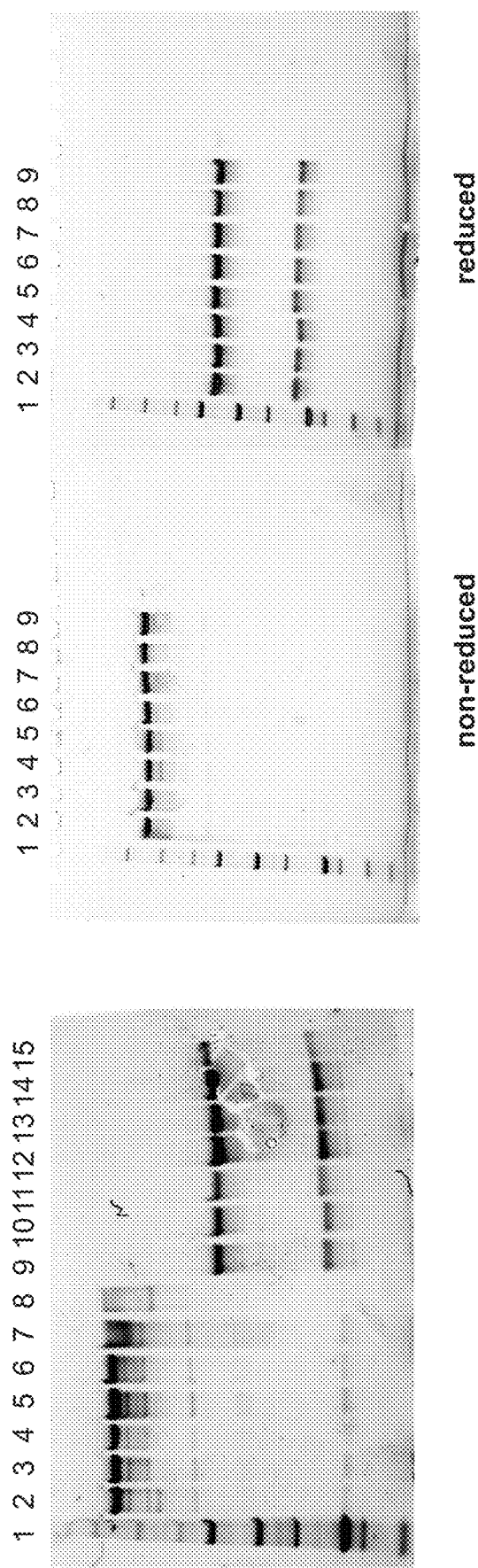
FIG. 7 shows SDS-PAGE gel analysis of expression and folding of Wnt signaling enhancer molecules comprising the indicated combinations of point mutations as compared to the initial αASGR1-RSPO2 Wnt signaling enhancer molecule (left panel: lane 1=marker, lanes 2-8=EESY, EEAL, EEAE, EEAH, EEAT, EEAY, EEAR, respectively, non-reduced, and lanes 9-15=EESY, EEAL, EEAE, EEAH, EEAT, EEAY, EEAR, respectively, reduced; right panel: lane 1=marker, lanes 2-9=EESN, EEAN, EESL, EESE, EESH, EEST, EESR, EESK).

Wnt signaling enhancer molecules comprising various combinations of the preferred amino acid substitutions identified above were made and tested by STF assay, octet binding, and polyspecificity assays. These molecules comprised the following amino acids at positions 1-4 of Table 1: EESY, EEAL, EEAE, EEAH, EEAT, EEAY, EEAR, EESN, EEAN, EESL, EESE, EESH, EEST, EESR, and EESK. SDS-PAGE analysis under non-reducing and reducing conditions was performed to determine protein folding (FIG. 7: left panel: lane 1=marker, lanes 2-8=EESY, EEAL, EEAE, EEAH, EEAT, EEAY, EEAR, respectively, non-reduced, and lanes 9-15=EESY, EEAL, EEAE, EEAH, EEAT, EEAY, EEAR, respectively, reduced; right panel: lane 1=marker, lanes 2-9=EESN, EEAN, EESL, EESE, EESH, EEST, EESR, EESK).

STF assays were performed to assess the ability of these molecules to modulate Wnt signaling in Huh-7 STF Wnt responsive reporter cells in the presence of a supplied Wnt source. Only mutants 1R34-EEST/RA ("EEST"), 1R34-EESA/RA ("EESA"), 1R34-EESN/RA ("EESN"), 1R34-EEAN/RA ("EEAN"), 1R34-EEAT/RA ("EEAT"), and 1R34-EESK/RA ("EESK") had comparable STF activity as the 1R34-DDNN/RA starting molecule ("NG") (FIG. 8 and FIGS. 39A-C).

As summarized in FIG. 8, the EEST, EESN, EEAN, and EEAT mutants were all mono disperse and stable to freeze-thaw comprising three rounds of freeze-thaw between liquid nitrogen freezing to room temperature. Freeze-thaw stability was assayed by STF and SEC (data not shown). Binding to the ASGR1 antigen was also determined. As shown in FIG. 8 and FIG. 9, these four mutants and the parental molecule had similar binding affinities to ASGR1 antigen. Polyspecific binding to insulin, heparin, dsDNA, KLH, and LPS was also examined. ELISAs showed comparable interaction with heparin amongst the mutants. At high concentrations, the mutants also showed comparable, weak binding to dsDNA, KLH, and LPS, but no binding to insulin. Thus, these constructs showed comparable activity and stability.

Different point mutations were made at two highly conserved hydrophobic residues within the Fu2 domain of huRSPO2, F105 and F109, in order to abolish LGR binding by the RSPO2 polypeptide. In particular, these residues were replaced by either F105R and F109A or F105E and F109E. Table 2 shows the specific combinations of substitutions present in each of these variants.

TABLE 2

Constructs

αASGR1-RSPO2-EEST-EE (1R34-EEST/EE)
αASGR1-RSPO2-EEST-RA (1R34-EEST/RA)
αASGR1-RSPO2-EEAT-EE (1R34-EEAT-EE)
αASGR1-RSPO2-NG (WT) (1R34-DDNN/NG)

The sequences of the light chain and heavy chain:RSPO2 fusion proteins present in each of these molecules is shown below.

The sequence of the light chains of the αASGR1-RSPO2-EEST-EE (1R34-EEST/EE) molecule is provided below with the CDRs underlined:

(SEQ ID NO: 7)
SSELTQDPAVSVALGQTVRITCQGESLRSYYASWYQQKPGQAPVLVIYG

KSNRPSGIPDRFSGSSSGNTASLTITGAQAEDEADYYCTSLERIGYLSY

VFGGGTKLTVLGQPKAAPSVTLFPPSSEELQANKATLVCLISDFYPGAV

TVAWKADSSPVKAGVETTTPSKQSNNKYAASSYLSLTPEQWKSHRSYSC

QVTHEGSTVEKTVAPTECS.

The sequence of the heavy chains with the fused RSPO2 sequence for the αASGR1-RSPO2-EEST-EE molecule is shown below with the CDRs underlined, the RSPO2 sequence italicized, and the linker sequence in bold:

(SEQ ID NO: 8)
NPICKGCLSCSKDNGCSRCQQKLFFFLRREGMRQYGECLHSCPSGYYGH

RAPDMNRCARCRIENCDSCRSKDACTKCKVGFYLHRGRCFDECPDGFA

PLEETMECVEGGGGSGGGGSGGGGSEVQLLESGGGLVQPGGSLRLSCAA

SGFTFSSYAMSWVRQAPGKGLEWVSAISGSGGSTYYAESVKGRFTISRD

NSKNTLYLQMNSLRAEDTAVYYCAKDFSSRRWYLEYWGQGTLVTVSSAS

TKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDV

SHEDPEVKFNWYVDGVEVHNAKTKPREEQYGSTYRVVSVLTVLHQDWLN

GKEYKCKVSNKALPAPIEKTISKAKGQPREPQVYTLPPSREEMTKNQVS

LTCLVKGFYPSDIAVEWESNGQPENNYKTTPPVLDSDGSFFLYSKLTVD

KSRWQQGNVFSCSVMHEALHNHYTQKSLSLSPGK.

Two amino acid substitutions as compared to the wild type human RSPO2 sequence are shown as bold, italicized, and underlined.

The sequence of the light chains of the αASGR1-RSPO2-EEST-RA molecule is provided below with the CDRs underlined:

(SEQ ID NO: 9)
SSELTQDPAVSVALGQTVRITCQGESLRSYYASWYQQKPGQAPVLVIYG

KSNRPSGIPDRFSGSSSGNTASLTITGAQAEDEADYYCTSLERIGYLSY

VFGGGTKLTVLGQPKAAPSVTLFPPSSEELQANKATLVCLISDFYPGAV

TVAWKADSSPVKAGVETTTPSKQSNNKYAASSYLSLTPEQWKSHRSYSC

QVTHEGSTVEKTVAPTECS.

The sequence of the heavy chains with the fused RSPO2 sequence for the αASGR1-RSPO2-EEST-RA molecule is shown below with the CDRs underlined, the RSPO2 sequence italicized, and the linker sequence in bold:

(SEQ ID NO: 10)
NPICKGCLSCSKDNGCSRCQQKLFFFLRREGMRQYGECLHSCPSGYYGH

RAPDMNRCARCRIENCDSCRSKDACTKCKVGFYLHRGRCFDECPDGFA

PLEETMECVEGGGGSGGGGSGGGGSEVQLLESGGGLVQPGGSLRLSCAA

SGFTFSSYAMSWVRQAPGKGLEWVSAISGSGGSTYYAESVKGRFTISRD

NSKNTLYLQMNSLRAEDTAVYYCAKDFSSRRWYLEYWGQGTLVTVSSAS

TKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDV

SHEDPEVKFNWYVDGVEVHNAKTKPREEQYGSTYRVVSVLTVLHQDWLN

GKEYKCKVSNKALPAPIEKTISKAKGQPREPQVYTLPPSREEMTKNQVS

LTCLVKGFYPSDIAVEWESNGQPENNYKTTPPVLDSDGSFFLYSKLTVD

KSRWQQGNVFSCSVMHEALHNHYTQKSLSLSPGK.

Two amino acid substitutions as compared to the wild type human RSPO2 sequence are shown as bold, italicized, and underlined.

The sequence of the light chains of the αASGR1-RSPO2-EEAT-EE molecule is provided below with the CDRs underlined:

(SEQ ID NO: 11)
SSELTQDPAVSVALGQTVRITCQGESLRSYYASWYQQKPGQAPVLVIYG

KANRPSGIPDRFSGSSSGNTASLTITGAQAEDEADYYCTSLERIGYLSY

VFGGGTKLTVLGQPKAAPSVTLFPPSSEELQANKATLVCLISDFYPGAV

TVAWKADSSPVKAGVETTTPSKQSNNKYAASSYLSLTPEQWKSHRSYSC

QVTHEGSTVEKTVAPTECS.

The sequence of the heavy chains with the fused RSPO2 sequence for the αASGR1-RSPO2-EEAT-EE molecule is shown below with the CDRs underlined, the RSPO2 sequence italicized, and the linker sequence in bold:

(SEQ ID NO: 12)
NPICKGCLSCSKDNGCSRCQQKLFFFLRREGMRQYGECLHSCPSGYYGH

RAPDMNRCARCRIENCDSCRSKDACTKCKVGFYLHRGRCFDECPDGFA

PLEETMECVEGGGGSGGGGSGGGGSEVQLLESGGGLVQPGGSLRLSCAA

SGFTFSSYAMSWVRQAPGKGLEWVSAISGSGGSTYYAESVKGRFTISRD

NSKNTLYLQMNSLRAEDTAVYYCAKDFSSRRWYLEYWGQGTLVTVSSAS

TKGPSVFPLAPSSKSTSGGTAALGCLVKDYFPEPVTVSWNSGALTSGVH

-continued
```
TFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDV

SHEDPEVKFNWYVDGVEVHNAKTKPREEQYGSTYRVVSVLTVLHQDWLN

GKEYKCKVSNKALPAPIEKTISKAKGQPREPQVYTLPPSREEMTKNQVS

LTCLVKGFYPSDIAVEWESNGQPENNYKTTPPVLDSDGSFFLYSKLTVD

KSRWQQGNVFSCSVMHEALHNHYTQKSLSLSPGK.
```

Two amino acid substitutions as compared to the wild type human RSPO2 sequence are shown as bold, italicized, and underlined.

Figure 10:
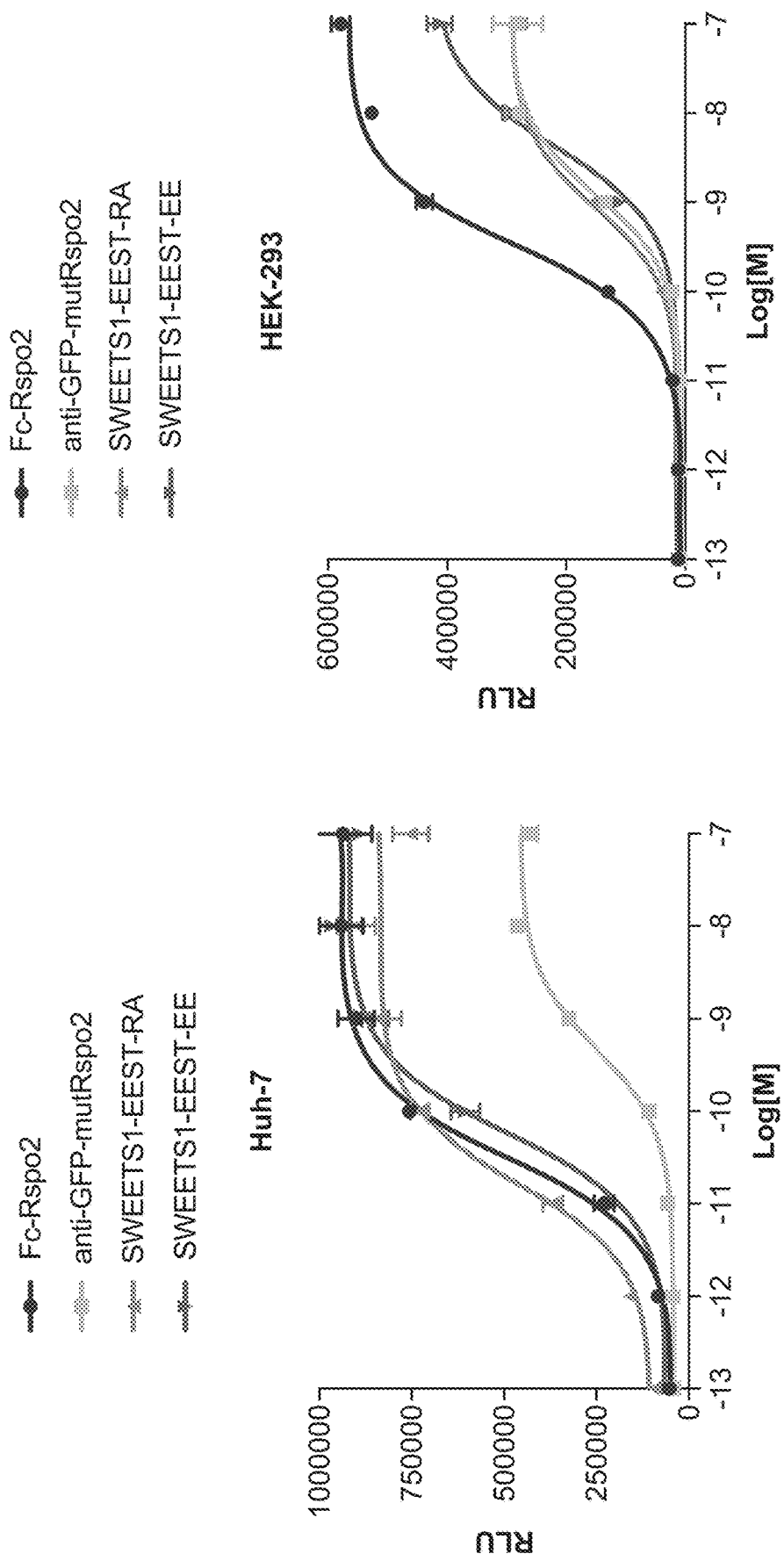
FIG. 10 provides graphs showing the results of STF assays of Wnt signaling enhancer molecules comprising the indicated combinations of point mutations in Huh-7 (left panel) and Hek-203 (right panel) cells.

As shown in FIG. 10, the F105E and F109E combination of mutations (SWEETS-1_RSPO2EE_NG_EEST_G4S; 1R34-EEST/EE) had less in vitro activity in the STF assay as compared to the F105R and F109A combination of mutations (SWEETS-1_NG_EEST_G4S; 1R34-EEST/RA), particularly in Huh-7 cells, where the latter was almost six-fold more potent. However, surprisingly, this greater in vitro activity did not translate to increased in vivo activity for the F105R and F109A combination of mutations. Instead, when Axin mRNA expression levels were analyzed in non-human primates treated with SWEETS-1_NG_EEST_G4S (1R34-EEST/RA) or SWEETS-1_RSPO2EE_NG_EEST_G4S (1R34-EEST/EE), the F105E and F109E combination of mutations showed equal or greater increases in Axin2 expression as compared to the F105R and F109A combination of mutations (FIG. 11), which is opposite of in vitro potency.

8M24-v1 Molecule Modifications

Various amino acid modifications of the 8M24-based αASGR1-RSPO2 Wnt signaling enhancer molecule (8M24-v1) were made and tested to identify molecules with improved properties.

Initially, the VH and VL domains of the starting 8M24 antibody sequences were each humanized two different ways (H1, H2, V1 and V2). The original and humanized VH and VL sequences are shown in FIG. 25 (SEQ ID NOs:13-18). Various combinations of the humanized VH and VL sequences were combined and tested for their binding affinity to human ASGR1 as compared to the parental 8M24 VH and VL sequences, in the context of the parental 8M24 IgG1 constant regions. As shown in Table 3, the combination of the L1 and H1 humanized VL and VH chains was selected based on their minimally affecting kinetic binding to human ASGR1.

TABLE 3

| VH and VL | KD | kon | koff |
|---|---|---|---|
| Parental | <1E-12 | 5.89E5 | <1E-7 |
| L1H1 | 5.73E-12 | 4.6E5 | 2.64E-6 |
| L1H2 | <1E-12 | 5.11E5 | <1E-7 |
| L2H1 | <1E-12 | 4.89E5 | <1E-7 |
| L2H2 | 1.10E-10 | 5.73E5 | 6.29E-5 |

Figure 27:
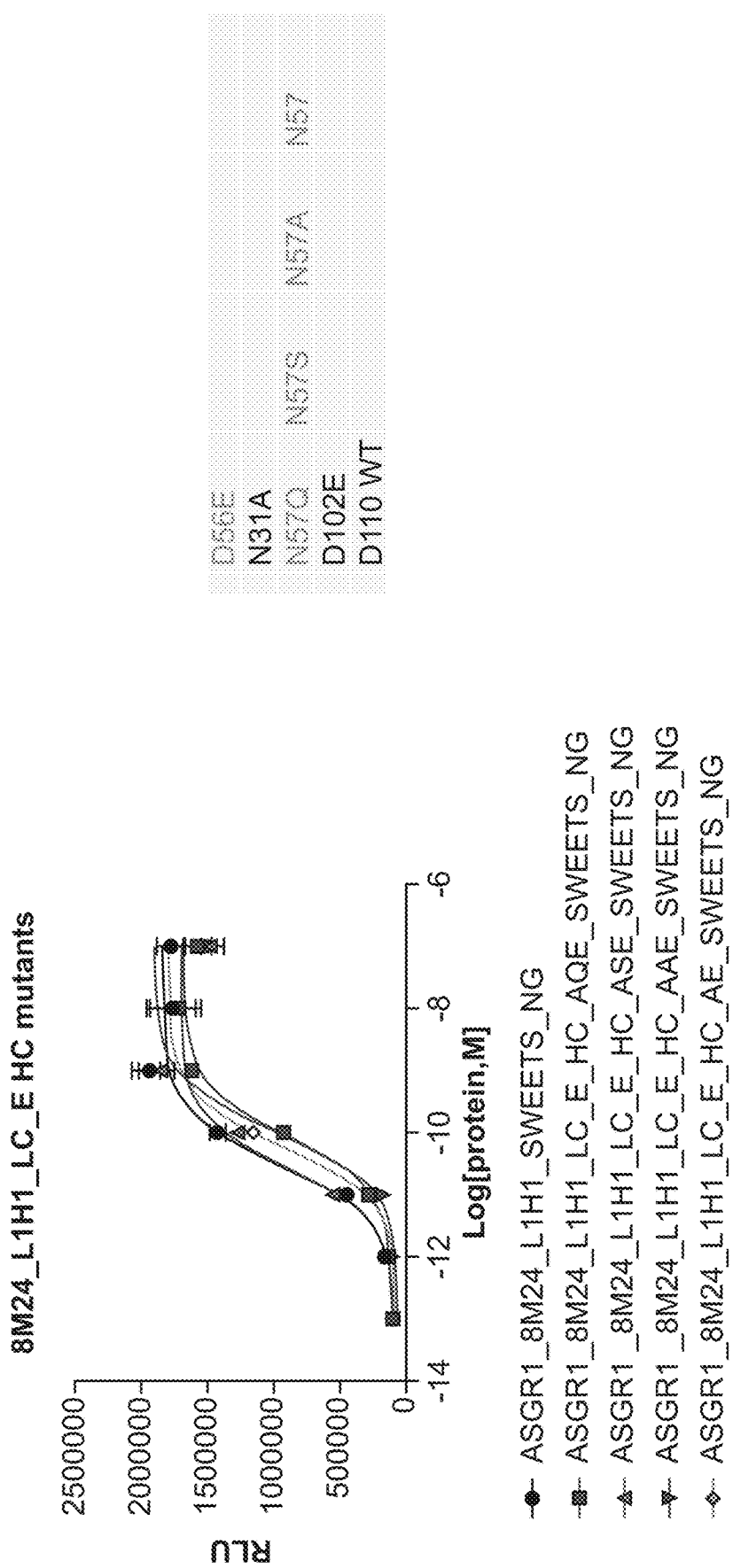
FIG. 27 is a graph showing the results of STF assays of 8M24 Wnt signaling enhancer molecules comprising the indicated point mutations at N57.

Potential deamidation or Asp isomerization liabilities were identified in the CDRs of the 8M24 ASGR1 binding IgG portion of the Wnt signaling enhancer molecules (shown in bold in FIG. 26). Each of these amino acids was substituted by the various amino acids shown in FIG. 26 and tested in the context of L1H1-humanized 8M24-based (αASGR1-RSPO2 Wnt signaling enhancer molecules in STF assays, as described above. The RSPO2 sequence included the F105R and F109A substitutions described above. When tested in the context of single mutations, the light chain D56E mutant was selected, and the heavy chain N31A mutant was the most potent of the mutations at that positions and was selected. The heavy chain N57Q, S, and A mutants all worked about equally well. The D102E mutant was also selected. All three mutations at D110 had poor potency, so the wild type D110 residue was selected (data not shown). Light chains comprising the D56E mutation were tested in combination with various heavy chain mutations identified above, which are shown in FIG. 27. As shown in FIG. 27, the mutant comprising the heavy chain mutations at N31A, N57S, and D102E (EASE) had the best activity. Various combination mutants were tested in a variety of other assays, including protein folding, HIC, polyspecificity, Tm/Tagg, stability and octet Kd. The results of these assays is summarized in FIG. 28. The EASE mutant had the best combination of activity and octet Kd. The sequence of its light chain variable domain polypeptides is shown below, with CDRs underlined:

```
                                    (SEQ ID NO: 19)
DIQMTQSPSSLSASVGDRVTITCRISENIYSNLAWYQQKPGKAPKLLIY

AAINLAEGVPSRFSGSGSGTDFTLTISSLQPEDFATYYCQHFWGTPFTF

GQGTKLEIK
```

The sequences of its heavy chain variable domain fused to the RSPO2 variant sequence is shown below, with the RSPO2 sequence in italics, the linker in bold, and the CDRs underlined:

```
                                    (SEQ ID NO: 20)
NPICKGCLSCSKDNGCSRCQQKLFFFLRREGMRQYGECLHSCPSGYYGH

RAPDMNRCARCRIENCDSCRSKDACTKCKVGFYLHRGRCFDECPDGFA

PLEETMECVEGGGGSGGGGSGGGGSEVQLVQSGAEVKKPGSSVKVSCKA

SGYTFTAYGINWVRQAPGQGLEWMGEIFPRSDSTFYAQKFQGRVTITAD

KSTSTAYMELSSLRSEDTAVYYCARKGREYGTSHYFDYWGQGTTVTVS

S.
```

The full heavy chain also included the constant region sequences as shown in ID NO:.

Based on the above studies, Wnt signal enhancer molecules with specific combinations of mutations that could only be determined empirically to provide superior properties were identified.

Example 2

In Vivo Liver Effect of Liver-Specific Wnt Signal Enhancing Molecules

To demonstrate that αASGR1-RSPO2 constructs described in Example 1 could activate the Wnt-signaling pathway in a tissue specific manner in vivo, mice were treated with the various constructs.

Figure 12:
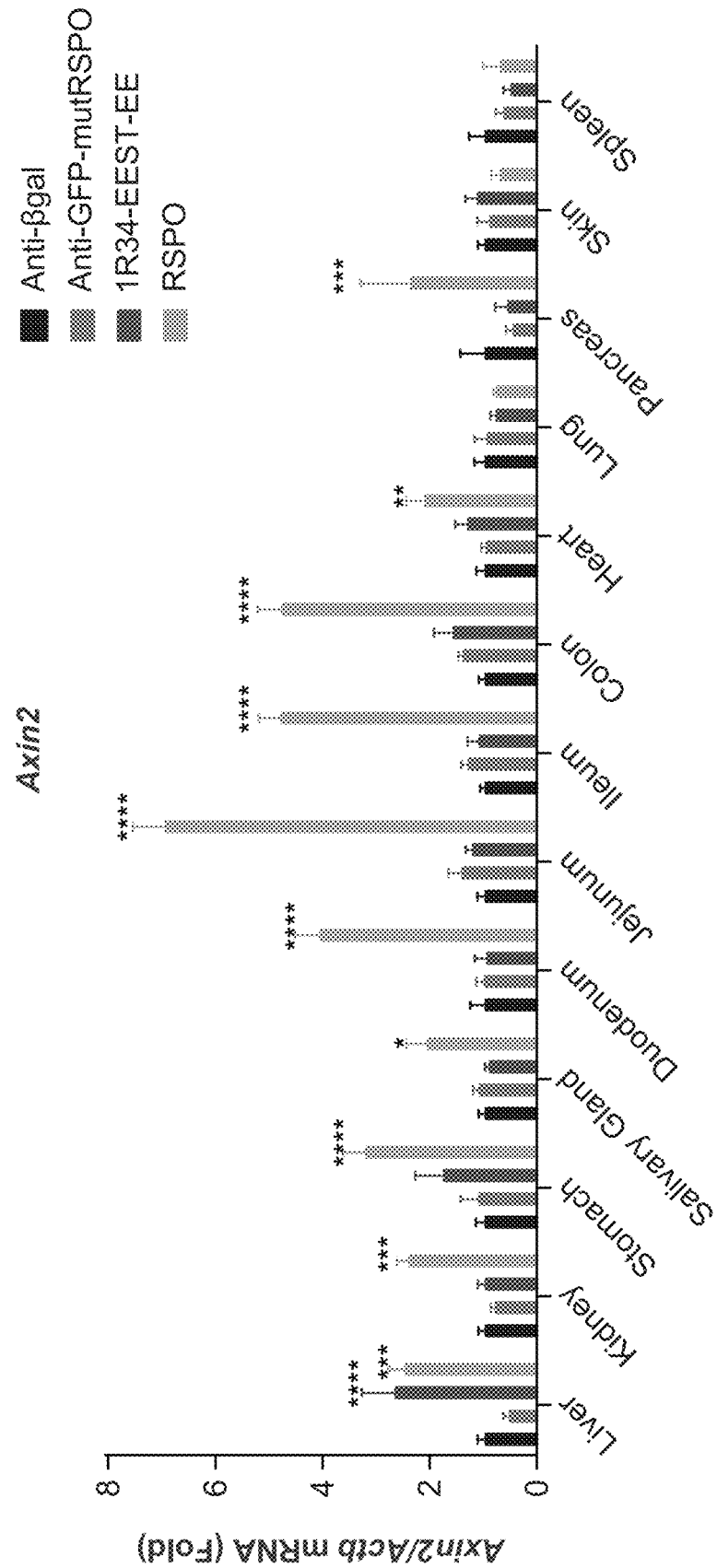
FIG. 12 is a graph showing increased expression of Axin2 in various tissues isolated from animals treated with anti-bgal, anti-GFP-mutRSPO, the EEST-EE Wnt signaling enhancer molecule (1R34-EEST-EE), or Rspo2 (left to right for each tissue).
Figure 21:
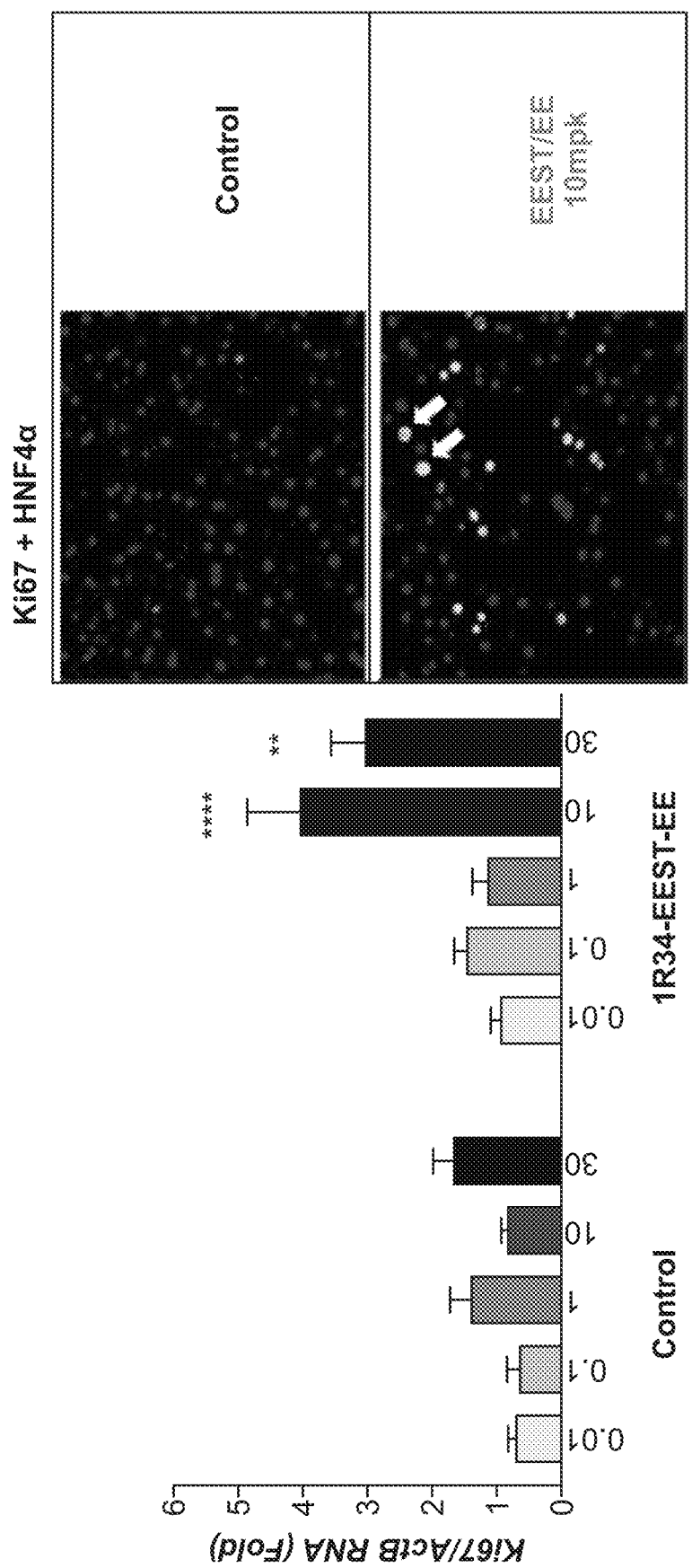
FIG. 21 is a graph showing expression of the proliferation marker, Ki67, in the liver of animals treated with control or αASGR1-RSPO2-EEST-EE.
Figure 22:
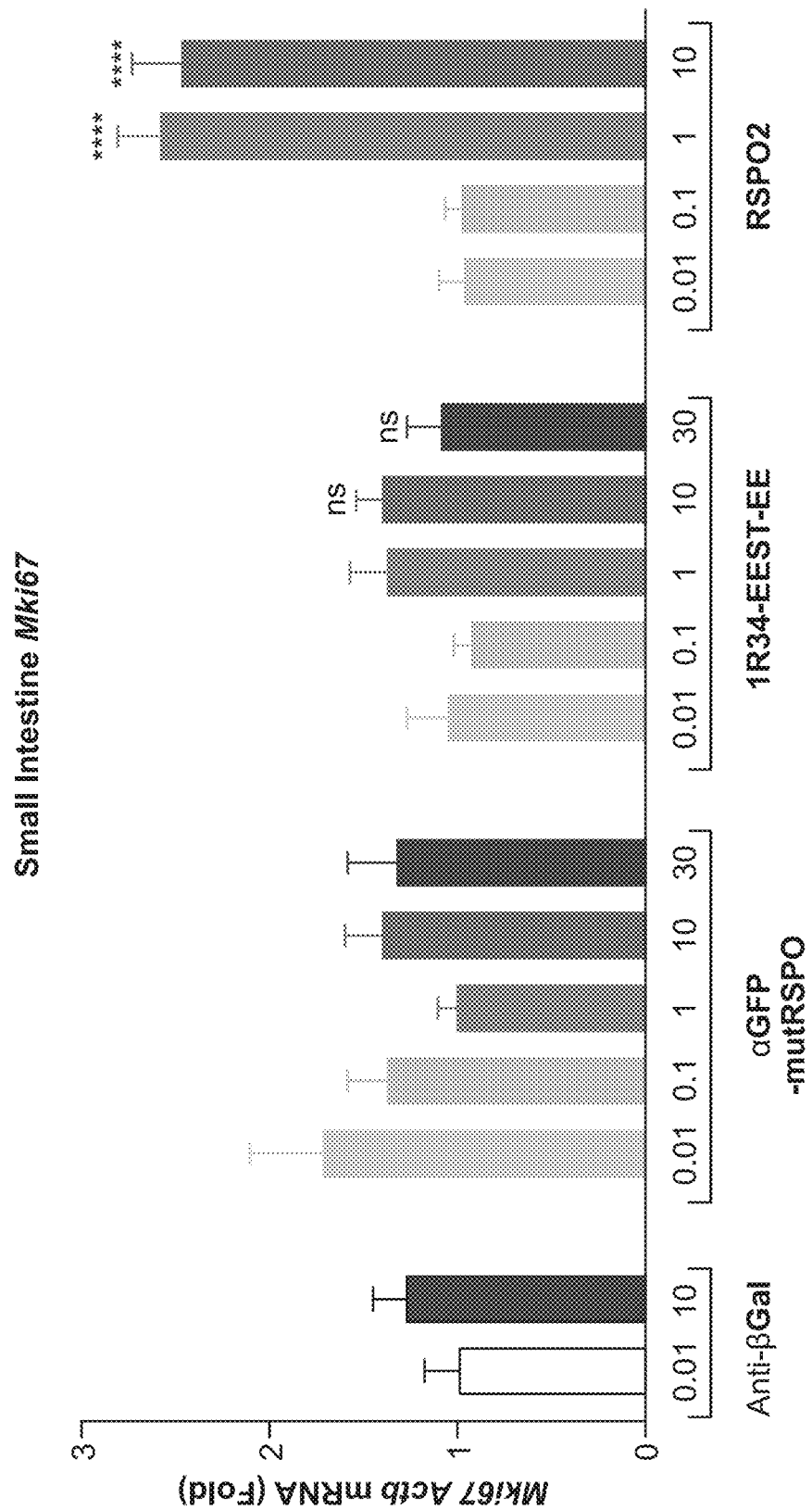
FIG. 22 is a graph showing expression of the proliferation marker, Ki67, in the small intestine of animals treated with control or αASGR1-RSPO2-EEST-EE.
Figure 23:
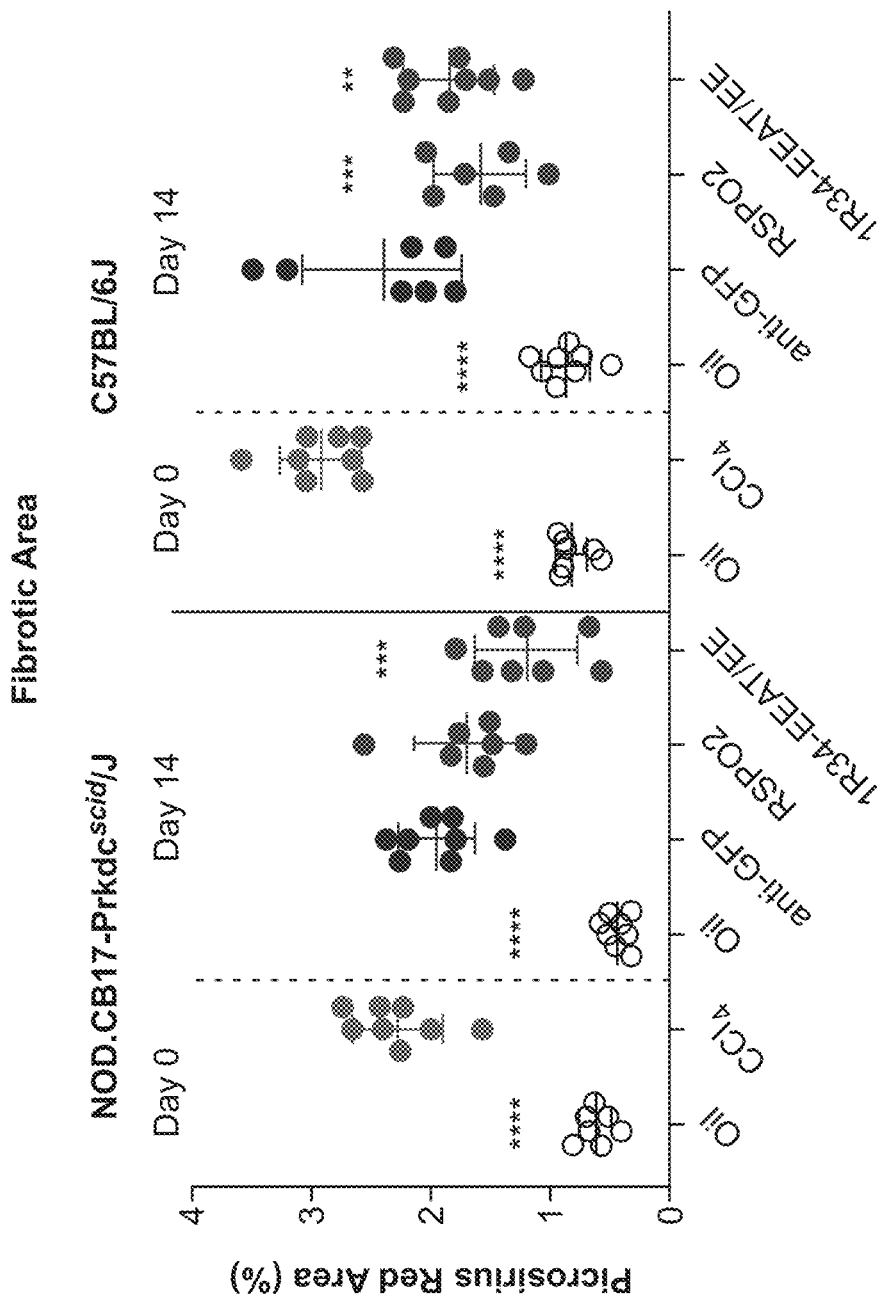
FIG. 23 is a graph showing fibrotic area in animals treated with control (anti-GFP), Rspo2, or αASGR1-RSPO2-EEAT-EE following treatment with $CCl_4$.

To analyze tissue specific activation of the Wnt-signaling pathway by Wnt signaling enhancer molecules, naïve mice received a single i.p. dose of 10 mg/kg of αASGR1-RSPO2-EEST-EE (1R34-EEST/EE), R-spo2, or control (anti-βgal or anti-GFP-mutRSPO) (n=5 mice per group). EEST indicates the substitutions present at positions 1-4 of FIG. 1, and the following EE indicates the N105E and N109E substitutions in the RSPO2 region. 48 hours after treatment, various organs and tissues were collected for analysis. Axin2/ActB gene expression was determined and normalized to control. Axin2 mRNA levels were significantly increased in most tissues following treatment with Rspo2. However, αASGR1-RSPO2-EEST-EE only resulted in an increase of Axin2 mRNA in the liver (FIG. 12). For each tissue, from left to right is shown anti-bgal, anti-GFP-mutRSPO, αASGR1-RSPO2-EEST-EE, and RSPO2. The resulting data showed that the Wnt signal enhancing molecule selectively activates the Wnt pathway in the liver (FIG. 12).

mRNA and protein expression of Ki67 in the liver and small intestine were determined by RT-PCR and immunofluorescence, and protein expression of HNF4c was determined by immunofluorescence. Antigen Ki-67 is a nuclear protein that is associated with and used as a cellular marker of proliferation, and hepatocyte nuclear factor 4a (HNF4a) is an orphan nuclear receptor that plays a major role in hepatic differentiation. As shown in FIGS. 21 and 22, αASGR1-RSPO2-EEST-EE (EE) stimulated proliferation of hepatocytes (FIG. 21) but not small intestine cells (FIG. 22). In addition, the livers of animals treated with αASGR1-RSPO2-EEST-EE showed expression of Ki67 and HNF4ae by immunofluorescence.

To analyze expression of genes upregulated upon activation of the Wnt-signaling pathway, naïve mice received a single i.p. dose of 10 mg/kg of αASGR1-RSPO2-EEST-EE (1R34-EEST/EE), αASGR1-RSPO2-EEST-RA (1R34-EEST/RA), or αGFP-IgG (n=20 mice per group). Serum and liver samples were collected 1 hr, 4 hrs, 24 hrs, and 72 hrs after protein dosing for expression analysis (n=5 for each group, at each timepoint). mRNA expression was analyzed by qPCR, and samples were normalized to ActB. The relative fold was calculated by setting the average of the anti-GFP group at 1 hour, to a value of 1.

Figure 13:
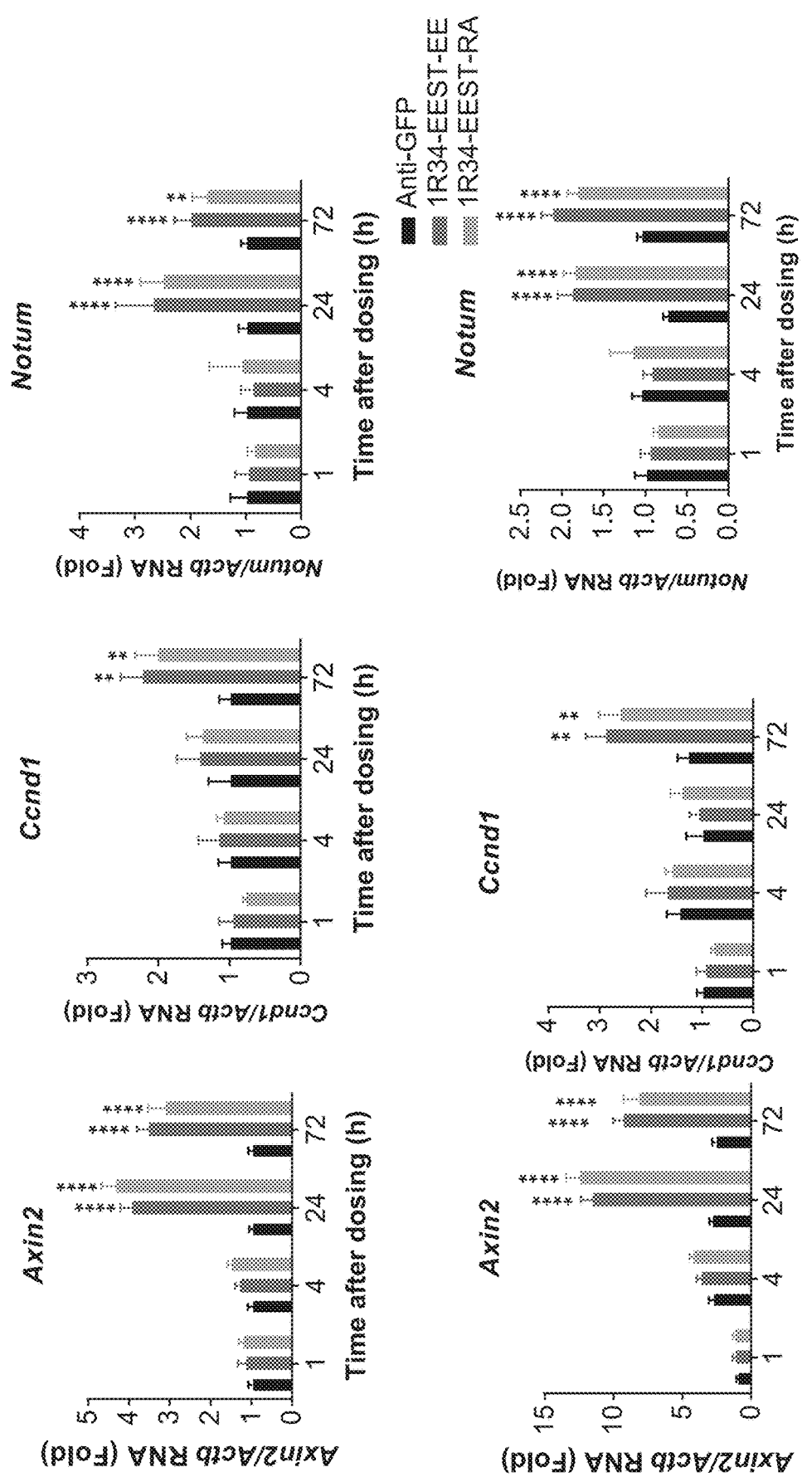
FIG. 13 provides graphs showing increased expression in the liver of the indicated Wnt target genes in animals treated with αGFP-IgG, αASGR1-RSPO2-EEST-EE, or αASGR1-RSPO2-EEST-RA Wnt signaling enhancer molecule (left to right) for the indicated times.

Treatment with αASGR1-RSPO2-EEST-EE or αASGR1-RSPO2-EEST-RA induced expression of liver Axin2, Ccnd1, and Notum significantly when compared to expression in mice treated with the αGFP-IgG negative control (FIG. 13; left to right at each time point: αGFP-IgG, αASGR1-RSPO2-EEST-EE, and αASGR1-RSPO2-EEST-RA; 2-way ANOVA, Holm-Sidak multiple comparisons to anti-GFP, * p<0.05,  p<0.01, * p<0.001, **** p<0.0001). These results demonstrate that αASGR1-RSPO2 variants activate the Wnt pathway in liver in vivo.

Figures 14A, 14B:
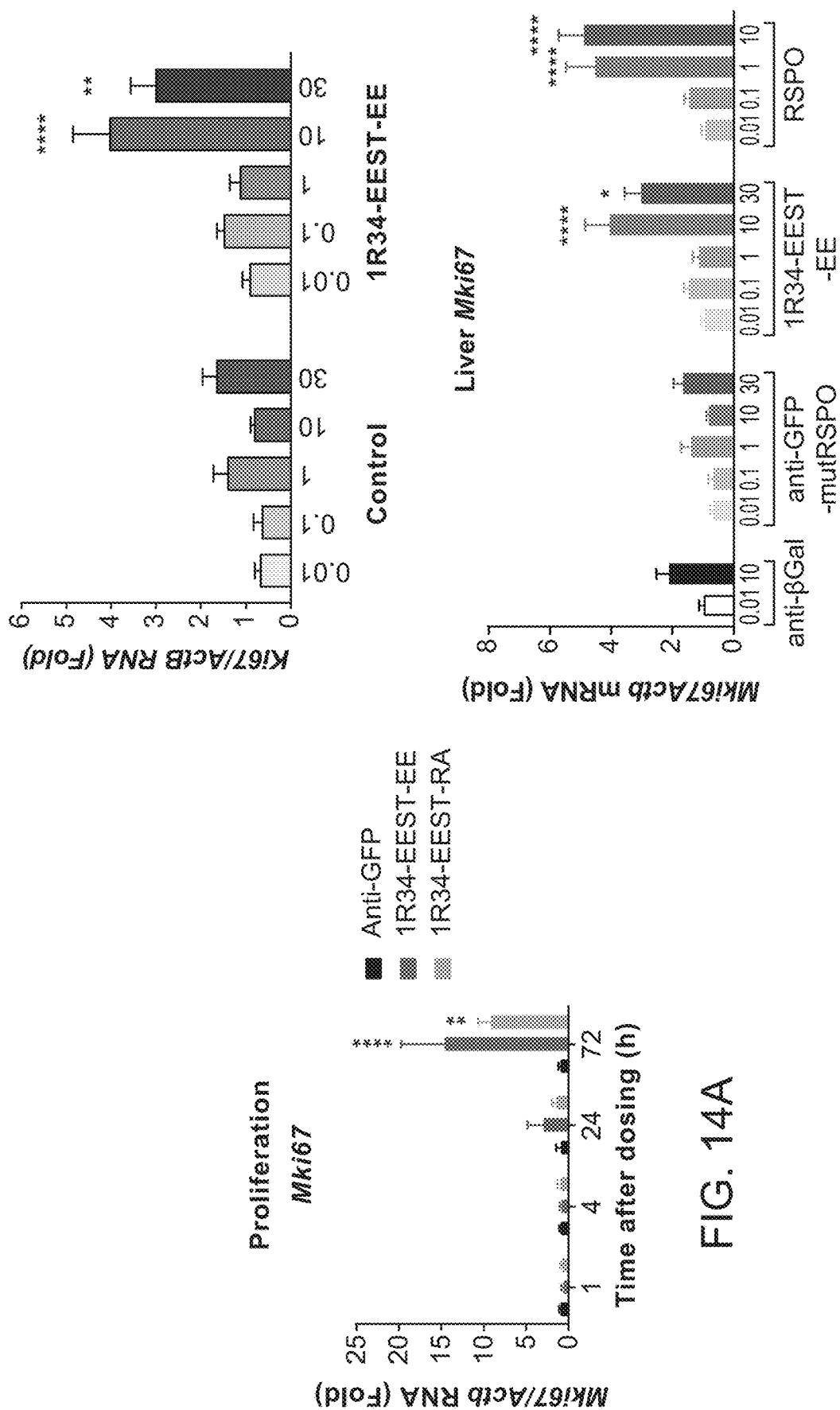
FIG. 14A shows increased expression of the proliferation marker, Ki67, in the liver of animals treated of αGFP-IgG, αASGR1-RSPO2-EEST-EE, or αASGR1-RSPO2-EEST-RA (left to right) at the indicated timepoints.
FIG. 14B shows increased expression of the proliferation marker, Ki67, in the liver of animals treated with the indicated dosages of αASGR1-RSPO2-EEST-EE or control.

In another study, mice received a single i.p. dose of 10 mg/kg of αASGR1-RSPO2-EEST-EE, αASGR1-RSPO2-EEST-RA, or αGFP-IgG (n=5 mice per group). Liver samples were collected 1 hr, 4 hrs, 24 hrs, and 72 hrs later for expression analysis and histoimmunochemistry. Treatment with αASGR1-RSPO2-EEST-EE or αASGR1-RSPO2-EEST-RA induced expression of the cellular proliferation marker gene Mki67 when compared to mice treated with the αGFP-IgG negative control (FIG. 14A; left to right at each time point: αGFP-IgG, αASGR1-RSPO2-EEST-EE, and αASGR1-RSPO2-EEST-RA; 2-way ANOVA, Holm-Sidak multiple comparisons to anti-GFP, * p<0.05,  p<0.01, * p<0.001, **** p<0.0001). These results demonstrate that αASGR1-RSPO2 variants can stimulate proliferation in liver parenchymal cells. Additional studies showed that this effect was dose dependent (FIG. 14B).

Expression of human ASGR1 in mouse liver was induced by IV injection of ssAAV8-CAG-hASGR1, using $1\times10^1$ genomic particles per mouse, a dose shown to achieve transgene expression levels equivalent to the endogenous liver Asgr1 mRNA, 7 days prior to treatment with the αASGR1-RSPO2 constructs (data not shown).

Figure 29:
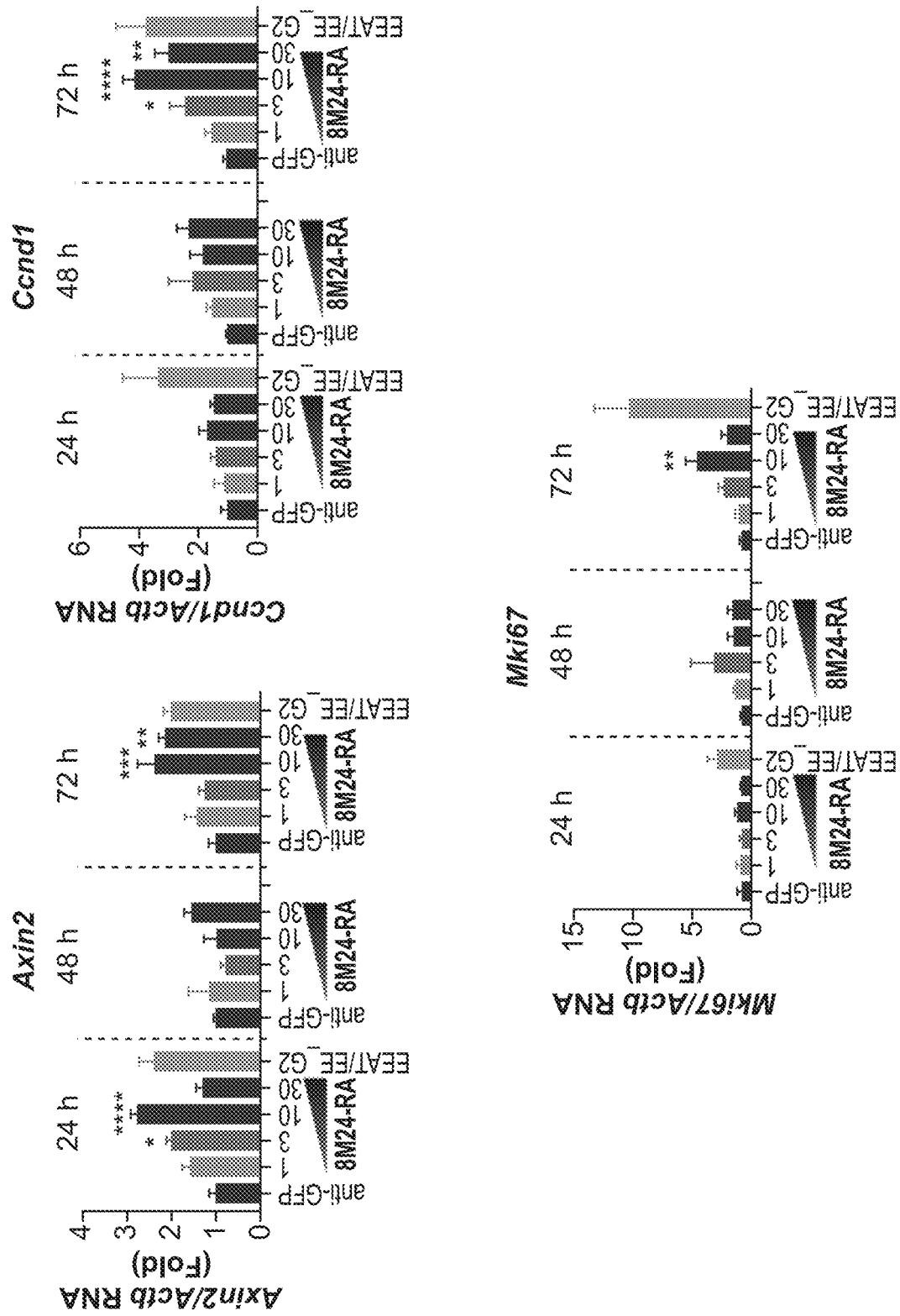
FIG. 29 provides graphs showing Axin2, Cend, and Ki67 expression in animals treated with the initial 8M24-RA Wnt signal enhancing molecule or the EEST-EE IgG2 format Wnt signal enhancing molecule (1R34-EEST/EE IgG2) at various dosages.
Figure 30:
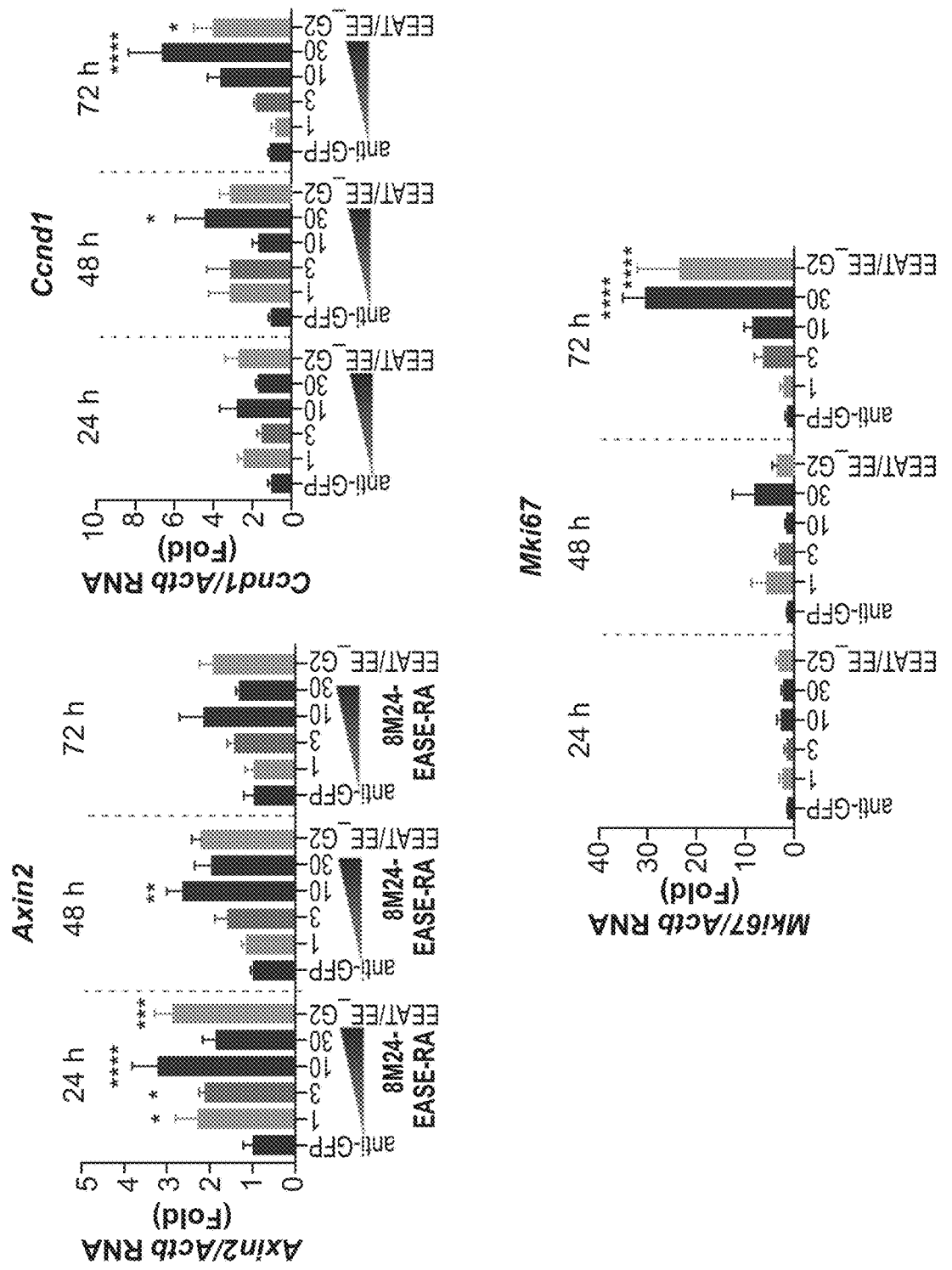
FIG. 30 provides graphs showing Axin2, Cend, and Ki67 expression in animals treated with the 8M24-EASE-RA Wnt signal enhancing molecule or the EEST-EE IgG2 format Wnt signal enhancing molecule (1 R34-EEST/EE IgG2) at various dosages.

The ability of the original 8M24-RA molecule (8M24-v1) and the 8M24-RA EASE mutant (8M24-EASE) to induce expression of genes regulated by the Wnt signaling pathway was demonstrated. Mice received a single i.p. dose of 8M24-RA (8M24-v1) or 8M24-RA EASE (8M24-EASE-RA; 1, 3, 10 or 30 mg/kg), anti-GFP (10 mg/kg), or αASGR1-RSPO2-EEST-EE (1R34-EEST/EE) in an IgG2 format instead of its normal IgG1 format. Serum and liver samples were collected 24 h, 48 h or 72 h after treatment (n=4 at each timepoint). mRNA expression by qPCR was normalized to Actb. The relative fold was calculated by setting the average of the anti-GFP group at 1 for each timepoint. As shown in FIG. 29, 8M24-RA induced the Wnt signal target genes Axin2 and Ccnd1 and expression of proliferation marker Mki67. As shown in FIG. 30, 8M-24-EASE-RA also induced expression of the Wnt signal target genes Axin2 and Ccnd1, and the proliferation marker Mki67. 8M24-RA and 8M-24-EASE-RA both also induced a small but significant dose-dependent increase in ALP, consistent with the role of ASGR in the elimination of serum ALP (data not shown).

Example 3

Pharmacokinetic Profile of Liver-Specific Wnt Signal Enhancing Molecules

The pharmacokinetic profile of the Wnt signal enhancing molecules was examined in mice. Mice were divided into six groups (n=25 per group) and received a single dose of the EEST-EE construct either IV at 3, 10, 30, 100 mg/kg or i.p. at 10 or 30 mg/kg. Serum samples (sparse) were collected at 5 and 30 min (IV) 30 min and 1 h (i.p.) and 2 h, 6 h, 24 h, day 4, day 7, day 10 or day 14 (IV and i.p.) after protein dosing (n=5 for each group), at each timepoint. Serum levels of EEST-EE were quantified by performing ELISA with either an ASGR1 or RNF43 capture ligand. Clearance, terminal half-life, Cmax and MRT are shown in the tables in FIG. 15. Liver samples were collected at termination at 30 min (IV), 1 h (i.p.), 6 h, 24 h, day 7 or day 14 (IV and i.p.) after protein dosing (n=5 for each timepoint). The relative fold was calculated by setting the average of the anti-GFP group at 1 for each timepoint. As shown in FIG. 15, 1R34-EEST/EE showed a non-linear PK response to increasing doses. Comparison of the AUC obtained between IV and i.p. dosing showed high bioavailability.

Figure 31:
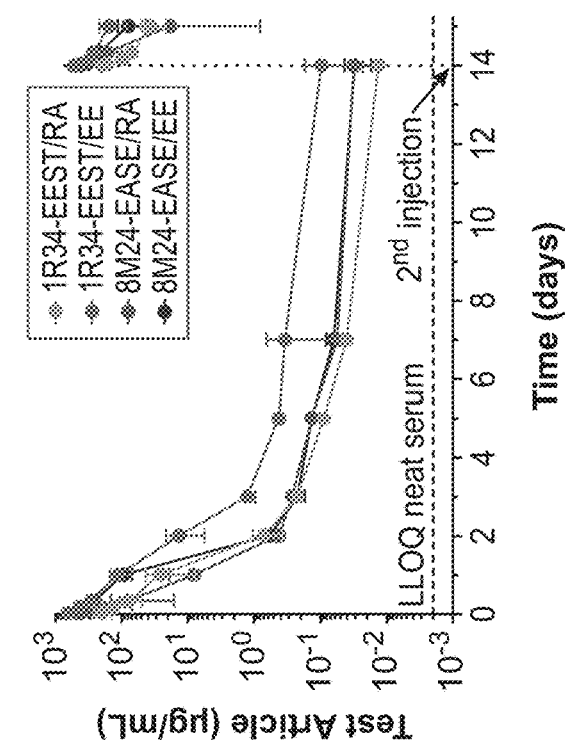
FIG. 31 provides the pharmacokinetic profile of the EEST-RA (1R34-EEST/RA), EEST-EE (1R34-EEST/EE), 8M24-EASE-RA, or 8M24-EASE-EE Wnt signal enhancing molecules in mice.

Similar studies were performed to compare the 1R34-EEST/RA, 1R34-EEST/EE, 8M24-EASE-RA, and 8M24-EASE-EE constructs. The results are provided in FIG. 31.

Example 4

Liver-Targeted Wnt Signal Enhancing Molecules Improve Liver Function in Mouse Models of Liver Fibrosis The effect of the Wnt signaling enhancer molecules on liver function was examined in two mouse models of liver fibrosis.

The chronic thioacetamide-induced mouse model of liver fibrosis was used. Six-week old C57Bl/6J male mice were treated with thioacetamide (TAA). TAA was added to drinking water at a concentration of 200 mg/L for thirteen weeks to induce liver fibrosis. In addition, during the last eight weeks of TAA conditioning, mice were administered with TAA i.p. 3 times weekly. TAA treatment was discontinued 2 days prior to dosing with αASGR1-RSPO2 proteins, and mice returned to purified, laboratory-grade acidified drinking water. Mice were injected intraperitoneally (i.p.) with recombinant αASGR1-RSPO2-EEST-EE (1R34-EEST/EE) or αASGR1-RSPO2-EEST-RA (1R34-EEST/RA) daily, or with αGFP-IgG or Rspo2 twice weekly for one week, as diagrammed in FIG. 16.

Figure 16:
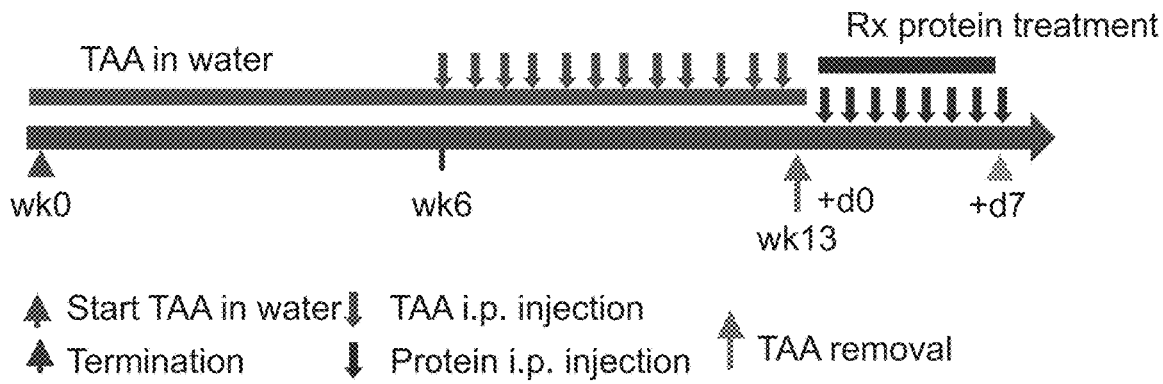
FIG. 16 is a diagram of the chronic thioacetamide-induced mouse model of liver fibrosis and the various Wnt signal enhancing molecules tested.
Figure 17A:
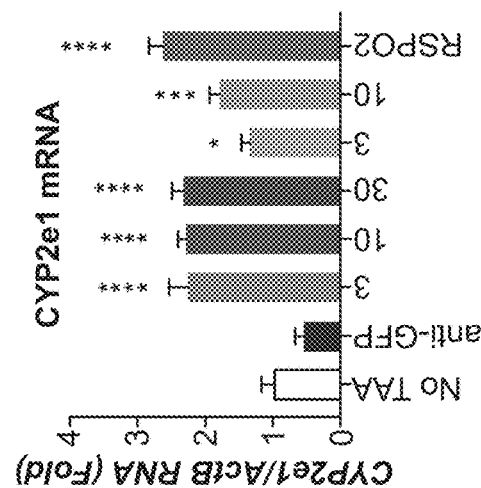
FIGS. 17A-17C show INR (FIG. 17A), Axin2 (FIG. 17B), and CYP2e1 mRNA (FIG. 17C) following administration of the indicated amounts of the Wnt signal enhancing molecules, EEST-EE or EEST-RA.
Figure 17B:
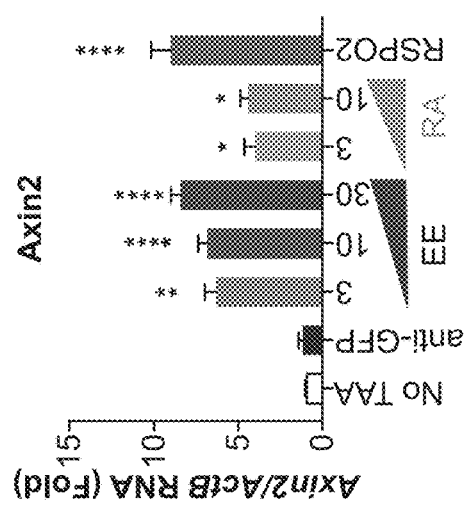
Figure 17C:
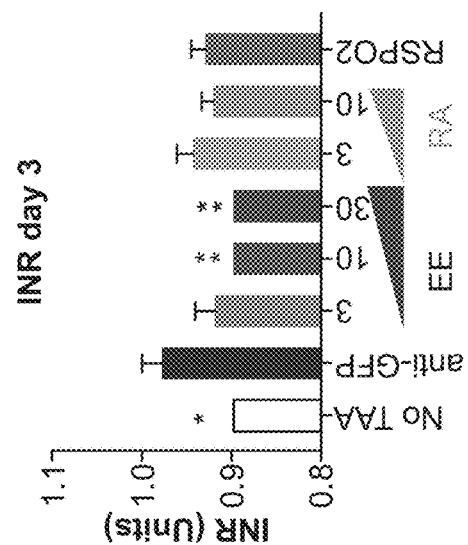
Figure 18:
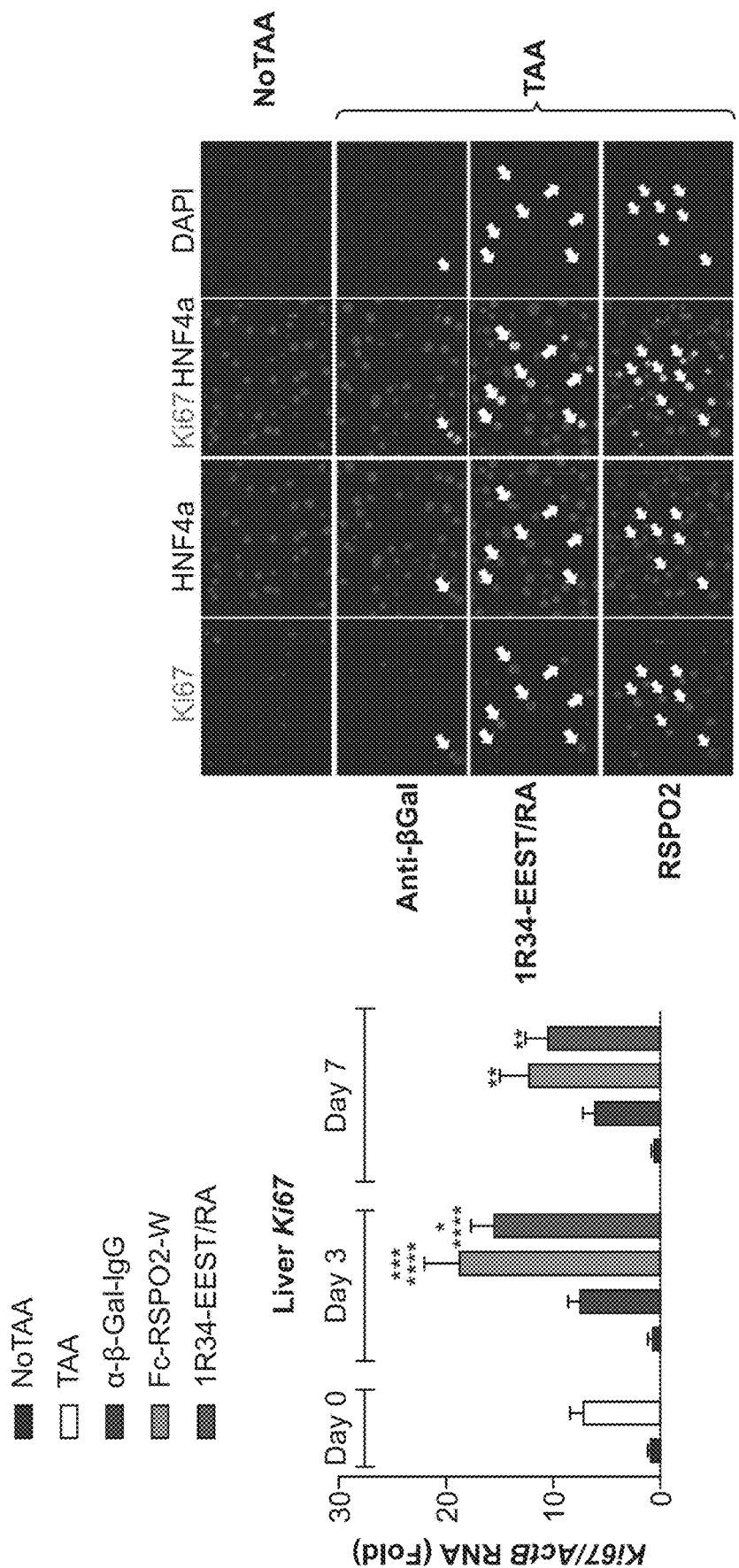
FIG. 18 shows expression of Ki67 in the liver of animals treated with control (anti-bgal), EEST-EE, or Rspo2, in the presence or absence of TAA.

At the times indicated in FIG. 16, INR was measured using the Roche CoaguChek-XS Plus. At 3, 10 and/or 30 days after beginning dosing, mice were anesthetized with isoflurane and blood was removed by cardiac puncture. A portion of the left liver lobe and duodenum were collected for analysis. Formalin-fixed and paraffin-embedded liver samples were sectioned and stained with the anti-Ki-67 rabbit antibodies (Abcam, ab15580). The number of Ki-67-positive nuclei per randomly chosen field (100× magnification using 10× objective) were counted using Image J. Treatment with αASGR1-RSPO2-EEST-EE (1R34-EESD/EE) led to a significant decrease in INR, whereas treatment with αASGR1-RSPO2-EEST-RA (1R34-EEST/RA) or Rspo2 did not (FIG. 17A; 1-way ANOVA, comparisons to anti-GFP; (*) $p<0.05$, () $p<0.01$, (*) $p<0.001$, (****) $p<0.0001$). Treatment with αASGR1-RSPO2-EEST-EE or Rspo2 also led to a significant increase in axin2 and CYP2e1 mRNA expression, whereas treatment with αASGR1-RSPO2-EEST-RA showed a smaller, but significant increase in axin2 and CYP2e1 mRNA expression (FIGS. 17B and 17C; (*) $p<0.05$, () $p<0.01$, (*) $p<0.001$, (****) $p<0.0001$). Ki67 immunofluorescence staining also confirmed hepatocyte specificity in the TAA-induced injury model (FIG. 18).

The effect of αASGR1-RSPO2-EEST-EE was also examined in the $CCl_4$-induced injury model. $CCl_4$ i.p. C57BL/6J male mice received $CCl_4$ i.p. injections twice weekly for 11 weeks. A control group of mice received olive oil i.p. injections only (n=8). $CCl_4$ treatment was discontinued and mice were divided in 10 groups (n=8) and dosed daily or q.o.d. with αASGR1-RSPO2-EEST-EE or αASGR1-RSPO2-EEST-RA at various dosages (mg/kg), or twice weekly with anti-GFP (10 mg·kg) or RSPO2 (4.6 mg/kg). Blood and liver samples were collected at termination at day 7 or at day 14.

Figure 20:
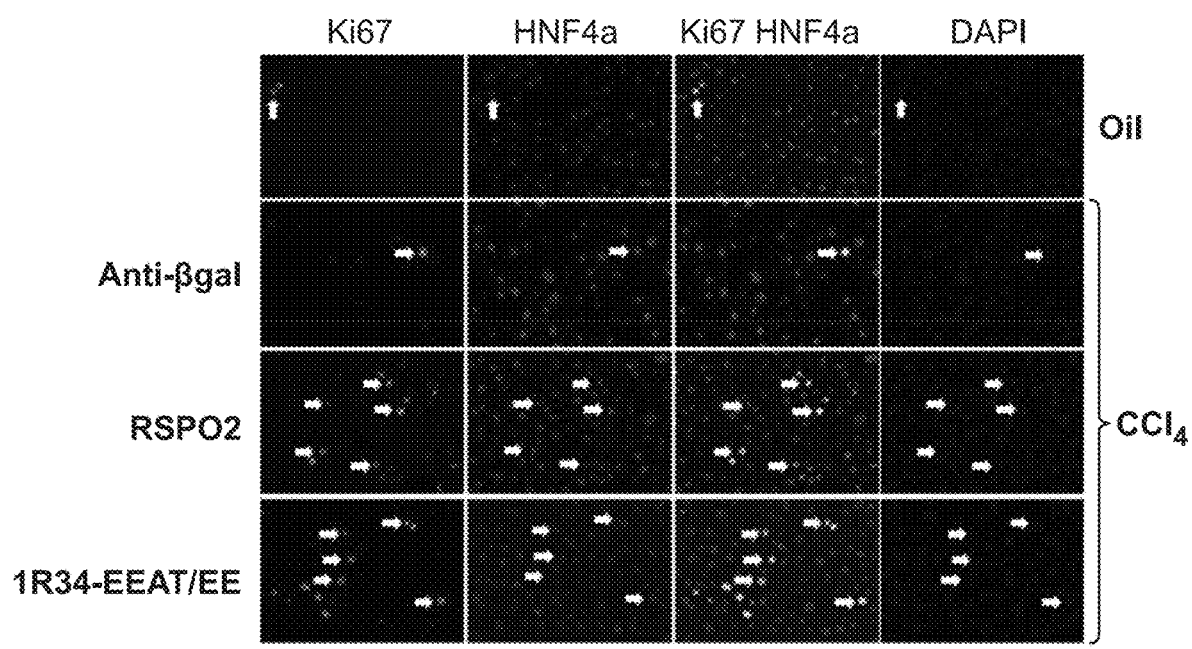
FIG. 20 shows expression of Ki67 in the liver of animals treated with control (anti-bgal), EEAT-EE (αASGR1-RSPO2-EEAT-EE or 1R34-EEAT/EE), or Rspo2, in the presence or absence of $CCl_4$.

As shown in FIG. 19, αASGR1-RSPO2-EEST-EE significantly induced levels of Axin 2 and Mki67 mRNA at day 7. Greater increases in Axin2, Ccnd1 and Mki67 mRNA were observed with αASGR1-RSPO2-EEST-EE than with αASGR1-RSPO2-EEST-RA. In addition, immunofluorescence confirmed that the increase was hepatocyte-specific (FIG. 20).

Example 5

Wnt Signal Enhancing Molecules Improve Liver Synthetic Function and Reduces Fibrosis Six-week old C57Bl/6J male mice were treated with thioacetamide (TAA). TAA was added to drinking water at a concentration of 200 mg/L for eighteen weeks to induce liver fibrosis. In addition, during the last seven weeks of TAA conditioning, mice were administered TAA i.p. 3 times weekly, resulting in liver fibrosis. TAA treatment was discontinued 2 days prior to dosing with αASGR1-RSPO2-EEST-EE (1R34-EEST/EE), and mice returned to purified, laboratory-grade acidified drinking water. Mice were injected intraperitoneally (i.p.) with recombinant αASGR1-RSPO2-EEST-EE or negative control daily at 10 mg/kg for 14 days.

At the times indicated in FIG. 16A, INR was measured using the Roche CoaguChek-XS Plus. INR (Internalized Normalized Ratio) measures the speed of blood clot formation. High INR levels reflect liver disease or cirrhosis and indicate an associated inability to produce normal amounts of proteins and less optimal blood clotting. At 3, 7, and 14 days after beginning dosing, mice were anesthetized with isoflurane and blood was removed by cardiac puncture. Treatment with αASGR1-RSPO2-EEST-EE led to a significant decrease in INR as compared to control (FIG. 16B). In this mouse model of fibrosis, short-term treatment with both Rspo and αASGR1-RSPO2-EEST-EE resulted in modest, variable, reductions in fibrosis (data not shown).

Example 6

Effect of Tissue-Targeted Rspo Mimetics on Liver Function in a Chronic $CCl_4$-Induced Mouse Model of Liver Fibrosis Liver fibrosis was also examined using a chronic CCl4-induced mouse model of liver fibrosis. In particular, the effect of 1R23-EEAT/EE on $CCl_4$-induced hepatic fibrosis was compared in immunodeficient and immunocompotent mice.

Thirty-two 6-week-old C57BL/6J males (Jackson Laboratories) and thirty-two NOD.CB17-Prkdc$^{scid}$/J (SCID) were injected intraperitoneally with $CCl_4$ (0.5 mL/kg, twice/week) for 10 weeks. Sixteen mice of each strain were injected intraperitoneally with olive oil carrier (0.5 mL/kg). Following $CCl_4$ treatment, eight mice of each strain, with or without $CCl_4$ treatment were terminated and blood and tissues were collected for baseline measurements. The remaining $CCl_4$ treated mice were randomized into treatment groups based on body weight (Table 4) and dosed with proteins for 2 weeks. Treatment groups are as follows for each strain: 20 mg/kg 1 R34-EEAT/EE, n=8 (daily dosing); 4.6 mg/kg Fc-RSPO2-WT, n=8 (twice/week dosing); 10 mg/kg anti-GFP, n=8 (twice/week dosing). An additional control groups previously injected with oil only, n=8, was included. Blood was drawn from mice on day 7 (first day of protein dosing denotes as Day 0) for serum chemistry testing. Mice were terminated at Day 14. Total body and liver weights were measured, blood, liver tissues were collected and preserved for testing.

Table 4 provides a description of treatment groups for the $CCl_4$-induced mouse fibrosis model. Immunodeficient, NOD.CB17-Prkdc$^{scid}$/J, or immunocompetent, C57BL/6J, males were preconditioned with $CCl_4$ diluted in olive oil carrier, or with olive oil alone. Mice were divided in groups A to L as indicated. Mice were then injected with test articles at the dose and frequency indicated, followed by termination either at baseline on day 0, or 14 days after the start of test articles dosing.

TABLE 4

CCl4-induced fibrosis treatment groups

| Group | Strain | N | CCl$_4$ | Test Article | Dose (mpk) | Frequency | Termination |
|---|---|---|---|---|---|---|---|
| A | NOD.CB17- | 8 | Oil | none | 0 | N/A | Baseline |
| B | Prkdc$^{scid}$/J | 8 | ✓ | none | 0 | | Baseline |
| C | | 8 | Oil | none | 0 | | Day 14 |
| D | | 8 | ✓ | Anti-GFP | 10 | 2×/wk | Day 14 |
| E | | 8 | ✓ | EEAT/EE | 20 | q.d. | Day 14 |
| F | | 8 | ✓ | RSPO2 | 4.6 | 2×/wk | Day 14 |
| G | C57BL/6J | 8 | Oil | none | 0 | N/A | Baseline |
| H | | 8 | ✓ | None | 0 | | Baseline |
| I | | 8 | Oil | none | 0 | | Day 14 |
| J | | 8 | ✓ | Anti-GFP | 10 | 2×/wk | Day 14 |
| K | | 8 | ✓ | EEAT/EE | 20 | q.d. | Day 14 |
| L | | 8 | ✓ | RSPO2 | 4.6 | 2×/wk | Day 14 |

Figure 32:
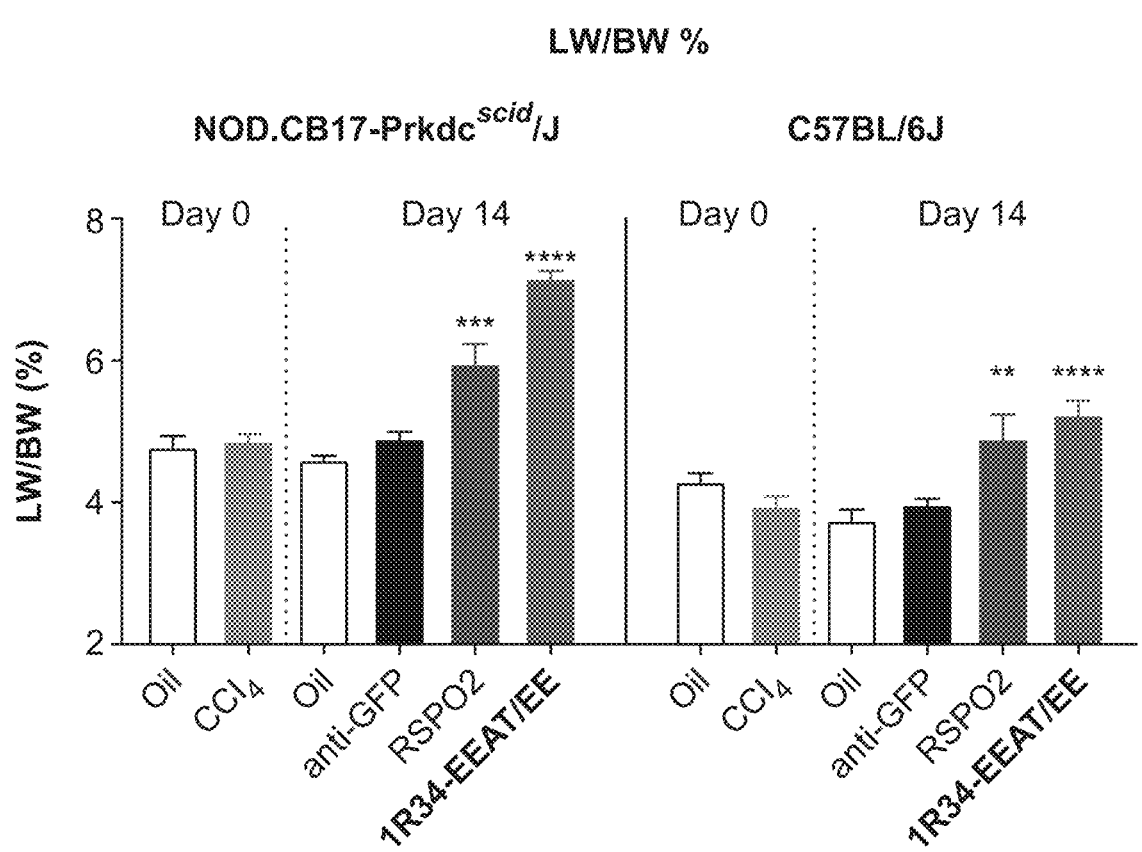
FIG. 32 shows the percentage of liver to body weight ratio at termination. Statistical Analyses: One-way ANOVA (GraphPad Prism), * $p<0.05$,  $p<0.01$, * $p<0.001$, **** $p<0.0001$, Error bars: Mean with SEM.

Liver to body weight ratios were significantly elevated in groups treated with RSP02 positive control as well as those treated with the RSPO mimetic, 1R34-EEAT/EE (FIG. 32).

Figure 33A:
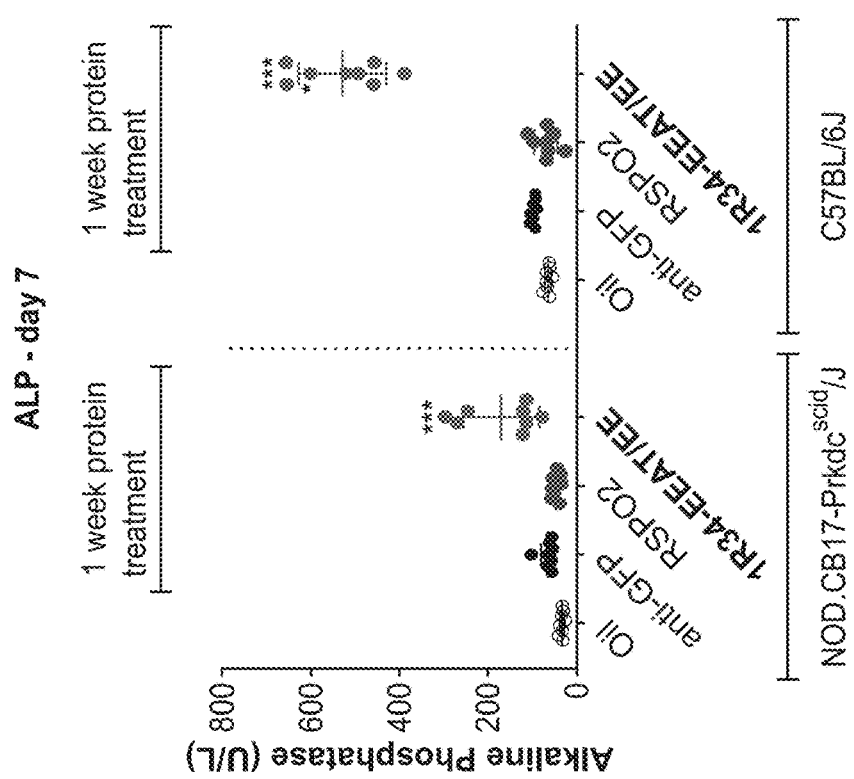
FIGS. 33A-B shows serum ALP (FIG. 33A) and albumin (FIG. 33B) at day 7 and day 14 after the start of test articles dosing.
Figure 33B:
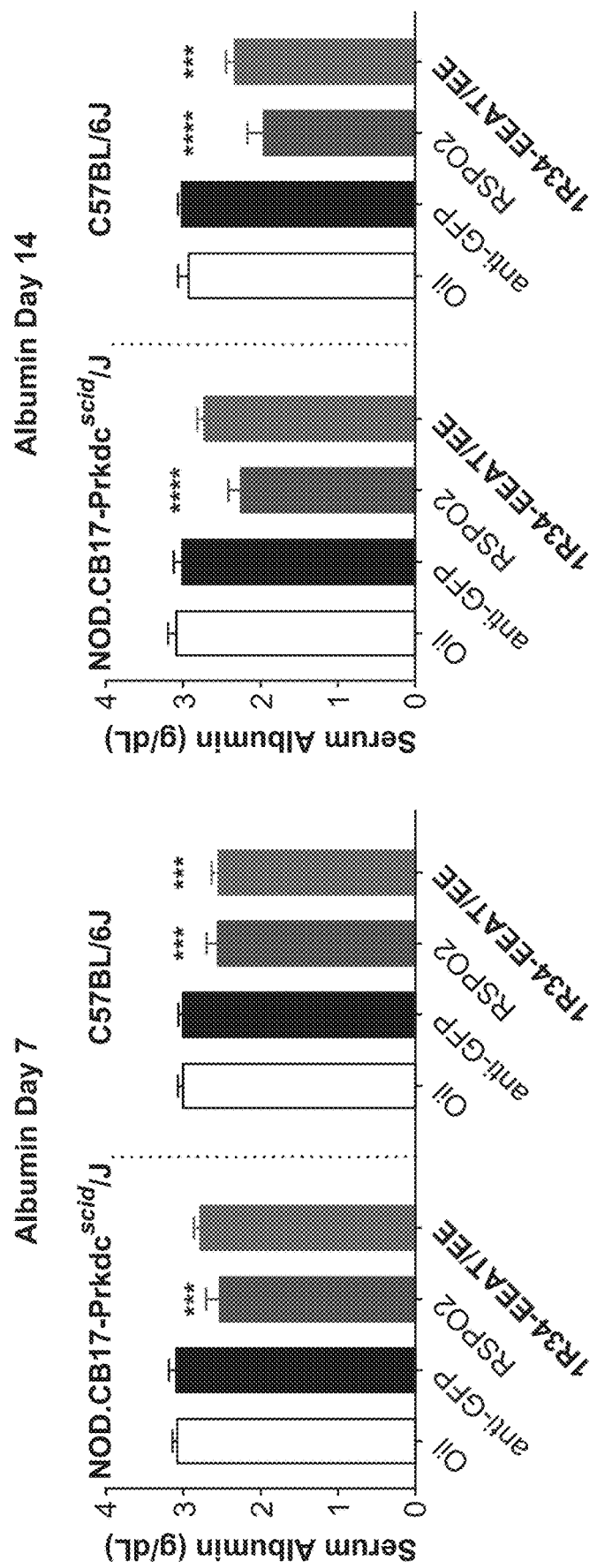

At timepoints after one and two weeks of protein treatment, serum alkaline phosphatase (ALP) and albumin were measured. The mouse serum was collected from tail bleed at Day 7 and terminal bleed at Day 14 and analyzed using a VetAxcel (Alfa-Wasserman). The data is presented in FIGS. 33A and 33B. Serum ALP was statistically higher at both one-week and two-week timepoints, consistent with the upregulation of the alkaline phosphatase protein levels due to the elimination of ASGR receptor as described in an ASGR1-KO mouse model (see, e.g., Cell Host Microbe. 2018 Oct. 10; 24(4):500-513). Serum albumin levels were significantly reduced in response to RSPO2 and 1R34-EEAT/EE. This result suggests an expected temporary reduction in function of periportal hepatocytes due to increased pericentral hepatocyte expansion, induced by increased Wnt signaling.

Quantitative PCR was used to measure changes in hepatic gene expression. Treatment of mice with RSP02 or 1R34-EEAT/EE led to increased expression of the Wnt-inducible Axin2 gene in the SCID mice but not in the C57BL/6J mice at day 14. These results suggest that the test articles activity is sustained in immunodeficient mice, but not in immunocompetent mice, after two weeks.

Figure 34:
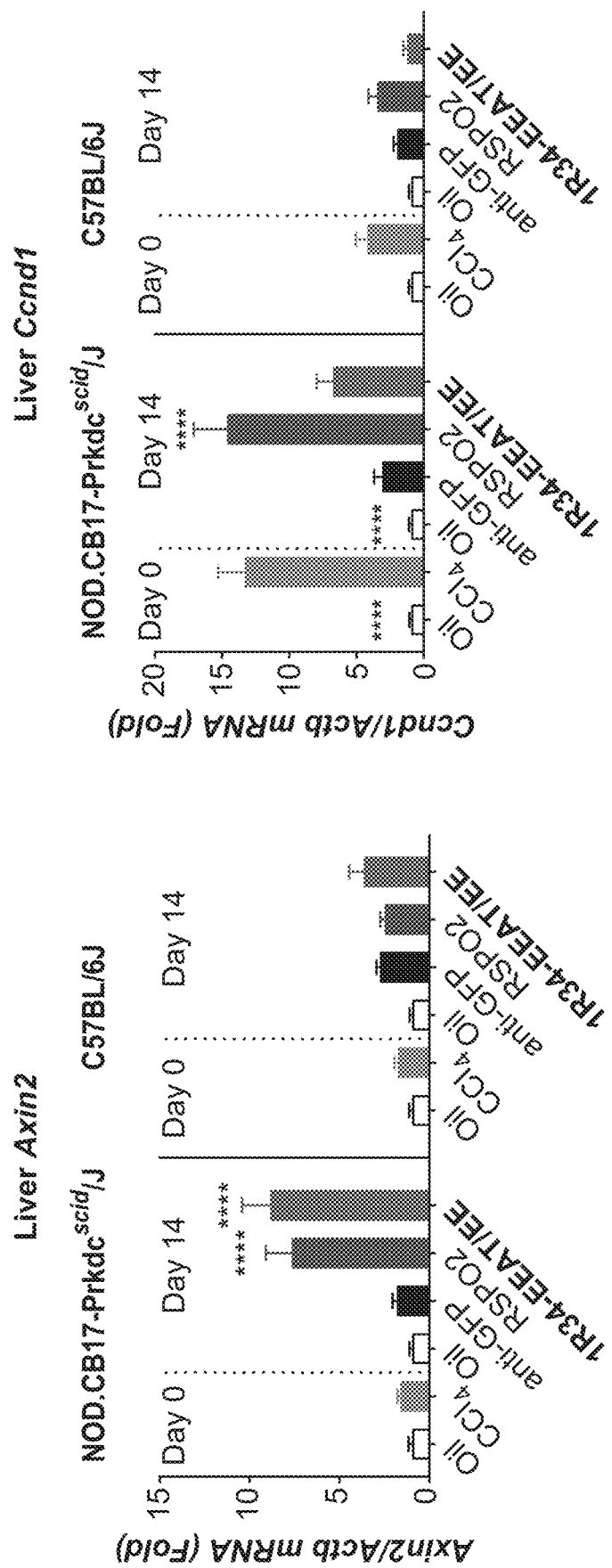
FIG. 34 shows expression analysis of liver RNA for the Axin2, Ccnd1 and Mki67 genes as measured by qPCR.
Figure 34:
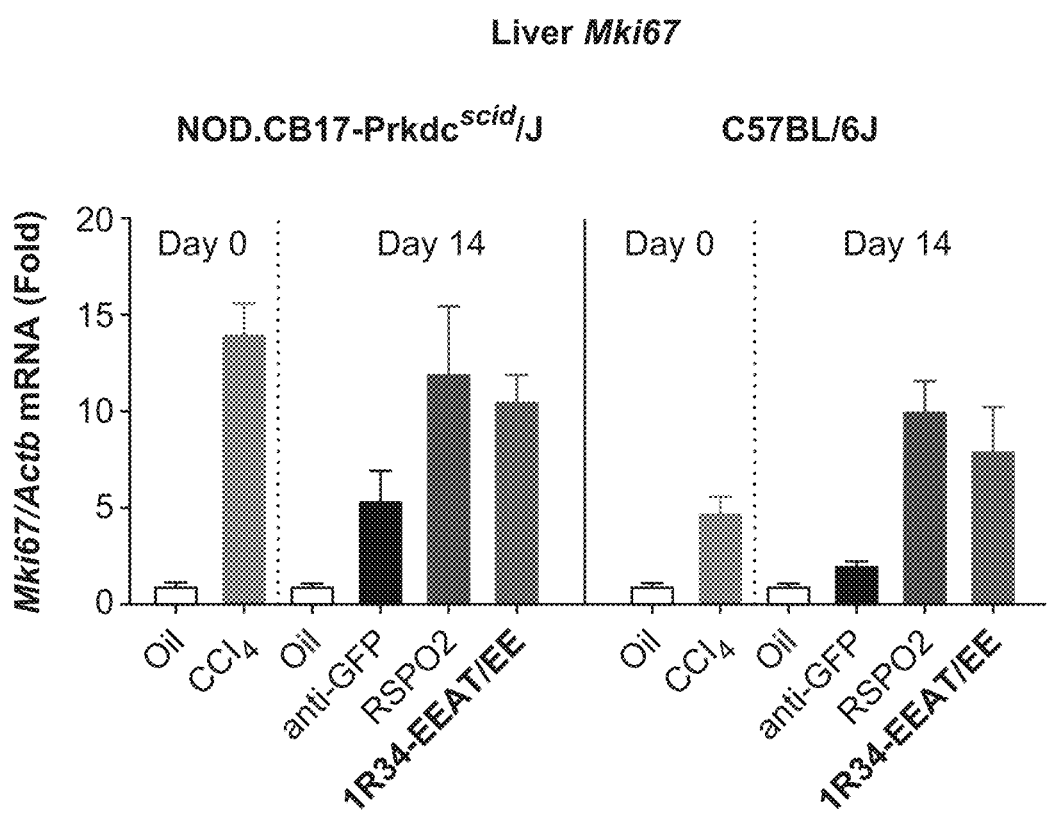
Figure 35:
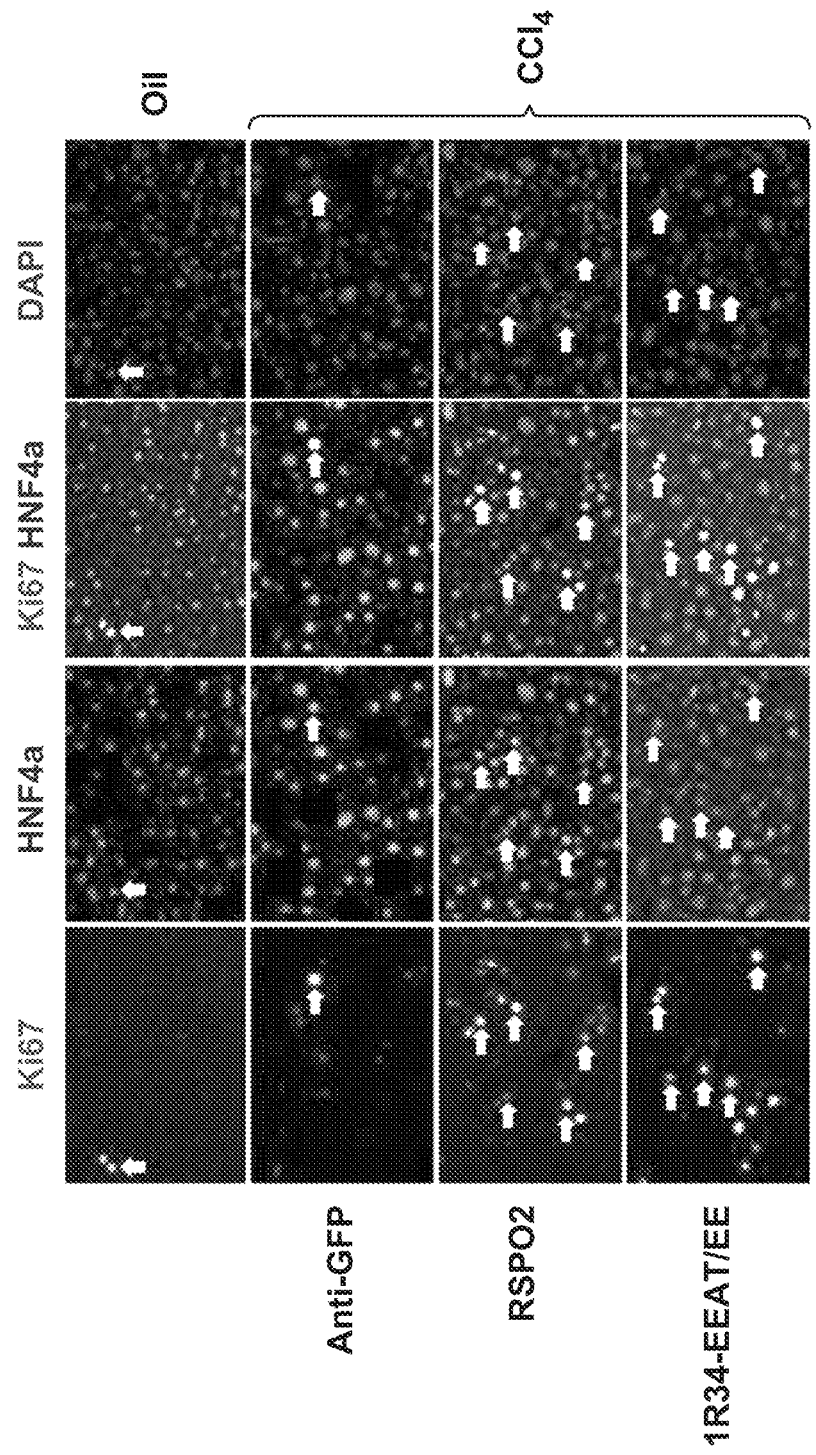
FIG. 35 shows immunofluorescence staining of liver sections from mice treated with SZN-043.v2, RSPO2, anti-GFP after $CCl_4$ treatment, or control sections from mice injected with olive oil only. Staining with a proliferation marker, anti-Ki67 nuclear antigen (green), a hepatocyte-specific marker, anti-HNF4α (red) DNA staining with DAPI (blue).

Treatment with RSPO2 and 1R34-EEAT/EE also revealed a trend toward an increase in Mki67 and Cyclin DI (Ccnd1) proliferation markers in the liver after 1R34-EEAT/EE treatment, and a significant increase after RSPO2 treatment (FIG. 34). Immunofluorescence staining of liver sections showed that the number of Ki67-HNF4a double positive cells were increased in RSPO2 and 1R34-EEAT/EE liver samples from SCID mice (FIG. 35). Similar results were obtained with liver samples from C57BL/6J mice (data not shown). These results suggest that the RSPO2 and 1R34-EEAT/EE promote the proliferation of hepatocytes.

Figure 36A:
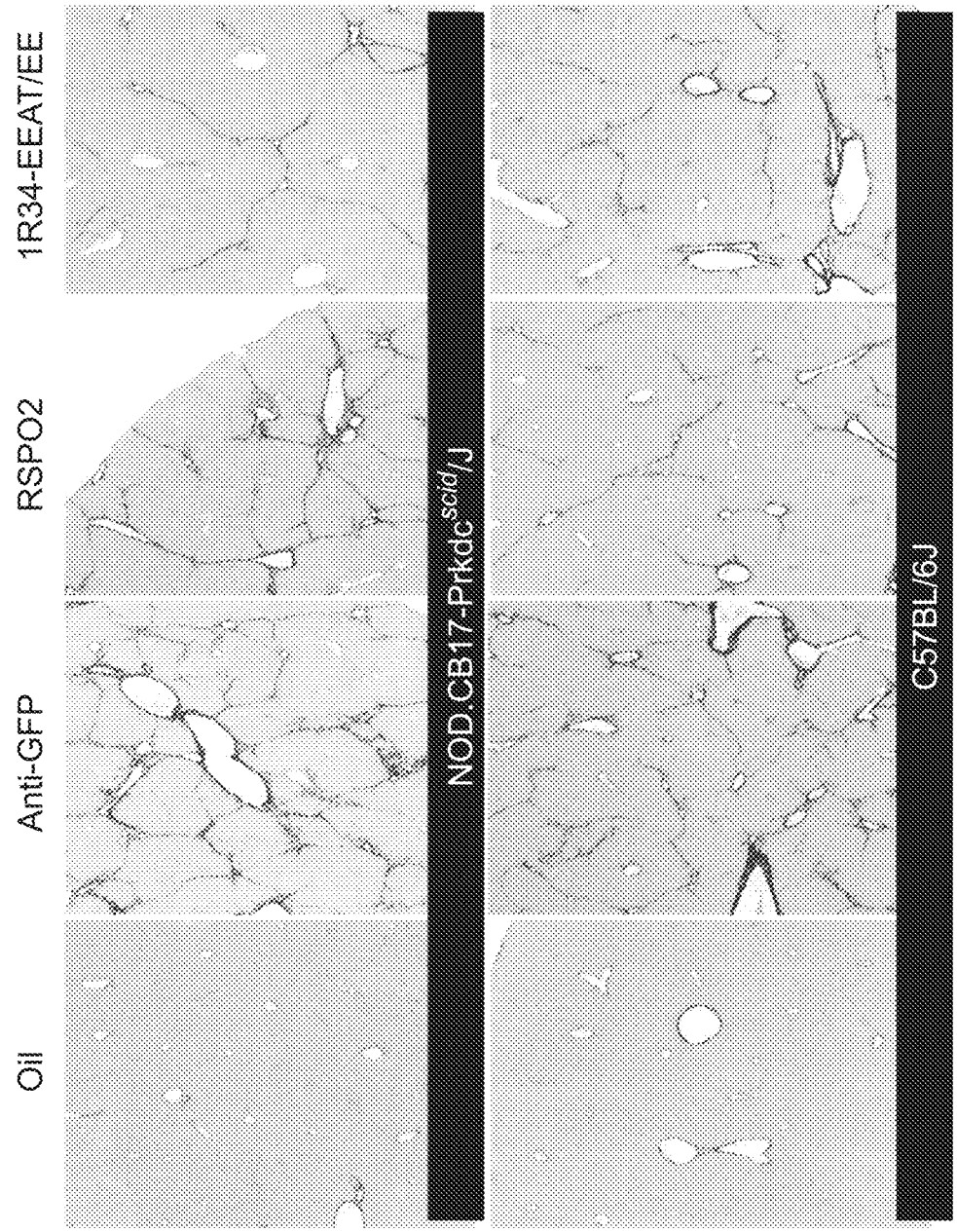
FIGS. 36A-B shows percentage fibrotic area measured by Picro-Sirius red staining (FIG. 36A) followed by quantification using Image J (FIG. 36B).
Figure 36B:
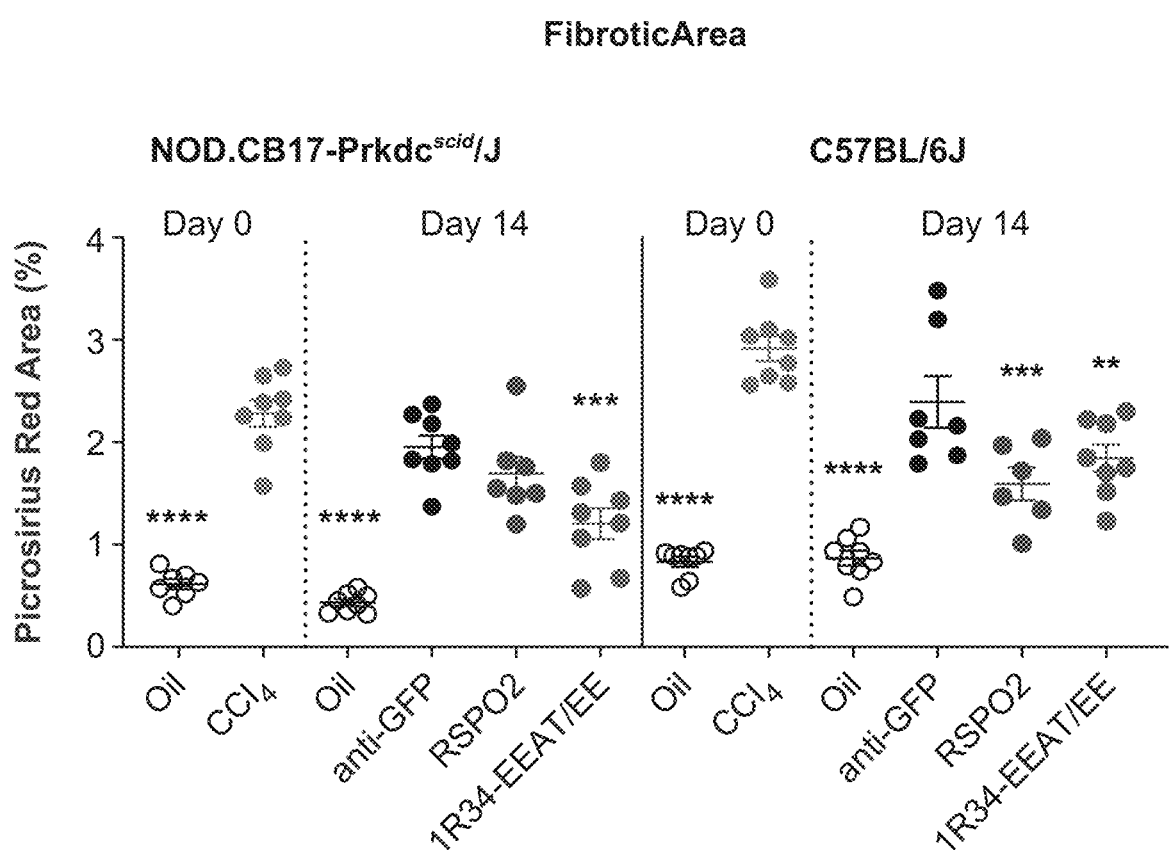

Histological liver sections were stained with Sirius red to measure the levels of fibrosis (FIG. 36A). The Sirius red stained area was quantitated by Image J (NIH) (FIG. 36B). These results show that 1R34-EEAT/EE reduced significantly the percentage area of Sirius Red stained collagen fibers in both immunocompetent and immunodeficient mice. RSPO2 reduces the percentage area stained with Sirius red also, albeit not significantly in the SCID mice.

Together these data suggest that the RSPO mimetic, 1R34-EEAT/EE, has a significant impact on the rate at which mouse livers can resolve fibrosis and regenerate functional hepatocytes.

Example 7

Liver-Targeted RSPO Wnt Signal Enhancing Molecules Activate Wnt Signalling and Engage Targets in Non-Human Primates Non-human female primates were treated with 10 mg/kg of either αASGR1-RSPO2-EEST-EE (1R34-EEST/EE), αASGR1-RSPO2-EEST-RA (1R34-EEST/RA), 8M24 αASGR1-RSPO2-EASE-RA (M24-EASE/RA), 8M24-EASE-RSPO2-EASE-EE (8M24/EASE/EE) or vehicle control by intravenous bolus at day 1 and day 15, and then terminated 24 hours after the second dose at day 16. Liver samples were obtained and subjected to hematological analysis and histopathology. Liver samples were analyzed by qPCR for AXIN2 expression and normalized to the ACTB expression. The relative fold was calculated by setting the average value of the vehicle group as 1. Average+/−SEM. 1-way ANOVA, Holm-Sidak multiple comparisons to vehicle, * p<0.05.

Figure 11:
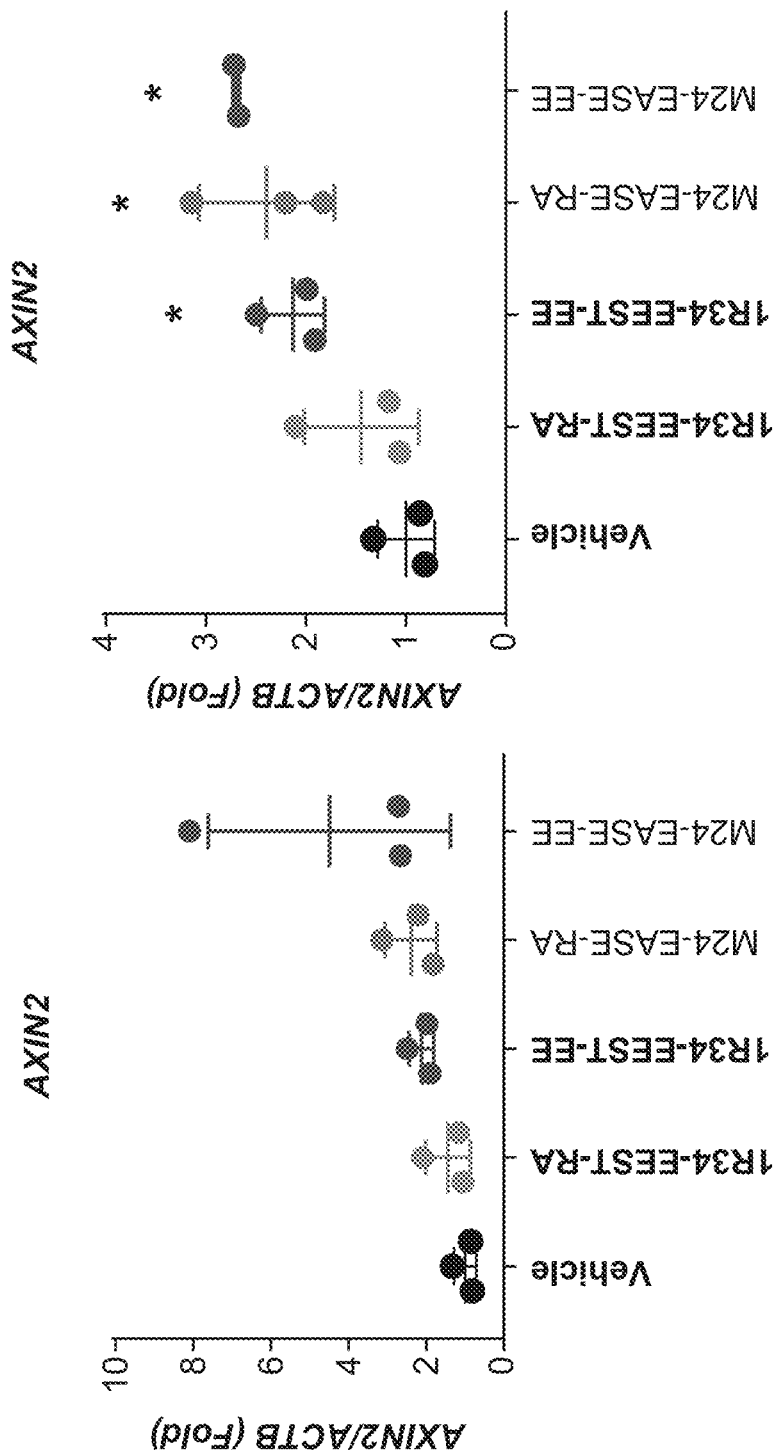
FIG. 11 provides graphs showing Axin2/ActB expression in animals treated with vehicle or the indicated Wnt signaling enhancer molecules. Data is presented with (left panel) or without (right panel) the value for the injured animal, treated daily with rimadyl.
Figure 24:
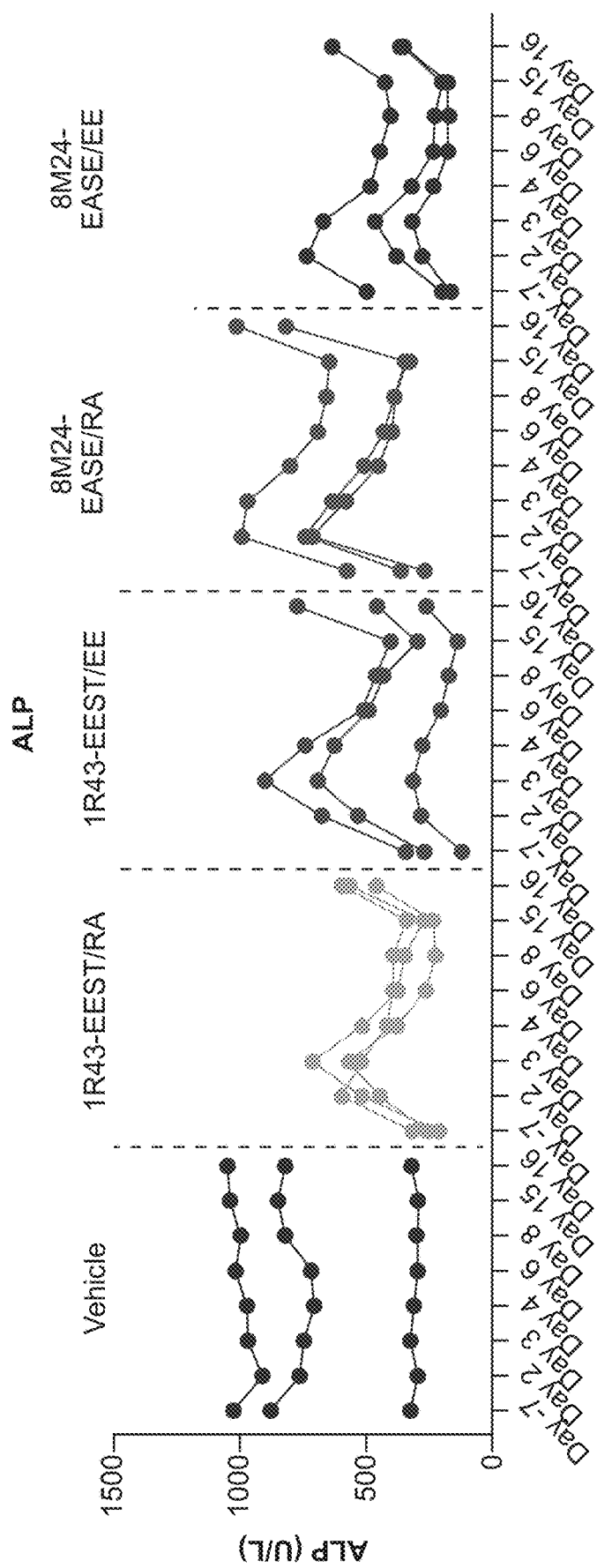
FIG. 24 is a graph showing expression of ALP following treatment with vehicle, EEST-RA, EEST-EE, 8M24-EASE-RA, or 8M24-EASE-EE.

Treatment with αASGR1-RSPO2-EEST-EE, αASGR1-RSPO2-EEST-RA, 8M24 αASGR1-RSPO2-EASE-RA, or 8M24-EASE-RSPO2-EASE-EE resulted in no unscheduled deaths, no abnormal clinical observations, and no changes in body weight or food consumption. Axin2 mRNA levels were significantly increased in the liver, and were slightly higher following treatment with αASGR1-RSPO2-EEST-EE, 8M24 αASGR1-RSPO2-EASE-RA, or 8M24-EASE-RSPO2-EASE-EE than with αASGR1-RSPO2-EEST-RA (FIG. 11). With respect to clinical pathology, there were no substantive changes in hematology, but there was a substantive, transient increase in ALP consistent with binding of the molecules to ASGR1, thus inhibiting clearance of ALP by this receptor (FIG. 24).

These studies demonstrate that the Wnt signaling enhancer molecules are well-tolerated and active in non-human primates.

Example 8

Crystal Structure of Human ASGR1-CBD:8M24 Complex

Asialoglycoprotein receptor (ASGR; ASGPR), a C-type lectin mainly expressed in mammalian liver cells (hepatocytes), mediate clearance of desialylated, galactose- or N-acetylgalactosamine-terminating plasma glycoproteins via receptor mediated endocytosis. Assembly of ASGR is thought to be a hetero-trimer made up two ASGR1 and one ASGR2 polypeptides referred to as H1 and H2, respectively. Structurally, both ASGR1 (H1) and ASGR2 (H2) polypeptides are type-II membrane proteins with a short N-terminal cytosolic domain followed by a single-transmembrane helix, and exoplasmic region comprising of an helical stalk-region that mediate oligomerization via a coiled-coiled structure and a carbohydrate binding domain (CBD) at their C-terminus. Human ASGR1 and ASGR2 share 54% sequence identity between them.

The crystal structure of human ASGR1-CBD (HuASGR1-CBD) domain (residues 154 to 291 of uniprot entry P07306; https://www.dot.uniprot.org/uniprot/P07306) complexed with the Fab domain of the antibody named 8M24 was determined. The sequence of the HuASGR1-CBD construct used for the structural studies contained an octa-Histidine motif and a biotin acceptor peptide (BAP) at its N-terminus is as follows:

```
HuASGR1-CBD_P07306_154-291
                                         (SEQ ID NO: 52)
HHHHHHHHGSGSGLNDIFEAQKIEWHESGSGCPVNWVEHERSCYWFSRS

GKAWADADNYCRLEDAHLVVVTSWEEQKFVQHHIGPVNTWMGLHDQNGP

WKWVDGTDYETGFKNWRPEQPDDWYGHGLGGGEDCAHFTDDGRWNDDVC

QRPYRWVCETELDKASQEPPLL.
```

Expression and Purification of HuASGR1-CBD for Structural Studies

Plasmid expressing HuASGR1-CBD was transfected for expression in Expi293 cells (ThermoFisher USA), typically at 1000 mL scale, using FectoPro transfection agent following standard protocols from the manufacturer (Polyplus Transfection NY USA). After 4 days of continuous cell growth, media were harvested by centrifugation, HuASGR1-CBD was purified from media by incubation with HisComplete resin (1 mL per L of culture; Roche) pre-equilibrated in 50 mM sodium di-hydrogen phosphate pH 8.0, 300 mM NaCl, washed with 10 mM imidazole, and eluted with 250 mM imidazole in the equilibration buffer. Elutions were concentrated to 5 mL, and further polished on a HiLoad 16/600 Superdex 200 pg column (GE Life Sciences) pre-equilibrated with HBS (20 mM HEPES pH 7.4, and 150 mM sodium chloride). Fractions near main peak was further analyzed by SDS-Polyacrylamide Gel Electrophoresis (SDS-PAGE; Tris-HCl 4-15% gel from Bio-Rad, Hercules, CA) to confirm the content. The samples were prepared in Laemmli sample buffer and heated at 100° C. for 5 min. Fractions containing HuASGR1-CBD were concentrated to 1.78 mg/mL and frozen in the presence of 10% glycerol for storage at −80 C until further use. Protein concentrations were determined using a NanoDrop Spectrophotometer (Thermo Scientific) by the direct UV A280 method. The relationship of absorbance to protein concentration is linear based on Beer-Lamber equation, $A=\varepsilon l c$; A is the absorbance value, s is the wavelength-dependent extinction coefficient, 1 is the path length in centimeters, and c is the protein concentration. The extinction coefficients of all produced proteins were estimated by their amino acid sequences.

Expression and Purification of 8M24 Fab

Plasmids expressing light-chain and heavy-chain (with hexa-histidine tag at its C-terminus) of 8M24 Fab (L1H1 version corresponding to SZP19057+19056) were transfected for expression in Expi293 cells (ThermoFisher USA), typically at 1000 mL scale, using FectoPro transfection agent following standard protocols from the manufacturer (Polyplus Transfection NY USA). After 4 days of continuous cell growth, media were harvested by centrifugation, and bound to Complete-His resin (2.5 mL per 1L culture; Roche) pre-equilibrated in PBS and eluted under gravity-flow using 250 mM imidazole in PBS. Elutions containing Fab binders were concentrated to ~5 mL, and further polished on a HiLoad 16/600 Superdex 200 pg column (GE Life Sciences) column pre-equilibrated with HBS. Fractions near main peak was further analyzed by SDS-Polyacrylamide Gel Electrophoresis (SDS-PAGE; Tris-HCl 4-15% gel from Bio-Rad, Hercules, CA) to confirm the content. The samples were prepared in Laemmli sample buffer and heated at 100° C. for 5 min. Fractions containing 8M24 Fab were concentrated to 7.12 mg/mL and frozen in the presence of 10% glycerol for storage at −80 C until further use. Protein concentrations were determined using a NanoDrop Spectrophotometer (Thermo Scientific) by the direct UV A280 method. The relationship of absorbance to protein concentration is linear based on Beer-Lamber equation, $A=\varepsilon l c$; A is the absorbance value, $\varepsilon$ is the wavelength-dependent extinction coefficient, 1 is the path length in centimeters, and c is the protein concentration. The extinction coefficients of all produced proteins were estimated by their amino acid sequences.

HuASGR1-CBD:8M24 Complex Formation, Crystallization, and Structure Determination Purified HuASGR2-CBD and 8M24 Fab were mixed at 1.1:1 molar ratio (little excess of the HuASGR1-CBD), and incubated with carboxy-peptidase A and B at a w/w ratio of 100:1 for over-night at 4° C. Complex formation was confirmed by observation of a single-major peak on SuperdexS200 Increase (10/300 GL) column pre-equilibrated in HBS. Fractions containing complexes were further checked by SDS-PAGE and concentrated to ~20 mg/mL for crystallization screens. Crystallization screen, using commercially available MCSG1, MCSG2, MCSG3, MCSG4, PACT (Molecular Dimensions USA), PEGs I, and PEGs II (Qiagen USA) screens were performed using Mosquito (TTP LabTech) liquid handler and equilibrated at 18° C. inside an EchoTherm incubator (Torrey Pines Scientific USA). 96-well plate crystal screening experiments were periodically monitored manually via a DiscoveryV20 stereomicroscope (Zeiss USA), and crystals were frozen for data collection by plunging into liquid nitrogen in the presence of various cryo-protectants (typically 15 to 30% v/v of glycerol or ethyleneglycol). X-ray diffraction datasets were collected at the Berkeley Center for Structural Biology at the Advanced Light Source (ALS), Berkeley CA, and processed with XDS [XDS. Kabsch W. (2010) Acta Cryst. D66, 125-132], and xdsme [Legrand P. (2017) XDSME: XDS Made Easier GitHub repository, https://github.com/legrandp/xdsme DOI 10.5281/zenodo.837885]programs. Structure of HuASGR1-CBD:8M24 complex was determined by molecular replacement method using Phaser [Phaser crystallographic software. McCoy A J, Grosse-Kunstleve R W, Adams P D, Winn M D, Storoni L C, and Read R J. (2007) J Appl Crystallogr 40, 658-674] with poly-alanine model of published structure of ASGR1-CBD [PDB code: 5JPV; Efficient Liver Targeting by Polyvalent Display of a Compact Ligand for the Asialoglycoprotein Receptor. Sanhueza C A, Baksh M M, Thuma B, Roy M D, Dutta S, Preville C, Chrunyk B A, Beaumont K, Dullea R, Ammirati M, Liu S, Gebhard D, Finley J E, Salatto C T, King-Ahmad A, Stock I, Atkinson K, Reidich B, Lin W, Kumar R, Tu M, Menhaji-Klotz E, Price D A, Liras S, Finn M G, Mascitti V. (2017) J. Am. Chem. Soc. 139: 3528-3536] and variable and constant domains of previously determined crystals structure of an unrelated Fab at Surrozen Inc, followed by refinement and validation by MolProbity as implemented in Phenix [PHENIX: a comprehensive Python-based system for macromolecular structure solution. P. D. Adams, P. V. Afonine, G. Bunkoczi, V. B. Chen, I. W. Davis, N. Echols, J. J. Headd, L. W. Hung, G. J. Kapral, R. W. Grosse-Kunstleve, A. J. McCoy, N. W. Moriarty, R. Oeffner, R. J. Read, D. C. Richardson, J. S. Richardson, T. C. Terwilliger, and P. H. Zwart. (2010) Acta Cryst D66, 213-221; MolProbity: all-atom structure validation for macromolecular crystallography. Chen V B, Arendall W B, Headd J J, Keedy D A, Immormino R M, Kapral G J, Murray L W, Richardson J S, and Richardson D C. (2010) Acta Cryst. D66, 12-21]. Crystallography models were manually inspected and built using COOT [Features and development of Coot. Emsleym P, Lohkamp B, Scott W G, and Cowtan K. (2010) Acta Cryst. D66, 486-501]. Analyses of refined crystal structures, and image creations were performed using MOE (CCG) and PyMol (Schrodinger).

Structure of HuASGR2-CBD:8M24 Complex

The sequence of the light chain and heavy chain of the 8M24 Fab used for the structural studies are shown below.

8M24L1 Light-chain:
(SEQ ID NO: 53)
DIQMTQSPSSLSASVGDRVTITCRISENIYSNLAWYQQKPGKAPKLLIY

AAINLADGVPSRFSGSGSGTDFTLTISSLQPEDFATYYCQHFWGTPFTF

GQGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.

8M24H1 Heavy-chain:
(SEQ ID NO: 54)
EVQLVQSGAEVKKPGSSVKVSCKASGYTFTNYGINWVRQAPGQGLEWMG

EIFPRSDNTFYAQKFQGRVTITADKSTSTAYMELSSLRSEDTAVYYCAR

KGRDYGTSHYFDYWGQGTTVTVSSASTKGPSVFPLAPSSKSTSGGTAAL

GCLVKDYFPEPVTVSWNSGALTSGVHTFPAVLQSSGLYSLSSVVTVPSS

SLGTQTYICNVNHKPSNTKVDKKVEPKSCGSGSGHHHHHH.

Diffraction quality crystals of HuASGR1-CBD:8M24 complex (concentration=20 mg/mL) grew in PACT-A6 crystallization condition containing 0.1 M SPG (Succinic Acid, sodium phosphate monobasic monohydrate, Glycine buffer) pH 9.0 and 25% w/v PEG 1500. Crystal was cryo-protected using 20% glycerol in the well-solution. HuASGR1-CBD:8M24 complex crystallized in the P $2_1 2_1 2_1$ space group (a=38.91 Å, b=90.32 Å, c=167.80 Å) with one complex molecules per asymmetric unit. Structure of HuASGR1-CBD:8M24 complex was determined at a resolution of 1.7 Å and refined to $R_{cryst}$ and $R_{free}$ factors of 17.3% and 20.5%, respectively.

Figure 37A:
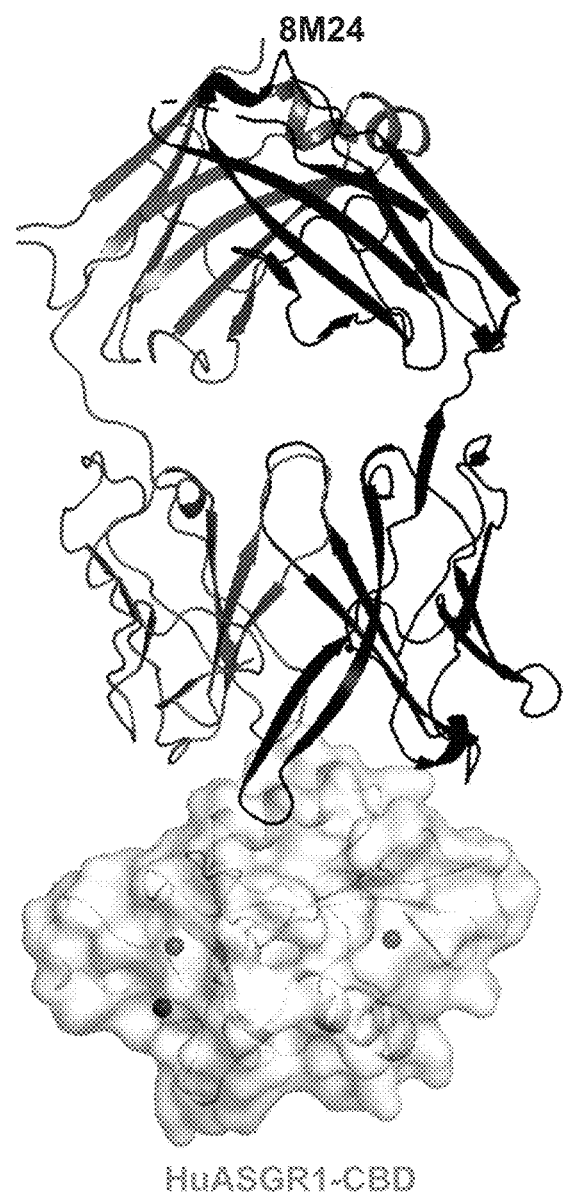
FIG. 37A shows the overall structure of the HuASGR1-CBD:8M24 complex. The molecular-surface of HuASGR1-CBD is shown in light-gray transparent surface. The heavy and light chains of 8M24 are colored in shades of darker and lighter black, respectively. Three structural calcium ions are shown as dark spheres.
Figure 37B:
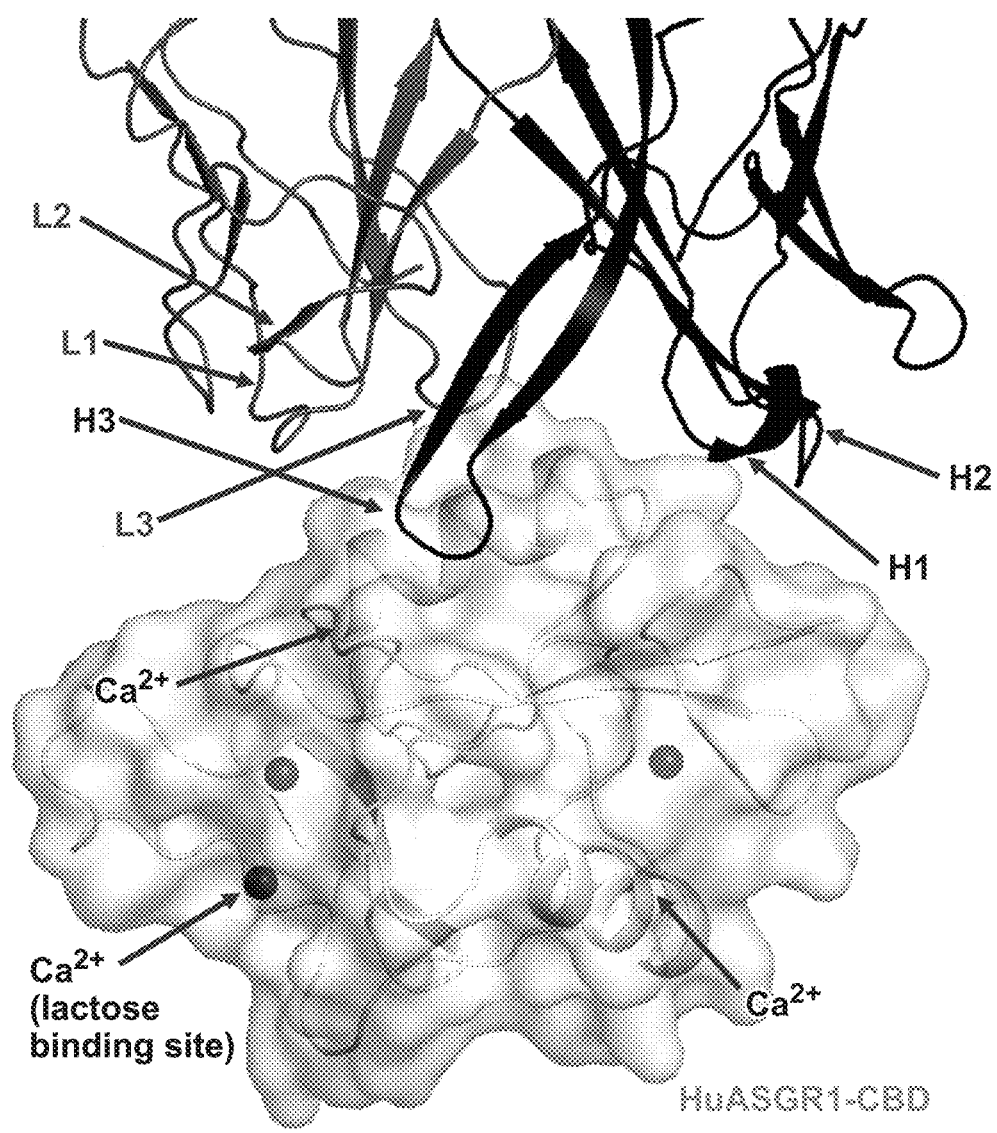
FIG. 37B shows a close-up view of the HuASGR1-CBD:8M24 interface with positions of CDR loops H1, 112, H3 of heavy-chain, L1, L2, and L3 of light-chain marked.
Figure 39B:
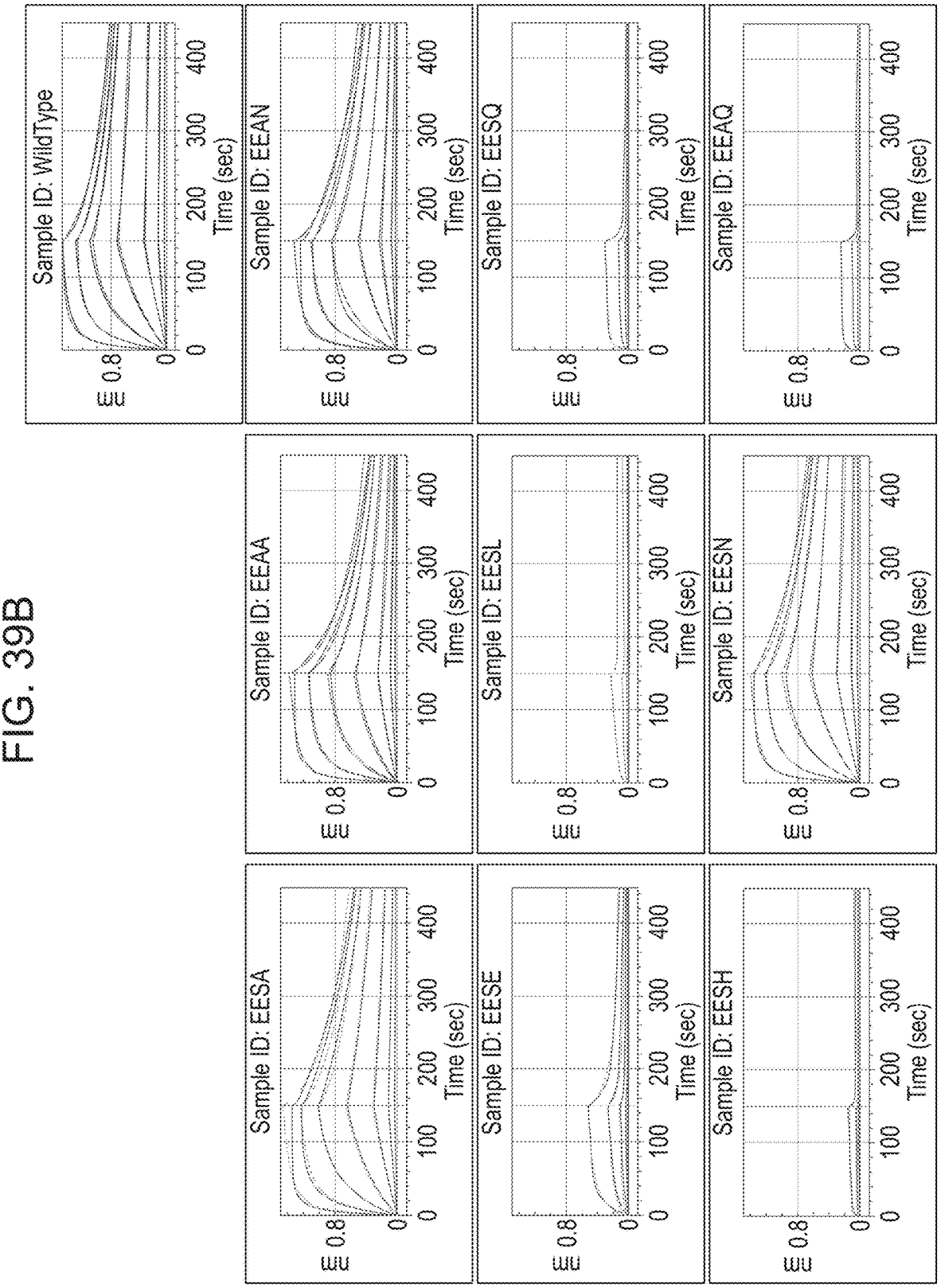
Figure 39C:
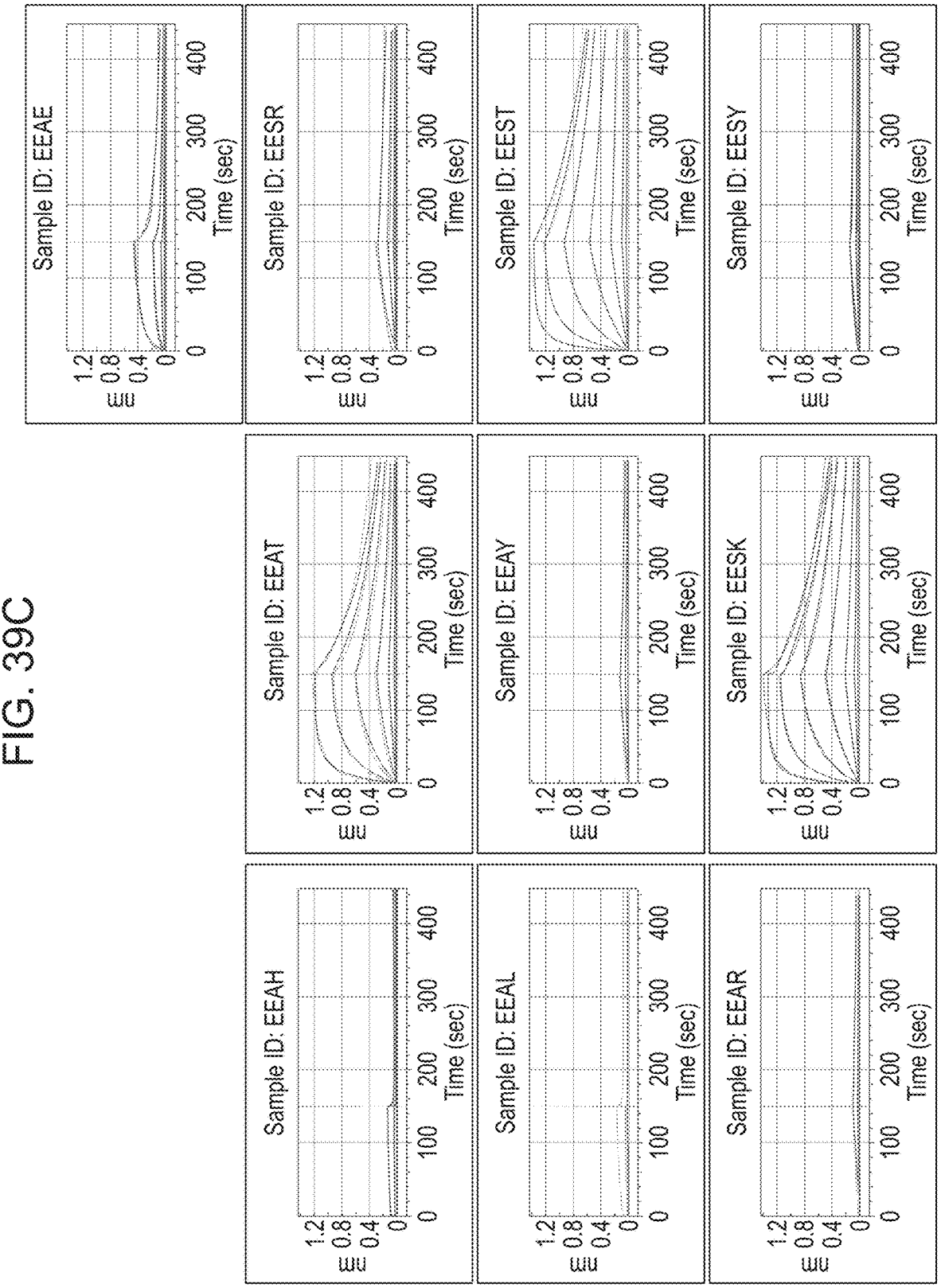
Figure 40A:
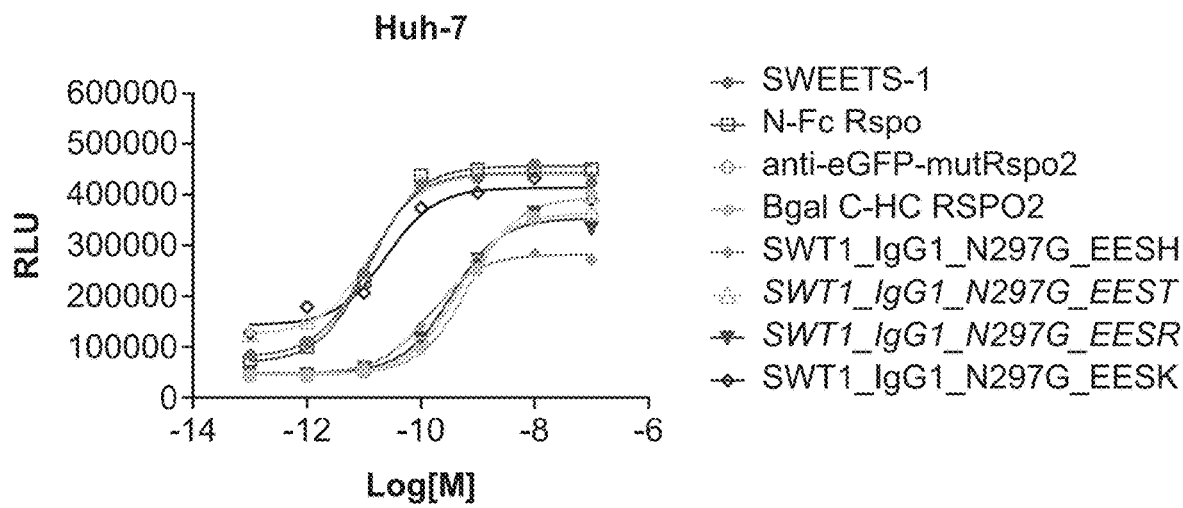
FIGS. 40A-40D show the STF activity of various combinations of mutations in Huh-7 (FIGS. 40A and 40C) and Hek-293 (FIGS. 40B and 40D) cells
Figure 40B:
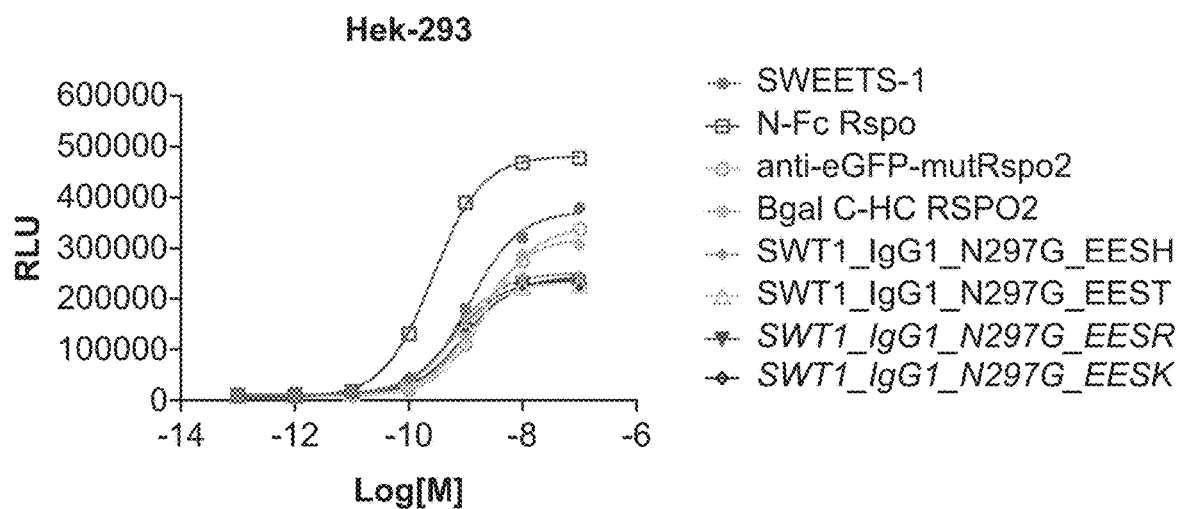
Figures 40C, 40D:
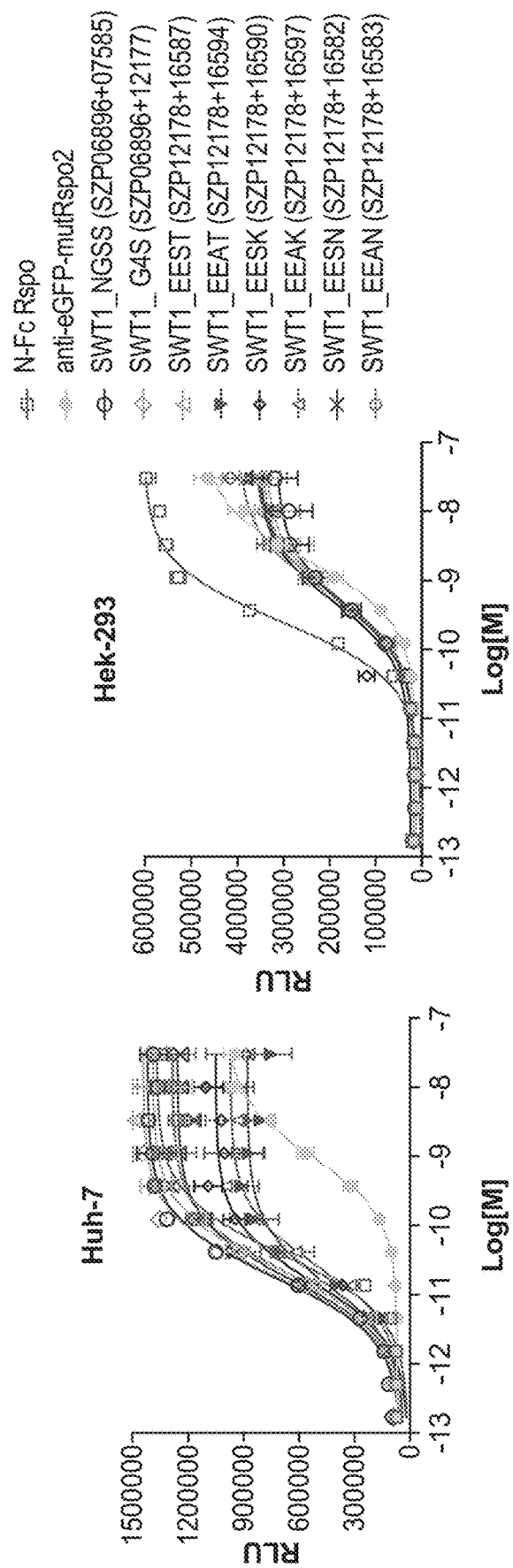

The overall structure of the HuASGR1-CBD:8M24 complex is shown in FIG. 37A. Structural analyses of HuASGR1-CBD revealed that both its overall fold and three $Ca^{2+}$ ions important for structural stability of CBD are similar to its previously published structure [PDB Code: 1DV8; Crystal structure of the carbohydrate recognition domain of the H1 subunit of the asialoglycoprotein receptor. Meier M, Bider M D, Malshkevich V N, Spiess M, and Burkhard P. (2012) J Mol Biol 300, 857-865]. The structure also revealed that the 8M24 epitope on ASGR1 is located away from $Ca^{2+}$ ion that is part of the natural ligand binding site (FIG. 37B).

The structure of the complex was used to identify epitopes on human ASGR1 for 8M24, with the following residue defining the core interaction-site (5A cut-off): Gly163, Pro165, Val166, Asn167, Cys175, Trp177, Ser181, Lys183, Ala184, Ala186, Asp187, Asn190, Tyr191, Arg193, Leu194, Glu195, Asp196, Trp285, Thr289, Glu290, and Leu291.

In addition, the following residues on human ASGR1 were identified as immediate-interaction site for 8M24 (inter-atomic distances >5.0 Å and <=8.0 Å): Cys164, Trp168, Arg173, Ser174, Phe178, Ser179, Arg180, Gly182, Trp185, Ala188, Asp189, Cys192, Ala197, Gln227, Cys279, Gln280, Arg281, Cys287, and Glu288.

The structure of the HuASGR1-CBD:8M24 complex was used to identify the following residues of 8M24 at less-than or equal to 5.0 Å from any atoms of human ASGR1: 8M24 heavy chain: Asn31, Phe52, Arg54, Ser55, Asn57, Phe59, Lys99, Arg101, Asp102, Tyr103, Gly104, Thr105, Ser106, and His107. 8M24 light chain: Tyr30, Ser31, Asn32, Phe91, Trp92, Gly93, and Phe96.

Further, the structure of the HuASGR1-CBD:8M24 complex revealed the following residues of 8G8 to be immediate-interaction site for human ASGR1 with inter-atomic distances >5.0 Å and <=8.0 Å:

8M24 heavy chain: Thr28, Thr30, Tyr32, Gly33, Asn35, Glu50, Ile51, Pro53, Asp56, Thr58, Gly100, Tyr108 and Phe109.

8M24 light chain: Ile2, Asn28, Ile29, Ala50, His90, and Thr94.

Example 9

Effect of Hepatocyte-Targeted Rspo Mimetics on Liver Function and Tissue Repair after Acetaminophen-Induced Liver Injury The mouse model of acetaminophen (APAP) hepatoxicity is a well-established model of acute liver injury and the mechanisms and severity are similar between mice and humans. The ability of 1R34-EEAT-EE to repair the hepatoxic effects of APAP-induced liver injury was examined.

100 male C57BL/6J mice (aged 9 weeks) were randomized, based upon body weight, into 10 study groups (Groups A-J) and then, fasted overnight. To induce liver injury, mice were administered a single intraperitoneal (IP) dose of APAP 300 mg/kg (Groups B-J, n=90); the control group (Group A, n=10) was administered IP saline. Following this, mice were returned to their cages and food was available ad libitum. Two hours following APAP administration and according to randomization group, mice in Groups B-J received a single IP injection of one of the following treatments: anti-GFP 10 mg/kg (negative control), N-acetylcysteine (NAC) 1200 mg/kg (positive control), or 1R34-EEAT-EE 10 mg/kg. Group A mice continued to be followed, with no additional injection of vehicle administered. Mice were then followed for up to 72 hours, with termination occurring 24, 48, or 72 hours post treatment.

At the respective termination timepoints, blood and livers were collected for clinical chemistry and immunohistopathological analysis. Quantitative polymerase chain reaction (qPCR) analysis of liver mRNA measured Wnt target genes and the expression levels of key cytochrome P450 (CYP) metabolic enzymes.

TABLE 5

APAP-induced liver injury treatment groups

| Group | APAP | N | Test Article | Dose (mpk) | Route | Frequency | Termination |
|---|---|---|---|---|---|---|---|
| A | none | 10 | none | N/A | | Single | 24 h |
| B | ✓ | 10 | Anti-GFP | 10 | i.p. | Dose | 24 h |
| C | ✓ | 10 | Nac | 1200 | | | 24 h |
| D | ✓ | 10 | EEAT-EE | 10 | | | 24 h |
| E | ✓ | 10 | Anti-GFP | 10 | | | 48 h |
| F | ✓ | 10 | Nac | 1200 | | | 48 h |
| G | ✓ | 10 | EEAT-EE | 10 | | | 48 h |
| H | ✓ | 10 | Anti-GFP | 10 | | | 72 h |
| I | ✓ | 10 | Nac | 1200 | | | 72 h |
| J | ✓ | 10 | EEAT-EE | 10 | | | 72 h |

Figure 43:
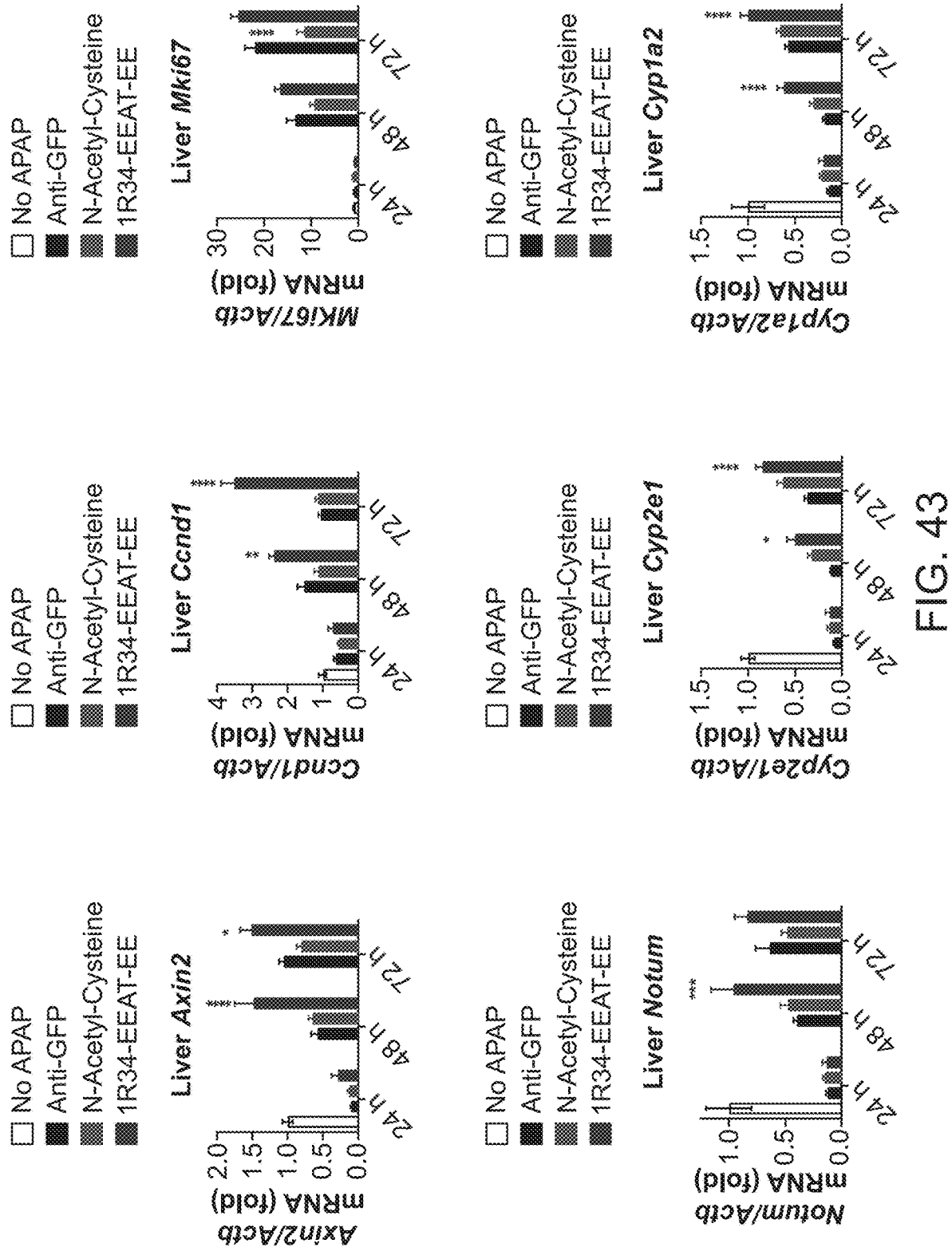
FIG. 43 provides graphs showing expression levels of the indicated Wnt target genes and cytochrome P450 (CYP) metabolic enzymes in livers of uninjured animals or APAP-injured livers of animals treated with αGFP-IgG, Nac, or (αASGR1-RSPO2-EEAT-EE Wnt signaling enhancer molecule (left to right) at the indicated times.

1R-34 EEAT-EE activated the Wnt/β-catenin signaling pathway, as shown by the increase in liver mRNA expression of Axin2, a marker of Wnt/p-catenin activation, and the induction of cyclin D1 (Ccnd1), a Wnt target gene and proliferation marker of the G1/S phase transition of the cell cycle (FIG. 43). In addition, Notum, a Wnt target gene and physiologic negative regulator of Wnt ligands, was induced by 1R34-EEAT-EE.

The expression of the Cyp1a2 and Cyp2e1 genes were markedly reduced in all groups after APAP-induced liver injury (FIG. 43). 1R34-EEAT-EE treatment resulted in a significantly higher level of Cyp1a2 and Cyp2e1 expression at 48 and 72 hours after dosing.

Figure 44:
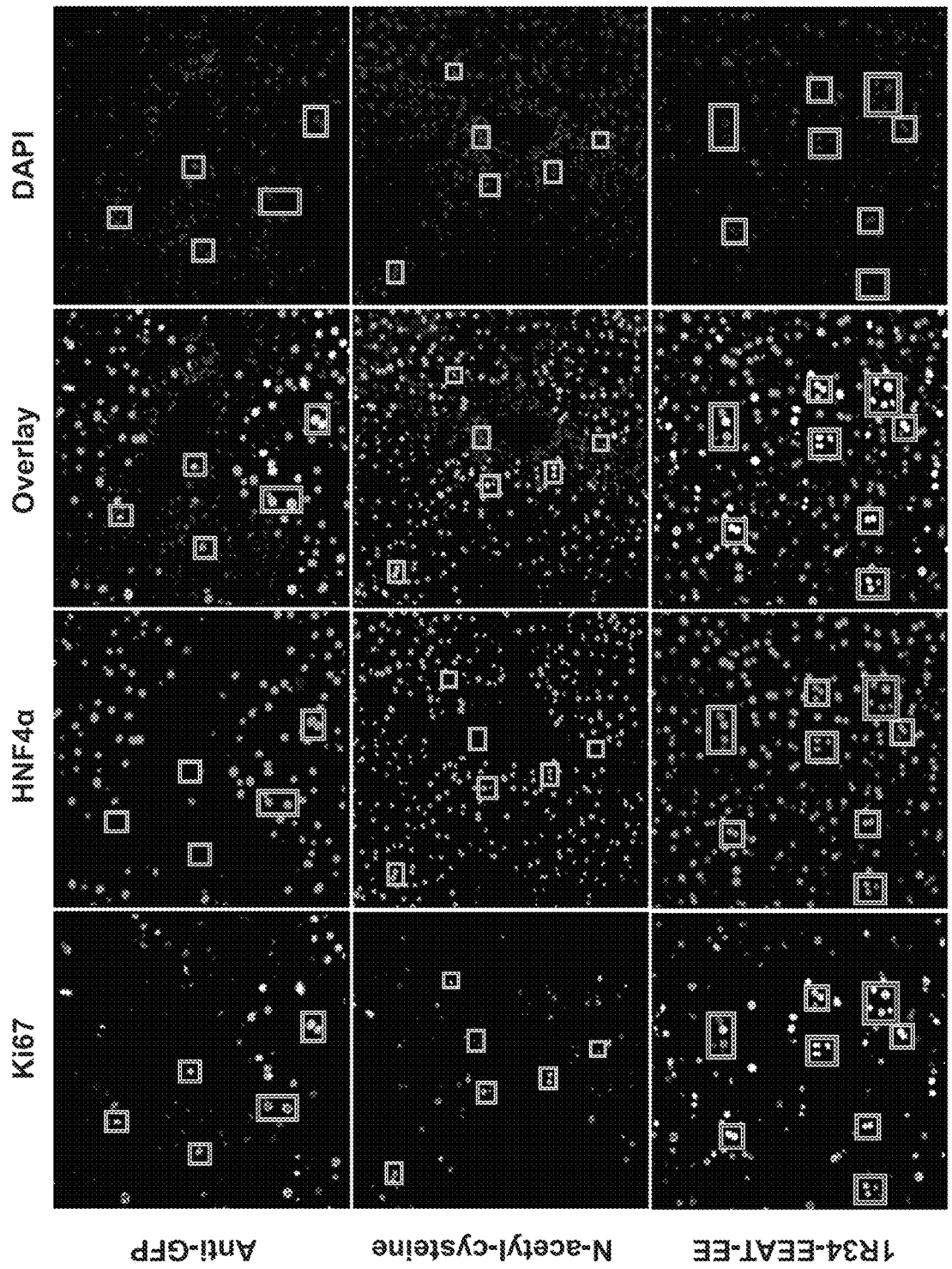
FIG. 44 provides micrographs showing Ki67 and HNF4a expression in hepatocytes of livers treated with the indicated agents following acetaminophen-induced liver injury.
Figure 45:
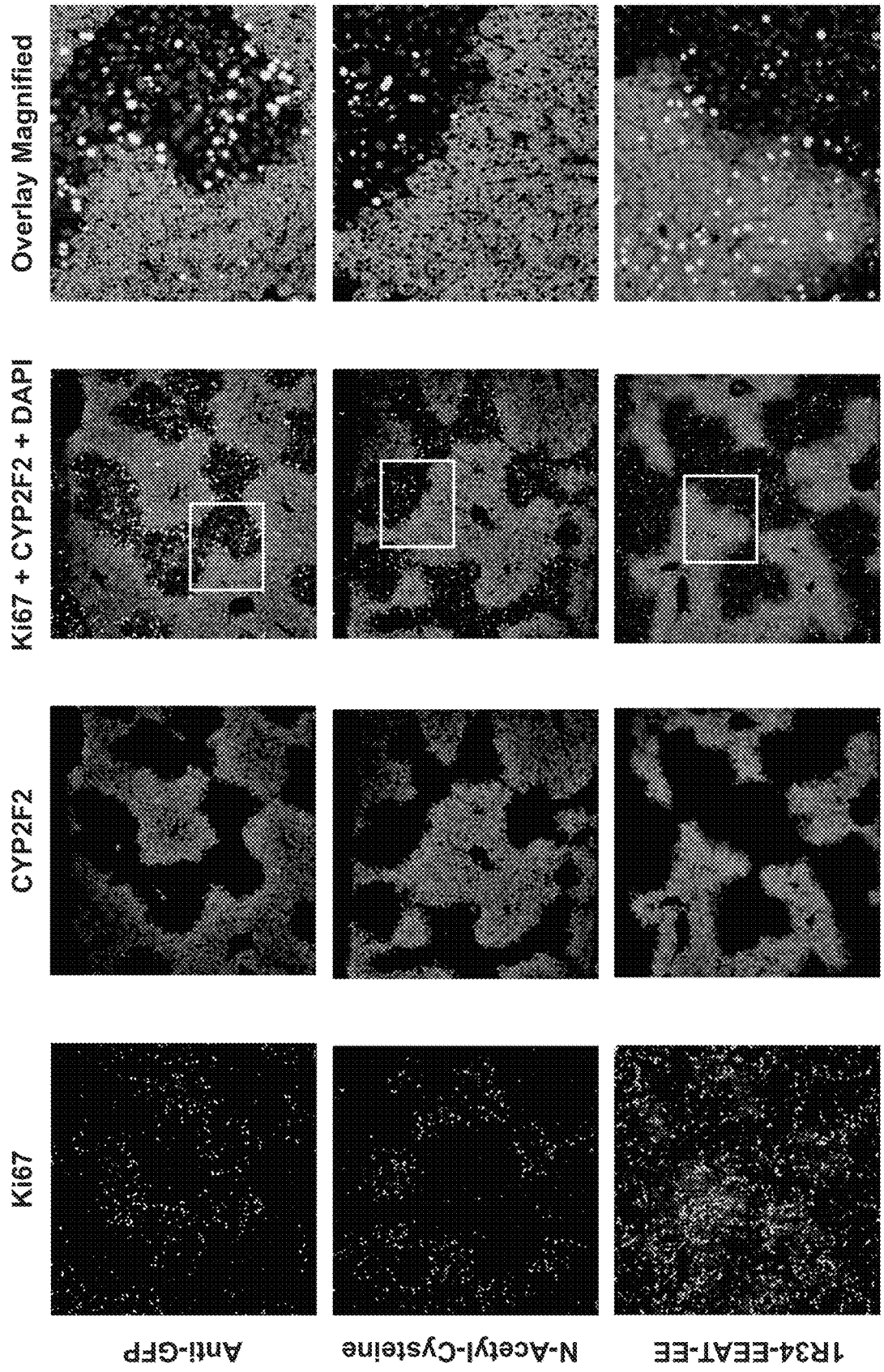
FIG. 45 provides micrographs showing Ki67 and CYP2F2 expression in hepatocytes of livers treated with the indicated agents following acetaminophen-induced liver injury.

At 72 hours post treatment, spontaneous repair, as evidenced by the presence of immunoreactive Ki67+ nuclei, was observed by immunofluorescence in the pericentral regions of livers treated with anti-GFP. The regenerative capacity of 1R34-EEAT-EE was demonstrated by an increase in Ki67+/HNF4α+ double-positive hepatocytes (FIG. 44), white squares) beyond that which occurs spontaneously, with uniform distribution in all hepatic zones, including the periportal region, as shown by the double immunofluorescence staining with Ki-67 and the periportally expressed CYP2F2 (FIG. 45). In contrast, a significant proportion of non-hepatocytes appeared to proliferate in the anti-GFP and N-acetylcysteine groups, based on the presence of Ki67+ nuclei with undetectable HNF4a (yellow squares).

Figure 46:
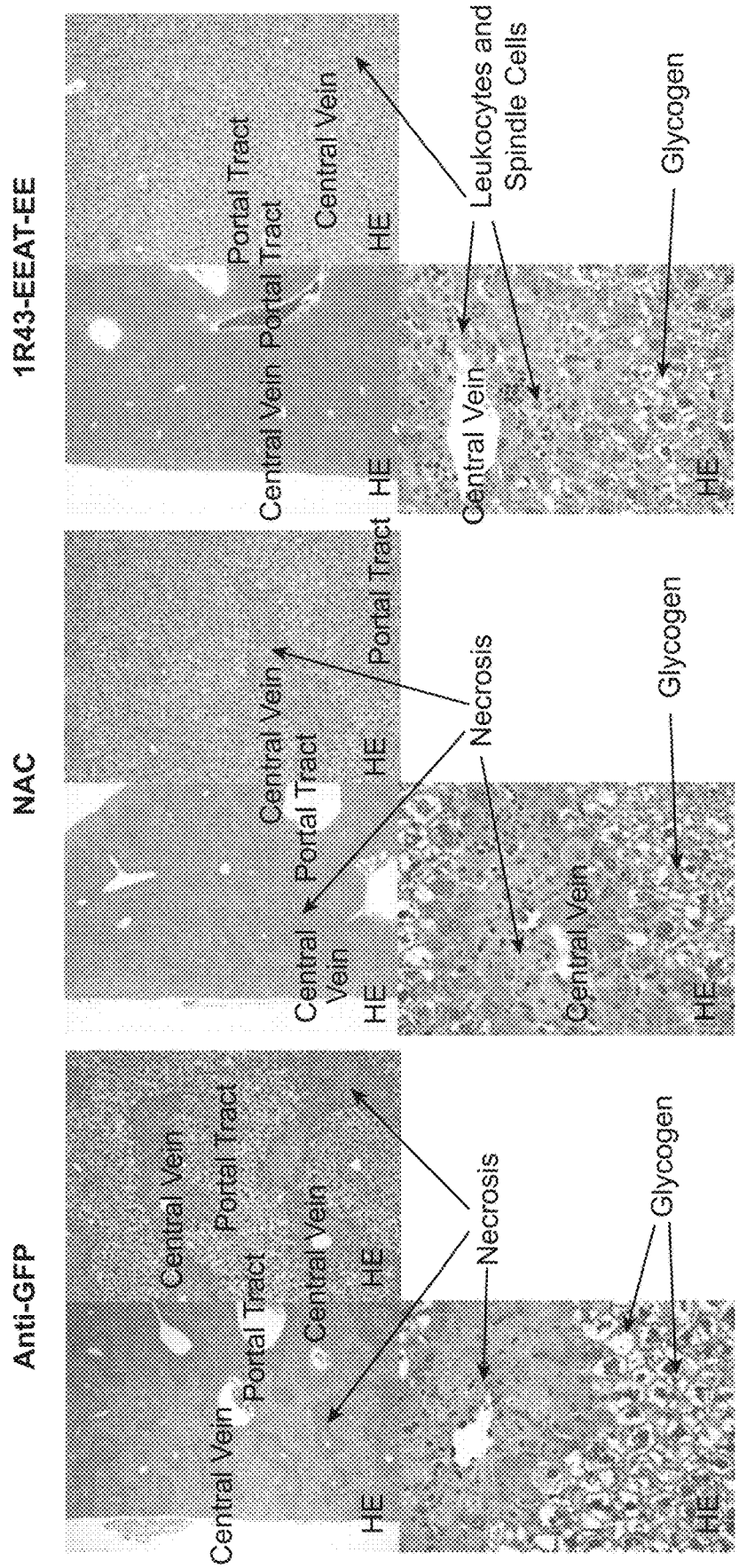
FIG. 46 provides micrographs showing histology of livers treated as indicated. Areas of necrosis following anti-GFP or Nac treatment are indicated.

Histological analysis showed large regions of diffuse necrosis in the pericentral regions of the liver in the control group, but reduced necrosis in 1R34-EEAT-EE treated livers (FIG. 46).

Figure 47:
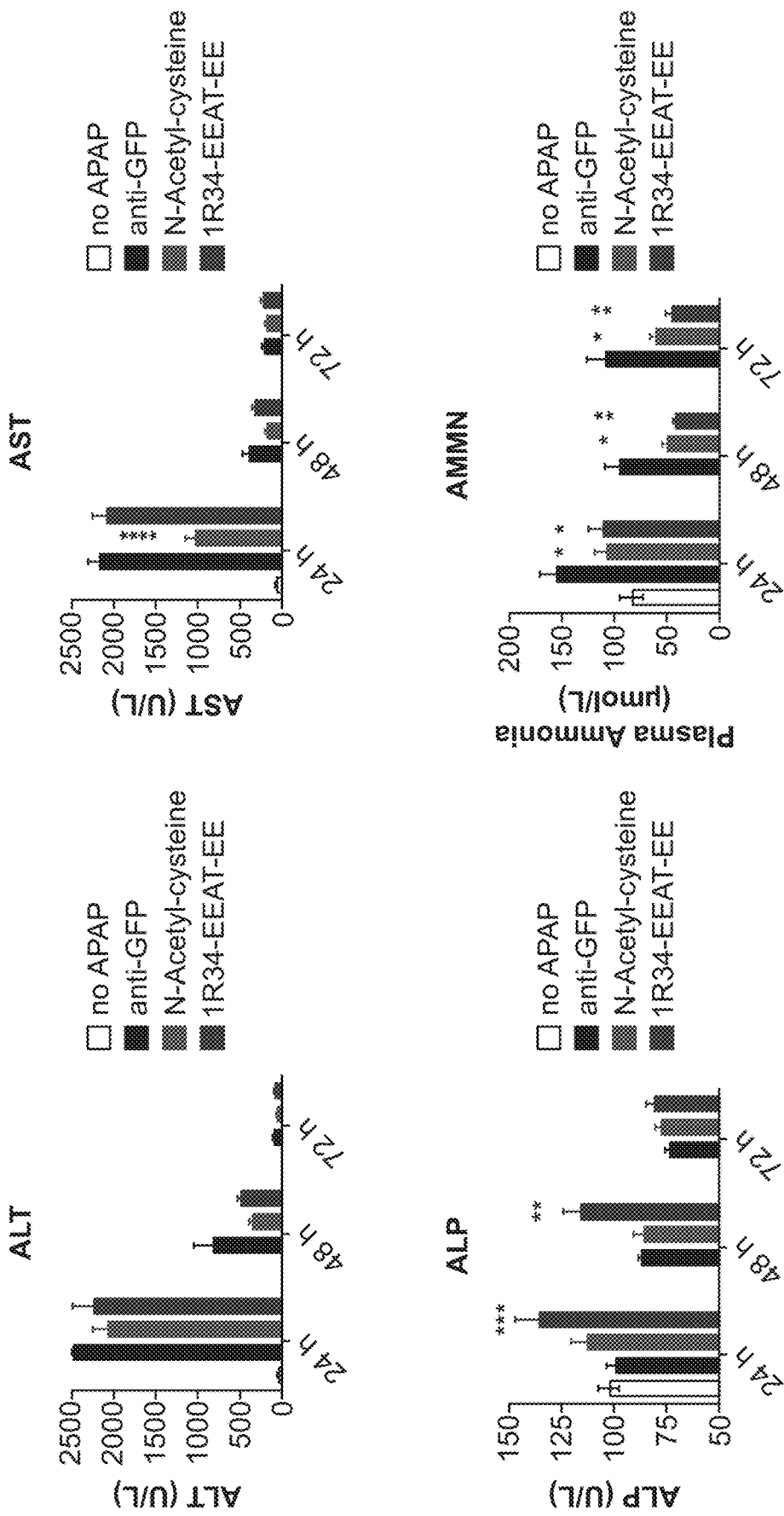
FIG. 47 provides graphs showing ALT, AAST, ALP, and AMMN levels in livers of uninjured animals or APAP-injured livers treated with αGFP-IgG, Nac, or αASGR1-RSPO2-EEAT-EE Wnt signaling enhancer molecule (left to right) at the indicated times

Serum alkaline phosphatase (ALP) was significantly increased at 24 and 48 hours post treatment, which is consistent with ASGR1 occupancy by 1R34-EEAT-EE and the known role of the ASGR in ALP clearance (FIG. 47). Plasma ammonia levels were significantly reduced by 1R34-EEAT-EE compared to anti-GFP at all measured timepoints. There were no significant differences in serum levels of AST or ALT between 1R34-EEAT-EE and anti-GFP at any measured timepoint.

This study in a murine model of APAP-induced liver injury demonstrated that 1R34-EEAT-EE alleviated APAP-induced hepatotoxicity through targeted activation of Wnt/β-catenin signaling in the liver and stimulation of hepatocyte-specific regeneration.

Example 10

Effect of Hepatocyte-Targeted RSPO Mimetics on Liver Function and Tissue Repair after Chronic-Binge Ethanol-Induced Liver Injury Animal models of alcoholic liver injury reproduce, to various degrees, many features of AH in patients, such as steatosis and elevated liver expression of inflammasome components, such as IL-1β. The chronic-binge model is a commonly used model, composed of voluntary feeding using a Lieber-DeCarli liquid ethanol (EtOH)-containing diet and ethanol delivered by oral gavage (Bertola et al. 2013). This study examined the effects of 1R34-EEST-EE on hepatocyte expansion and function in a prolonged chronic, multiple-binge, acute alcoholic hepatitis (AAH) model in aged mice, where the spontaneous regenerative capacity of the mouse liver is significantly impaired.

Figure 48:
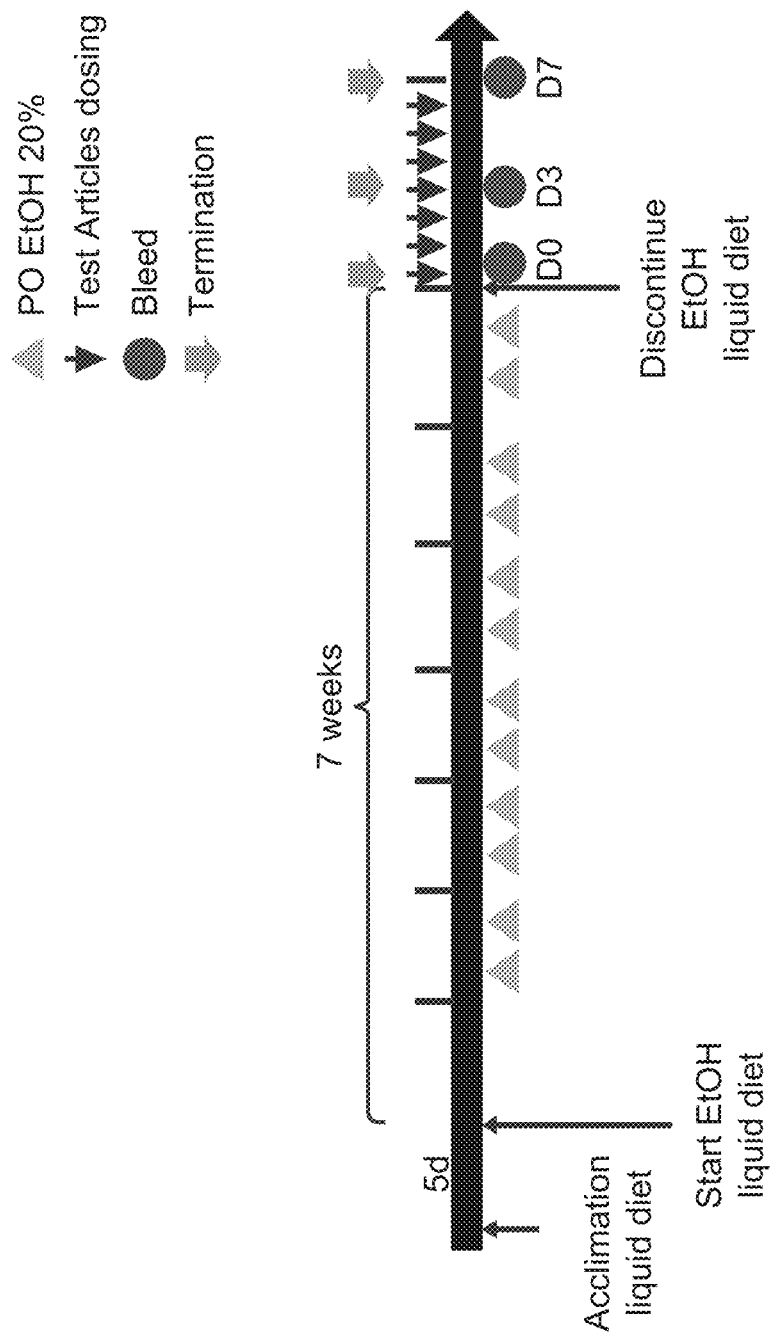
FIG. 48 is a diagram of a study of the effect of 1R34-EEST-EE on liver function and tissue repair in an animal model of chronic-binge ethanol-induced liver injury.

11-month-old C57BL/6J female mice were fed the control Lieber-DeCarli diet ad libitum for five days to acclimatize them to a liquid diet and tube feeding (FIG. 48). All mice were then randomized (FIG. 55). Mice in the EtOH-fed groups were allowed free access to the Lieber-DeCarli (L-D) diet containing 5% (vol/vol) EtOH for seven weeks, and the pair-fed group received the L-D control diet in which an isocaloric amount of maltose dextrin was substituted for ethanol. Beginning with Week 2 and continuing through Week 7 of the feeding period, EtOH-fed and pair-fed mice received twice weekly gavage doses of EtOH 20% (5.23 g/kg body weight) or isocaloric maltose dextrin, respectively. Upon completion of the EtOH feeding period, mice were returned to the control L-D liquid diet and randomized to treatment with 1R34-EEST-EE (30 mg/kg) or anti-GFP (10 mg/kg); treatments were administered once daily via intraperitoneal injection. Mice were then terminated after either 3 or 7 days of treatment.

TABLE 6

Ethanol-induced injury treatment groups

| Group | EtOH | n | Test Article | Dose (mpk) | Route | Frequency | Termination * |
|---|---|---|---|---|---|---|---|
| B | none | 6 | none | | N/A | | Day 0 |
| C | ✓ | 6 | none | | | | Day 0 |
| D | ✓ | 7 | Anti-GFP | 10 | i.p. | 2× weekly | Day 3 |
| E | ✓ | 7 | EEST-EE | 30 | | daily | Day 3 |
| F | ✓ | 7 | Anti-GFP | 10 | | 2× weekly | Day 7 |
| G | ✓ | 7 | EEST-EE | 30 | | daily | Day 7 |

At the respective termination timepoints, blood and tissue samples were collected for clinical chemistry analysis. Activation of Wnt pathway, proliferation and inflammation markers were examined by quantitative polymerase chain reaction (qPCR) analysis of liver mRNA.

Figure 49:
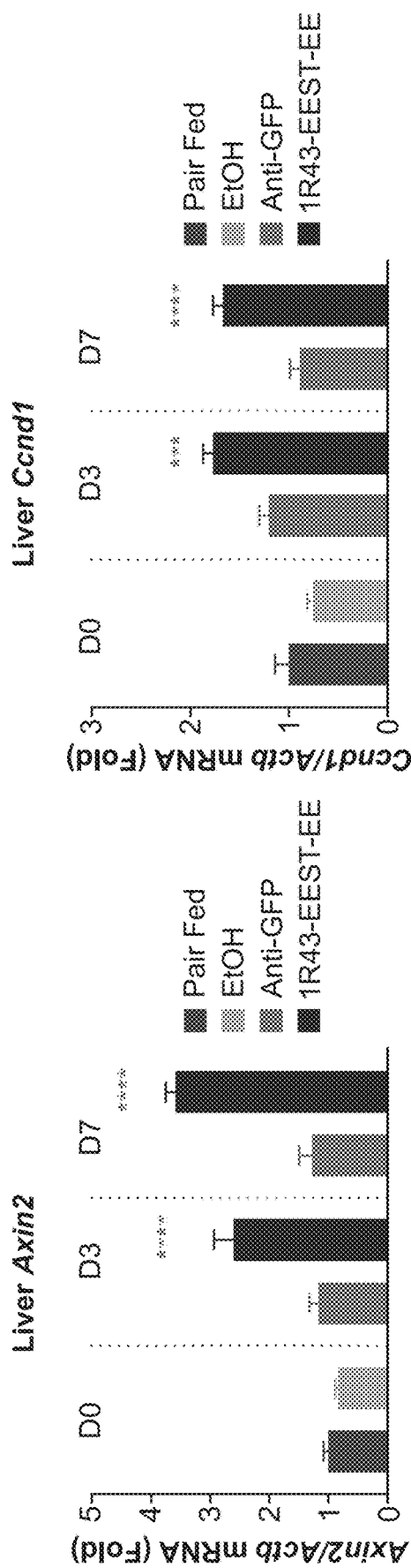
FIG. 49 provides graphs showing expression of the indicated Wnt target genes at day 0, day 3 or day 7 following treatment. At day 0, the bars from left to right correspond to pair fed and EtOH, at day 3, and at days 3 and 7, the bars from left to right correspond to treatment with anti-GFP or 1R43-EEST-EE.
Figure 50:
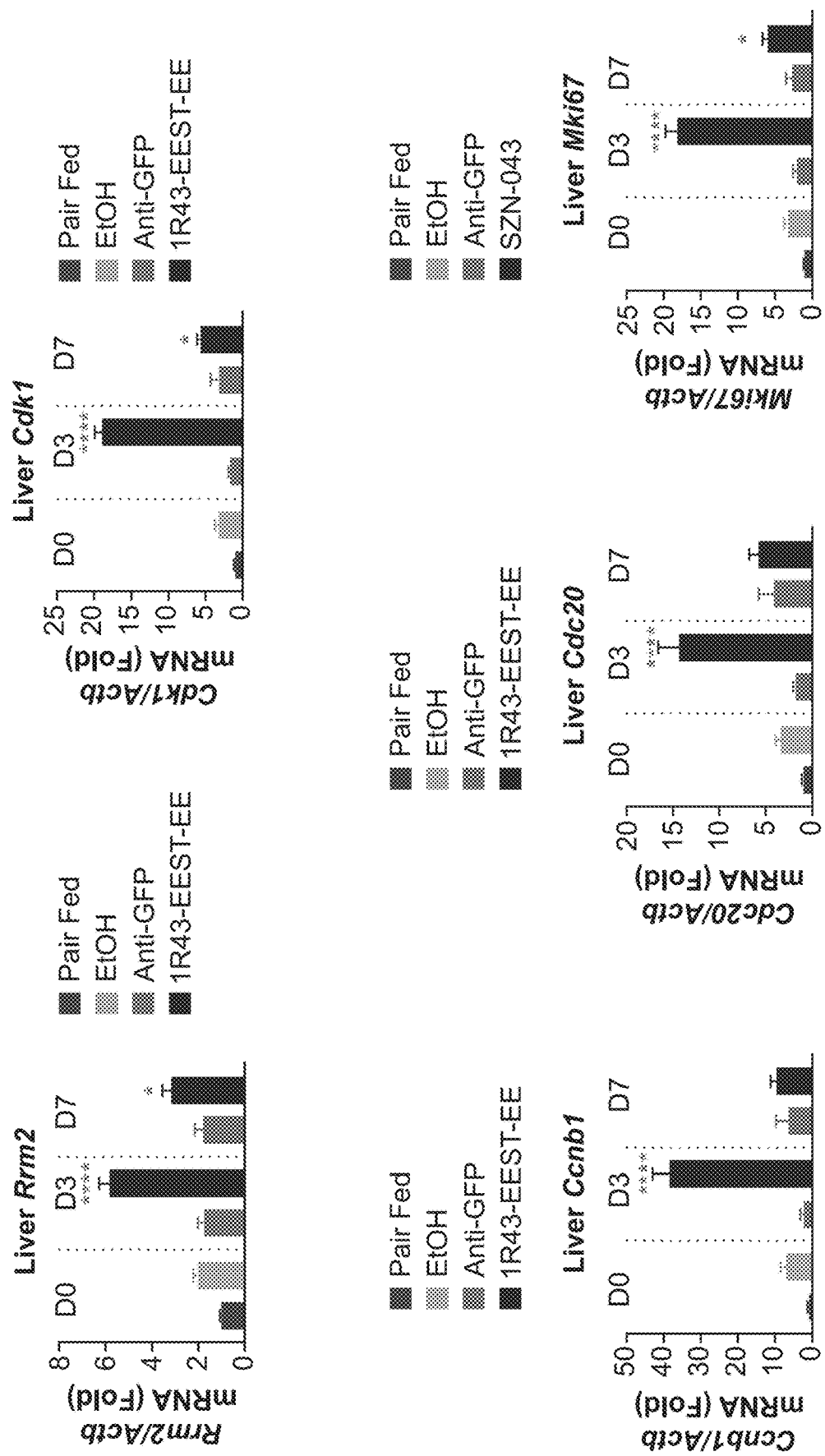
FIG. 50 provides graphs showing expression of the indicated hepatic proliferation markers at day 0, day 3 or day 7 following treatment. At day 0, the bars from left to right correspond to pair fed and EtOH, at day 3, and at days 3 and 7, the bars from left to right correspond to treatment with anti-GFP or 1R43-EEST-EE FIG. 51 provides micrographs showing immunofluorescent staining of Ki67 or HNF4A.
Figure 51:
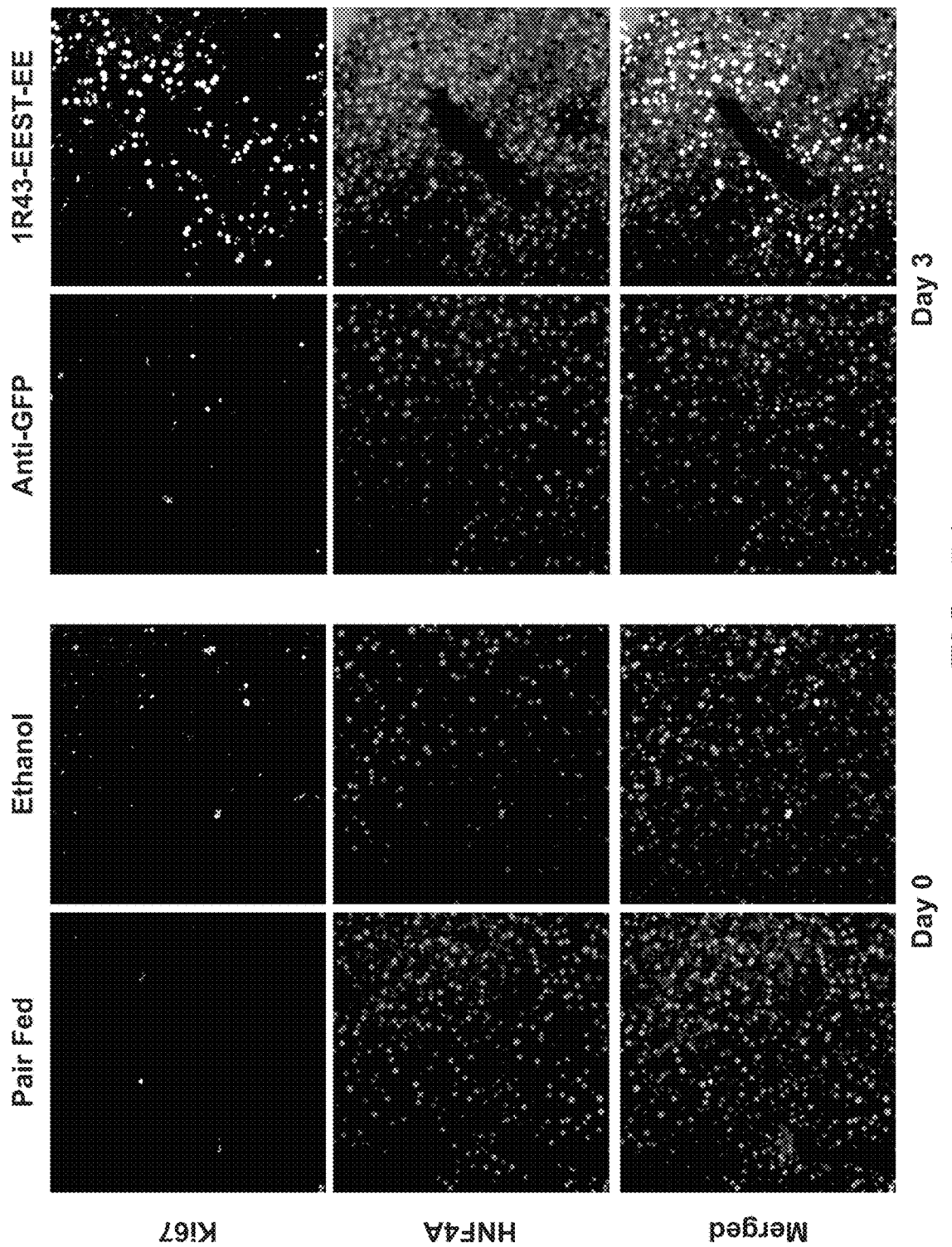

1R34-EEST-EE activated the Wnt/p-catenin signaling pathway, as shown by the increase in liver mRNA expression of Axin2 and Ccnd1, two Wnt target genes (FIG. 49), and the induction of hepatic proliferation markers, such as Rrm2, Cdk1, Ccnb1, Cdc20 and Mki67 (FIG. 50). The hepatocyte-specific regenerative activity of 1R34-EEST-EE was confirmed by double immunofluorescence staining with the proliferation marker, Ki67, and the hepatocyte-specific marker HNF4A (FIG. 51).

Figure 53:
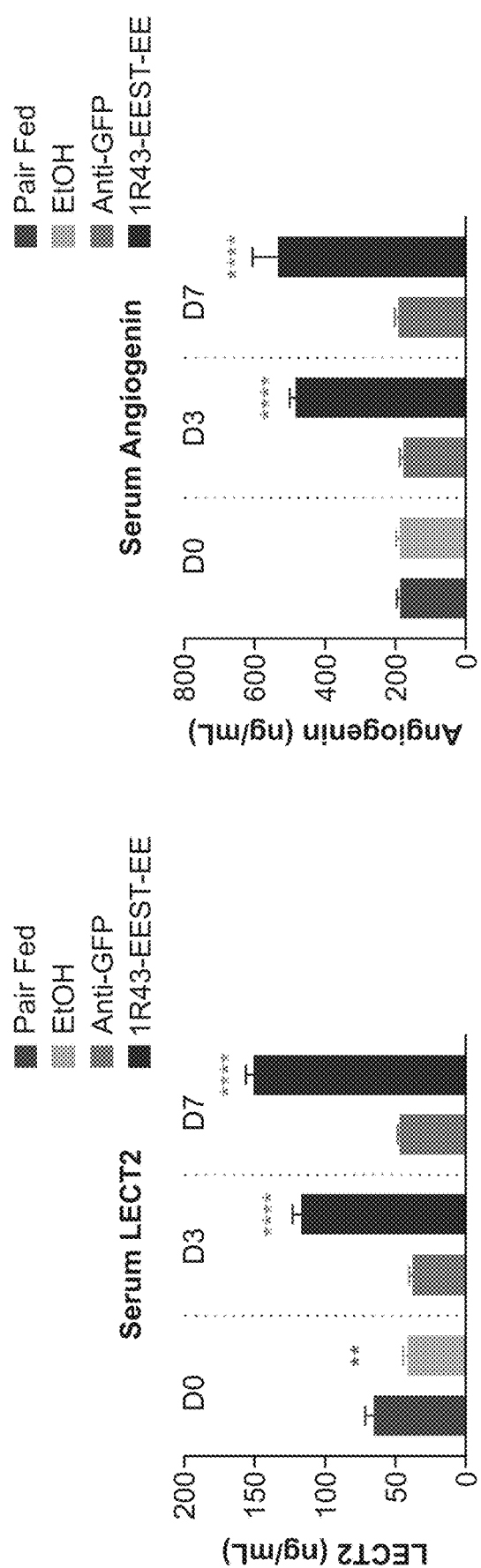
FIG. 53 is a graph showing expression of Lect2 and angiogenin at day 0, day 3 or day 7 following treatment. At day 0, the bars from left to right correspond to pair fed and EtOH, at day 3, and at days 3 and 7, the bars from left to right correspond to treatment with anti-GFP or 1R43-EEST-EE.

In addition, 1R34-EEST-EE significantly increased two serum biomarkers of Wnt activation, leukocyte cell-derived chemotaxin-2 (Lect2) and angiogenin, as measured by enzyme-linked immunosorbent assay (ELISA) (FIG. 53).

Figure 52:
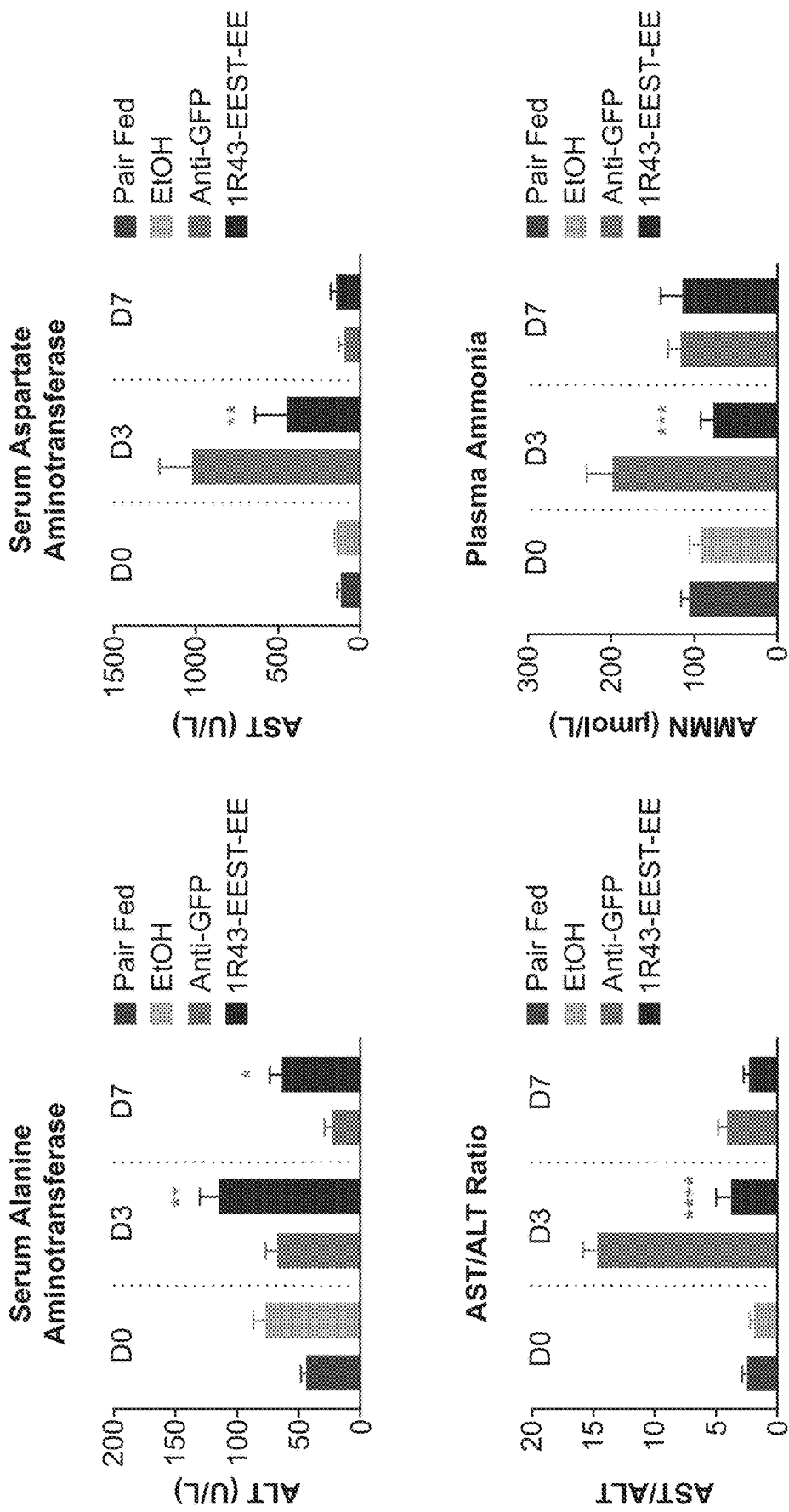
FIG. 52 provides graphs showing expression of the indicated molecules at day 0, day 3 or day 7 following treatment. At day 0, the bars from left to right correspond to pair fed and EtOH, at day 3, and at days 3 and 7, the bars from left to right correspond to treatment with anti-GFP or 1R43-EEST-EE.
Figure 54:
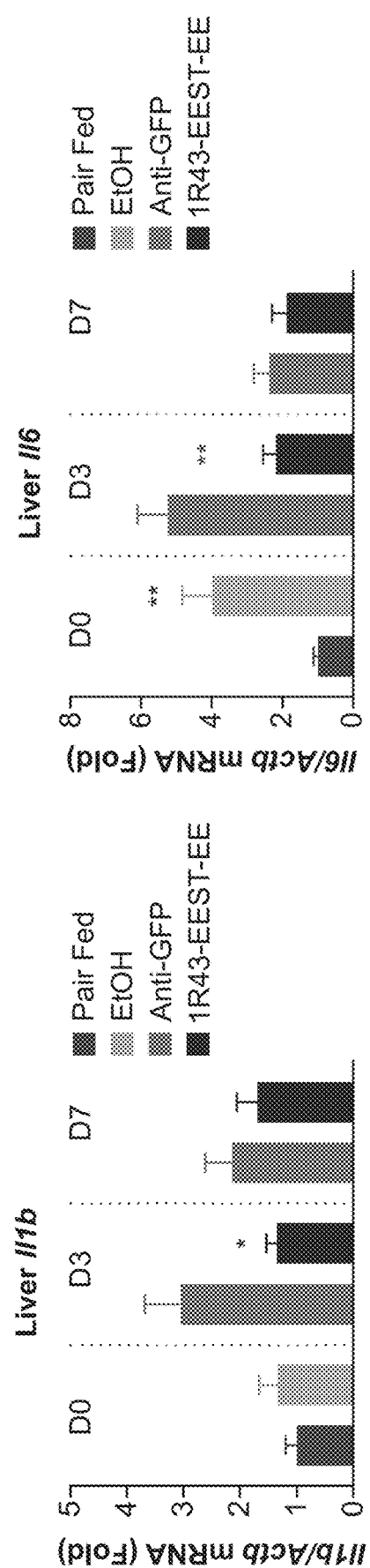
FIG. 54 provides graphs showing expression of the inflammatory markers, interleukins IL1b and IL6 at day 0, day 3 or day 7 following treatment. At day 0, the bars from left to right correspond to pair fed and HOH, at day 3, and at days 3 and 7, the bars from left to right correspond to treatment with anti-GFP or 1R43-EEST-EE.

1R34-EEST-EE also reduced mRNA expression of the inflammatory markers, interleukins Il1b and Il6 (FIG. 54) ALT was mildly elevated and AST significantly reduced in response to 1T34-EEST-EE, when compared to anti-GFP (control group), significant changes were observed after 3 days of treatment with 1R34-EEST-EE resulting in a strong reduction of the AST/ALT ratio (FIG. 52). In addition, circulating ammonia was significantly decreased by 1R34-EEST-EE compared to anti-GFP at Day 3 (FIG. 52).

In conclusion, 1R34-EEST-EE induced liver-specific Wnt/p catenin signaling in a model of AAH in aged mice. Further, 1R34-EEST-EE stimulated hepatocyte-specific cell regeneration. These data provide proof-of-concept that 1R34-EEST-EE stimulates hepatocyte expansion under conditions of impaired proliferation due to age and alcohol use.

Example 11

Biomarkers for Regeneration in Drug-Induced Liver Failure

Acute liver failure (ALF) due to acetaminophen (APAP) overdose or other drug-induced liver injury (DILI) has limited treatment options. Although 65% of patients with APAP-induced ALF spontaneously survive, there are approximately 500 deaths due to APAP hepatotoxicity annually in the US. In DILI, survival without transplant is approximately 25% with estimates of 300-500 deaths in the US. Patients who are not expected to recover following first-line therapy such as intravenous N-acetylcysteine are listed for liver transplant. Due to the increasing demand and limited supply of liver transplants, a reliable test that predicts liver recovery is desired.

Wnt signaling plays a central role in hepatocyte expansion during development and tissue repair. Downstream canonical Wnt signaling mediated by p-catenin stabilization correlates with increased regeneration in ALF patients (Apte 2009, Bhushan 2014).

Here, the difference in serum levels of liver injury biomarkers (alpha-fetoprotein and cholinesterase) and markers of Wnt signaling (angiogenin and leukocyte cell derived chemotaxin 2) between ALF patients who did not receive a liver transplant and those who went on to liver transplant or died were determined.

Alpha-Fetoprotein (AFP) is secreted by proliferating immature hepatocytes and is elevated in liver injury. In ALF, spontaneous survivors had higher day 3-to-day 1 AFP ratios than patients who died or were transplanted, suggesting a prognostic value of the change in AFP level (Schiot 2006).

Butyrylcholinesterase (BChE) is a nonspecific esterase produced by the liver and is decreased in many liver dysfunctions, including acute and chronic liver damage, inflammation, and infection.

Angiogenin is a direct Wnt target secreted primarily by hepatocytes. Angiogenin induces angiogenesis and plays a role in cell growth and survival. It has not been reported if there is a link between angiogenin and ALF outcome.

Leukocyte cell derived chemotaxin 2 (LECT2) is a hepatokine secreted nearly exclusively by hepatocytes and is a direct Wnt target. LECT2 plays a key role in liver regeneration: specific to ALF, LECT2 levels increased when liver function recovered (Sato 2004), but low LECT2 levels during the first 3 days following injury correlated to higher probability of survival (Slowik 2019).

Serum samples were selected from the US Adult Acute Liver Failure Study Group Registry (NCT 00518440). The etiology of liver failure was divided into two groups as adjudicated by the ALFSG: APAP or DILI/other/indeterminate. Spontaneous survivors (SS) were defined as patients who recovered without transplant and were compared to patients who went on to transplant or died (LT/D). There were samples from 10 patients with APAP overdose and 5 DILI patients in the SS group drawn on days 1, 3, and 7 following enrollment, and 10 APAP and 10 DILI patients in the LT/D group drawn on days 1 and 3 (see Table 7).

TABLE 7

Survival of liver failure patients

| Days following enrollment | APAP Spontaneous | DILI Survival | APAP Transplanted | DILI or Died |
|---|---|---|---|---|
| Day 1 | N = 11 | N = 4 | N = 10 | N = 9 |
| Day 3 | N = 10 | N = 5 | N = 10 | N = 9 |
| Day 7 | N = 10 | N = 5 | | |

AFP, angiogenin, and LECT2 were measured by enzyme-linked immunosorbent assay (ELISA), and BChE was measured by enzymatic activity assay.

Time since study enrollment represented different times in clinical course among patients. To account for this, biomarker levels were interpreted in the context of time since hospital admission. The log scale of biomarker levels were modeled by conducting a random-mixed effect model, with covariates including the terms for time since hospital admission and status group indicating SS or LT/D. Unstructured correlation was assumed to account for correlation due to repeated measurements over time within the same patient. Point estimates and 95% confidence intervals (CI) for least squared means for each status group and the difference between the two statuses were estimated.

The profiles of AFP, angiogenin, LECT2, and BChE were plotted against time from hospital admission, separately for SS and LT/D. Point estimates and 95% CI of least squared means were compared between SS and LT/D. Fold differences for SS vs LT/D are summarized in Table 8.

TABLE 8

AFP, angiogenin, LECT2, and BChE profiles

| Analyte | Fold SS vs LT/D | 95% CI | P-value |
|---|---|---|---|
| AFP | 1.72 | (0.53, 5.57) | 0.3583 |
| Angiogenin | 2.63 | (1.76, 3.93) | <0.0001 |
| LECT2 | 6.26 | (1.68, 23.39) | 0.0078 |
| BChE | 1.84 | (0.96, 3.53) | 0.0663 |

The fold differences in point estimates for angiogenin and LECT2 between SS and LT/D were significant, while the fold differences for AFP and BChE were not significant.

Fold differences in point estimates were compared between SS and LT/D separately for etiology of liver failure (APAP and DILI/other). There were significant fold differences for both angiogenin and LECT2 in APAP patients, but only a significant fold difference for angiogenin in DILI/other patients (Table 9).

TABLE 9

AFP, angiogenin, LECT2, and BChE profiles

| Analyte | Etiology | Fold SS vs LT/D | 95% CI | P-value |
|---|---|---|---|---|
| AFP | APAP | 2.24 | (0.79, 6.33) | 0.1246 |
| AFP | DILI/other | 0.98 | (0.07, 13.54) | 0.9874 |
| Angiogenin | APAP | 2.09 | (1.31, 3.34) | 0.0032 |
| Angiogenin | DILI/other | 2.55 | (1.23, 5.30) | 0.0154 |
| LECT2 | APAP | 3.64 | (2.10, 6.33) | <0.0001 |

TABLE 9-continued

AFP, angiogenin, LECT2, and BChE profiles

| Analyte | Etiology | Fold SS vs LT/D | 95% CI | P-value |
|---|---|---|---|---|
| LECT2 | DILI/other | 0.98 | (0.28, 3.42) | 0.9766 |
| BChE | APAP | 1.16 | (0.79, 1.73) | 0.4349 |
| BChE | DILI/other | 1.35 | (0.70, 2.63) | 0.3445 |

In ALF, a >2.5-fold increase in circulating angiogenin and a >6-fold increase in circulating LECT2 was seen early after hospital admission in patients who recovered without a liver transplant. These results suggest the serum markers may function as prognostic indicators of regeneration and could function as biomarkers for the activation of Wnt signaling. Furthermore, since 1R34-EEST-EE was shown to have significantly increased LECT2 and angiogenin in Example 10, these data suggest that treatment with 1R34-EEST is associated with increased Wnt signaling and regeneration.

REFERENCES

Acute liver failure induced by idiosyncratic reaction to drugs: challenges in diagnosis and therapy. Authors: Tujios, S; Lee, W. Journal Title: Liver International. Publisher: Wiley. Publication Date: 01/2018. Volume: 38. Issue: 1. Pages: 6-14. DOI: 10.1111/liv.13535. PMID: 28771932.

Beta-catenin activation promotes liver regeneration after acetaminophen-induced injury. Authors: Apte, U; Singh, S; Zeng, G; Cieply, B; Virji, M; Wu, T; Monga, S. Journal Title: The American Journal of Pathology. Publisher: Elsevier. Publication Date: 09/2009. Volume: 175. Issue: 3. Pages: 1056-1065. DOI: 10.2353/ajpath.2009.080976. PMID: 19679878.

Pro-regenerative signaling after acetaminophen-induced acute liver injury in mice identified using a novel incremental dose model. Authors: Bhushan, B; Walesky, C; Manley, M; Gallagher, T; Borude, P; Edwards, G; Monga, S; Apte, U. Journal Title: The American Journal of Pathology. Publisher: Elsevier. Publication Date: 11/2014. Volume: 184. Issue: 11. Pages: 3013-3025. DOI: 10.1016/j.ajpath.2014.07.019. PMID: 25193591.

Alpha-fetoproitein and prognosis in acute liver failure. Authors: Schiot, F; Ostapowicz, G; Murray, N; Satyanarana, R; Zaman, A; Munoz, S; Lee, W. Journal Title: Liver Transplantation. Publisher: Wiley. Publication Date: 12/2006. Volume: 12. Issue: 12. Pages: 1776-1781. DOI: 10.1002/lt.20886. PMID: 17133565.

Serum LECT2 level as a prognostic indicator in acute liver failure. Authors: Sato, Y.; Watanabe, H.; Kameyama, H.; Kobayashi, T.; Yamamoto, S.; Takeishi, T.; Hirano, K.; Oya, H.; Nakatsuka, H.; Watanabe, T.; Kokai, H.; Yamagoe, S.; Suzuki, K.; Oya, K.; Kojima, K.; Hatakeyama, K. Journal Title: Transplantation Proceedings. Publisher: Elsevier. Publication Date: 10/2004. Volume: 36. Issue: 8. Pages: 2359-2361. DOI: 10.1016/j.transproceed.2004.07.007. PMID: 15561249.

Leukocyte cell derived chemotaxin-2 (Lect2) as a predictor of survival in adult acute liver failure. Authors: Slowik, V; Borude, P; Jaeschke, H; Woolbright, B; Lee, W; Apte, U, the Acute Liver Failure Study Group. Journal Title: Translational Gastroenterology and Hepatology. Publisher: AME Publishing Company. Publication Date: 03/2019. Volume: 4. Issue: 17. Pages: 2359-2361. DOI: 10.21037/tgh.2019.03.03. PMID: 30976720.

The various embodiments described above can be combined to provide further embodiments.

Aspects of the embodiments can be modified to employ concepts of the various patents, application and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

All of the U.S. patents, U.S. patent application publications, U.S. patent application, foreign patents, foreign patent application and non-patent publications referred to in this specification and/or listed in the Application Data Sheet are incorporated herein by reference, in their entirety.

The invention claimed is:

1. A liver-specific Wingless-related integration site (Wnt) signal enhancing molecule, or a pharmaceutically acceptable salt thereof, comprising:
(a) a first domain comprising two modified human R-spondin 2 polypeptides, wherein the modified R-spondin 2 polypeptides comprise amino acid substitutions at positions F105 and F109 of SEQ ID NO:48, or fragments thereof comprising the furin 1 and furin 2 domains of the modified human R-spondin 2 polypeptides, wherein the first domain specifically binds one or more-transmembrane E3 ubiquitin ligases, wherein the one or more transmembrane E3 ubiquitin ligases are Zinc and Ring Finger 3 (ZNRF3) and Ring Finger Protein 43 (RNF43); and
(b) a second domain comprising an Immunoglobulin G (IgG) antibody comprising two heavy chain polypeptides and two light chain polypeptides, wherein the heavy chain polypeptides comprise a CDRH1 sequence of SYAMS (SEQ ID NO: 34), a CDRH2 sequence of AISGSGGSTYYAESVKG (SEQ ID NO: 63), and a CDRH3 sequence of DFSSRRWYLEY (SEQ ID NO: 36), and the light chain polypeptides comprise a CDRL1 sequence of QGESLRSYYAS (SEQ ID NO: 37), a CDRL2 sequence of YGKSNRPS (SEQ ID NO: 38), and a CDRL3 sequence of CTSLERIGYLSYV (SEQ ID NO: 39), wherein the second domain specifically binds a tissue-specific cell surface molecule, wherein the tissue specific cell surface molecule is an asialoglycoprotein receptor I (ASGRI),
wherein the first modified human R-spondin 2 polypeptides or fragments thereof of the first domain is fused to the N-terminus of the first heavy chain polypeptides of the second domain, and the second modified human R-spondin 2 polypeptide or fragment thereof of the first domain is fused to the N-terminus of the second heavy chain polypeptide of the second domain.

2. The molecule of claim 1, wherein the amino acid substitutions at positions F105 and F109 are: F105E and F109E.

3. The molecule of claim 1, comprising two antibody light chain polypeptides and two fusion polypeptides, wherein each fusion polypeptide comprises the modified human R-spondin 2 polypeptide or fragment thereof fused to the N-terminus of the IgG antibody heavy chain polypeptide via a peptidyl linker sequence, wherein the two fusion polypeptides are linked to each other, and the two antibody light chain polypeptides are each linked to different heavy chain polypeptides of the fusion polypeptides.

4. The molecule of claim 3, wherein the peptidyl linker sequences comprise one or more amino acids selected from the group consisting of: Glycine, Asparagine, Serine, Threonine and Alanine.

5. A pharmaceutical composition comprising the molecule of claim 1 and a pharmaceutically acceptable diluent, adjuvant or carrier.

6. The molecule of claim 3, wherein:
(i) the two antibody light chain polypeptides comprise a variable region sequence having at least 95% identity to the variable region sequence set forth in SEQ ID NO: 27; and/or
(ii) the two antibody heavy chain polypeptides comprise a variable region sequence having at least 95% identity to the variable region sequence set forth in amino acids 123-242 of SEQ ID NO: 8.

7. The molecule of claim 1 comprising:
(i) two polypeptides having at least 95% identity to SEQ ID NO: 7; and
(ii) two polypeptides having at least 95% identity to SEQ ID NO: 8.

8. The molecule of claim 6, comprising:
(i) two polypeptides of SEQ ID NO: 7; and
(ii) two polypeptides of SEQ ID NO: 8.

9. A pharmaceutical composition comprising the molecule of claim 7 and a pharmaceutically acceptable diluent, adjuvant or carrier.

10. The pharmaceutical composition of claim 9, wherein the molecule comprises:
(i) two polypeptides of SEQ ID NO: 7; and
(ii) two polypeptides of SEQ ID NO: 8.

* * * * *

UNITED STATES PATENT AND TRADEMARK OFFICE
CERTIFICATE OF CORRECTION

| | |
|---|---|
| PATENT NO. | : 12,240,876 B2 |
| APPLICATION NO. | : 18/311082 |
| DATED | : March 4, 2025 |
| INVENTOR(S) | : Yang Li et al. |

It is certified that error appears in the above-identified patent and that said Letters Patent is hereby corrected as shown below:

In the Claims

At Column 112, Claim number 1, Line number 60, please replace "human R-spondin 2 polypeptides" with --human R-spondin 2 polypeptide--;

At Column 112, Claim number 1, Line number 65, please replace "or fragments thereof" with --or fragment thereof--;

At Column 112, Claim number 1, Line number 66, please replace "first heavy chain polypeptides" with --first heavy chain polypeptide--;

At Column 114, Claim number 7, Line number 10, please replace "claim 1" with --claim 3--;

At Column 114, Claim number 8, Line number 15, please replace "claim 6" with --claim 7--.

Signed and Sealed this
Sixth Day of May, 2025

Coke Morgan Stewart
*Acting Director of the United States Patent and Trademark Office*